US006352982B1

(12) United States Patent
Mabuchi et al.

(10) Patent No.: US 6,352,982 B1
(45) Date of Patent: Mar. 5, 2002

(54) 4,1-BENZOXAZEPINES, THEIR ANALOGUES, AND THEIR USE AS SOMATOSTATIN AGONISTS

(75) Inventors: Hiroshi Mabuchi, Nara; Nobuhiro Suzuki, Tsukuba; Takashi Miki, Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/403,066

(22) PCT Filed: Apr. 20, 1998

(86) PCT No.: PCT/JP98/01797

§ 371 Date: Oct. 14, 1999

§ 102(e) Date: Oct. 14, 1999

(87) PCT Pub. No.: WO98/47882

PCT Pub. Date: Oct. 29, 1998

(30) Foreign Application Priority Data

Apr. 21, 1997 (JP) .............................................. 9-103138
Nov. 20, 1997 (JP) .............................................. 9-319545

(51) Int. Cl.$^7$ ...................... C07D 267/14; A61K 31/55; A61P 5/50
(52) U.S. Cl. .................. 514/211.05; 540/490
(58) Field of Search ....................... 540/490; 514/211.05

(56) References Cited

U.S. PATENT DOCUMENTS 3,458,501 A  7/1969 Bell et al. ................ 260/239.3

FOREIGN PATENT DOCUMENTS

| EP | 0567026 A1 | 10/1993 |
| EP | 0645377 A1 | 3/1995 |
| EP | 0645378 A1 | 3/1995 |
| EP | 0705607 A2 | 4/1996 |
| FR | 2733984 | 11/1996 |
| JP | 57-035576 | 2/1982 |
| JP | 7-97371 | 4/1995 |
| JP | 08259447 | 10/1996 |
| WO | WO 93/07129 | 4/1993 |
| WO | WO 95/14470 | 6/1995 |
| WO | WO 96/09827 | 4/1996 |
| WO | WO 97/10224 | 3/1997 |
| WO | WO 98/00406 | 1/1998 |

OTHER PUBLICATIONS

A. Walser et al., "Quinazolines and 1,4–Benzodiazepines . . . " *J. Org. Chem.*, vol. 38, No. 20, (1973), pp. 3502–3507.

Y. Masuoka et al., "Syntheses of Medium–Sized Heterocycles . . . " *Chemical Pharmaceutical Bulletin*, vol. 34, (1986), pp. 140–149.

M. Ankersen et al., "Discovery of a Novel Non–Peptide Somatostatin Agonist . . . " *J. Am. Chem. Soc.* (1998), 120, pp. 1368–1373.

*Primary Examiner*—Bruck Kifle
*Assistant Examiner*—Hong Liu
(74) *Attorney, Agent, or Firm*—Philippe Y. Riesen; Mark Chao

(57) ABSTRACT

The present invention provides a compound of the formula:

(I)

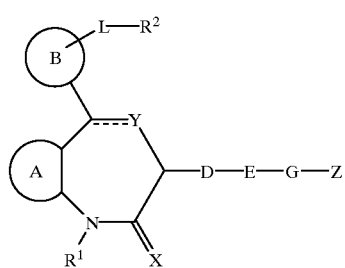

wherein ring A is an optionally substituted aromatic hydrocarbon ring or aromatic heterocyclic ring; ring B is an optionally substituted aromatic hydrocarbon ring or aromatic heterocyclic ring; Z is an optionally substituted cyclic group or linear hydrocarbon group; $R^1$ is a hydrogen atom, an optionally substituted hydrocarbon group or heterocyclic ring; $R^2$ is an optionally substituted amino group; D is a bond or an optionally substituted divalent hydrocarbon group; E is a bond, —CON($R^a$)—, —N($R^a$)CO—, —N($R^b$)CON($R^c$)—, —N($R^d$)COO—, —N($R^e$)SO$_2$—, —COO—, —N($R^f$)—, —O—, —S— —SO—, —SO$_2$—,

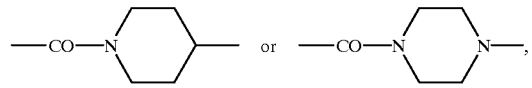

(in which $R^a$, $R^b$, $R^c$, $R^d$, $R^e$ and $R^f$ are respectively a hydrogen atom or an optionally substituted hydrocarbon group); G is a bond or an optionally divalent substituted hydrocarbon group; L is a divalent group;

ring B may form an optionally substituted non-aromatic condensed nitrogen-containing heterocyclic ring by combining with $R^2$; X is two hydrogen atoms, an oxygen atom or a sulfur atom; === is a single bond or a double bond, and Y is a nitrogen atom when === is a double bond, or an oxygen atom, —N($R^4$)— (in which $R^4$ is a hydrogen atom, an optionally substituted hydrocarbon group or an acyl group) or S(O)$_n$ (in which n is 0, 1 or 2) when === is a single bond, or a salt thereof, which have somatostatin receptor agonistic action.

31 Claims, No Drawings

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Oligomer SL-1 based on human SSTR1c DNA

<400> SEQUENCE: 1
ggtcgacctc agctaggatg ttccccaatg                                    30

<210> SEQ ID NO 2
<211> LENGTH: 28
<212> TYPE: DNA
<213> ORGANISM: Artificial Sequence
<220> FEATURE:
<223> OTHER INFORMATION: oligomer SL-2 based on human SSTR1c DNA
      sequence

<400> SEQUENCE: 2
ggtcgacccg ggctcagagc gtcgtgat                                      28

<210> SEQ ID NO 3
<211> LENGTH: 28
<212> TYPE: DNA
<213> ORGANISM: Artificial Sequence
<220> FEATURE:
<223> OTHER INFORMATION: oligomer PT-1 based on human SSTR2 cDNA
      sequence

<400> SEQUENCE: 3
ggtcgacacc atggacatgg cggatgag                                      28

<210> SEQ ID NO 4
<211> LENGTH: 26
<212> TYPE: DNA
<213> ORGANISM: Artificial Sequence
<220> FEATURE:
<223> OTHER INFORMATION: oligomer PT-2 based on human SSTR2 cDNA
      sequence

<400> SEQUENCE: 4
ggtcgacagt tcagatactg gtttgg                                        26

<210> SEQ ID NO 5
<211> LENGTH: 30
<212> TYPE: DNA
<213> ORGANISM: Artificial Sequence
<220> FEATURE:
<223> OTHER INFORMATION: oligomer S3-1 based on human SSTR3c DNA
      sequence
```

<400> SEQUENCE: 5
ggtcgacctc aaccatggac atgcttcatc          30

<210> SEQ ID NO 6
<211> LENGTH: 29
<212> TYPE: DNA
<213> ORGANISM: Artificial Sequence
<220> FEATURE:
<223> OTHER INFORMATION: oligomer S3-2 based on human SSTR3c DNA
      sequence

<400> SEQUENCE: 6
ggtcgacttt ccccaggccc ctacaggta           29

<210> SEQ ID NO 7
<211> LENGTH: 28
<212> TYPE: DNA
<213> ORGANISM: Artificial Sequence
<220> FEATURE:
<223> OTHER INFORMATION: oligomer S4-1 based on human SSTR4 DNA
      sequence

<400> SEQUENCE: 7
ggctcgagtc accatgagcg cccectcg            28

<210> SEQ ID NO 8
<211> LENGTH: 27
<212> TYPE: DNA
<213> ORGANISM: Artificial Sequence
<220> FEATURE:
<223> OTHER INFORMATION: oligomer S4-2 based on human SSTR4 DNA
      sequence

<400> SEQUENCE: 8
gggctcgagc tcctcagaag gtggtgg             27

<210> SEQ ID NO 9
<211> LENGTH: 28
<212> TYPE: DNA
<213> ORGANISM: Artificial Sequence
<220> FEATURE:
<223> OTHER INFORMATION: oligomer S5-1 based on human SSTR5c DNA
      sequence

<400> SEQUENCE: 9
ggtcgaccac catggagccc ctgttccc            28

<210> SEQ ID NO 10
<211> LENGTH: 26
<212> TYPE: DNA
<213> ORGANISM: Artificial Sequence
<220> FEATURE:
<223> OTHER INFORMATION: oligomer S5-2 based on human SSTR5c DNA
      sequence

<400> SEQUENCE: 10
ccgtcgacac tctcacagct tgctgg              26

4,1-BENZOXAZEPINES, THEIR ANALOGUES, AND THEIR USE AS SOMATOSTATIN AGONISTS

This application is the National Stage of International Application No. PCT/JP98/01797, filed on Apr. 20, 1998.

TECHNICAL FIELD

This invention relates to novel condensed cyclic compounds having somatostatin receptor agonistic activity, a process for producing their compounds and a pharmaceutical composition characterized by containing them.

BACKGROUND ART

Somatostatin was first isolated from ovine hypothalamic tissues as a peptide (SST-14) consisting of 14 amino acids having inhibitory action on the secretion of growth hormone. At present, a somatostatin (SST-28) consisting of 28 amino acids has also been isolated. This somatostatin is a brain-gut peptide widely distributed not only in the hypothalamus but also in other organs such as cerebrum, limbic system, spinal cord, vagus nerve, autonomic nerve nodule, gastrointestinal mucosa and islets of Langerhans in the pancreas. It inhibits the secretion of pituitary/gastrointestinal hormones such as growth hormones, thyroid-stimulating hormones, gastrin, insulin and glucagon. It also inhibits the secretion of gastric acid, pancreatic exocrine secretion and movement/blood flow of the intestines.

As somatostatin receptors have so far been made known Types 1 to 5 (SSTR1, SSTR2, SSTR3, SSTR4 and SSTR5). They have been recognized to show different expressions in each part of the central and peripheral regions [Life Sciences, Vol. 57, No. 13, p1249 (1995)].

At present, compounds analogous to the peptide-form somatostatins having specific hormone-inhibitory actions are under clinical development.

Condensed 4,1-benzoxazepine compounds having a substituent at the 3-position have been published in Chem. Pharm. Bull. 34 (1), p140–149 (1986), official gazettes of Japanese Published Unexamined Patent Application No. S57(1982)-35576, Japanese Published Unexamined Patent Application No. H6(1994)-239843(corresponding to EP-A-0567026), Japanese Published Unexamined Patent Application No. H7(1995)-179429(corresponding to EP-A-0645378), Japanese Published Unexamined Patent Application No. H7(1995)-179444(corresponding to EP-A-0645377), Japanese Published Unexamined Patent Application No. H7(1995)-267939, WO93/07129, WO96/09827, Japanese Published Unexamined Patent Application No. H8(1996)-259447, Japanese Published Unexamined Patent Application No. H8(1996)-157369.

2,3,4,5-Tetrahydro-2-oxo(or thioxo)-1H-1,4-condensed diazepine compounds having substituents at the 3- and 5-positions were published in J. Org. Chem., 38(20), 1973.

4,1-Benzoxazepine compounds having substituents at the 3- and 5-positions were published in Japanese Published Unexamined Patent Application No. H8(1996)-259447, WO96/09827.

DISCLOSURE OF THE INVENTION

The compounds now under development as somatostatin receptor agonists are peptide-form compounds. They have therefore many problems in various aspects such as duration of efficacy, dosing method, specificity and adverse drug reactions. In order to solve these problems, it is of great significance to originate and develop a non-peptide-form compound having an excellent somatostatin receptor agonistic action.

The present inventors have conducted extensive studies, in view of the above circumstances, to synthesize compounds represented by the following formula (I) or salts thereof for the first time. It is characterized by the chemical structure in which an amino group is bound via a divalent radical with the aromatic ring B in the formula (I):

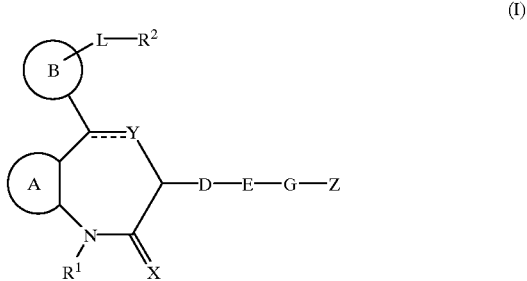

wherein ring A is an optionally substituted aromatic hydrocarbon ring or an optionally substituted aromatic heterocyclic ring, ring B is an optionally substituted aromatic hydrocarbon ring or an optionally substituted aromatic heterocyclic ring, Z is an optionally substituted cyclic group or an optionally substituted linear hydrocarbon group, $R^1$ is a hydrogen atom, an optionally substituted hydrocarbon group or an optionally'substituted heterocyclic ring, $R^2$ is an optionally substituted amino group, D is a bond or an optionally substituted divalent hydrocarbon group, E is a bond, —CON($R^1$)—, —N($R^a$)CO—, —N($R^b$)CON($R^c$)—, —N($R^d$)COO—, —N($R^e$)SO$_2$—, —COO—, —N($R^f$)—, —O—, —S—, —SO—, —SO$_2$—,

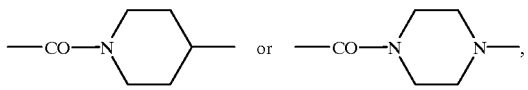

(in which $R^a$, $R^b$, $R^c$, $R^d$, $R^e$ and $R^f$ are respectively a hydrogen atom or an optionally substituted hydrocarbon group), G is a bond or an optionally divalent substituted hydrocarbon group, L is a divalent group, ring B may form an optionally substituted non-aromatic condensed nitrogen-containing heterocyclic ring by combining with $R^2$, and X is two hydrogen atoms, an oxygen atom or a sulfur atom, === is a single bond or a double bond, and Y is a nitrogen atom when === is a double bond, or an oxygen atom, —N($R^4$)— (in which $R^4$ is a hydrogen atom, an optionally substituted hydrocarbon group or an acyl group) or S(O)$_n$ (in which n is 0, 1 or 2) when === is a single bond, or a salt thereof, and where the compounds have excellent properties as drugs with their specific chemical structures, such as, unexpectedly preferred somatostatin receptor agonistic action with low toxicity. The present invention has been completed based on these findings.

Namely, the present invention relates to 1) the above-mentioned compound (I) or a salt thereof,
2) a compound described in the above item 1, wherein Z is an optionally substituted cyclic group, G is an optionally divalent substituted hydrocarbon group and ring B does not form a non-aromatic condensed nitrogen-containing heterocyclic ring by combining with $R^2$,
3) a compound described in the above item 2, wherein Y is a nitrogen atom when === is a double bond, or an oxygen atom or —$N(R^4)$— (in which $R^4$ is a hydrogen atom, an optionally substituted hydrocarbon group or an acyl group) when === is a single bond,
4) a compound described in the above item 1, wherein === is a single bond,
5) a compound described in the above item 1, wherein ring B is an optionally substituted benzene ring,
6) a compound described in the above item 1, wherein ring B is an optionally substituted aromatic heterocyclic ring,
7) a compound described in the above item 1, wherein ring B is a benzene ring or a thiophene ring,
8) a compound described in the above item 1, wherein ring A is an optionally substituted benzene ring,
9) a compound described in the above item 1, wherein ring A is a benzene ring which may be substituted with halogen, hydroxy or $C_{1-6}$ alkoxy,
10) a compound described in the above item 1, wherein R is an optionally substituted hydrocarbon group,
11) a compound described in the above item 1, wherein $R^1$ is a $C_{1-6}$ alkyl group or a $C_{7-14}$ aralkyl group, which may be substituted with hydroxy, phenyl or amino which may be substituted with $C_{1-6}$ alkyl-carbonyl or $C_{1-6}$ alkylsulfonyl,
12) a compound described in the above item 1, wherein X is an oxygen atom,
13) a compound described in the above item 1, wherein Y is an oxygen atom,
14) a compound described in the above item 1, wherein L is a hydrocarbon group which may be mediated by —O— or —S— and may be substituted,
15) a compound described in the above item 1, wherein L is a $C_{1-6}$ alkylene group,
16) a compound described in the above item 1, wherein Z is an optionally substituted phenyl group,
17) a compound described in the above item 1, wherein Z is a phenyl group which is substituted with halogen,
18) a compound described in the above item 1, wherein D is an optionally substituted divalent hydrocarbon group.
19) a compound described in the above item 1, wherein D is a $C_{1-6}$ alkylene group,
20) a compound described in the above item 1, wherein E is —$CON(R^a)$— (in which Ra is a hydrogen atom or an optionally substituted hydrocarbon group),
21) a compound described in the above item 1, wherein E is —CONH—,
22) a compound described in the above item 1, wherein G is a $C_{1-6}$ alkylene group,
23) a compound described in the above item 1, wherein $R^2$ is an unsubstituted amino group,
24) a compound described in the above item 1, wherein ring B forms a tetrahydroisoquinoline ring by combining with $R^2$,
25) a compound described in the above item 1, wherein ring A is an optionally substituted benzene ring, ring B is an optionally substituted benzene ring, Z is an optionally substituted phenyl group, D is a $C_{1-6}$ alkylene group, G is a $C_{1-6}$ alkylene group, R is an 2. optionally substituted hydrocarbon group, R is an unsubstituted amino group, E is —CONH—, L is a $C_{1-6}$ alkylene group, X is an oxygen atom,
=== is a single bond and Y is an oxygen atom,
26) a compound described in the above item 25, wherein ring A is a benzene ring which may be substituted with halogen, hydroxy or $C_{1-6}$ alkoxy, ring B is a benzene ring, Z is a phenyl group which may be substituted with halogen and $R^1$ is a $C_{7-14}$ aralkyl group which may be substituted with hydroxy, phenyl or amino which may be substituted with $C_{1-6}$ alkyl-carbonyl or $C_{1-6}$ alkylsulfonyl,
27) a compound described in the above item 1, wherein ring A is an optionally substituted benzene ring, ring B is an optionally substituted aromatic heterocyclic ring, Z is an optionally substituted phenyl group, D is a $C_{1-6}$ alkylene group, G is a $C_{1-6}$ alkylene group, $R^1$ is an optionally substituted hydrocarbon group, $R^2$ is an unsubstituted amino group, E is —CONH—, L is a $C_{1-6}$ alkylene group, X is an oxygen atom, === is a single bond and Y is an oxygen atom,
28) a compound described in the above item 27, wherein ring A is a benzene ring which may be substituted with halogen, hydroxy or $C_{1-6}$ alkoxy, ring B is a thiophene ring, Z is a phenyl group which may be substituted with halogen and $R^1$ is a $C_{7-14}$ aralkyl group which may be substituted with hydroxy, phenyl or amino which may be substituted with $C_{1-6}$ alkyl-carbonyl or $C_{1-6}$ alkylsulfonyl,
29) a compound described in the above item 1, wherein ring A is a benzene ring which may be substituted with halogen, hydroxy, $C_{1-6}$ alkoxy, halogeno-$C_{1-6}$ alkoxy, $C_{7-14}$ aralkyloxy, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy or hydroxyphenyl-$C_{1-6}$ alkoxy, ring B is a benzene ring or a thiophene ring, which may be substituted with $C_{1-6}$ alkoxy, or a tetrahydroisoquinoline ring by combining with $R^2$, Z is a $C_{6-14}$ aryl group, a $C_{3-10}$ cycloalkyl group, a piperidyl group, a thienyl group, a furyl group, a pyridyl group, a thiazolyl group, an-indolyl group or a $C_{1-6}$ alkyl group, which may have 1 to 3 substituents selected from halogen, formyl, halogeno-$C_{1-6}$ alkyl, $C_{1-6}$ alkoxy and $C_{1-6}$ alkoxy-carbonyl, oxo and pyrrolidinyl D is a $C_{1-6}$ alkylene group, G is a bond or a $C_{1-6}$ alkylene group which may have phenylene and which may be substituted with phenyl, $R^1$ is a hydrogen atom, a $C_{1-6}$ alkyl group, a $C_{2-6}$ alkenyl group, a $C_{6-14}$ aryl group or a $C_{7-14}$ aralkyl group, which may be substituted with (1)halogen, (2)nitro, (3)amino which may have 1 to 2 substituents selected from $C_{1-6}$ alkyl which may be substituted with $C_{1-6}$ alkyl-carbonyl, benzyloxycarbonyl and $C_{1-6}$ alkylsulfonyl, (4)hydroxy which may be substituted with (i)$C_{1-6}$ alkyl which may be substituted with hydroxy, $C_{1-6}$ alkyl-carbonyl, carboxy or $C_{1-6}$ alkoxy-carbonyl, (ii)phenyl which may be substituted with hydroxy, (iii)benzoyl or (iv)mono- or di-$C_{1-6}$ alkylamino-carbonyl, (5)$C_{3-6}$ cycloalkyl, (6)phenyl which may be substituted with hydroxy or halogeno-$C_{1-6}$ alkyl, or (7)thienyl, furyl, thiazolyl, indolyl or benzyloxycarbonylpiperidyl, $R^2$ is (1) an unsubstituted amino group, (2) a piperidyl group or (3) an amino group which have 1 to 2 substitutents selected from (i) benzyl, (ii) $C_{1-6}$ alkyl which may be substituted with amino or phenyl, (iii)

mono- or di-$C_{1-6}$ alkylcarbamoyl, (iV) $C_{1-6}$ alkoxycarbonyl, (V) $C_{1-6}$ alkyl-sulfonyl, (vi) piperidylcarbonyl and (vii) $C_{1-6}$ alkyl-carbonyl which may be substituted with halogen or amino, E is a bond, —CON($R^a$)—, —N($R^a$)CO—, —N($R^b$)CON ($R^c$)—, —COO—, —CO—N⟨ ⟩   or   —CO—N⟨ ⟩N—, in which $R^a$, $R^b$ and $R^c$ is a hydrogen atom or a $C_{1-6}$ alkyl group, L is a $C_{1-6}$ alkylene group which may be mediated by —O— and may be substituted with $C_{1-6}$ alkyl, X is an oxygen atom, and === is a single bond or a double bond, and Y is a nitrogen atom when === is a double bond, or an oxygen atom, —N($R^4$)— (in which R is a hydrogen atom, an optionally substituted hydrocarbon group or an acyl group) or $S(O)_n$ (in which n is 0, 1 or 2) when === is a single bond, 30) a compound described in the above item 1, which is
3,5-trans-N-(2-fluorobenzyl)-5-(3-aminomethylphenyl)-1-(4-biphenylmethyl)-7-chloro-2-oxo-1,2,3,5-tetrahydro-4,1-benzoxazepine-3-acetamide or a salt thereof, (3S,5S)-N-(2-fluorobenzyl)-5-(3-aminomethylphenyl)-7-chloro-1-neopentyl-2-oxo-1,2,3,5-tetrahydro-4,1-benzoxazepine-3-acetamide or a salt thereof, 3,5-trans-N-(2-fluorobenzyl)-5-(3-aminomethylphenyl)-1-[2-(4-biphenyl)ethyl]-7-chloro-2-oxo-1,2,3,5-tetrahydro-4,1-benzoxazepine-3-acetamide or a salt thereof, 3,5-trans-N-(2-fluorobenzyl)-5-(4-aminomethylphenyl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(2-aminomethylthiophen-5-yl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-[3-[(1-amino-1-methyl)ethyl]phenyl]-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-hydroxybenzyl)-2-oxo-1,2,3,5-tetrahydro-4,1-benzoxazepine-3-acetamide or a salt thereof, 3,5-trans-N-(2-fluorobenzyl)-1-(4-acetylaminobenzyl)-5-(3-aminomethylphenyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-methanesulfonylaminobenzyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-hydroxybenzyl)-7-methyloxy-2-oxo-1,2,3,5-tetrahydro-4,1-benzoxazepine-3-acetamide or a salt thereof, 3,5-trans-N-(2-fluorobenzyl)-5-[4-[(1-amino-1-methyl)ethyl]phenyl]-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-[2-(4-hydroxyphenyl)ethyl]-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-7-hydroxy-2-oxo-1,2,3,5-tetrahydro-4,1-benzoxazepine-3-acetamide or a salt thereof, or 3,5-trans-N-(2-fluorobenzyl)-1-(4-biphenylmethyl)-7-chloro-2-oxo-1,2,3,5-tetrahydro-5-(1,2,3,4-tetrahydroisoquinolin-5-yl)-4,1-benzoxazepine-3-acetamide or a salt thereof, 31) a process for producing the compound of the formula:

(I)

wherein the symbols are as defined in claim 1, or a salt thereof, which comprises reacting a compound of the formula:

wherein the symbols are as defined in claim 1, or a salt thereof, with a compound of the formula:

$R^a$
|
H-N—G—Z wherein the symbols are as defined in claim 1, or a salt thereof, 32) a pharmaceutical composition which comprises a compound (I) described in the above item 1 or a salt thereof in admixture with a pharmaceutically acceptable carrier or excipient, 33) a pharmaceutical composition described in the above item 32, which is a somatostatin receptor agonist, 34) a pharmaceutical composition described in the above item 32, which is for treating or preventing diabetes, obesity, diabetic complication or inveterate diarrhea, 35) use of a compound (I) described in the above item 1 or a salt thereof for manufacturing a pharmaceutical composition, 36) use of a compound (I) described in the above item 1 or a salt thereof for manufacturing a pharmaceutical composition which is a somatostatin receptor agonist, 37) use of a compound (I) described in the above item 1 or a salt thereof for manufacturing a pharmaceutical composition for treating or preventing diabetes, obesity, diabetic complication or inveterate diarrhea, 38) a method for activating somatostatin receptors in a mammal which comprises administering an effective amount of a compound (I) described in the above item 1 or a salt thereof to said mammal, 39) a method for using a compound (I) described in the above item 1 or a salt thereof as somatostatin receptor agonists in a mammal which comprises administering an effective amount of a compound of claim 1 or a salt thereof to said mammal, and 40) a method for treating or preventing diabetes, obesity, diabetic complication or inveterate diarrhea in a mammal which comprises administering an effective amount of a compound (I) described in the above item 1 or a salt thereof to said mammal.

In the formula mentioned above, ring A stands for an optionally substituted aromatic hydrocarbon group or an optionally substituted aromatic heterocyclic ring. As ring A is preferably used, for example, an optionally substituted aromatic hydrocarbon group is used. Especially an optionally substituted benzene ring is frequently used.

As said "aromatic hydrocarbon group" represented by ring A are mentioned aromatic hydrocarobons consisting of 6 to 14 carbon atoms (for example, $C_{6-14}$ aryl such as benzene, naphthalene, anthracene and phenanthrene). Especially benzene is frequently used.

As said "aromatic heterocyclic ring" represented by ring A are mentioned, for example, monocyclic aromatic heterocyclic ring and polycyclic aromatic condensed heterocyclic ring. As said "monocyclic aromatic heterocyclic ring" are mentioned 5- or 6-membered monocyclic aromatic heterocyclic rings having 1 to 4 hetero atoms selected from nitrogen, oxygen and sulfur in addition to carbon atoms. More specifically, furan, thiophene, pyrrole, oxazole, isooxazole, thiazole, isothiazole, imidazole, pyrazole, 1,2,3-oxadiazole, 1,2,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine and triazine are used for example. As said "polycyclic aromatic condensed heterocyclic ring" are mentioned, for example, bi- or tri-cyclic aromatic condensed heterocyclic ring which is formed by the condensation of the benzene ring and said "monocyclic aromatic heterocyclic rings". More specifically, benzofuran, isobenzofuran, benzo[b]thiophene, indole, isoindole, 1H-indazole, benzimidazole, benzoxazole, 1,2-benzoisoxazole, benzthiazole, 1,2-benzisothiazole, 1H-benzotriazole, quinoline, isoquinoline, cinnolin, quinazoline, quinoxaline, phthalazine, naphthylidine, purine, pteridine, carbazole, α-carbolin, β-carbolin, γ-carbolin, acridine, phenoxazine, phenothiazine, phenazine, phenoxathine, thianthrene, phenatrizine, phenanthroline, indolidine, pyrrolo[1,2-b]pyridazine, pyrazolo[1,5-a)pyridine, imidazo[1,2-a]pyridine, imidazo[1,5-a]pyridine, imidazo(1,2-a]pyridazine, imidazo[1,2-a]pyrimidine, 1,2,4-triazolo[4,3-a]pyridine and 1,2,4-triazolo[4,3-b]pyridazine are used for example. As said "aromatic heterocyclic ring" represented by ring A is preferably used, for example, said "monocyclic aromatic heterocyclic ring". Especially, furan, thiophene and pyridine are frequently used for example.

As the substituents that said "aromatic hydrocarbon group", "aromatic heterocyclic ring" and "benzene ring" may have are mentioned, for example, halogen atom (for example, fluorine, chlorine, bromine and iodine), $C_{1-6}$ alkyl (for example, methyl, ethyl, propyl, butyl, sec-butyl, t-butyl and isopropyl), halogeno-$C_{1-6}$ alkyl (for example, $C_{1-6}$ alkyl groups substituted with 1 to 5 said "halogen atoms" such as trifluoromethyl), phenyl, benzyl, $C_{1-6}$ alkoxy (for example, methoxy, ethoxy, propoxy, butoxy, sec-butoxy, t-butoxy and isopropoxy), halogeno-$C_{1-6}$ alkoxy (for example, $C_{1-6}$ alkoxy groups substituted with 1 to 5 said "halogen atoms" such as trifluoromethoxy and chloropropyloxy), phenoxy, $C_{7-14}$ aralkyloxy (for example, benzyloxy, phenethyloxy and phenylpropyloxy), formyloxy, $C_{1-6}$ alkyl-carbonyloxy (for example, acetyloxy), $C_{1-6}$ alkylthio (for example, methylthio, ethylthio, propylthio, butylthio, sec-butylthio, t-butylthio and isopropylthio), halogeno-$C_{1-6}$ alkylthio (for example, $C_{1-6}$ alkylthio groups substituted with 1 to 5 said "halogen atoms" such as trifluoromethylthio), hydroxy, mercapto, cyano, nitro, carboxy, formyl, $C_{1-6}$ alkyl-carbonyl (for example, acetyl and propionyl), benzoyl, $C_{1-6}$ alkoxy-carbonyl (for example, methoxycarbonyl, ethoxycarbonyl and propoxycarbonyl), phenoxycarbonyl, amino, mono- or di-$C_{1-6}$ alkylamino (for example, methylamino, ethylamino, dimethylamino and diethylamino), formylamino, $C_{1-6}$ alkyl-carbonylamino (for example, acetylamino, propyonylamino and butyrylamino), carbamoyl, mono- or di-$C_{1-6}$ alkyl-carbamoyl (for example, N-methylcarbamoyl, N-ethylcarbamoyl, N,N-dimethylcarbamoyl and N,N-diethylcarbamoyl), sulfo, $C_{1-6}$ alkylsulfonyl (for example, methylsulfonyl, ethylsulfonyl and propylsulfonyl), benzoyl-$C_{1-6}$ alkoxy (for example, hydroxyethyloxy), hydroxy-$C_{1-6}$ alkoxy (for example, hydroxyethyloxy), $C_{1-6}$ alkoxy-carbonyl-$C_{1-6}$ alkoxy (for example, methoxycarbonylmethyloxy), $C_{3-14}$ cycloalkyl-$C_{1-6}$ alkoxy (for example, cyclohexylmethyloxy), imidazol-1-yl-$C_{1-6}$ alkoxy (for example, imidazol-1-ylpropyloxy), $C_{7-14}$ aralkyloxy-carbonyl-$C_{1-6}$ alkoxy (for example, benzyloxycarbonylmethyloxy), hydroxyphenyl-$C_{1-6}$ alkoxy (for example, [3-(4-hydroxyphenyl)propyl]oxy), $C_{7-14}$ aralkyloxy-carbonyl (for example, benzyloxy-carbonyl), mono- or di-$C_{1-6}$ alkylamino-$C_{1-6}$ alkoxy (for example, methylaminomethoxy, ethylaminoethoxy, dimethylaminomethoxy) and mono- or di-$C_{1-6}$ alkylamino-carbonyloxy (for example, methylaminocarbonyloxy, ethylaminocarbonyloxy, dimethylaminocarbonyloxy). Especially, said "halogen atom" is frequently used. Said "aromatic hydrocarbon ring", "aromatic heterocyclic ring" and "benzene ring" may have 1 to 4 substituents selected from their substituents.

A preferable example of ring A is an optionally substituted benzene ring and more preferably, a benzene ring which may be substituted with halogen, hydroxy, $C_{1-6}$ alkoxy, halogeno-$C_{1-6}$ alkoxy, $C_{7-14}$ aralkyloxy, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy or hydroxyphenyl-$C_{1-6}$ alkoxy. The most preferable examples of ring A are a benzene ring which may be substituted with halogen (preferably, chlorine and etc.), hydroxy or $C_{1-6}$ alkoxy (preferably, methoxy and etc.).

Preferable position of substituents for ring A is 7- or 8-position.

Preferable number of substituents for ring A is 1 or 2.

In the formula mentioned above, ring B stands for an optionally substituted aromatic hydrocarbon group or an optionally substituted aromatic heterocyclic ring. As ring B, an optionally substituted aromatic hydrocarbon group is preferably used for example. Especially an optionally substituted benzene ring is frequently used.

As said "aromatic hydrocarbon groups" represented by ring B are mentioned, for example, an aromatic hydrocarbon group consisting of 6 to 14 carbon atoms ($C_{6-14}$ aryl groups of, for example, benzene, naphthalene, anthracene and phenanthrene). Especially benzene is frequently used.

As said "aromatic heterocyclic ring" represented by ring B are mentioned, for example, monocyclic aromatic heterocyclic rings and polycyclic aromatic condensed heterocyclic rings. As said "monocyclic aromatic heterocyclic ring" are mentioned 5- or 6-membered monocyclic aromatic heterocyclic rings having 1 to 4 hetero atoms selected from nitrogen, oxygen and sulfur in addition to carbon atoms. More specifically, furan, thiophene, pyrrole, oxazole, isooxazole, thiazole, isothiazole, imidazole, pyrazole, 1,2,3-oxadiazole, 1,2,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine and triazine are used for example. As said "polycyclic aromatic condensed heterocyclic ring" are mentioned, for example, bi- or tricyclic aromatic condensed heterocyclic rings which are formed by the condensation of the benzene ring and said "monocyclic aromatic heterocyclic ring". More specifically, benzofuran, isobenzofuran, benzo[b]thiophene, indole, isoindole, 1H-indazole, benzimidazole, benzoxazole, 1,2-benzisooxazole, benzothiazole, 1,2-benzisothiazole, 1H-benzotriazole, quinoline, isoquinoline, cinnolin, quinazoline, quinoxaline, phthalazine, naphthylidine, purine, pteridine, carbazole, α-carbolin, β-carbolin, γ-carbolin, acridine, phenoxazine, phenothiazine, phenazine, phenoxathine, thianthorene, phenatrizine, phenanthroline, indolidine, pyrrolo[1,2-b]pyridazine, pyrazolo[1,5-a]pyridine, imidazo[1,2-a]pyridine, imidazo[1,5-a]pyridine, imidazo[1,2-a]pyridazine, imidazo[1,2-a]pyrimidine, 1,2,4-triazolo[4,3-a]pyridine and 1,2,4-triazolo[4,3-b]pyridazine are used for example. As said "aromatic heterocyclic ring" represented by ring B is preferably used, for example, "monocyclic aromatic heterocyclic ring". Especially, furan, thiophene and pyridine(more especially, thiophene) are frequently used.

As the substituents that said "aromatic hydrocarbon ring", "aromatic heterocyclic ring" and "benzene ring" may have are mentioned, for example, the same substituents that said "aromatic hydrocarbon" at ring A may have. Said "aromatic hydrocarbon ring", "aromatic heterocyclic ring" and "benzene ring" may have 1 to 4 substituents selected from these substituents.

Preferable example of ring B are an optionally substituted benzene ring or aromatic heterocyclic ring and more preferably, a benzene ring or a thiophene ring, which may be substituted with $C_{1-6}$ alkoxy. The most preferable example of ring B is an unsubstituted benzene ring or an unsubstituted thiophene ring.

In the formula mentioned above, ring B may form an optionally substituted non-aromatic condensed nitrogen-containing heterocyclic ring by combining with $R^2$.

Examples of non-aromatic condensed nitrogen-containing heterocyclic rings formed when ring B combines with $R^2$ include bi-cyclic non-aromatic condensed nitrogen-containing heterocyclic ring which is formed by the condensation of benzene ring and the 5- or 6-membered monocyclic non-aromatic heterocyclic ring having 1 to 3 hetero atoms selected from nitrogen, oxygen and sulfur and preferably, tetrahydroisoquinoline (for example, 1,2,3,4-tetrahydroisoquinoline), tetrahydroquinoline (for example, 1,2,3,4-tetrahydroquinoline), isoindoline, indoline, 2,3-dihydrobenzthiazole, 2,3-dihydrobenzoxazole, 3,4-dihydro-2H-1,4-benzthiazine, 3,4-dihydro-2H-1,4-benzoxazine, 1,2,3,4-tetrahydroquinoxaline, 2,3,4,5-tetrahydro-1,4-benzoxazepine and more preferably, tetrahydroisoquinoline.

As the substituents that said "non-aromatic condensed nitrogen-containing heterocyclic ring" may have are mentioned, for example, the same substituents that said "aromatic hydrocarbon ring, aromatic heterocyclic ring and benzene ring" represented by ring B may have. The said "non-aromatic condensed nitrogen-containing heterocyclic ring" may have 1 to 4 substituents selected from the above.

In the formula mentioned above, Z stands for an optionally substituted cyclic group or an optionally substituted linear hydrocarbon group. As said "cyclic !D group" represented by Z are mentioned cyclic hydrocarbon group and heterocyclic group, for example. As ring Z is preferably used an optionally substituted aromatic hydrocarbon group and an optionally substituted aromatic heterocyclic group for example. Especially, an optionally substituted phenyl group is frequently used.

Said "cyclic hydrocarbon group" is represented by alicyclic hydrocarbon group consisting of 3 to 14 carbon atoms or aromatic hydrocarbon group consisting of 6 to 14 carbon atoms. As said "alicyclic hydrocarbon group" are mentioned, for example, $C_{3-14}$ cycloalkyl (for example, cyclopropyl, cyclobutyl, cyclopentyl and cyclohexyl), $C_{3-14}$ cycloalkenyl (for example, cyclopentenyl and cyclohexenyl), $C_{5-14}$ cycloalkadienyl (for example, 2,4-cycloptentadienyl and 1,3-cyclohexadienyl) and indanyl. As said "aromatic hydrocarbon group" are mentioned $C_{6-14}$ aryl (for example, phenyl, naphthyl, anthracenyl and phenanthrenyl) for example.

As said "heterocyclic group" are mentioned, for example, monocyclic heterocyclic group and polycyclic condensed heterocyclic group. As said "monocyclic heterocyclic group" are mentioned 5- or 6-membered monocyclic heterocyclic group having 1 to 4 hetero atoms selected from nitrogen, oxygen and sulfur in addition to carbon atoms, for example. More specifically, monocyclic aromatic heterocyclic group (for example, furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl and triazinyl), monocyclic non-aromatic heterocyclic group (for example, oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl) are used for example. As said "polycyclic condensed heterocyclic group" are mentioned, for example, bi- or tri-cyclic aromatic condensed heterocyclic group which is formed by the condensation of benzene ring and said "monocyclic aromatic heterocyclic ring" or these partial reduction. More specifically, polycyclic aromatic condensed heterocyclic groups (for example, benzofuryl, isobenzofuryl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthorenyl, phenatrizinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazine, imidazo[1,2-a]pyrimidine, 1,2,4-triazolo[4,3-a]pyridyl, 1,2,4-triazolo[4,3-b]pyridazinyl) and polycyclic non-aromatic condensed heterocyclic groups (for example, isochromanyl, chromanyl, indolinyl, isoindolinyl, 1,2,3,4-tetrahydroisoquinolinyl and 1,2,3,4-tetrahydroquinolinyl) are used.

As the substituents that said "cyclic group" represented by Z may have are mentioned, for example, the same substituents that said "aromatic hydrocarbon group" in ring A may have, oxo and thioxo. Said "cyclic group" may have 1 to 5 substituents selected from these substituents.

As said "linear hydrocarbon group" represented by Z are mentioned, for example, "aliphatic hydrocarbon group" of "hydrocarbon group" represented by $R^1$. As the substituents that "linear hydrocarbon group" represented by Z may have are mentioned, for example, the same substituents that said "aromatic hydrocarbon group" represented by R may have.

Preferable examples of Z is a $C_{6-14}$ aryl group (preferably, phenyl), a $C_{3-10}$ cycloalkyl group, a piperidyl group, a thienyl group, a furyl group, a pyridyl group, a thiazolyl group, an indolyl group or a $C_{1-6}$ alkyl group, which may have 1 to 3 substituents selected from halogen, forymyl, halogeno-$C_{1-6}$ alkyl, $C_{1-6}$ alkoxy, $C^{1-6}$ alkoxy-carbonyl, oxo and pyrrolidinyl, and more preferably, a phenyl group substituted with halogen (preferably, fluorine).

Preferable position of substituents for cyclic group represented by Z is ortho-position.

Preferable number of substituents for cyclic group represented by Z is one.

In the formula mentioned above, D stands for a bond or an optionally substituted divalent hydrocarbon group, preferably divalent hydrocarbon groups.

As said "divalent hydrocarbon group" represented by D is used a straight chain divalent hydrocarbon group with 1 to 10 carbons, for example. Specifically, $C_{1-10}$ alkylene (for example, methylene, ethylene, propylene, butylene, pentamethylene, hexamethylene, peptamethylene and octamethylene) is mentioned for example. More specifically, $C_{1-6}$ alkylene (for example, methylene, ethylene, propylene, butylene, pentamethylene, hexamethylene) is mentioned. Said "divalent hydrocarbon group" may have a $C_{3-6}$ cycloalkylene (for example, 1,4-cyclohexylene), phenylene (for example, 1,4-phenylene and 1,2-phenylene), for example, at any position.

As the substituents that said "divalent hydrocarbon group" represented by D may have are mentioned, for example, $C_{1-6}$ alkyl (for example, methyl, ethyl, propyl and isopropyl), halogeno-$C_{1-6}$ alkyl (for example, $C_{1-6}$ alkyl substituted by said 1 to 5 "halogen atoms" such as trifluoromethyl), phenyl and benzyl. Said "divalent hydrocarbon group" may have 1 to 3 of these substituents.

As D, $C_{1-6}$ alkylene (for example, methylene, ethylene and propylene, preferably methylene) is frequently used.

In the formula mentioned above, G stands for a bond or an optionally substituted divalent hydrocarbon group. As the "optionally substituted divalent hydrocarbon group" represented by G is used the same as the above-mentioned "optionally substituted divalent hydrocarbon group" represented by D for example.

Preferable examples of G are a bond or a $C_{1-6}$ alkylene group which may have phenylene and which may be substituted with phenyl and $C_{1-6}$ alkylene (for example, methylene, ethylene, propylene) is frequently used as G. $C_{1-6}$ alkylene represented by G may be mediated by phenylene between G and E or Z, or may include phenylene in $C_{1-6}$ alkylene.

In the formula mentioned above, $R^1$ stands for hydrogen atom, an optionally substituted hydrocarbon group or an optionally substituted heterocyclic ring. As $R^1$ is preferably used an optionally substituted hydrocarbon group.

As said "hydrocarbon group" represented by $R^1$ are mentioned, for example, aliphatic hydrocarbon groups, alicyclic hydrocarbon groups, aryl groups and aralkyl groups. Especially, aliphatic hydrocarbon is frequently used.

As said "aliphatic hydrocarbon group" are mentioned aliphatic hydrocarbon groups having 1 to 10 carbon atoms (for example, $C_{1-10}$ alkyl, $C_{2-10}$ alkenyl and $C_{2-10}$ alkynyl). As said "$C_{1-10}$ alkyl", are mentioned, for example, methyl, ethyl, propyl, isopropyl, butyl, isobutyl, sec-butyl, t-butyl, pentyl, isopentyl, neopentyl, 1-methylpropyl, hexyl, isohexyl, 1,1-dimethylbutyl, 2,2-dimethylbutyl, 3,3-dimethylbutyl, 3,3-dimethylpropyl, 2-ethylbutyl and heptyl. Preferably, $C_{3-5}$ alkyl (for example, propyl, isopropyl, isobutyl and neopentyl) is mentioned. Especially, isobutyl and neopentyl are frequently used. As said "$C_{2-10}$ alkenyl", are mentioned, for example, vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. More specifically, $C_{2-6}$ alkenyl (for example, vinyl, allyl, isopropenyl, 2-methylallyl, 2-methyl-1-propenyl, 2-methyl-2-propenyl and 3-methyl-2-butenyl) is frequently used for example. As said "$C_{2-10}$ alkynyl" are mentioned, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Especially, $C_{2-6}$ alkynyl (for example, ethynyl, 1-propynyl and 2-propynyl) is frequently used for example.

As said "alicyclic hydrocarbon" are mentioned, for example, alicyclic hydrocarbon with 3 to 10 carbons (for example, $C_{3-10}$ cycloalkyl, $C_{3-10}$ cycloalkenyl and $C_{5-10}$ cycloalkadienyl). As said "$C_{3-10}$ cycloalkyl" are mentioned, for example, cyclopropyl, cyclobutyl, cyclopentyl, cyclohexyl, cycloheptyl, cyclooctyl and cyclononyl). As said "$C_{3-10}$ cycloalkenyl" are mentioned, for example, 1-cyclobuten-1-yl, 1-cyclopenten-1-yl, 2-cyclopenten-1-yl, 3-cyclopenten-1-yl, 2-cyclohexen-1-yl and 3-cyclohexen-1-yl. As said "$C_{5-10}$ cycloalkadienyl" are mentioned, for example, 2,4-cyclopentadien-1-yl and 2,5-cyclohexadien-1-yl.

As said "aryl" are mentioned, for example, $C_{6-14}$ aryl (for example, phenyl, naphtyl, anthryl, phenanthryl and acenaphthylenyl).

As said "aralkyl" are mentioned, for example, $C_{7-14}$ aralkyl (for example, benzyl, phenethyl, 3-phenylpropyl, 4-phenylbutyl and 2-naphthylmethyl).

As the substituents that said "hydrocarbon group" may have are mentioned, for example, halogen atoms, nitro, cyano, imino, optionally substituted amino, optionally substituted hydroxy group, optionally substituted carboxy, cycloalkyl, cycloalkenyl and optionally substituted heterocyclic. The group containing aromatic ring in said "hydrocarbon group" may have alkyl, halogenoalkyl and optionally substituted aryl in addition to the substituents described before. These substituents may be substituted by 1 to 5 (preferably 1 to 3) said "hydrocarbon groups".

As said "halogen atom" that is the substituent of said "hydrocarbon group" are mentioned fluorine, chlorine, bromine and iodine for example.

As said "optionally substituted amino group" that is the substituent of said "hydrocarbon group" are mentioned, for example, (1) amino group that may have 1 to 2 substituents selected from (i) $C_{1-6}$ alkyl that may be substituted by 1 to 5 said "halogen atoms" (for example, methyl, ethyl, propyl, isopropyl and trifluoromethyl), phenyl and benzyl, (ii) formyl, $C_{1-6}$ alkyl-carbonyl (for example, acetyl, propyonyl, butyryl), benzoyl, (iii) $C_{1-6}$ alkoxy-carbonyl (for example, methoxycarbonyl, ethoxycarbonyl, propoxycarbonyl, sec-propoxycarbonyl and butoxycarbonyl) and $C_{7-14}$ aralkyloxy-calbonyl (for example, benzyloxycarbonyl), (iv)

sulfo group and $C_{1-6}$ alkylsulfonyl (for example, methylsulfonyl, ethylsulfonyl, propylsulfonyl, sec-propylsulfonyl, butylsulfonyl and t-butylsulfonyl), and (v) $C_{1-6}$ alkylaminocarbonyl (for example, methylaminocarbonyl, ethylaminocarbonyl, propylaminocarbonyl, butylaminocarbonyl and dimethylaminocarbonyl), and (2) pyrrolidinyl, piperidyl, morpholinyl, thiomorpholinyl, 4-methylpiperidyl and 4-phenylpiperidyl.

As the substituents that said "optionally substituted hydroxy group" may have are mentioned, for example, (i) optionally substituted $C_{1-6}$ alkyl, (ii) optionally substituted $C_{6-10}$ aryl, (iii) optionally substituted $C_{7-14}$ aralkyl and (iv) acyl. As "$C_{1-6}$ alkyl" in said "optionally substituted $C_{1-6}$ alkyl" are mentioned, for example, methyl, ethyl, propyl, isopropyl, butyl and pentyl. Said "$C_{1-6}$ alkyl" may have 1 to 3 substituents selected from, for example, halogen atoms (for example, fluorine, chlorine, bromine and iodine), hydroxy, $C_{1-6}$ alkoxy (for example, methoxy, ethoxy, propoxy and isopropoxy), formyl, $C_{1-6}$ alkyl-carbonyl (for example, acetyl, propyonyl and butyryl), carboxyl, $C_{1-6}$ alkoxy-carbonyl (for example, methoxycarbonyl, ethoxycarbonyl, propoxycarbonyl, sec-propoxycarbonyl and butoxycarbonyl), amino, mono- or di-$C_{1-6}$ alkylamino (for example, methylamino, ethylamino, dimethylamino and diethylamino), pyrrolidyl, piperidyl, morpholinyl, thiomorpholinyl, 4-methylpiperidyl, 4-phenylpiperidyl, carbamoyl, mono- or di-$C_{1-6}$ alkyl-carbamoyl (for example, N-methylcarbamoyl, N-ethylcarbamoyl, N,N-dimethylcarbamoyl and N,N-diethylcarbamoyl), phenoxy, mono- or di-$C_{1-6}$ alkyl-carbamoyloxy (for example, N-methylcarbamoyloxy, N-ethylcarbamoyloxy, N,N-dimethylcarbamoyloxy, N,N-diethylcarbamoyloxy), formylamino, $C_{1-6}$ alkyl-carbonylamino (for example, acetylamino, propionylamino and butyrylamino), formyloxy and $C_{1-6}$ alkyl-carbonyloxy (for example, acetoxy). As "$C_{6-10}$ aryl" in said "optionally substituted $C_{6-10}$ aryl" are mentioned, for example, phenyl and naphthyl. Said "$C_{6-10}$ aryl" may have 1 to 5 substituents selected from, for example, $C_{1-6}$ alkyl (for example, methyl, ethyl, propyl and isopropyl) and halogeno-$C_{1-6}$ alkyl (for example, $C_{1-6}$ alkyl substituted by 1 to 5 said "halogen atoms", such as trifluoromethyl) in addition to the substituents that said "$C_{1-6}$ alkyl" may have. As said "optionally substituted $C_{7-14}$ aralkyl" are mentioned, for example, benzyl and phenethyl. As said substituents that "$C_{7-14}$ aralkyl" may have are mentioned those that said "$C_{6-10}$ aryl" may have. The number of substituents is 1 to 5. As said "acyl" are mentioned, for example, formyl, $C_{1-6}$ alkyl-carbonyl (for example, acetyl, propyonyl, butyryl and t-butylcarbonyl), benzoyl, $C_{1-6}$ alkoxy-carbonyl (for example, methoxycarbonyl, ethoxycarbonyl, propoxycarbonyl, sec-propoxycarbonyl, butoxycarbonyl and t-butoxycarbonyl), benzyloxycarbonyl, $C_{1-6}$ alkylsulfonyl (for example, methylsulfonyl, ethylsulfonyl, propylsulfonyl, sec-propylsulfonyl, butylsulfonyl and t-butylsulfonyl), carbamoyl and mono- or di-$C_{1-6}$ alkyl-carbamoyl (for example, N-methylcarbamoyl, N-ethylcarbamoyl, N,N-dimethylcarbamoyl and N,N-diethylcarbamoyl). These may have 1 to 3 substituents selected from, for example, halogen atoms (for example, fluorine, chlorine, bromine and iodine), hydroxy, $C_{1-6}$ alkoxy (for example, methoxy, ethoxy, propoxy and isopropoxy), formyl, $C_{1-6}$ alkyl-carbonyl (for example, acetyl, propyonyl and butyryl), carboxyl, $C_{1-6}$ alkoxy-carbonyl (for example, methoxycarbonyl, ethoxycarbonyl, propoxycarbonyl, sec-propoxycarbonyl and butoxycarbonyl), amino group, mono- or di-$C_{1-6}$ alkylamino group (for example, methylamino, ethylamino, dimethylamino and diethylamino), pyrrolidinyl, piperidyl, morpholinyl, thiomorpholinyl, 4-methylpiperidyl, 4-phenylpiperidyl, 4-benzyloxycarbonylpiperidyl, carbamoyl, mono- or di-$C_{1-6}$ alkyl-carbamoyl (for example, methylcarbamoyl, ethylcarbamoyl, dimethylcarbamoyl and diethylcarbamoyl), phenoxy, mono- or di-$C_{1-6}$ alkyl-carbamoyloxy (for example, methylcarbamoyloxy, ethylcarbamoyloxy, dimethylcarbamoyloxy and diethylcarbamoyloxy), formylamino, $C_{1-6}$ alkyl-carbonylamino group (for example, acetylamino, propyonylamino and butyrylamino), formyloxy and $C_{1-6}$ alkyl-carbonyloxy (for example, acetoxy).

As the substituents that said "optionally substituted carboxyl" that is the substituent of said "hydrocarbon group." may have are mentioned, for example, $C_{1-6}$ alkyl (for example, methyl, ethyl, propyl, isopropyl, butyl and t-butyl), benzyl and mono- or di-$C_{1-6}$ alkylamino group (for example, methylamino, ethylamino, dimethylamino and diethylamino).

As said "cycloalkyl" which is the substituent of said "hydrocarbon group" are mentioned, for example, $C_{3-6}$ cycloalkyl such as cyclopropyl, cyclobutyl, cyclopentyl and cyclohexyl.

As said "cycloalkenyl" which is the substituent of said "hydrocarbon group" are mentioned, for example, $C_{3-6}$ cycloalkenyl such as 1-cyclobuten-1-yl, 1-cyclopenten-1-yl, 2-cyclopenten-1-yl, 3-cyclopenten-1-yl, 2-cyclohexen-1-yl and 3-cyclohexen-1-yl.

As "heterocyclic ring" in said "optionally substituted heterocyclic ring" that is the substituents of said "hydrocarbon group" are mentioned, for example, 5- or 6-membered monocyclic heterocyclic ring having 1 to 4 hetero atoms selected from nitrogen, oxygen and sulfur in addition to carbon atom (for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyi, oxylanyl, azetidinyl, oxetanyl, thietanyl, pyrrolidinyl, tetrahydrofuranyl, thiolanyl, piperidyl, tetrahydro-pyranyl, morpholinyl, thiomorpholinyl and piperadinyl), and benzene ring, bi- or tri-cyclic condensed heterocyclic ring which is formed by the condensation of above-described "5- or 6-membered monocyclic heterocyclic ring" (for example, benzofuranyl, isobenzofuryl, benzo[b]thienyl, indolyl, isoindolyl, 1H-indazolyl, benzimidazolyl, benzoxazolyl, 1,2-benzoisoxazolyl, benzthiazolyl, 1,2-benzoisothiazolyl, lH-benzotriazolyl, quinolyl, isoquinolyl, cinnolinyl, quinazolinyl, qunoxalinyl, phthalazinyl, naphthyldinyl, purinyl, puteridinyl, carbazolyl, α-carbolinyl, β-carbolinyl, γ-carbolinyl, acridinyl, phenoxazinyl, phenothiazinyl, phenazinyl, phenoxanthinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]-pyridazinyl, isochromanyl, chromanyl, indolinyl and isoindolinyl). As the substituents which said "heterocyclic ring" may have are mentioned, for example, oxo and pyrrolidinyl, in addition to the same substituents as those for said "aromatic hydrocarbon group" in ring A. Said "heterocyclic ring" may have 1 to 4 substituents selected from the substituents mentioned above, As said "alkyl" which is the substituent of said "hydrocarbon group" are mentioned, for example, $C_{1-6}$ alkyl such as methyl, ethyl, propyl, isopropyl, butyl, isobutyl, sec-butyl and t-butyl.

As said "halogenoalkyl" which is the substituent of said "hydrocarbon group" are mentioned, for example, $C_{1-6}$ alkyl substituted by 1 to 5 halogen atoms (for example, fluorine, chlorine, bromine and iodine) (for example, trifluoromethyl and trichloromethyl).

As "aryl" in said "optionally substituted aryl" which is the substituent of said "hydrocarbon group" are mentioned, for example, $C_{6-14}$ aryl such as phenyl, naphthyl, 2-biphenyl, 3-biphenyl, anthryl, phenanthryl and acenaphthylenyl. Said "phenyl", may have 1 to 5 substituents which are selected from, for example, halogen atoms (for example, fluorine, chlorine, bromine and iodine), $C_{1-6}$ alkyl (for example, methyl, ethyl, propyl, isopropyl, butyl and t-butyl), halogeno-$C_{1-6}$ alkyl (for example, $C_{1-6}$ alkyl substituted by 1 to 5 said "halogen atoms" such as trifluoromethyl), $C_{1-6}$ alkoxy (for example, methoxy, ethoxy, propoxy, isopropoxy and t-butoxy), $C_{7-14}$ aralkyloxy (for example, benzyloxy), hydroxy, amino, mono- or di-$C_{1-6}$ alkylamino (for example, methylamino, ethylamino, dimethylamino and diethylamino), carboxy, $C_{1-6}$ alkyl-carbonyl (for example, acetyl, propyonyl and butyryl), $C_{1-6}$ alkoxy-carbonyl (for example, methoxycarbonyl, ethoxycarbonyl, propoxycarbonyl, sec-propoxycarbonyl and butoxycarbonyl), nitro and cyano.

As "optionally substituted heterocyclic ring" represented by $R^1$ is used the same substituent as "optionally substituted heterocyclic ring" exemplified as the substituent on above "hydrocarbon group".

Preferable examples of $R^1$ are a hydrogen atom, a $C_{1-6}$ alkyl group, a $C_{2-6}$ alkenyl group, a $C_{6-14}$ aryl group or a $C_{7-14}$ aralkyl group, which may be substituted with (1)halogen, (2)nitro, (3)amino which may have 1 to 2 substituents selected from $C_{1-6}$ alkyl which may be substituted with $C_{1-6}$ alkyl-carbonyl, benzyloxycarbonyl and $C_{1-6}$ alkylsulfonyl, (4)hydroxy which may be substituted with (i)$C_{1-6}$ alkyl which may be substituted with hydroxy, $C_{1-6}$ alkyl-carbonyl, carboxy or $C_{1-6}$ alkoxy-carbonyl, (ii)phenyl which may be substituted with hydroxy, (iii)benzoyl or (iv)mono- or di-$C_{1-6}$ alkylamino-carbonyl, (5)$C_{3-6}$ cycloalkyl, (6)phenyl which may be substituted with hydroxy or halogeno-$C_{1-6}$ alkyl, or (7)thienyl, furyl, thiazolyl, indolyl or benzyloxycarbonylpiperidyl, and more preferably, a $C_{1-6}$ alkyl group or a $C_{7-14}$ aralkyl group, which may be substituted with hydroxy, phenyl or amino which may be substituted with $C_{1-6}$ alkyl-carbonyl or $C_{1-6}$ alkyl-sulfonyl.

Preferable position of substituents for aralkyl group represented by $R^1$ is para-position.

In the formula mentioned above, R stands for an amino group that may be substituted. As said "optionally substituted amino group" are mentioned, for example, (i) unsubstituted amino, (ii) optionally substituted hydrocarbon group, optionally substituted heterocyclic ring and amino group having 1 to 2 substituents selected from acyl groups, and (iii) optionally substituted nitrogen-containing heterocyclic ring.

As said "optionally substituted hydrocarbon group", the same substituent as said "optionally substituted hydrocarbon group" represented by $R^1$ is frequently used for example.

As said "heterocyclic ring which may have substituents" is used the same substituent as "heterocyclic ring which may have substituents" represented by $R^1$.

As said "acyl" are mentioned, for example, formyl, $C_{1-6}$ alkyl-carbonyl (for example, acetyl, propionyl and butyryl), benzoyl, $C_{1-6}$ alkoxy-carbonyl (for example, methoxycarbonyl, ethoxycarbonyl, propoxycarbonyl, sec-propoxycarbonyl, butoxycarbonyl and t-butoxycarbonyl), $C_{7-14}$ aralkyloxy-carbonyl (for example, benzyloxycarbonyl), piperidin-4-ylcarbonyl, $C_{1-6}$ alkylsulfonyl (for example, methylsulfonyl, ethylsulfonyl, propylsulfonyl, sec-propylsulfonyl, butylsulfonyl and t-butylsulfonyl), carbamoyl and mono- or di-$C_{1-6}$ alkyl-carbamoyl (for example, methylcarbamoyl, ethylcarbamoyl, dimethylcarbamoyl and diethylcarbamoyl). These may have 1 to 3 substituents which are selected from, for example, halogen atoms (for example, fluorine, chlorine, bromine and iodine), hydroxy, $C_{1-6}$ alkoxy (for example, methoxy, ethoxy, propoxy and isopropoxy), formyl, $C_{1-6}$ alkyl-carbonyl (for example, acetyl, propionyl and butyryl), carboxy, $C_{1-6}$ alkoxy-carbonyl (for example, methoxycarbonyl, ethoxycarbonyl, propoxycarbonyl, sec-propoxycarbonyl and butoxycarbonyl), amino, mono- or di-$C_{1-6}$ alkylamino (for example, methylamino, ethylamino, dimethylamino and diethylamino), pyrrolidinyl, piperidyl, morphorinyl, thiomorphorinyl, 4-methylpiperidyl, 4-phenylpiperidyl, carbamoyl, mono- or di-$C_{1-6}$ alkyl-carbamoyl (for example, methylcarbamoyl, ethylcarbamoyl, dimethylcarbamoyl and diethylcarbamoyl), phenoxy, mono- or di-$C_{1-6}$ alkyl-carbamoyloxy (for example, methylcarbamoyloxy, ethylcarbamoyloxy, dimethylcarbamoyloxy and diethylcarbamoyloxy), formylamino, $C_{1-6}$ alkyl-carbonylamino (for example, acetylamino, propionylamino and butyrylamino), formyloxy and $C_{1-6}$ alkyl-carbonyloxy (for example, acetoxy).

As "nitrogen-containing heterocyclic ring" in said "optionally substituted nitrogen-containing heterocyclic ring that may have substituents" are mentioned, for example, 5- to 7-membered nitrogen-containing heterocyclic rings having 1 to 4 hetero atoms selected from nitrogen, oxygen and sulfur other than nitrogen with a bond (for example, 1-imidazolyl, 1-pyrazolyl, 1-pyrrolyl, 1-pyrrolidinyl, 1-piperidyl, morpholinyl, thiomorpholinyl) or 5 to 7-membered nitrogen-containing heterocyclic rings condensed by benzene or pyridine (for example, 1-benzimidazolyl, 1,2,3,4-tetrahydroisoquinolin-2-yl, 1,2,3, 4-tetrahydro-quinolin-1-yl and 1-indolyl).

As the substituent that said "nitrogen-containing heterocyclic ring" may have is used the same substituent as the substituent that said "aromatic hydrocarbon group" in ring A may have. They are preferably halogen atoms (for example, fluorine, chlorine, bromine and iodine), $C_{1-6}$ alkyl (for example, methyl, ethyl, propyl, butyl, sec-butyl, t-butyl and isopropyl) and $C_{1-6}$ alkoxy (for example, methoxy, ethoxy, propoxy, butoxy, sec-butoxy, t-butoxy and isopropoxy). The number of the substituents is 1 to 5.

Preferable example of $R^2$ are an unsubstituted amino group, a piperidyl group or an amino group which have 1 to 2 substitutents selected from benzyl, $C_{1-6}$ alkyl which may be substituted with amino or phenyl, mono- or di-$C_{1-6}$ alkyl-carbamoyl, $C_{1-6}$ alkoxy-carbonyl, $C_{1-6}$ alkyl-sulfonyl, piperidylcarbonyl and $C_{1-6}$ alkyl-carbonyl which may be substituted with halogen or amino and more preferably, an unsubstituted amino group.

In the formula mentioned above, E represents a bond, —CON($R^a$)—, —N($R^a$)CO—,

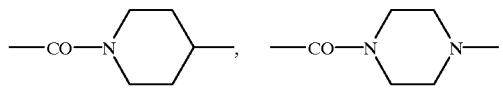

—N($R^b$)CON($R^c$)—, —N($R^d$)COO—, —N($R^e$)SO$_2$—, —COO—, —N($R^f$)—, —O—, —S—, —SO— to —SO$_2$— ($R^a$, $R^b$, $R^c$, $R^d$, $R^e$ and $R^f$ represent hydrogen or optionally substituted hydrocarbon groups, and hydrogen or $C_{1-6}$ alkyl (for example, methyl) is preferably used, especially hydrogen is frequently used, as $R^a$, $R^b$, $R^c$, $R^d$, $R^e$ and $R^f$).

As said "optionally substituted hydrocarbon group" is preferably used, for example, the same hydrocarbon group as the above-described "optionally substituted hydrocarbon group" represented by $R^1$.

Preferable example of E are a bond, —CON($R^a$)—, —N($R^a$)CO—, —N($R^b$)CON($R^c$)—, —COO—,

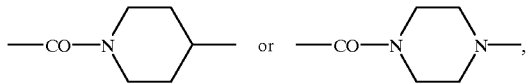

(in which $R^a$, $R^b$ and $R^c$ stands for the same as described above and preferably, a hydrogen atom or a $C^{1-6}$ alkyl group), —CON($R^a$)— (in which Ra stands for the same as described above and preferably, a hydrogen atom or a $C_{1-6}$ alkyl group) is preferably used. Especially, —CONH is frequently in use.

In the formula mentioned above, L stands for a divalent group, As said "divalent group" are mentioned, for example, divalent optionally substituted hydrocarbon groups which may be mediated by —O— to —S—.

L is preferably an optionally substituted divalent hydrocarbon group, for example. Especially, optionally substituted $C_{1-6}$ alkylene is frequently used.

As said "optionally substituted divalent hydrocarbon group" is used the same hydrocarbon group as the above-described "optionally substituted divalent hydrocarbon group" represented by D. As "$C_{1-6}$ alkylene group" in "optionally substituted $C_{1-6}$ alkylene" are mentioned, for example, methylene, ethylene, propylene and butylene. Said "$C_{1-6}$ alkylene" may have 1 to 5 $C_{1-6}$ alkyl groups (for example, methyl, ethyl, propyl, isopropyl and butyl) for example.

Preferable examples of L are a $C_{1-6}$ alkylene group which may be mediated by —O— and may be substituted with $C_{1-6}$ alkyl and more preferably, a $C_{1-6}$ alkylene group(for example, preferably methylene).

In the formula mentioned above, X stands for two hydrogen atoms, an oxygen atom or a sulfur atom, preferably an oxygen atom or a sulfur atom. Especially, oxygen atom is frequently used.

In the formula mentioned above, === stands for a single or a double bond. Preferably, a single bond is frequently used.

In the formula mentioned above, Y stands for nitrogen atom when === represents a double bond, and oxygen, —N($R^4$)— (in which $R^4$ stands for a hydrogen atom, an optionally substituted hydrocarbon group or an acyl group) or $S(O)_n$ (in which n is 0, 1 or 2) when === represents a single bond.

As said "optionally substituted hydrocarbon group" represented by $R^4$ is used the same group as said "optionally substituted hydrocarbon group" described in $R^1$.

As said "acyl" represented by $R^4$ are mentioned, for example, formyl, $C_{1-6}$ alkyl-carbonyl (for example, acetyl, propionyl and butyryl), benzoyl, $C_{1-6}$ alkoxy-carbonyl (for example, methoxycarbonyl, ethoxycarbonyl, propoxycarbonyl, sec-propoxycarbonyl, butoxycarbonyl and t-butoxycarbonyl), benzyloxycarbonyl, $C_{1-6}$ alkylsulfonyl (for example, methylsulfonyl, ethyl-sulfonyl, propylsulfonyl, sec-propylsulfonyl, butysulfonyl and t-butylsulfonyl), carbamoyl and mono- or di-$C_{1-6}$ alkyl-carbamoyl (for example, methylcarbamoyl, ethylcarbamoyl, dimethylcarbamoyl and diethylcarbamoyl). They may have 1 to 3 substituents selected from, for example, halogen atoms (for example, fluorine, chlorine, bromine and iodine), hydroxy, $C_{1-6}$ alkoxy (for example, methoxy, ethoxy, propoxy and isopropoxy), formyl, $C_{1-6}$ alkyl-carbonyl (for example, acetyl, propionyl and butyryl), carboxyl, $C_{1-6}$ alkoxy-carbonyl (for example, methoxycarbonyl, ethoxycarbonyl, propoxycarbonyl, sec-propoxycarbonyl and butoxycarbonyl), amino, mono- or di-$C_{1-6}$ alkylamino (for example, methylamino, ethylamino, dimethylamino and diethylamino), pyrrolidyl, piperidyl, morpholinyl, thiomorpholinyl, 4-methylpiperidyl, 4-phenylpiperidyl, carbamoyl, mono- or di-$C_{1-6}$ alkyl-carbamoyl (for example, methylcarbamoyl, ethylcarbamoyl, dimethylcarbamoyl and diethylcarbamoyl), phenoxy, mono- or di-$C_{1-6}$ alkyl-carbamoyloxy (for example, methylcarbamoyloxy, ethylcarbamoyloxy, dimethylcarbamoyloxy and diethylcarbamoyloxy), formylamino, $C_{1-6}$ alkyl-carbonylamino (for example, acetylamino, propionylamino and butyrylamino), formyloxy and $C_{1-6}$ alkyl-carbonyloxy (for example, acetoxy).

As $R^4$ is preferably used, for example, hydrogen or $C_{1-6}$ alkyl (for example, methyl, ethyl, propyl, isopropyl and butyl).

Preferable examples of Y is a nitrogen atom when === is a double bond, or an oxygen atom, —N($R^4$)— (in which $R^4$ is a hydrogen atom, an optionally substituted hydrocarbon group or an acyl group) or S(O), (in which n is 0, 1 or 2) when === is a single bond, and preferably, an oxygen atom when === is a single bond.

Preferable examples of compounds of the formula (I) or a salt thereof include compounds wherein ring A is a benzene ring which may be substituted with halogen, hydroxy, $C_{1-6}$ alkoxy, halogeno-$C_{1-6}$ alkoxy, $C_{7-14}$ aralkyloxy, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy or hydroxyphenyl-$C_{1-6}$ alkoxy, ring B is a benzene ring or a thiophene ring, which may be substituted with $C_{1-6}$ alkoxy, or a tetrahydroisoquinoline ring by combining with $R^2$, Z is a $C_{6-14}$ aryl group, a $C_{3-10}$ cycloalkyl group, a piperidyl group, a thienyl group, a furyl group, a pyridyl group, a thiazolyl group, an indolyl group or a $C_{1-6}$ alkyl group, which may have 1 to 3 substituents selected from halogen, formyl, halogeno-$C_{1-6}$ alkyl, $C_{1-6}$ alkoxy and $C_{1-6}$ alkoxy-carbonyl, oxo and pyrrolidinyl, D is a $C_{1-6}$ alkylene group, G is a bond or a $C_{1-6}$ alkylene group which may have phenylene and which may be substituted with phenyl, $R^1$ is a hydrogen atom, a $C_{1-6}$ alkyl group, a $C_{2-6}$ alkenyl group, a $C_{6-14}$ aryl group or a $C_{7-14}$ aralkyl group, which may be substituted with (1)halogen, (2)nitro, (3)amino which may have 1 to 2 substituents selected from $C_{1-6}$ alkyl which may be substituted with $C_{1-6}$ alkyl-carbonyl, benzyloxycarbonyl and $C_{1-6}$ alkylsulfonyl, (4)hydroxy which may be substituted with (i)$C_{1-6}$ alkyl which may be substituted with hydroxy, $C_{1-6}$ alkyl-carbonyl, carboxy or $C_{1-6}$ alkoxy-carbonyl, (ii)phenyl which may be substituted with hydroxy, (iii)benzoyl or (iv)mono- or di-$C_{1-6}$ alkylamino-carbonyl, (5)$C_{3-6}$ cycloalkyl, (6)phenyl which may be substituted with hydroxy or halogeno-$C_{1-6}$ alkyl, or (7)thienyl, furyl, thiazolyl, indolyl or benzyloxycarbonylpiperidyl, R² is (1) an unsubstituted amino group, (2) a piperidyl group or (3) an amino group which have 1 to 2 substitutents selected from (i) benzyl, (ii) C₁₋₆ alkyl which may be substituted with amino or phenyl, (iii) mono- or di-C₁₋₆ alkyl-carbamoyl, (iv) C₁₋₆ alkoxy-carbonyl, (v) C₁₋₆ alkyl-sulfonyl, (vi) piperidylcarbonyl and (vii) C₁₋₆ alkyl-carbonyl which may be substituted with halogen or amino, E is a bond, —CON(Rᵃ)—, —N(Rᵃ)CO—, —N(Rᵇ)CON(Rᶜ)—, —COO—,

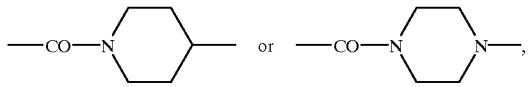

in which Rᵃ, Rᵇ and Rᶜ is a hydrogen atom or a C¹⁻⁶ alkyl group,

L is a C₁₋₆ alkylene group which may be mediated by —O— and may be substituted with C₁₋₆ alkyl, X is an oxygen atom, and === is a single bond or a double bond, and Y is a nitrogen atom when === is a double bond, or an oxygen atom, —N(R⁴)— (in which R⁴ is a hydrogen atom, an optionally substituted hydrocarbon group or an acyl group) or S(O)ₙ (in which n is 0, 1 or 2) when === is a single bond.

More preferable examples of compounds of the formula (I) include compounds wherein ring A is a benzene ring which may be substituted with halogen, hydroxy or C₁₋₆ alkoxy, ring B is a benzene ring or a thiophene ring, or a tetrahydroisoquinoline ring by combining with R², Z is a phenyl group which may be substituted with halogen, D is a C₁₋₆ alkylene group, G is a C₁₋₆ alkylene group, R¹ is a C₁₋₆ alkyl group or a C₇₋₁₄ aralkyl group, which may be substituted with hydroxy, phenyl or amino which may be substituted with C₁₋₆ alkyl-carbonyl or C₁₋₆ alkylsulfonyl, R² is an unsubstituted amino group, E is —CONH—, L is a C₁₋₆ alkylene group, X is an oxygen atom, and Y is an oxygen atom when === is a single bond. iMore preferable examples of compounds of the formula (I) include compounds wherein the substituent (—D—E—G—Z) at 3-position of benzoxazepine ring is S-configuration, and relative configuration between the substituent at 3-position and the substituent (ring B) at 5-position is trans.

Most preferable examples of compounds of the formula-(I) or a salt thereof include 3,5-trans-N-(2-fluorobenzyl)-5-(3-aminomethylphenyl)-1-(4-biphenylmethyl)-7-chloro-2-oxo-1,2,3,5-tetrahydro-4,1-benzoxazepine-3-acetamide or a salt thereof, (3S,5S)-N-(2-fluorobenzyl)-5-(3-aminomethylphenyl)-7-chloro-1-neopentyl-2-oxo-1,2,3,5-tetrahydro-4,1-benzoxazepine-3-acetamide or a salt thereof, 3,5-trans-N-(2-fluorobenzyl)-5-(3- aminomethylphenyl)-1-[2-(4-biphenyl)ethyl]-7-chloro-2-oxo-1,2,3,5-tetrahydro-4,1-benzoxazepine-3-acetamide or a salt thereof, 3,5-trans-N-(2-fluorobenzyl)-5-(4-aminomethylphenyl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(2-aminomethylthiophen-5-yl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-[3-[(1-amino-1-methyl)ethyl]phenyl]-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-hydroxybenzyl)-2-oxo-1,2,3,5-tetrahydro-4,1-benzoxazepine-3-acetamide or a salt thereof, 3,5-trans-N-(2-fluorobenzyl)-1-(4-acetylaminobenzyl)-5-(3-aminomethylphenyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-methanesulfonylaminobenzyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-hydroxybenzyl)-7-methyloxy-2-oxo-1,2,3,5-tetrahydro-4,1-benzoxazepine-3-acetamide or a salt thereof, 3,5-trans-N-(2-fluorobenzyl)-5-[4-[(1-amino-1 -methyl)ethyl]phenyl]-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-[2-(4-hydroxyphenyl)ethyl]-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-7-hydroxy-2-oxo-1,2,3,5-tetrahydro-4,1-benzoxazepine-3-acetamide or a salt thereof, and 3,5-trans-N-(2-fluorobenzyl)-1-(4-biphenylmethyl)-7-chloro-2-oxo-1,2,3,5-tetrahydro-5-(1,2,3,4-tetrahydroisoquinolin-5-yl)-4,1-benzoxazepine-3-acetamide or a salt thereof.

The compound or a salt thereof represented by the formula (I) may be manufactured using the following method or a method corresponding thereto.

In the compounds represented by the formula (I), a compound represented by the formula (Ia):

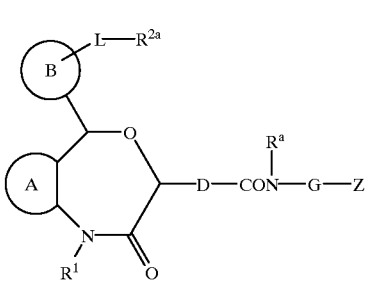

(Ia)

wherein, R²ᵃ stands for the group having a protecting group (for example, t-butoxycarbonyl, benzyloxycarbonyl and trityl) in the above-described R², and the other symbols have the same meaning as described above, or a salt thereof, can be produced by allowing a compound represented by the formulae (IIIa), (IIIb) or (IIIc) obtained by the methods (Method A), (Method B) and (Method C) shown below as intermediate to react with the a compound represented by the formula (IV), (IV') or (IV"):

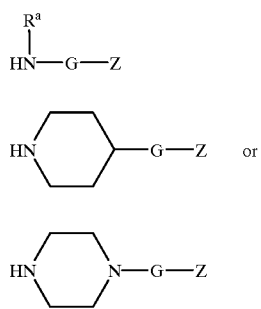

wherein the symbols have the same meaning as described above or a salt thereof.

Method A

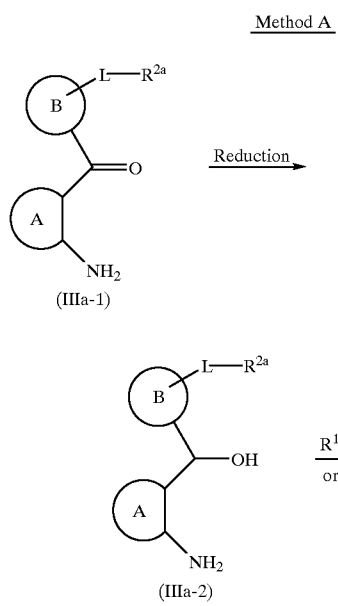

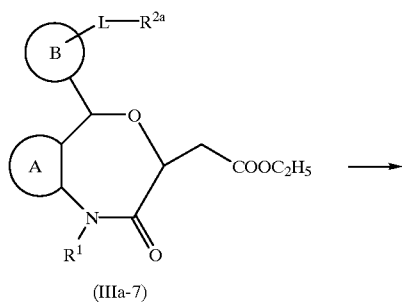

Le stands for an elimination radical (for example, chlobrine, bromine, iodine, methylsulfonyloxy and toluenesulfonyloxy); $R^{1a}$ stands for an optionally substituted hydrocarbon group represented by RI excluding its methylene group and the other symbols stand for the same meaning as described above.

Method B

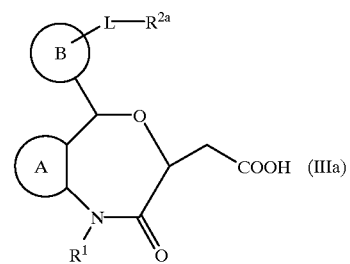

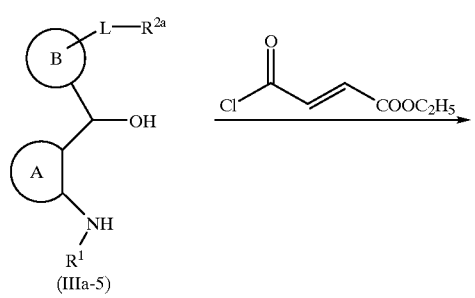

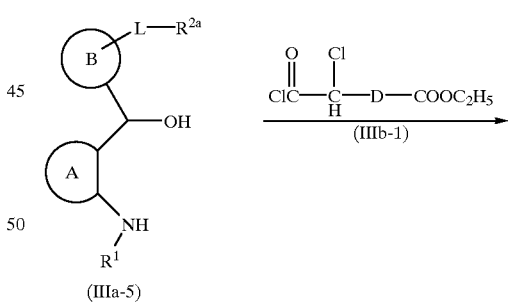

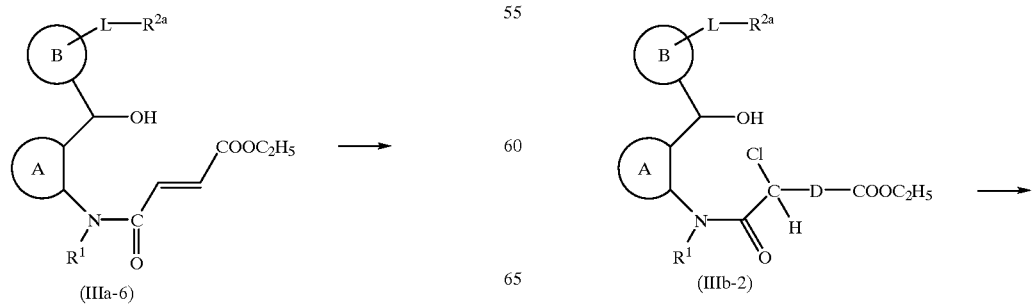

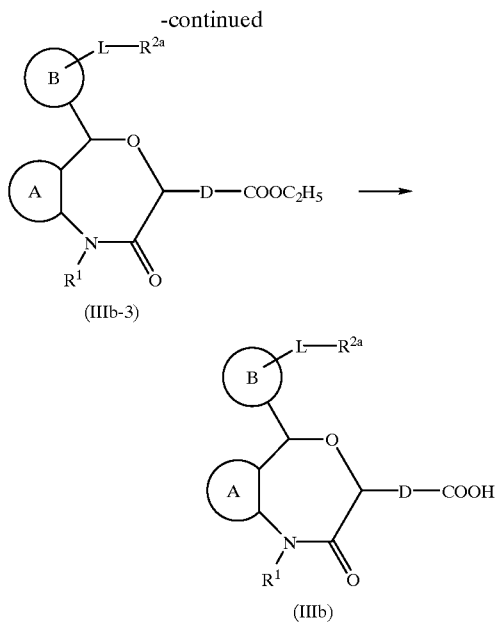

(IIIb-3)

(IIIb)

These symbols have the same meaning as described above.

In the reaction of the compound represented by the formula (IIIa-1) or a salt thereof in the above-mentioned (Method A) to give the compound represented by the formula-(IIIa-2) or a salt thereof, the reduction reaction of the carbonyl in the compound represented by the formula (IIIa-1) or a salt thereof may be carried out by treating the compound, for example, with a metal-hydrogen complex (for example, aluminum lithium hydride, aluminum sodium hydride, triethoxy aluminum sodium hydride and boron sodium hydride), in a solvent, for example, selected from proton solvents (for example, methanol, ethanol, propanol and butanol), or non-proton solvents (for example, ethylether, tetrahydrofuran and dioxane). Such a metal-hydrogen complex is used in a quantity of approximately 0.3 to 5 mol equivalent, preferably approximately 0.5 to 2 mol per 1 mol of the compound represented by the formula (IIIa-1) or a salt thereof. The reaction temperature is about −20 to 100° C., preferably about 20 to. 50° C., and the reaction time is about 0.5 to 24 hours.

The reaction of the compound represented by the formula (IIIa-2) or a salt thereof in the above-mentioned (Method A) to give the compound represented by the formula (IIIa-5) or a salt thereof may be carried out in solvent selected, for example, from ether solvents (for example, diethyl ether, tetrahydrofuran and dioxane), hydrocarbon solvents (for example, benzene, toluene, hexane and heptane), alcohol solvents (for example, methanol, ethanol and propanol), acetone and dimethylformamide optionally in the presence of a base (for example, sodium hydrogen carbonate, potassium hydrogen carbonate, sodium carbonate, potassium carbonate, sodium hydride and potassium hydride). For this reaction, approximately 1 to 10 mol equivalent, preferably approximately 1 to 2 mol equivalent of the compound represented by the formula (IIIa-3) or a salt thereof is used for 1 mol of the compound represented by the formula (IIIa-2) or a salt thereof. The reaction temperature at that time is about 0 to 100° C., preferably about 20 to 50° C. The reaction time is about 1 to 24 hours, preferably about 3 to 10 hours. The compound represented by the formula (IIIa-5) or a salt thereof can be manufactured by subjecting the compound represented by the formula (IIIa-2) or a salt thereof and the compound represented by the formula (IIIa-4) or a salt thereof to catalytic reduction and reductive amidation using boron sodium hydride or sodium boron cyanohydride, for example, in a solvent selected from, for example, ether solvents (for example, diethylether, tetrahydrofuran and dioxane), hydrocarbon solvents (for example, benzene, toluene, hexane and heptane), alcohol: solvents (for example, methanol, ethanol, propanol and butanol). At that time approximately 1 to 10 mol equivalent, preferably approximately 0.5 to 1 mol equivalent of the compound represented by the formula (IIIa-4) or a salt thereof is used to 1 mol of the compound represented by the formula (IIIa-2) or a salt thereof. The reaction temperature at that time is about 0 or 100° C., preferably about 10 to 70° C. The reaction time is about 1 to 24 hours, preferably about 3 to 10 hours.

The reaction of the compound represented by the formula (IIIa-5) or a salt thereof in the above-described (Method A) with fumaric chloride monoethyl ester and the reaction of the compound represented by the formula (IIIa-5) or a salt thereof in the above-described (Method B) with the compound represented by the formula (IIIb-1) or a salt thereof can be carried out using a per se known acylation reaction. This acylation reaction may be carried out, for example, in a solvent selected from ether solvents (for example, diethylether, tetrahydrofuran and dioxane), haloid solvents (for example, dichlormethane, dichlorethane and chloroform and.carbon tetrachloride), hydrocarbon solvents (for example, benzene, toluene, hexane and heptane), dimethylformamide, dimethylsulfoxide ester solvents (for example, ethyl acetate, methyl acetate) optionally in the presence of water and a base (for example, 4-dimethylaminopyridine, triethylamine, triethylenediamine, tetramethylethylenediamine, sodium hydrogen carbonate, potassium hydrogen carbonate, sodium carbonate, potassium carbonate, sodium hydride and potassium hydride). At that time, approximately 1 to 10 mol equivalent, preferably approximately 1 to 3 mol equivalent of the compound represented by the formula (IIIb-1) or a salt thereof and an acid chloride (for example, fumaric chloride monoethyl ester) are used for 1 mol of the compound represented by the formula (IIIa-5) or a salt thereof. The reaction temperature at that time is about −50 to 100° C., preferably about 0 to 50° C. The reaction time is about 1 to 48 hours, preferably about 5 to 10 hours.

The cyclization of the compound represented by the formula (IIIa-6) or a salt thereof in the above-described (Method A) to give the compound represented by the formula (IIIa-7) or a salt thereof may be carried out, for example, in a solvent selected from ether solvents (for example, diethylether, tetrahydrofuran and dioxane), hydrocarbon solvents (for example, benzene, toluene, hexane and heptane), alcohol solvents (for example, methanol, ethanol, propanol and butanol), acetone and dimethylformamide optionally in the presence of a base (for example, sodium hydrogen carbonate, potassium hydrogen carbonate, sodium carbonate, potassium carbonate, sodium hydride and potassium hydride). At that time, approximately 1 to 5 mol equivalent, preferably approximately 1 to 2 mol equivalent of these bases is used for 1 mol of the compound represented by the formula (IIIa-6) or a salt thereof. The reaction temperature at that time is about −20 to 200° C., preferably about 20 to 100° C. The reaction time is about 1 to 20 hours, preferably about 2 to 5 hours.

The cyclization of the compound represented by the formula (IIIb-2) in the above-described (Method B) to give the compound represented by the formula (IIIb-3) or a salt thereof may be carried out, for example, in a solvent selected from ether solvents (for example, diethylether, tetrahydrofuran and dioxane), hydrocarbon solvents (for example, benzene, toluene, hexane and heptane), alcohol solvents (for example, methanol, ethanol, propanol and butanol), acetone, dimethylformamide optionally in the presence of a base (for example, sodium hydrogen carbonate, potassium hydrogen carbonate, sodium carbonate, potassium carbonate, sodium hydride and potassium hydride). At that time, approximately 1 to 5 mol equivalent, preferably approximately 1 to 2 mol equivalent of these bases is used for 1 mol of the compound represented by the formula (IIIb-2) or a salt thereof. The reaction temperature is about −20 to 100° C., preferably about 20 to 100° C. Reaction time is about 1 to 20 hours, preferably about 2 to 5 hours.

The compounds represented by the formula (IIIa) or a salt thereof in the above-described (Method A) and the compounds represented by the formula (IIIb) or a salt thereof in the above-described (Method B) are m; manufactured by treating the compound represented by the formula of either (IIIa-7) or (IIIb-3) or a salt thereof with an acid or a base. Namely, the compound can be produced from the compound represented by the formula (IIIa-7) or (IIIb-3) or a salt thereof in an aqueous solution of, for example, a mineral acid (for example, nitric acid, hydrochloric acid, hydrobromic acid, hydroiodic acid and sulfuric acid) or an alkaline metal hydroxide (for example, sodium hydroxide, barium hydroxide and-lithium hydroxide) at the temperature of about 0 to 150° C., preferably about 20 to 50° C. At that time, the intensity of the acid and the base is about 1 to 10 normal, preferably about 4 to 10 normal. The reaction time at that time is about 1 to 24 hours, preferably about 2 to 10 hours.

The compound represented by the formula (Ia) or a salt thereof can be produced by allowing the compound represented by the formula (IIIa) or (IIIb) or a salt thereof to react with the compound represented by the formula (IV), (IV') or (IV") or a salt thereof in a solvent optionally in the presence of a base using a condensing agent. The solvent used therein is selected from, for example, ether solvents (for example, diethylether, tetrahydrofuran and dioxane), hydrocarbon solvents (for example, benzene, toluene, hexane and heptane), haloid solvents (for example, dichlormethane, dichlorethane and chloroform and carbon tetrachloride), acetonitrile and dimethylformamide. As the base used therein are mentioned, for example, triethylamine, 4-dimethylaminopyridine, triethylenediamine and tetramethylethylenediamine. As the condensing agent are mentioned, for example, condensing agents used for peptide synthesis. More specifically, dicyclohexylcarbodiimide, diethyl cyanophosphate and 1-ethyl-3-(3-dimethylaminopropyl)-carbodiimide are frequently used for example. At that time, approximately 0.5 to 2 mol equivalent, preferably approximately 1 to 1.2 mol equivalent of the compound represented by the formula (IV) or a salt thereof is used for 1 mol of the compound represented by the formula (IIIa) or (IIIb) or a salt thereof, and about 0.5 to 5 mol equivalent, preferably about 1 to 2 mol equivalent of the condensing agent is used. The reaction temperature at that time is about 0 to 100° C., preferably about 20 to 50° C. The reaction time is about 0.5 to 24 hours, preferably about I to 5 hours. In the compounds represented by the formula (I), a compound shown by the formula (Ib):

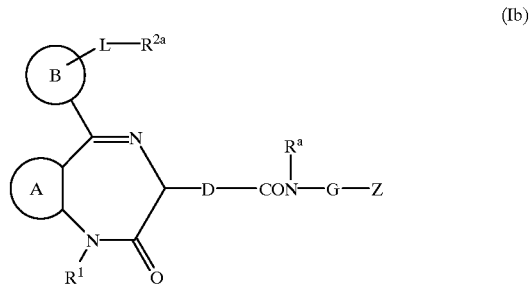

(Ib)

wherein the symbols have the same meaning as described above, or a salt thereof can be produced by allowing the compound represented by the formula (IIIc) or a salt thereof obtained by (Method C) and (Method D) described below as the intermediate to react with a compound represented by the formula (IV).

Method C

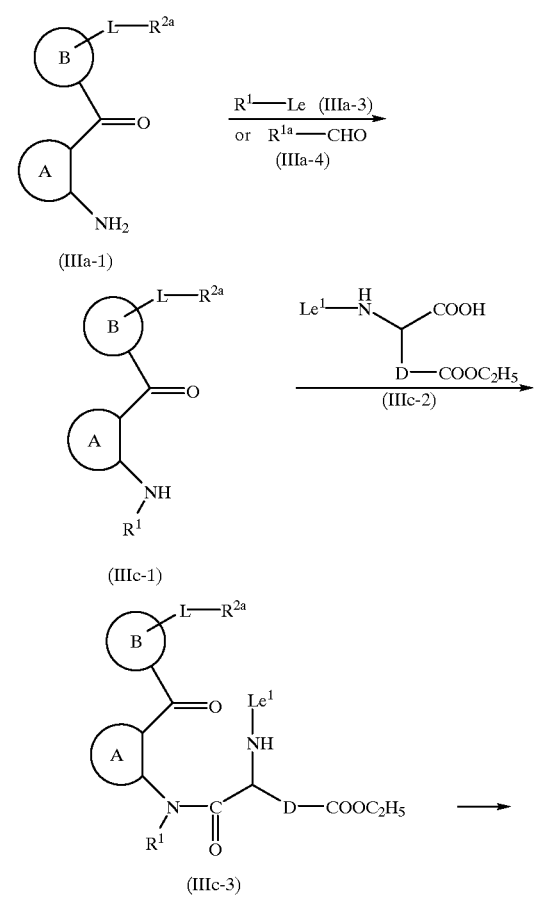

-continued

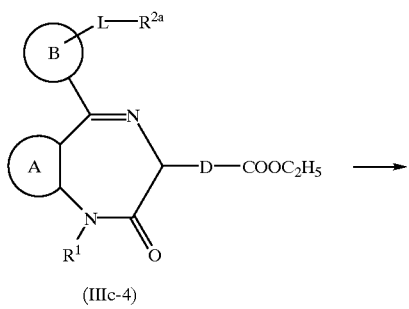

(IIIc-4)

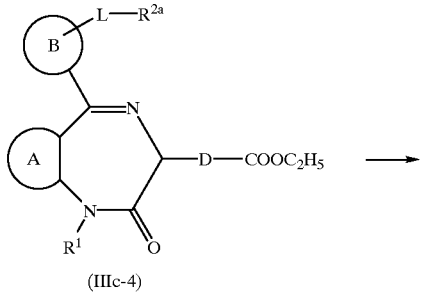

(IIIc-4)

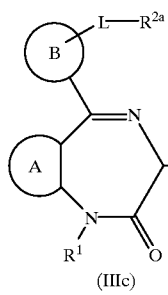

(IIIc)

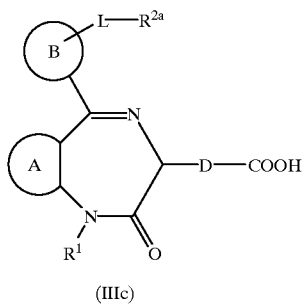

(IIIc)

Le¹ has the same meaning as Le. However, Le¹ and Le are not the same at the same time. The other symbols have the same meaning as described above or a salt thereof.

Method D

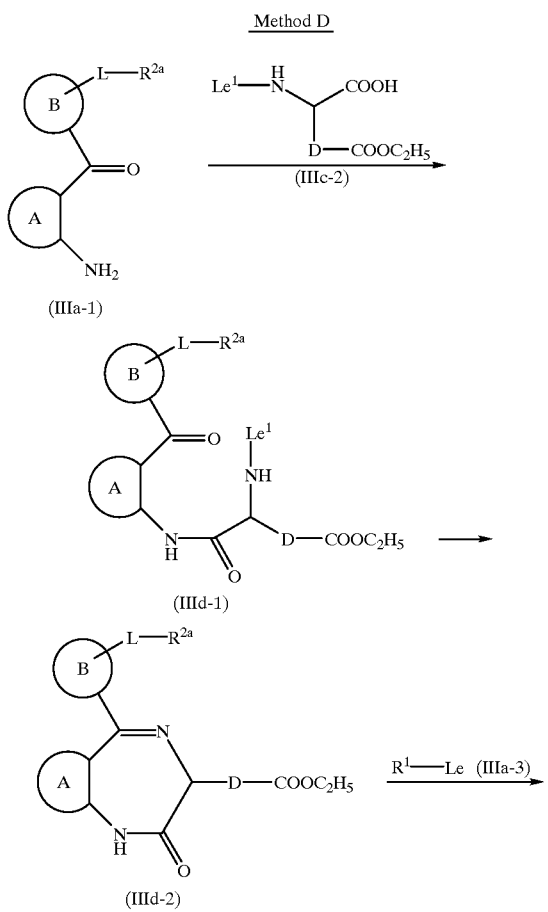

These symbols have the same meaning as described above.

The production of the compound represented by the formula (IIIc-1) or a salt thereof from the compound represented by the.formula (IIIa-1) or a salt thereof in the above-described (Method C) is carried out by the method similar to that for producing the compound represented by the formula (IIIa-5) or a salt thereof by, for example, allowing the compound represented by the formula (IIIa-2) or a salt thereof shown in the above-described (Method A) to react with the compound represented by the formula (IIIa-3) or (IIIa-4) or a salt thereof. The production of the compound represented by the formula (IIIc-3) or a salt thereof from the compound represented by the formula (IIIc-1) or a salt thereof, and the compound represented by the formula (IIId-1) or a salt thereof from the compound represented by the formula (IIIa-1) or a salt thereof in the above-described (Method C) and (Method D) is carried out in solvent selected from, for example, ether solvents (for example, diethylether, tetrahydrofuran and dioxane), hydrocarbon solvents (for example, benzene, toluene, hexane and heptane), haloid solvents (for example, dichlormethane, dichlorethane and chloroform), acetonitrile and dimethylformamide using condensing agent (for example, diethyl cyano-phosphate and dicyclohexylcarbodiimide) optionally in the presence of a base (for example, triethylamine, 4-dimethylaminopyridine and N-methylpiperidine). Approximately 1 to 5-mol equivalent, preferably 1 to 1.5 mol equivalent of the compound represented by the formula (IIIc-2) or a salt thereof is used for 1 mol of the compound represented by the formula (IIIc-1) or (IIIa-1) or a salt thereof. The reaction temperature at that time is about 0 to 100 IC, preferably about 20 to 50° C. The reaction time is about 1 to 24 hours, preferably about 2 to 5 hours. At that time about 1 to 5 mol equivalent, preferably about 1 to 2 mol equivalent of a condensing agent is used for 1 mol of the compound represented by the formula (IIIc-1) or (IIIa-1).

The production of the compound represented by the formfula (IIIc-4) or a salt thereof from the compound represented by the formula (IIIc-3) or a salt thereof in the above-described (Method C) or the compound represented by the formula (IIId-2) or a salt thereof from the compound represented by the formula (IIId-1) or a salt thereof in the above-described (Method D) is carried out by a per se known method in a solvent selected, for example, from ether solvents (for example, diethylether, tetrahydrofuran and dioxane), hydrocarbon solvents (for example, benzene, toluene, hexane and heptane), alcohol solvents (for example, methanol, ethanol, propanol and butanol), haloid solvents (for example, dichlormethane, dichlorethane and chloroform), acetone, acetonitrile and dimethylformamide. When $Le^1$ is carbobenzyloxy, for example, $Le^1$ is liberated by catalytic reduction using, for example paradium and platinum, and when $Le^1$ is t-butoxycarbonyl, for example, $Le^1$ is liberated by dissolving in an acid (for example, hydrochloric acid, hydrobromic acid and trifluoroacetic acid) before the above production is carried out from the thus $Le^1$-liberated compound in a solvent selected from, for example, ether solvents (for example, diethylether, tetrahydrofuran and dioxane), hydrocarbon solvents (for example, benzene, toluene, hexane and heptane), alcohol solvents (for example, methanol, ethanol, propanol and butanol), acetonitrile and dimethylformamide optionally in the presence of an acid (for example, hydrochloric acid, hydrobromic acid, propionic acid, methanesulfonic acid, toluenesulfonic acid and sulfuric acid). The reaction temperature at that time is about 0 to 100° C., preferably about 30 to 70° C. The reaction time is about 1 to 24 hours, preferably about 3 to 10 hours. For the production of the compound represented by the formula (IIIc-4) or a salt thereof from the compound represented by the formula (IIId-2) in the above-described (Method D) is used a method similar to that for the reaction between the compound represented by the formula (IIIa-2) or a salt thereof in the above-described (Method A) and the compound represented by the formula (IIIa-3) or a salt thereof. Also, for the production of the compound represented by the formula (IIIc) or a salt thereof from the compound represented by the formula (IIIc-4) in the above-described (Method C) and (Method D) is used a method similar to that for the production of the compound represented by the formula (IIIa) or a salt thereof from the compound represented by the formula (IIIa-7) or a salt thereof in the above-described (Method A).

In the compounds represented by the formula (I), a compound represented by the formula (Ic):

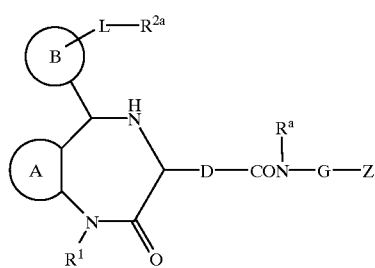

(Ic)

wherein the symbols have the same meaning as described above, or a salt thereof can.be produced by reducing the compound represented by the formula (Ib) or a salt thereof. Namely, the compound can be produced in a solvent selected from, for example water, ether solvents (for example, diethylether, tetrahydrofuran and dioxane), hydrocarbon solvents (for example, benzene, toluene, hexane and heptane), alcohol solvents (for example, methanol, ethanol, propanol and butanol), haloid solvents (for example, dichlormethane, chloroform) using a reducing agent such as sodium boron hydride, aluminum lithium hydride and sodium boron cyanohydride. In this reaction, approximately 0.2 to 5 mol equivalent, preferably approximately 0.3 to 1 mol equivalent of the reducing agent is used for 1 mol of the compound represented by the formula (Ib) or a salt thereof. The reaction temperature at that time is about 0 to 100° C., preferably about 20 to 50° C. The reaction time is about 0.5 to 10 hours, preferably about 1 to 3 hours.

In the compounds represented by the formula (I) or salts thereof, a compound represented by the formula (Id):

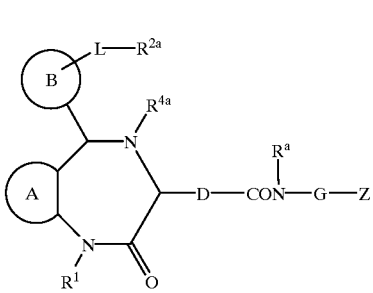

(Id)

wherein $R^{4a}$ stands for optionally substituted hydrocarbon group and the other symbols in the formula have the same meaning as described above, or a salt thereof is produced by the reaction between the compound represented by the formula (Ic) or a salt thereof, and a compound represented by the formula (IVa) or (IVb):

$$R^{4a}\text{—Le} \tag{IVa}$$

or $$R^{4aa}\text{—N}=\text{C}=\text{O} \tag{IVb}$$

wherein $R^{4aa}$ stands for optionally substituted hydrocarbon group and the other symbols in the formula have the same meaning as described above, or a salt thereof. For example, the reaction between the compound represented by the formula (Ic) or a salt thereof and the compound represented by the formula (Iva) or a salt thereof may be carried out by the method similar to that for the reaction between the compound represented by the formula (IIIa-2) or a salt thereof and the compound represented by the formula (IIIa-3) or a salt thereof in the above-described (Method A). Further, the reaction between the compound represented by the formula (Ic) or a salt thereof and the compound represented by the formula (IVb) or a salt thereof may be carried in a solvent selected from, for example, ether solvents (for example, diethylether, tetrahydrofuran and dioxane), haloid solvents (for example, dichlormethane, dichlorethane and chloroform), acetonitrile and dimethylformamide, optionally using a base. As the base used therein are mentioned organic bases such as triethylamine, 4-dimethylaminopyridine, triethylenediamine, and tetramethylethylenediamine. In this reaction approximately 0.5 to 3 mol equivalent, preferably approximately 1 to 1.5 mol equivalent of the compound represented by the formula (IVb) or a salt thereof is used for 1 mol of the compound represented by the formula (Ic). The reaction temperature at that time is about 0 to 150° C., preferably about 30 to 100° C. The reaction time is about 0.5 to 24 hours, preferably about 1 to 3 hours.

In the compounds represented by the formula (I) or salts thereof, a compound represented by the formula (Ie):

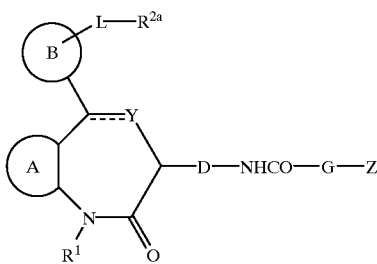
(Ie)

wherein the symbols have the same meaning as described above or a salt thereof is produced by, for example, introducing a compound represented by the formula (V):

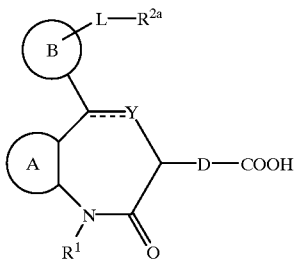
(V)

wherein the symbols have the same meaning as described above or a salt thereof to a compound represented by the formula (VI):

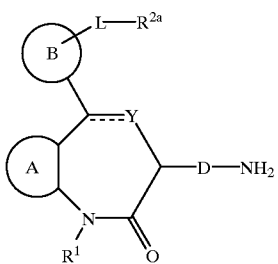
(VI)

wherein the symbols have the same meaning as described above or a salt thereof, and allowing this to react with a compound of the formula (VII):

Z—G—COOH     (VII)

wherein the symbols have the same meaning as described above or a salt thereof.

The compound represented by the formula (VI) or a salt thereof can be produced by allowing the compound represented by the formula (V) or a salt thereof to react with diphenylphosphorylazide in solvent in the presence of a base and treating the obtained product in solvent with an acid. As the solvent used in the reaction between the compound of the formula (V) or a salt thereof with diphenylphosphorylazide are mentioned, for example, ether solvents (for example, diethylether, tetrahydrofuran and dioxane), haloid solvents (for example, dichlormethane, dichlorethane and chloroform) and dimethylformamide. As the base used therein are mentioned, for example, triethylamine, 4-dimethylaminopyridine, triethylenediamine and tetramethylene-diamine. In this reaction, approximately 1 to 10 mol equivalent, preferably approximately 1.5 to 3 mol equivalent of diphenylsulfonylazide is used for the compound of the formula (V). The reaction temperature at that time is about −20 to 50° C., preferably about 0 to 20° C. The reaction time is about 0.5 to 5 hours, preferably about 1 to 2 hours.

As the solvent used for treating the above reaction products with an acid are mentioned, for example, water, dioxane and dimethylformamide and as the acid used are mentioned mineral acids such as sulfuric acid, hydrochloric acid, nitric acid and hydrobromic acid. The reaction temperature at that time is about 20 to 200° C., preferably about 50 to 100° C. The reaction time is about 0.5 to 5 hours, preferably about 1 to 2 hours. The condensation reaction of the compound represented by the formula (VI) or a salt thereof with the compound represented by the formula (VII) or a salt thereof is conducted under conditions similar to that for the condensation reaction between, for example, the compound represented by the formula (IIIa) or (IIIb) or a salt thereof and the compound represented by the formula (IV) or a salt thereof to give the compound represented by the formula (Ia) or a salt thereof.

In the compounds represented by the formula (I) or salts thereof, a compound represented by the formula (If):

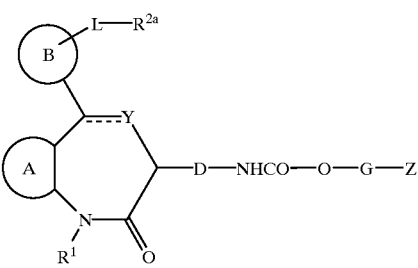
(If)

wherein the symbols have the same meaning as described above, or a salt thereof, or a compound represented by the formula (Ig):

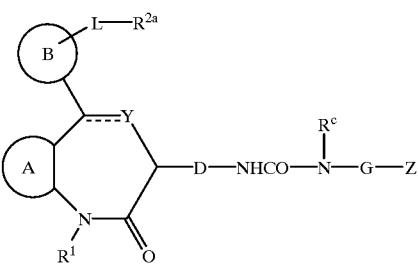
(Ig)

wherein the symbols have the same meaning as described above, or a salt thereof is produced under conditions similar to that for producing the compound represented by the formula (VI) or a salt thereof, for example, by allowing the compound represented by the formula (V) or a salt thereof to react with diphenylphosphorylazide to give an intermediate compound of the formula (VIII):

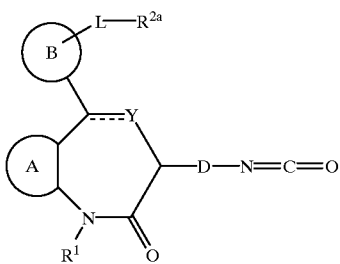

(VIII)

wherein the symbols have the same meanig as described above and allowing this to react with a compound represented by the formula (IX) or (X):

Z—GAOH    (IX)

or

Z—G—NHR$^c$    (X)

wherein the symbols have the same meaning as described above, or a salt thereof. The production may be carried out under conditions similar to the reaction between the compound represented by the formula (Ic) or a salt thereof and the compound represented by the formula (IVb) or a salt thereof.

In the compounds represented by the formula (I) or salts thereof, a compound represented by the formula (Ih):

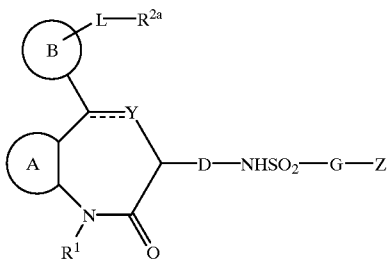

(Ih)

wherein the symbols have the same meaning as described above or a salt thereof is produced by the reaction between the compound represented by the formula (VI) or a salt thereof and a compound represented by the formula (XI):

Z—SO$_2$Cl    (XI)

wherein the symbols have the same meaning as described above, or a salt thereof. This reaction may be carried out in a solvent selected from, for example, ether solvents (for example, dimethylether, tetrahydrofuran and dioxane), alcohol solvents (for example, methanol, ethanol, propanol and butanol), acetone and dimethylformamide optionally in the presence of a base (for example, sodium hydrogen carbonate, potassium hydrogen carbonate, sodium carbonate, potassium carbonate, sodium hydride and triethylamine). In this reaction, approximatelyl to 10 mol equivalent, preferably approximately 1 to 2 mol equivalent of the compound represented by the formula (XI) or a salt thereof are used for 1 mol of the compound represented by the formula (VI). The reaction temperature at that time is about 0 to 100° C., preferably about 20 to 50° C. The reaction time is about 1 to 24 hours, preferably about 3 to 10 hours.

In the compounds represented by the formula (I), a compound represented by the formula (Ii):

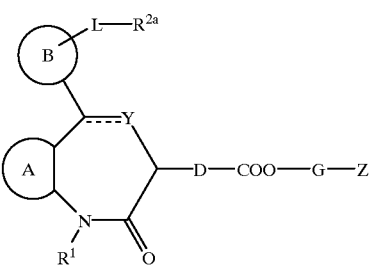

(Ii)

wherein the symbols have the same meaning as described above, or a salt thereof is produced by the reaction between the compound represented by the formula (V) or a salt thereof and a compound represented by the formula (XII):

Z—G—OH    (XII)

described above, or a salt thereof. It can be produced, for example, by allowing the compound represented by the formula (V) or a salt thereof to react with the compound represented by the formula (XII) or a salt thereof using a condensing agent in a solvent optionally in the presence of a base. As the solvent used therein are mentioned, for example, ether solvents (for example, diethylether, tetrahydrofuran and dioxane), haloid solvents (for example, dichlormethane, dichlorethane, chloroform and carbon tetrachloride), acetonitrile and dimethylformamid. As the base used therein are mentioned, for example, triethylamine, 4-dimethylaminopyridine, triethylenediamine, tetramethylethylenediamine. As condensing agent used therein are mentioned, for example, a condensing agent used for the synthesis of a peptide, more specifically, dicyclohexylcarbodiimide, diethyl cyanophosphate and 1-ethyl-3-(3-dimethylaminopropyl)carbodiimide. In this reaction approximately 0.5 to 2 mol equivalent, preferably approximately 1 to 1.2 mol equivalent of the compound represented by the formula (XII) or a salt thereof and approximately 0.5 to 5 mol equivalent, preferably approximately 1 to 2 mol equivalent of the condensing agent are used for 1 mol of the compound represented by the formula (V) or a salt thereof. The reaction temperature at that time is about 0 to 100° C., preferably about 20 to 50° C. The reaction time is about 0.5 to 24 hours, preferably about 1 to 5 hours.

In the compounds represented by the formula (I) or salts thereof, a compound represented by the formula (Ij):

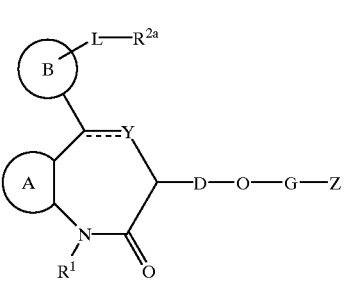

(Ij)

wherein the symbols have the same meaning as described above, or a salt thereof is produced by allowing a compound represented by the formula (XIII):

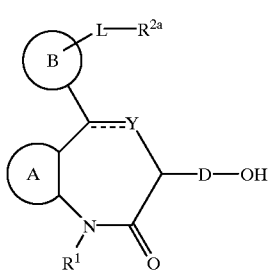

(XIII)

wherein the symbols have the same meaning as described above or a salt thereof to react with a compound represented by the formula (XIV):

$$Z-Le \quad (XIV)$$

wherein the symbols have the same meaning as described above or a salt thereof. The compound represented by the formula (XIII) or a salt thereof can be produced by treating the compound represented by the formula (V) or a salt thereof in a solvent selected from, for example, proton solvents (for example, methanol, ethanol, propanol and butanol) and non-proton solvents (for example, ethylether, tetrahydrofuran and dioxane) with, for example, a metal-hydrogen complex (for example, aluminum lithium hydride, aluminum sodium hydride and boron sodium hydride). The metal-hydrogen complex is used in quantity of approximately 0.3 to 5 mol equivalent, preferably approximately 0.5 to 2 mol equivalent for 1 mol of the compound represented by the formula (V). The reaction temperature at that time is about −20 to 100° C., preferably about 0 to 20° C. The reaction time is about 0.5 to 10 hours, preferably about 1 to 3 hours.

As the solvent used in the reaction between the compound represented by the formula (XIII) or a salt thereof and the compound represented by the formula (XIV) or a salt thereof may be mentioned, for example, non-proton solvents (for example, ethylether, tetrahydrofuran, dioxane, acetonitrile and dimethylformamide) optionally using, for example, an inorganic base (for example,: sodium hydrogen carbonate, potassium hydrogen carbonate, sodium carbonate and potassium carbonate), an organic base (for example, triethylamine, 4-dimethylaminopyridine, triethylenediamine and tetramethylethylenediamine), sodium hydroxide and cesium fluoride. In this reaction, approximately 0.5 to 5 mol equivalent, preferably approximately 1 to 2 mol equivalent of the compound represented by the formula (XIV) or a salt thereof is used for 1 mol of the compound represented by the formula (XIII) or a salt thereof. The reaction temperature at that time is about 0 to 2000C, preferably about 20 to 100° C. The reaction time is about 10 minutes to 5 hours, preferably about 30 minutes to 2 hours.

In the compounds represented by the formula (I) salts thereof, a compound represented by the formula (Ik):

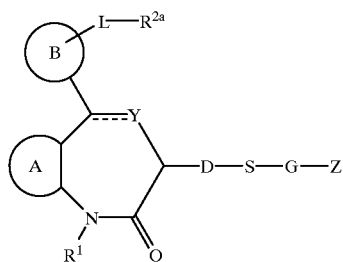

(Ik)

wherein the symbols have the same meaning as described above, or a salt thereof is produced by allowing a compound represented by the formula (XV):

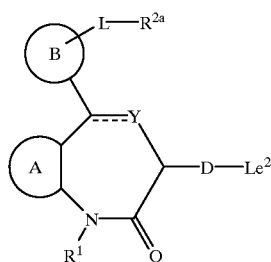

(XV)

wherein $Le^2$ is a halogen (for example, chlorine, bromine and iodine) and the other symbols have the same meaning as described above, or a salt thereof to react with a compound represented by the formula (XVI):

$$Z-SH \quad (XVI)$$

wherein the symbols have the same meaning as described above, or a salt thereof.

The compound represented by the formula (XV) or a salt thereof can be produced by, for example, diazotization of the compound represented by the formula (VI) or a salt thereof in, for example, hydrochloric acid, hydrobromic acid or hydroiodic acid with sodium nitrite followed by heating. The reaction temperature at that time is about 20 to 200° C., preferably about 50 to 100° C. The reaction time is about 5 minutes to 2 hours, preferably about 15 to 30 minutes. The reaction between the compound represented by the formula (XV) or a salt thereof and the compound represented by the formula (XVI) or a salt thereof may be carried out under conditions similar to that for production of the compound represented by the formula (Ij) or a salt thereof by reaction between the compound represented by the formula (XIII) or a salt thereof and the compound represented by the formula (XIV) or a salt thereof.

Of the compounds represented by formula (I) or salts thereof, a compound represented by the formula (Il):

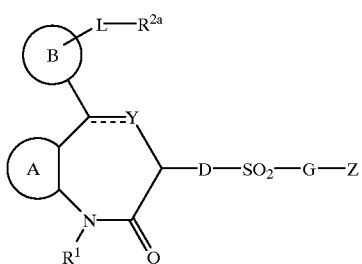
(II)

wherein the symbols have the same meaning as described above, or a salt thereof is produced by oxidizing the compound represented by the formula (Ik) or a salt thereof. In this reaction, approximately 1 to 5 mol equivalent, preferably approximately 2 to 3 mol equivalent of metachloroperbenzoic acid is used for 1 mol of the compound represented by the formula (Im) in a solvent selected from, for example, ether solvents (for example, diethylether, tetrahydrofuran and dioxane), hydrocarbon solvents (for example, benzene, toluene, hexane and heptane), haloid solvents (for example, dichlormethane, dichlorethane and chloroform), acetonitrile and dimethylformamide. The reaction temperature at that time is about 0 to 100° C., preferably about 0 to 30° C. The reaction time is about 1 to 10 hours, preferably about 1 to 2 hours.

In the compounds represented by the formula (I) or salts thereof, a compound represented by the formula (Im):

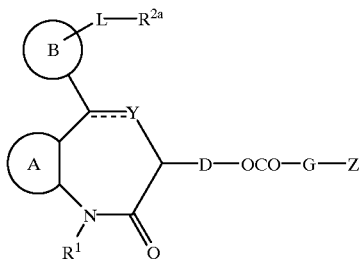
(Im)

wherein the symbols have the same meaning as described above, or a salt thereof is produced by allowing the compound represented by the formula (XIII) or a salt thereof to react with the compound represented by the formula (VII) or a salt thereof under conditions similar to that of the reaction of the compound represented by the formula (V) or a salt thereof and the compound represented by the formula (XII) or a salt thereof for the production of the compound represented by the formula (Ii) or a salt thereof.

In the compounds represented by the formula (I) or salts thereof, a compound represented by the formula (In):

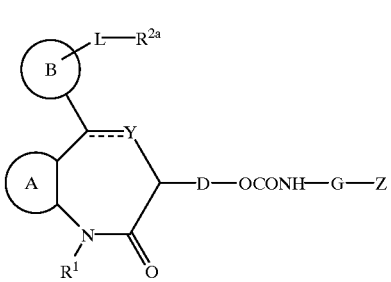
(In)

wherein the symbols have the same meaning as described above, or a salt thereof is produced by allowing the compound represented by the formula (XIII) or a salt thereof to react with a compound represented by the formula (XVII):

$$Z-N=C-O \qquad (XVII)$$

wherein the symbols have the same meaning as described above, or a salt thereof. As the solvent used in this reaction are mentioned, for example, ether solvents (for example, diethylether, tetrahydrofuran and dioxane), haloid solvents (for example, dichlormethane, dichlorethane and chloroform), acetonitrile and dimethylformamide. A base (for example, triethylamine, 4-dimethyl-aminopyridine, triethylenediamine, tetramethylethylenediamine) is optionally used. In this reaction, approximately 0.5 to 3 mol equivalent, preferably approximately 1 to 1.5 mol equivalent of the compound represented by the formula (XVII) or a salt thereof is used for 1 mol of the compound represented by the formula (XIII) or a salt thereof. The reaction temperature at that time is about 0 to 150° C., preferably about 30 to 100° C. The reaction time is about 0.5 to 24 hours, preferably about 1 to 3 hours.

In the compounds represented by the formula (I) or salts thereof, a compound represented by the formula (Io):

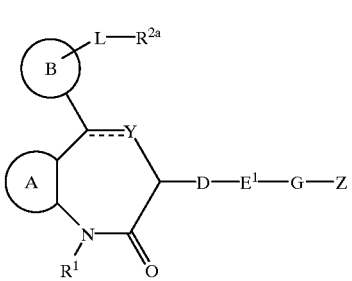
(Io)

wherein $E^1$ is —CON($R^a$)—, —N($R^b$)CON($R^c$)—, —N($R^d$)COO— or —N($R^e$)SO$_2$— and the other symbols have the same meaning as described above, or a salt thereof is produced by allowing, when $E^1$ is —CON($R^a$)— in the formula (Io), a compound represented by the formula (Iaa):

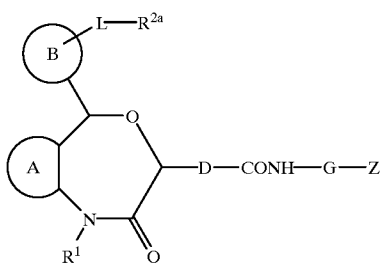

(Iaa)

wherein the symbols have the same meaning as described above, or a salt thereof, or a compound represented by the formula (Ibb):

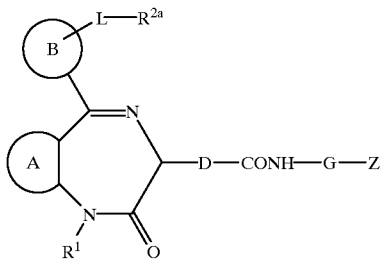

(Ibb)

wherein the symbols have the same meaning as described above, or a salt thereof, or a compound represented by the formula (Idd):

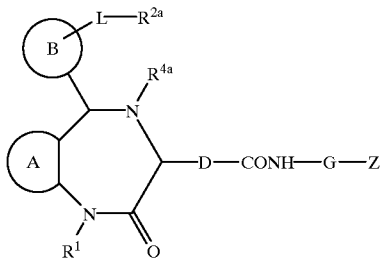

(Idd)

wherein the symbojshave the same meaning as described above, or a salt thereof to react with a compound represented by the formula (XIX):

$R^a$—Le     (XIX)

wherein the symbols have the same meaning as described above, or a salt thereof.

This reaction is carried out in, for example, ether solvents (for example, diethylether, tetrahydrofuran and dioxane), hydrocarbon solvents (for example, benzene, toluene, hexane and heptane), alcohol solvents (for example, methanol, ethanol and propanol), acetone and dimethylformamide, optionally in the presence of a base (for example, sodium hydrogen carbonate, potassium hydrogen carbonate, sodium hydrogen carbonate, potassium carbonate, sodium hydride and potassium hydride). In this reaction, approximately 1 to 10 mol equivalent, preferably approximately 1 to 2 mol equivalent of the compound of the formula (XIX) is used to react with 1 mol of the compound represented by the formula (Iaa), (Ibb) or (Idd) or a salt thereof. The reaction temperature at that time is about 0 to 100° C., preferably about 20 to 50° C. The reaction time is about 1 to 24 hours, preferably about 3 to 10 hours. The compounds are produced, when $E^1$ is —N($R^b$)CON($R^c$)—, —N($R^d$)COO— or —N($R^e$)SO$_2$— in the formula (Io), in a manner similar to that when $E^1$ is —CON($R^a$)—.

In the compounds represented by the formula (I) or salts thereof, a compound represented by the formula (Ip):

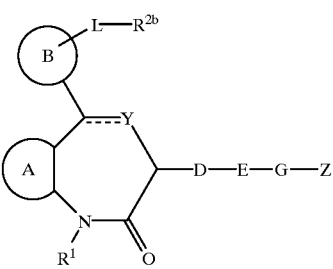

(Ip)

wherein $R^{2b}$ is a deprotected $R^{2a}$ and the other symbols have the same meaning as described above, or a salt thereof is produced by removing the protective group of a compound represented by the formula (Iq):

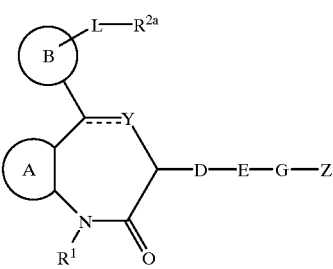

(Iq)

wherein the symbols have the same meaning as described above, or a salt thereof by a per se known method.

The removal of the protective group, when the protective group is t-butoxycarbonyl, trityl and benzyloxycarbonyl, can be done by treating the compound with an acid such as hydrogen chloride, hydrogen bromide, hydrochloric acid, hydrobromic acid, nitric acid, sulfuric acid and trifluoroacetic acid in a solvent selected from, for example, ether solvents (for example, diethylether, tetrahydrofuran and dioxane) and haloid solvents (for example, dichlormethane, dichlorethane and chloroform). Further, the removal of the protective group, when the protective group is benzyloxycarbonyl, can be done by hydrolyzing the compound by using, for example, a paradium catalyst (for example, metal paradium and paradium/charcoal) in a solvent selected from, for example, ether solvents (for example, diethylether, tetrahydrofuran and dioxane) alcoholic solvents (for example, methanol, ethanol, propanol), dimethylformamide, acetic acid ethylester and acetic acid. In this reaction, the reaction temperature is about −20 to 100° C., preferably about 0 to 30° C. when treated with an acid. The reaction time is about 0.1 to 5 hours, preferably about 0.5 to 1 hours. In this reaction, the reaction temperature is −20 to 150° C., preferably about 0 to 50° C. when hydrolysis is conducted. The reaction time is about 0.1 to 10 hours, preferably about 0.5 to 3 hours. The hydrogen pressure is about 1 to 100.atmospheric pressures, preferably about 1 to 3 atmospheric pressures. The catalysts are used at this time in approximately 0.001 to 0.5 mol equivalent, preferably approximately 0.01 to 0.1 mol equivalent for 1 mol of the compound represented by the formula (Ia) or a salt thereof.

In the compounds represented by the formula (I) or salts thereof, a compound represented by the formula (Ir):

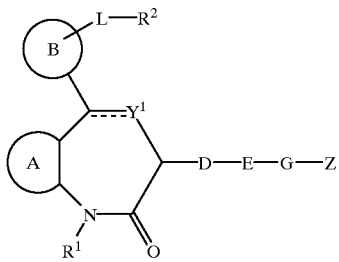

(Ir)

wherein $Y^1$ stands for oxygen or $-N(R^{4a})-$ (in which $R^{4a}$ stands for a hydrocarbon that may have substituents) and the other symbols have the same meaning as described above or a salt thereof is produced by allowing a compound represented by the formula (Is):

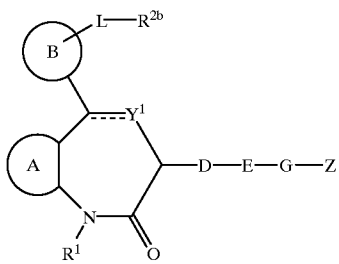

(Is)

wherein the symbols have the same meaning as described above, or a salt thereof to react with a compound represented by the formula (XX) or (XXI):

$R^{2c}$—Le          (XX)

or $R^{2d}$—N=C=O    (XXI)

wherein each of $R^{2c}$ and $R^{2d}$ is an optionally substituted hydrocarbon group, an optionally substituted heterocyclic group or acyl and the other symbols have the same meaning as described above, or a salt thereof. The reaction between the compound represented by the formula (Is) or a salt thereof and the compound represented by the formula (XX) or a salt thereof can be done under conditions similar to that for the reaction between the compound represented by the formula (IIIa-2) or a salt thereof and the compound represented by the formula (IIIa-3) or a salt thereof in the above-described (Method A). Further, the reaction between the compound represented by the formula (Is) or a salt thereof and the compound represented by the formula (XXI) or a salt thereof can be done under conditions similar to that of the production of the compound represented by the formula (Id) or a salt thereof by the reaction between the compound represented by the formula (Ic) or a salt thereof and the compound represented by the formula (IVb) or a salt thereof.

In the compounds represented by the formula (I) or salts thereof, a compound represented by the formula (It):

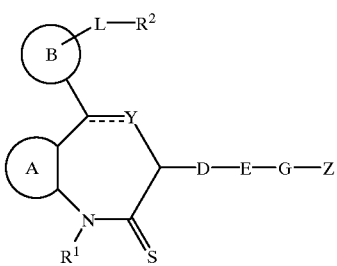

(It)

wherein the symbols have the same meaning as described above, or a salt thereof is produced by allowing the compound represented by the formula (I) in which X is oxygen or a salt thereof to react with Lawesson's reagent or phosphorus pentasulfide in a solvent selected from, for example, ether solvents (for example, diethylether, tetrahydrofuran and dioxane), hydrocarbon solvent (for example, benzene, toluene, hexane and heptane), alcohol solvents (for example, methanol, ethanol and propanol), haloid solvents (for example, dichlormethane and chloroform), hexamethylphosphoric triamide and dimethylsulfoxide. Lawesson's reagent or phosphorus pentasulfide is used at this time in quantity of approximately 1 to 10 mol equivalent, preferably approximately 1 to 3 mol equivalent for 1 mol of the compound represented by the formula (I) in which X is oxygen or a salt thereof. The reaction temperature at this time is about 0 to 150° C., preferably about 50 to 100° C. The reaction time is about 1 to 24 hours, preferably about 3 to 10 hours.

The compound represented by the formula (Iu) can be produced by using the intermediate (IIIe) and the compound of the formula (IV) in substantially the same method of producing the compound Ia as described in the foregoing.

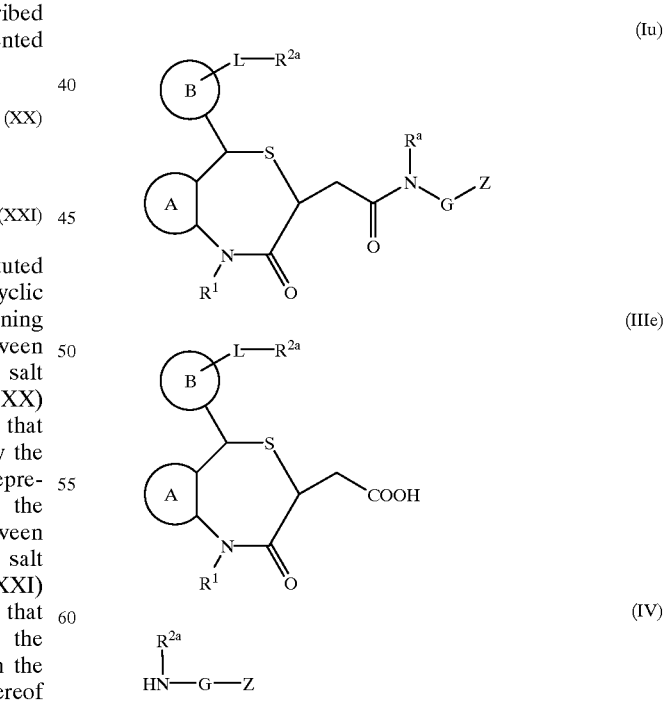

The intermediate represented by the formula (IIIe) can be produced by the following method. Namely, the reaction for producing the compound represented by the formula (IIIe-1)

or a salt thereof from the compound represented by the formula (IIIa-5) or a salt thereof can be conducted by allowing the starting compound to react with mercaptosuccinic acid in a hydrocarbon solvent (for example benzene, toluene and xylene) in the presence of an organic acid (for example methanesulfonic acid, p-toluenesulfonic acid and oxalic acid). The amount of the organic acid to be employed ranges, relative to 1 equivalent of the compound of the formula (IIIa-5), from 0.05 to 5 equivalents, preferably (0.05 to 0.1 equivalent). The reaction time ranges from 1 to 24 hours, preferably from 1 to 2 hours. The reaction temperature ranges from 20 to 140° C., preferably from 80 to 100° C.

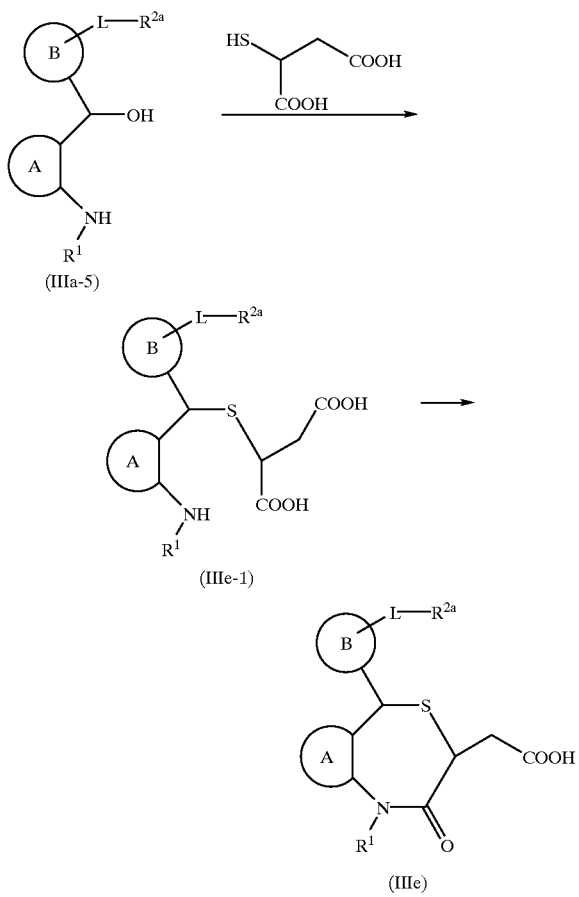

And, the reaction for producing the compound represented by the formula (IIIe) or a salt thereof from the compound represented by the formula (IIIe-1) or a salt thereof can be conducted in a hydrocarbon solvent (for example benzene, toluene and xylene). The reaction temperature ranges from 40 to 150° C., preferably from 100 to 140° C. The reaction time ranges from 1 to 24 hours, preferably from 12 to 20 hours.

And, the compound represented by the formula (Iv, Iw) can be produced by subjecting the compound represented by the formula (Iu) to oxidation. When this reaction is conducted by using m-chloro perbenzoic acid (1 to 1.2 equivalent), relative to 1 mol. of the compound represented by the formula (Iu), in a solvent such as an ether solvent (for example diethylether, tetrahydrofuran and dioxane) or a hydrocarbon solvent (for example dichloromethane, dichloroethane and chloroform) at —10 to 5° C., preferably 0° C. for 1 to 10 minutes, the compound represented by the formula (Iv) is obtained. While, in the case of conducting the reaction by using m-chloro perbenzoic acid (2 to 2.5 equivalents), relative to 1 mol. of the compound of the formula (Iu), at 10 to 50° C., preferably 10 to 20° C. for 2 to 5 hours, the compound represented by the formula (Iw) is produced.

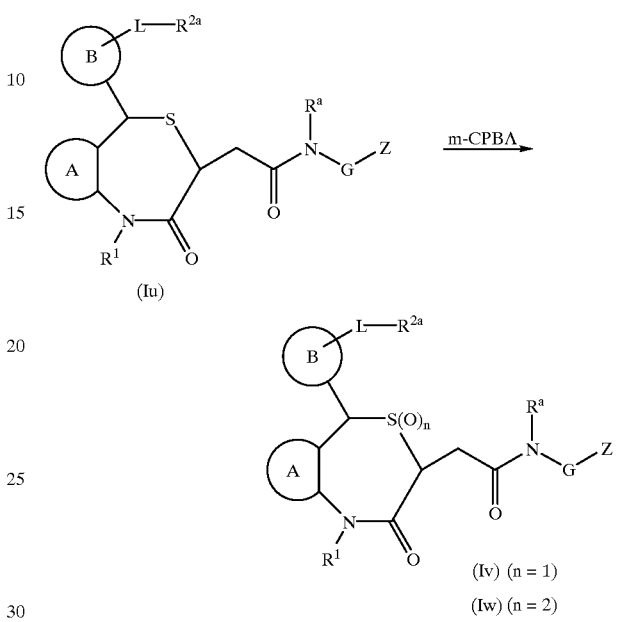

The starting compounds and intermediates of the present invention may be in form of salts but not specifically limited to them as the reaction proceeds. As salts of these compounds are used, for example, inorganic acid salts (for example, hydrochloride, sulfate, hydrobromide and phosphate), organic acid salts(for example, acetate, trifluoroacetate, succinate, maleate, fumarate, propionate, citrate, tartrate, malate, lactate, oxalate, methanesulfonate and p-toluene sulfonate), alkali metal salts (for example, sodium salt and potassium'salt), alkaline earth metal salts (for example, calcium salt and magnesium salt), organic base salts (for example, trimethylamine salt, triethylamine salt, pyridine salt, piperidine salt, ethanolamine salt), aluminum salt and ammonium salt. Further, the starting compounds and intermediates of the present invention may be used after isolation in usual manner. They may also be used without isolation for the subsquent reaction step.

When a compound has amino group, carboxy group and hydroxy group as the substituents in each of the above-mentioned reactions of the present invention, such protecting groups as those generally used in the peptide chemistry may be introduced to these groups. These protecting groups may be removed as occasion may demand to obtain an objective compound.

As the protecting group of the amino group are used, for example, formyl, $C_{1-6}$ alkyl-carbonyl (for example, acetyl and ethylcarbonyl), benzyl, t-butyloxycarbonyl, benzyloxycarbonyl, 9-fluorenylmethyloxycarbonyl, allyoxycarbonyl, phenylcarbonyl, $C_{1-6}$ alkyloxy-carbonyl (for example, methoxycarbonyl and ethoxy-carbonyl), $C_{7-10}$ aralkyl-carbonyl (for example, benzylcarbonyl), trityl, phthaloyl and N,N-dimethylaminomethylene. These groups may be substituted by, for example, 1 to 3 halogen atoms (for example, fluorine, chlorine and bromine) and nitro.

As the protecting group-of the carboxy group are used, for example, $C_{1-6}$ alkyl (for example, methyl, ethyl, propyl, isopropyl, butyl and t-butyl), phenyl, silyl and allyl. These groups may be substituted by, for example, 1 to 3 halogen atoms (for example, fluorine, chlorine and bromine) and nitro.

As the protecting group of the hydroxy group are used, for example, methoxymethyl, allyl, t-butyl, $C_{7-10}$ aralkyl (for example, benzyl), formyl, $C_{1-6}$ alkyl-carbonyl (for example, acetyl and ethylcarbonyl), benzolyl, furanyl and trialkylsilyl. These groups may be substituted by, for example, 1 to 3 halogen atoms (for example, fluorine, chlorine and bromine), $C_{1-6}$ alkyl (for example, methyl, ethyl, propyl, isopropyl, butyl, t-butyl), phenyl, $C_{7-10}$ aralkyl (for example, benzyl) and nitro.

As the method for removing these protecting groups is used a per se known method or a method corresponding thereoto, for example, a method employing acid, base, ultraviolet rays, hydrazine, phenylhydrazine, sodium N-methyldithiocarbamate, tetrabutylammonium fluoride and palladium acetate.

When a compound is obtained in the free form in each of the above-mentioned reactions of the present invention, the compound may be converted to a salt by a usual method and when obtained as a salt, it may be converted to the free form or to another salt.

A compound (I) of the present invention or a salt thereof thus obtained can be isolated and purified from the reaction solvent by known means, for example, phasic transfer, concentration, extraction by solvent, fractional distillation, crystallization, recrystallization and chromatography.

When a compound (I) of the present invention or a salt thereof is existing in the form of, for example, diastereomers and conformers, they may be isolated if required by a usual method for separation and purification. Further, when a compound (I) of the present invention or a salt thereof is a racemic compound, it may be separated into the d-compound and l-compound by usual optical resolution means.

When a compound (I) of the present invention contains a basic group, it may be obtained as a medically acceptable acid addition'salt by a method corresponding to the per se known methods. As acids used for formation of such acid addition salts are mentioned, for example, inorganic acid (for example, hydrochloric acid, sulfuric acid, phosphoric acid and hydrobromic acid), organic acids (for example, acetic acid, trifluoroacetic acid, succinic acid, maleic acid, fumaric acid, propionic acid, citric acid, tartaric acid, malic acid, lactic acid, oxalic acid, methanesulfonic acid, p-toluenesulfonic acid) and amino acids (for example, glutamic acid and asparaginic acid). Further, when a compound (I) of the present invention contains an acid group, it may be made into a medically acceptable salt with a base by a method corresponding to the per se known methods. As bases used for formation of such salts with bases are mentioned, for example, alkali metals (for example, sodium and potassium), alkaline earth metals (for example, calcium and magnesium), organic bases (for example, trimethylamine, triethylamine, pyridine, piperidine and ethanolamine), aluminum and ammonium.

The compounds (I) of the present invention or salts thereof may be used in a wide variety of prophylactic, diagnostic, and therapeutic treatments of mammals(for example, human, cattle, horse, dog, cat, monkey, mouse and rat, especially, human) with low toxicity and with less adverse reactions. The compounds (I) of the present invention or salts thereof inhibit or modulate production or secretion of a variety of hormones, growth factors and physiologically active substances of mammals. As said "hormones" are mentioned, for example, growth hormones (GH), thyroid stimulating hormones (TSH), prolactin, insulin and glucagon. As said "growth factors" are mentioned, for example, IGF-1. As said "physiologically active substances" are mentioned, for example, vasoactive intestinal polypeptide (VIP), gastcin, glucagon-like peptide-1, amylin, substance-P, CGRP, CCK(cholecystokinin) and amylase. And that said "physiologically active substance" includes cytokines such as interleukins and TNF-α. The compounds or salts thereof of this invention function through somatostatin receptors which couple to a variety of intracellular signal transduction systems. These systems include adenylyl cyclase, $K^+$ channels, $Ca^{2+}$ channels, protein phosphatases, phospholipaseC/IP3(inositol 1,4,5-trisphosphate), MAP kinase, a $Na^+/H^+$ exchanger, phospholipase A2, a transcription factor such as NF-κB. The compounds or salts thereof of this invention modulate directly or indirectly cell proliferation inhibitory action of somatostatin and modulate apoptosis induced or regulated by somatostatin. The compounds or salts thereof of this invention may be used in a variety of diseases associated with disorders of production or secretion of hormones, growth factors, and physiologically active substances, associated with disorders of intracellular signal transduction systems, or associated with disorders of regulating cell proliferation. Preferably, the compounds or salts thereof of this invention may be useful (1) for drugs for treatment of for example, tumors such as acromegaly, TSH-producing tumors, nonsecretory (afunctional) hypophysial tumors, ectopic ACTH (adrenocorticotrophic hormone)-producing tumors, medullar thyroid carcinoma, VIP-producing tumors, glucagon-producing tumors, gastrin-producing tumors, insulinoma and cartinoid tumor, (2) for drugs for treatment of insulin-dependent and non-insulin dependent diabetes mellitus or a variety of diseases associated with them, for example, diabetic retinopathy, diabetic nephropathy, diabetic neuropathy, Doan syndrome and orthostatic hypotension, (3) for drugs for improvement of hyperinsulinemia or for treatment of obesity, for example, by inhibition of appetite (4) for drug for treatment of, for example, acute pancreatitis, chronic pancreatitis, pancreato-intestinal fisutula, hemorrhagic ulcer, peptic ulcer, gastritis and hyperchylia by inhibition or modulation of the exocrine secretion in the digestive tracts, (5) for drugs for improvement of various symptoms associated with the *Helicobacter pylori* infection, for example, inhibitors of gastrin hypersecretion, (6) for drugs for inhibition of amylase secretion associated with endoscopic cholangiopancreatography, and drugs for prognostic treatment of surgical operation of pancreas, (7) for drugs for treatment of, for example, diarrhea due to intestinal malabsorption, promotion of secretion or dyskinesia of the digestive tracts(for example, short bowel syndrome), diarrhea due to the drugs for cancer chemotherapy, diarrhea due to AIDS, diarrhea due to graft versus host reaction (GVHR) associated with bone marrow transplantation, diarrhea due to diabetes mellitus, diarrhea due to celiac plexus blocking, diarrhea due to systemic sclerosis and diarrhea due to eosinophilia, (8) for drugs for treatment of, for example, dumping syndrome, irritable bowel syndrome, Crohn disease and inflammatory bowel disease, (9) for drugs for treatment of, for example, various cancers and tumors of which growth is dependent on insulin or IGF-1 or the other growth factors and various tumors and cancers associated with disorders of regulating cell proliferation caused by the other reasons (for example, thyroid cancer, colorectal cancer, breast cancer, prostatic cancer, small cell lung cancer, non-small cell cancer, pancreatic cancer, stomach cancer, cholangiocarcinoma, hepatic cancer, vesical cancer, ovarian cancer, melanoma, osteosarcoma, chondrosarcoma, malignant pheochromocytoma, neuro-blastoma, brain tumors, thymoma, renal cancers), leukemia (for example, leukemia of basophilic leukemia, chronic lymphocytic leukemia, chronic myeloid leukemia, Hodgkin disease, and non-Hodgkin lymphoma) (drugs for treatment of these cancers can be used for monotherapy or concomitant therapy with other anticancer drugs, for example, tamoxifen, LHRH agonists, LHRH antagonists, interferon-α, Interferon-β, interferon-γ and interleukin-2), (10) for drugs for prevention and treatment of, for example, hypertrophic cardiomyopathy, arteriosclerosis, valvulopathy, myocardiac infarction (especially, myocardiac infarction post percutaneous transluminal coronary arterioplasty) and reangioplasty, (11) for drugs for treatment of hemorrhage of esophageal varicosis, cirrhosis and peripheral blood vessel disorders, (12) for drugs for treatment of, for example, diseases associated with general or local inflammation, for example, polyarteritis, rheumatoid arthritis, psoriasis, sunburn, eczema and allergy (for example, asthma, atopic dermatitis and allergic rhinitis) because they inhibit or modulate the secretion of physiologically active substances acting on the immune system (for example, Substance P, tachykinin and cytokines), (13) for drugs for treatment of, for example, dementia (for example, Alzheimer disease, Alzheimer-type senile dementia, vascular/multi-infarct dementia), headache, migraine, schizophrenia, epilepsy, depression, generalized anxiety disorder, sleep disorder, and multiple sclerosis, because they give influence on the production and secretion of nerve regulators, (14) for analgesic drugs, (15) for drugs for treatment of, for example, acute bacterial meningitis, acute virus encephalitis, adult respiratory distress syndrome (ARDS), bacterial pneumonia, severe systemic mycotic infection, tuberculosis, spinal damage, bone fracture, hepatic failure, pneumonia, alcoholic hepatitis, virus A hepatitis, virus B hepatitis, virus C hepatitis, AIDS infection, human papilloma virus infection, influenza infection, metastasis of cancer, multiple myeloma, osteomalacia, osteoporosis, bone Paget disease, reflux esophagitis, nephritis, renal failure, sepsis, septic shock, hypercalcemia, hypercholesterolemia, hypertriglyceridemia, hyperlipemia, systemic lupus erythematosus, transient ischemic attach and alcoholic hepatitis, (16) for cure of, for example, organ trasplant, burns, trauma, and alopecia, (17) ocular diseases for example glaucoma, (18) for imaging of tumors having somatostain receptor after introducing a radioactive substance (for example, $^{123}$I, $^{125}$I, $^{111}$In) to the compounds of the present invention either directly or via a proper spacer, and (19) targeting tumors with somatostatin receptors using the compounds in the present invention conjugated with anti-cancer drugs directly or using an appropriate spacer.

The compounds (I) of the present invention or salts thereof may be used as it is. They are usually formulated into pharmaceutical compositions together with pharmaceutical carriers by a usual method. As said "pharmaceutical carriers" are used, for example, excipients (for example, calcium carbonate, kaolin, sodium hydrogen carbonate, lactose, D-mannitol, starches, crystalline cellulose, talc, granulated sugar and porous substances), binders (for example, dextrin, gums, a-converted starch, gelatin, hydroxypropylcellulose, hydroxypropylmethylcellulose, prulan), agglutinants (for example, natural gums, cellulose derivatives and acrylic acid derivatives), disintegrants (for example, carboxymethylcellulose calcium, Croscarmellose sodium, Crospovidone, low-substituted hydroxypropylceluloses and partially a-converted starch), solvents (for example, water for injection, alcohol, propyleneglycol, macrogol, sesame oil and corn oil), dispersants (for example, Tween 80, HCO 60, polyethyleneglycol, carboxymethylcellulose and sodium arginate), solubilizers (for example, polyethyleneglycol, propyleneglycol, D-mannitol, benzyl benzoate, ethanol, trisaminomethane, triethanolamine, sodium carbonate, sodium citrate), suspending agents (for example, stearyltriethanolamine, sodium laurylsulfate, benzalkonium chloride, polyvinyl alcohol and hydroxymethylcellulose), pain-killing agents (for example, benzyl alcohol), isotonicity agents (for example, sodium chloride and glycerin), buffers (for example, phosphates, acetates, carbonates and citrates), lubricants (for example, magnesium stearate, calcium stearate, talc, starch and sodium benzoate), colorants (for example, tar colors, caramel, red ferric oxide, titanium oxide, riboflavins). The medical preventive and curative drugs that may contain the above-described pharmaceutical carriers contain compounds (I) of the present invention or salts thereof in quantities required for prevention and treatment of a variety of diseases. The content of the compound (I) of the present invention or a medically acceptable salt thereof is usually about 0.1 to about 100 weight % of the whole pharmaceutical composition. As embodiments of the pharmaceutical compositions are used, for example, tablets (including sugar-coated tablets and film-coated tablets), pills, capsules (including microcapsules), granules, fine granules, powders, drip infusion preparations, syrups, emulsions, suspensions, injections, inhalants, ointments, suppositories, troches and poultices. These compositions are prepared according to a usual method (for example, the method described in the Japanese Pharmacopoeia 12th Edition).

The following are the methods for preparation of the main pharmaceutical compositions of the present invention, which naturally should not be construed as limiting thereto.

(1) Tablets

A compound of the present invention is mixed as it is or together with excipients, binders, disintegrating agents or other proper additives. The mixture is made into granules by a pertinent method. The granules are mixed with a lubricant and compressed into tablets. The tablets may be masked for taste or coated with a suitable coating material for the purpose of giving an enteric preparation or a sustained-release form.

(2) Injectables

A given amount of a compound of the present invention is dissolved, suspended or emulsified in, for example, water for injection, optionally adding to it a stabilizer, solubilizer, suspending agent, emulsifier, buffer and/or preservative to give a fixed dose.

(3) Suppository

An oily base, water-soluble base or other suitable base is optionally mixed with an emulsifier, suspending agent etc. A compound of the present invention is added to this, mixed and made into a proper form.

(4) Capsules

A compound of the present invention is mixed with an additive such as a proper excipient into a homogenous mixture or into granules by a proper method, or granules coated with a proper coating agent. The material thus obtained is softly filled in capsules as it is.

The pharmaceutical compositions of the present invention have a high safety with low toxicity and an excellent sbmatostatin agonistic action. They are therefore useful as drugs for prevention and treatment of the diseases mentioned above.

The quantities of the compounds of the present invention used in the above-mentioned pharmaceutical compositions may vary with animal species to be administered and frequency of the administration. They show efficacy over a wide range of the dosage. For example, the daily oral dosage of a pharmaceutical composition of the present invention in adult acromegaly patients of acromegaly, diabetes, obesity, diabetic complication or inveterate diarrhea is usually approximately 0.001 to 20 mg/kg body weight, preferably approximately 0.2 to 3 mg/kg body weight as the effective dose of the compound (I) of the present invention. When the compounds are used in parenteral form, in combination with other active ingredients or concomitantly with other drugs, the dosage is generally lower than these dosages. The dosage of the compound actually administered is decided by the compound selected, dosage forms, the age, body weight, gender and severity of the disease of the patients, administration routes and the period and interval of the administration. So it is possible to change the dosage at any time at the discretion of physicians.

The administration routes of the above-described pharmaceutical compositions are not particularly limited to a variety of situations. They can be administered, for example, by the oral route or by the parenteral routes. The parenteral routes mentioned here include, for example, intravenous, intramuscular, subcutaneous, intranasal, intrarectal, intravaginal and intraperioneal routes.

The duration and interval of treatment with the above-described pharmaceutical compositions may be changed according to a variety of situations and may be decided at any time at the discretion of physicians. There are methods of, for example, administration in divided doses, administration for consecutive days, intermittent administration, massive administration for a short period and repeated administration. In case of oral administration, for example, it is desirable that they are administered either in one dose to several divided doses per day (1 to 3 times a day). It is also possible to administer the pharmaceutical composition intravenously by drip infusion over a longer time.

BEST MODE FOR CARRYING OUT THE INVENTION

The present invention will be explained in more detail by the following examples and test examples. These are mere examples and are not intended to restrict the present invention, and may be modified within the range of not deviating from the scope of this invention.

In the examples and reference examples, abbreviations mean as follows.

s: singlet, d: doublet, t: triplet, q: quartet, dd: double doublet, m: multiplet, br broad, J: coupling constant, room temperature: 0–30° C.

EXAMPLES

Example 1

3,5-Trans-N-(2-fluorobenzyl)-1-benzyl-5-(3-tert-butoxycarbonylaminomethylphenyl)-7-chloro-2-oxo-1,2,3,5-tetrahydro-4,1-benzoxazepine-3-acetamide (A),
3,5-cis-N-(2-fluorobenzyl)-1-benzyl-5-(3-tert-butoxycarbonylaminomethylphenyl)-7-chloro-2-oxo-1,2,3,5-tetrahydro-4,1-benzoxazepine-3-acetamide (B)

(1) A solution of N-methyl-N-methyloxy-2-amino-5-chlorobenzamide (24.8 g) and N-tert-butoxycarbonyl-3-bromobenzylamine (22.0 g) in tetrahydrofuran (300 ml) was cooled to −78° C. To the solution was gradually added dropwise a hexane solution (1.6 mol./L)(240 ml) of n-butyl lithium. To the mixture were then added water (300 ml) and acetic acid ethyl ester (300 ml). The organic layer was washed with water, which was dried over anhydrous $MgSO_4$, then the solvent was distilled off. To the residual oily compound was added hexane (400 ml) to cause crystallization. The crystalline product was collected by filtration to give 2-amino-3'-tert-butoxycarbonylaminomethyl-5-chlorobenzophenone (12.5 g) as pale yellow crystals.

(2) To a solution of 2-amino-3'-tert-butoxycarbonylaminomethyl-5-chlorobenzophenone (7 g) in methanol (70 ml) was added sodium borohydride (1.1 g), and the mixture was stirred for 30 minutes at room temperature. To the reaction mixture was added acetic acid ethyl ester (100 ml). The mixture was washed with water and dried over anhydrous $MgSO_4$, followed by distilling off the solvent. The residue was purified by means of a silica gel column chromatography to give the object 2-amino-5-chloro-α-(3-tert-butoxycarbonylaminomethylphenyl)benzyl alcohol (6.9 g) as a colorless oily compound.

$NMR(CDCl_3)$ δ: 1.44(9H,s), 4.30(2H,d,J=5.8 Hz), 4.80–4.95(1H,br), 5.77(1H,s), 6.58(1H,d,J=8.4 Hz), 7.04–7.38(6H,m)

(3) To a solution of 2-amino-5-chloro-α-(3-tert-butoxycarbonylaminomethylphenyl)benzyl alcohol (0.7 g) in methanol (7 ml) were added benzaldehyde (229 mg) and acetic acid (130 mg). The mixture was stirred for 10 minutes at room temperature, to which was added sodium cyanoborohydride (135 mg). The mixture was stirred for 30 minutes at room temperature, to which was added ethyl acetate ester (50 ml). The mixture was washed with water and dried over anhydrous $MgSO_4$, followed by distilling off the solvent. The residue was purified by means of a silica gel column chromatography to give the object 2-benzylamino-5-chloro-α-(3-tert-butoxycarbonylaminomethylphenyl) benzyl alcohol (0.91 g) as a colorless oily compound.

$NMR(CDCl_3)$ δ: 1.44(9H,m), 2.55–2.65(1H,br), 4.24(2H,s), 4.28(2H,d,J=5.8 Hz), 4.70–4.97(2H,br), 5.80(1H,s), 6.52 (1H,d,J=8.8 Hz), 7.01–7.38(1H,m)

(4) To a solution of 2-benzylamino-5-chloro-α-(3-tert-butoxycarbonylaminomethylphenyl)benzyl alcohol (0.91 g) in acetic acid ethyl ester (10 ml) were added water (4 ml) and a 1N aqueous solution of sodium hydroxide (3 ml). To the mixture was added monoethyl fumarate ester chloride (330 mg), which was stirred for one hour under ice-cooling. To the mixture was added acetic acid ethyl ester (30 ml). The organic layer was washed with water and dried over anhydrous $MgSO_{41}$ followed by distilling off the solvent. The residue was dissolved in ethanol (10 mL), to which was added potassium carbonate (400 mg). The mixture was stirred overnight at room temperature. Insolubles were filtered off, and the solvent was distilled off. The residue was purified by means of a silica gel column chromatography to give ethyl ester of 1-benzyl-5-(3-tert-butoxycarbonylaminomethylphenyl)-7-chloro-2-oxo-1,2,3,5-tetrahydro-4,1-benzoxazepine-3-acetic acid (1.06 g).

$NMR(CDCl_3)$ δ: 1.24(3/10×3H,t,J=7.0 Hz), 1.25(7/10×3H,t, J=7.0 Hz), 2.76(7/10×1H,dd,J=5.4,16.8 Hz), 2.88(3/10×1H, dd,J=5.4,16.8 Hz), 3.13(7/10×1H,dd,J=8.4, 16.8 Hz), 3.22 (3/10×1H,dd,J=8.4,16.8 Hz), 3.68(3/10×1H, d,J=15.6 Hz), 4.14(2H,q,J=7.0 Hz), 4.20–4.32(2H,m), 4.44–4.90(3H,m), 5.37(7/10×1H,s), 5.44(7/10×1H,d,J-14.6 Hz), 5.89(3/10×1H,s), 6.50(7/10×1H,d,J=2/10 Hz), 6.97–7.39(11H+3/10×1H,m)

(5) To a solution of the compound obtained in (4) (0.98 g) in ethanol (10 ml) was added a 1N aqueous solution of sodium hydroxide (2 ml). The mixture was stirred for 3 hours at 60° C. To the reaction mixture was added acetic acid ethyl ester (50 ml), and ¹N hydrochloric acid, followed by extraction. The organic layer was washed with water and dried over anhydrous MgSO₄. The solvent was distilled off, and the residue was purified by means of silica gel column chromatography to give 1-benzyl-5-(3-tert-butoxycarbonylaminomethylphenyl)-7-chloro-2-oxo-1,2,3,5-tetrahydro-4,1-benzoxazepine-3-acetic acid (0.74 g) as a colorless amorphous solid product.

NMR(CD₃OD) δ: 1.39–1.45(9H,m), 2.72(1H,dd,J=5.6, 17.0 Hz), 3.01(1H,dd,J=8.4,17.0 Hz), 4.15–4.96(5H,m), 5.33 (⁷⁄₁₀×1H,s), 5.50(⁷⁄₁₀×1H,d, J=13.8 Hz), 5.70 (³⁄₁₀×1H,d,J=13.8 Hz), 6.39(³⁄₁₀×1H,s), 6.94–7.54(11H+³⁄₁₀×1H,m)

(6) To a solution of the compound obtained in (5) (0.74 g) and 2-fluorobenzylamine (184 mg) in dimethylformamide (7 ml) were added cyano diethyl phosphate (262 mg) and triethylamine (203 mg). The mixture was stirred for 30 minutes at room temperature, to which was added acetic acid ethyl ester (50 ml). The mixture was washed with water and dried over anhydrous MgSO₄. The solvent was distilled off, and the residue was purified by means of a silica gel column chromatography to give two species of colorless oily compounds, i.e. 3,5-trans-N-(2-fluorobenzyl)-1-benzyl-3-(3-tert-butoxycarbonylaminomethylphenyl)-7-chloro-2-oxo-1,2,3,5-tetrahydro-4,1-benzoxazepine-3-acetamide (A) (0.44 g) and 3,5-cis-N-(2-fluorobenzyl)-1-benzyl-5-(3-tert-butoxycarbonylaminomethylphenyl)-7-chloro-2-oxo-1,2,3, 5-tetrahydro-4,1-benzoxazepine-3-acetamide (B) (0.07 g).

(A), NMR(CDCl₃) δ: 1.45(9H,s), 2.70(1H,dd,J=5.8, 14.4 Hz), 2.93(1H,dd,J=7.4,14.4 Hz), 4.27(2H,d,J=5.4 Hz), 4.37–4.61(3H,m), 4.76–4.84(1H,br), 4.80(1H,d,J=14.6 Hz), 5.34(1H,s), 5.46(1H,d,J=14.6 Hz), 6.23–6.30(1H,br), 6.48 (1H,d,J=2.2 Hz), 6.93–7.34(15H,m)

(B), NMR(CDCl₃) δ: 1.42(9H,s), 2.83(1H,dd,J=5.8, 14.2 Hz), 3.04(1H,dd,J=7.2,14.2 Hz), 3.70(1H,d,J=13.8 Hz), 4.24 (2H,d,J=5.8 Hz), 4.48(2H,d,J=6.2 Hz), 4.60–4.72 (2H,m), 4.80–4.93(1H,br), 5.88(1H,s), 6.35–8.45(1H,br), 6.93–7.44 (15H,m)

EXAMPLE 2

3,5-Trans-N-(2-(fluorobenzyl)-5-(3-aminomethylphenyl)-1-benzyl-7-chloro-2-oxo-1,2,3,5-tetrahydro-4,1-benzoxazepine-3-acetamide•monohydrochloride In a 4N acetic acid ethyl ester solution of hydrogen chloride (45 ml) was dissolved 3,5-trans-N-(2-fluorobenzyl)-1-benzyl-5-(3-tert-butoxycarbonylaminomethylphenyl)-7-chloro-2-oxo-1,2,3, 5-tetrahydro-4,1-benzoxazepine-3-acetamide (0.44 g) produced in Example 1. The solution was stirred for 30 minutes at room temperature. The solvent was distilled off, and the residue was washed with diethyl ether/n-hexane. Insolubles were collected to give a colorless amorphous solid product (0.39 g).

NMR(CD₃OD) δ: 2.78(1H,dd,J=6.8,15.0 Hz), 2.91(1H, dd,J=6.8,15.0 Hz), 4.05(2H,s), 4.43(2H,s), 4.53(1H, t,J=6.8 Hz), 4.94(1H,d,J=15.0 Hz), 5.45(1H,s), 5.52(1H,d,J=15.0 Hz), 6.38(1H,d,J=2.2 Hz), 7.01–7.56(15H,m)

EXAMPLE 3

3,5-Cis-N-(2-fluorobenzyl)-5-(3-aminomethylphenyl)-1-benzyl-7-chloro-2-oxo-1,2,3,5-tetrahydro-4,1-benzoxazepine-3-acetamide•monohydrochloride In a solution of a 4N acetic acid ethyl ester of hydrogen chloride (1 ml) was dissolved 3,5-cis-N-(2-fluorobenzyl)-1-benzyl-5-(3-tert-butoxycarbonylaminomethylphenyl)-7-chloro-2-oxo-1,2,3,5-tetrahydro-4,1-benzoxazepine-3-acetamide (0.07 g) produced in Example 1. The solution was subjected to substantially the same procedure as in Example 2 to give a colorless amorphous solid product (0.05 g).

NMR(CD₃OD) δ: 2.89(1H,dd,J=6.6,15.4 Hz), 3.04(1H,dd, J=7.2,15.4 Hz), 3.89(1H,d,J=15.6 Hz), 4.06(2H,s), 4.37(1H, d,J=15.0 Hz), 4.49(1H,d,J=15.0 Hz), 4.60(1H,d, J=15.6 Hz), 4.74(1H,t,J=6.8 Hz), 6.02(1H,s), 6.97–7.66(1H,dd,J=6.6,7.2 Hz)

EXAMPLE 4

3,5-Trans-N-(2-fluorobenzyl)-1-(4-biphenylmethyl)-5-(3-tert-butoxycarbonylaminomethylphenyl)-7-chloro-2-oxo-1,2,3,5-tetrahydro-4,1-benzoxazepine-3-acetamide (1) To a solution of 2-amino-5-chloro-α-(3-tert-butoxycarbonylaminomethylphenyl)benzyl alcohol (4.0 g) in methanol (80 ml) were added 4-biphenylcarbaldehyde (2.2 g) and acetic acid (9.8 g). The mixture was stirred for 10 minutes at room temperature, to which was added cyano sodium borohydride (0.83 g). The mixture was stirred for 30 minutes at room temperature, to which was added acetic acid ethyl ester (50 ml). The mixture was washed with water and dried over anhydrous MgSO₄₁ followed by distilling off the solvent. The residue was dissolved in acetic acid ethyl ester (50 ml), to which was added 1N aqueous solution of sodium hydroxide (30 ml). To the mixture was added dropwise at room temperature, while stirring, a solution of monoethyl ester of fumaric chloride (1.9 g) in acetic acid ethyl ester (4 ml). The mixture was then stirred for one hour at room temperature, which was washed with water and dried over anhydrous MgSO₄. =The solvent was distilled off, and the residue was purified by means of a silica gel column chromatography to give an oily compound (5.0 g). This oily compound was dissolved in ethanol (120 ml), to which was added potassium carbonate (2.5 g). The mixture was stirred for 2 hours at 60° C. Insolubles were filtered off, and the solvent was distilled off. The residue was purified by means of a silica gel column chromatography to give ethyl ester of 3,5-trans-1-(4-biphenylmethyl)-5-(3-tert-butoxycarbonylaminomethylphenyl)-7-chloro-2-oxo-1,2,3, 5-tetrahydro-4,1-benzoxazepine-3-acetic acid (2.4 g) as a colorless oily product.

NMR(CDCl₃) δ: 1.26(3H,t,J=7 Hz), 1.44(9H,s), 2.77(1H, dd, J=5.2,15 Hz), 3.15(1H,dd,J=8.6,14.6 Hz), 4.0–4.3(4H, m), 4.5(1H,dd), 4.25(1H,m), 4.96(1H,d,J=14.6 Hz), 5.45 (1H, d,J=15 Hz), 5.39(1H,s), 6.50(1H,br s), 6.9–7.65(15H, m)

(2) The 3,5-trans-compound (2.0 g) produced in (1) was dissolved in a mixture of tetrahydrofuran (20 ml) and methanol (120 ml). To the solution was added a 1N aqueous solution of sodium hydroxide (15 ml). The mixture was stirred for 2 hours at 60° C. The reaction mixture was cooled, to which was added water (200 ml), which was neutralized with potassium hydrogensulfate, followed by extraction with acetic acid ethyl ester (50 ml×2). The extract was dried over anhydrous MgSO₄, and the solvent was distilled off. The residue was recrystallized from diethyl ether to give 3,5-trans-1-(4-biphenylmethyl)-5-(3-tert-butoxycarbonylaminomethylphenyl)-7-chloro-2-oxo-1,2,3, 5-tetrahydro-4,1-benzoxazepine-3-acetic acid (0.91 g) as colorless crystals, m.p.140–142° C.

(3) To a solution of the compound produced in (2) (0.9 g), 2-fluorobenzylamine (0.21 g) and triethylamine (0.27 g) in dimethylformamide (9 ml) was added cyano phosphoric acid diethyl ester (0.3 g). The mixture was stirred for 20 minutes at room temperature, to which was added water (50 ml), followed by extraction with acetic acid ethyl ester. The extract was washed with water and dried over anhydrous MgSO₄. The solvent was distilled off, and the residue was purified by means of a silica gel column chromatography to give a colorless amorphous solid product (0.93 g).

NMR(CDCl$_3$) δ: 1.43(9H,s), 2.72(1H,dd), 2.96(1H,dd), 4.2 (2H,m), 4.35–4.65(3H,m), 4.25(1H,m), 4.92(1H,d, J=15 Hz), 5.36(1H,s), 5.48(1H,d,J=16 Hz), 6.26(1H,t), 6.49(1H, d,J=1.8 Hz), 6.9–7.7(19H,m)

EXAMPLE 5

3,5-Trans-N-(2-fluorobenzyl)-5-(3-aminomethylphenyl)-1-(4-biphenylmethyl)-7-chloro-2-oxo-1,2,3,5-tetrahydro-4,1-benzoxazepine-3-acetamide•monohydrochloride The compound (0.9 g) produced in Example 4 was dissolved in a 4N acetic acid ethyl ester solution of hydrogen chloride (15 ml). The solution was stirred for one hour at room temperature. The solvent was distilled off, and the residue was recrystallized from diethyl ether to give colorless crystals (0.84 g), m.p.250–252° C.

NMR(DMSO-D$_6$) δ: 2.66(1H,dd,J=5.6,15.0 Hz), 2.886(1H, dd, J=7.8,15.0 Hz), 4.000(2H,s), 4.316(2H,d,J=5.6 Hz), 4.488(1H,t,J=5.8 Hz), 5.10(1H,d,J=15.2 Hz), 5.387(1H,d, J=15.2 Hz), 5.555(1H,s), 6.395(1H,d,J=2.2 Hz), 7.03–7.68 (19H,m), 8.25–8.62(3H,m)

EXAMPLE 6

3,5-Trans-N-(2-fluorobenzyl)-5-(3-aminomethylphenyl)-7-chloro-1-neopentyl-2-oxo-1,2,3,5-tetrahydro-4,1-benzoxazepine-3-acetamide•monohydrochloride (1) To a solution of 2-amino-5-chloro-α-(3-tert-butoxycarbonylaminomethylphenyl)benzyl alcohol (4.0 g) produced in Example 1-(2) in methanol (80 ml) were added trimethyl acetaldehyde:(1.04 g) and acetic acid (0.8 g). The mixture was stirred for 10 minutes at room temperature, to which was added cyano sodium borohydride (0.83 g). The mixture was stirred for 30 minutes at room temperature, to which was added acetic acid ethyl ester (50 ml). The mixture was washed with water and dried over anhydrous MgSO$_4$, followed by distilling off the solvent. The residue was dissolved in acetic acid ethyl ester (50 ml), to which was added a 1N aqueous solution of sodium hydroxide (30 ml). To the mixture was added dropwise, while stirring, an acetic acid ethyl ester (4 ml) solution of monoethyl ester of fumaric chloride (1.9 g). The mixture was then stirred for one hour at room temperature, which was washed with water and dried over anhydrous MgSO$_4$. The solvent was distilled off and the residue was purified by means of a silica gel column chromatography to give an oily compound (4.3 g). This oily compound was dissolved in ethanol (120 ml), to which was added potassium carbonate (2.5 g). The mixture was stirred for two hours at 60° C. Insolubles were filtered off, and the solvent was distilled off. The residue was purified by means of a silica gel column chromatography to give ethyl ester of 3,5-trans-5-(3-tert-butoxycarbonylaminomethylphenyl)-7-chloro-1-neopentyl-2-oxo-1,2,3,5-tetrahydro-4,1-benzoxazepine-3-acetic acid as a colorless oily product (2.6 g).

This compound (2.6 g) was dissolved in a mixture of tetrahydrofuran (20 ml) and methanol (120 ml), to which was added a iN aqueous solution of sodium hydroxide (15 ml). The mixture was stirred for 2 hours at 60° C., to which was added, after cooling, water (200 ml). The mixture was then neutralized with potassium hydrogensulfate, which was subjected to extraction with acetic acid ethyl ester (50 ml×2). The extract was dried over anhydrous MgSO$_4$, and, then, the solvent was distilled off. The residue was recrystallized from diethyl ether to give 3,5-trans-5-(3-tert-butoxycarbonylaminomethylphenyl)-7-chloro-1-neopentyl-2-oxo-1,2,3,5-tetrahydro-4,1-benzoxazepine-3-acetic acid (2.2 g) as colorless crystals, m.p.217–219° C. (2) To a solution of the compound (0.32 g) produced in (1), 2-fluorobenzylamine (0.11 g) and triethylamine (0.11 g) in dimethylformamide (5 ml) was added cyanophosphoric acid diethyl ester (0.12 g). The mixture was stirred for 20 minutes at room temperature, to which was added water (5 ml). The mixture was subjected to extraction with acetic acid ethyl ester. The extract was washed with water and dried over anhydrous MgSO$_4$. The solvent was distilled off, and the residue was purified by means of a silica gel column chromatography to give a colorless amorphous solid product (0.37 g).

This compound (0.24 g) was dissolved in a 4N acetic acid ethyl ester solution of hydrogen chloride (5 ml), which was stirred for 0.5 hour at room temperature. The solvent was distilled off to leave a colorless amorphous solid product (0.23 g). NMR(DMSO-d$_6$) δ: 0.88(9H,s), 2.60–2.80(2H,m), 3.26(1H,d, J=13.4 Hz), 4.00–4.10(2H,m), 4.26–4.20(4H,m), 5.08(1H, s), 6.41(1H,s), 7.13–7.80(11H,m), 8.15–8.60(3H, br)

EXAMPLE 7

3,5-Trans-N-(2-fluorobenzyl)-5-(3-tert-butoxycarbonylaminomethylphenyl)-1-(4-hydroxybenzyl)-2-oxo-7-(3-phenylpropyloxy)-1,2,3,5-tetrahydro-4,1-benzoxazepine-3-acetamide (1) 2-Amino-5-hydroxy-benzoic acid (3.0 g) was dissolved in a 1N aqueous solution of sodium hydroxide (50 ml), to which was added dropwise carbobenzyloxy chloride (3.5 g). The mixture was stirred for one hour at room temperature, which was neutralized with 1N hydrochloric acid, followed by extraction with ethyl acetate (100 ml). The organic layer was washed with water and dried over anhydrous sodium sulfate. The solvent was distilled under reduced pressure to leave 2-benzyloxycarbonylamino-5-hydroxybenzoic acid as blackish brown crystals (2.9 g).

2-Benzyloxycarbonylamino-5-hydroxybenzoic acid (6.0 g) and N,O-dimethylhydroxylamine hydrochloride (2.5 g) were dissolved in methylenb chloride (80 ml). To the solution were added 1-ethyl-3-(3-dimethylaminopropyl)-carbodiimide hydrochloride (4.6 g) and triethylamine (5 ml). The mixture was stirred for 2 hours at room temperature. The reaction mixture was concentrated under reduced pressure. To the concentrate was added water, which was subjected to extraction with ethyl acetate (200 ml). The organic layer was washed with water and dried over anhydrous sodium sulfate. The solvent was distilled off, and the residue was purified by means of a silica gel column chromatography to give N-methyl-N-methyloxy-2-benzyloxycarbonylamino-5-hydroxybenzamide as a yellow oily product (5.0 g).

NMR(CDCl$_3$) δ: 3.322(3H,s), 3.520(3H,s), 5.171(2H,s), 6.10(1H,m), 6.8–7.5(6H,m), 7.70–8.10(2H,m)

(2) A solution of N-methyl-N-methyloxy-2-benzyloxycarbonylamino-5-hydroxybenzamide (1.5 g), 3-phenylpropyl bromide (0.9 g) and potassium carbonate (0.6 g) in N,N-dimethylformamide (10 ml) was stirred for 3 hours at 70° C. The reaction mixture was poured into ice-water, which was subjected to extraction with ethyl acetate. The organic layer was washed with water and dried over anhydrous sodium sulfate. The solvent was distilled off, and the residue was purified by means of a silica gel column chromatography to give N-methyl-N-methyloxy-2-benzyloxycarbonylamino-S-(3-phenylpropyloxy) benzamide as a yellow oily product (1.4 g).

NMR(CDCl$_3$) δ: 2.0–2.2(2H,m), 2.803(2H,t,J=8 Hz), 3.34 (3H,s), 3.526(3H,s), 3.934(2H,t,J=6.2 Hz), 5.176(2H, s), 6.9–7.5(11H,m), 7.9–8.3(2H,m)

(3) N-Methyl-N-methyloxy-2-benzyloxycarbonylamino-5-(3-phenylpropyloxy)benzamide (1.4 g) was dissolved in a mixture of ethyl acetate (10 ml) and methanol (10 ml). To the solution was added 10% palladium-carbon (0.3 g). The mixture was stirred for 24 houks at room temperature under hydrogen atmosphere. The reaction mixture was subjected to filtration. From the filtrate was distilled off the solvent to leave N-methyl-N-methyloxy-2-amino-5-(3-phenylpropyloxy)benzamide as an orange oily product (1.0 g).

NMR(CDCl$_3$) δ: 2.05(2H,m), 2.794(2H,t,J=8 Hz), 3.342 (3H,s), 3.595(3H,s), 3.890(2H,t,J=6.2 Hz), 6.6–7.4(8H,m)

(4) N-Methyl-N-methyloxy-2-amino-5-(3-phenylpropyloxy)benzamide (1.0 g) and N-tert-butoxycarbonyl 3-bromobenzylamine (0.92 g) were dissolved in tetrahydrofuran (20 ml). The solution was cooled to −70° C., to which was added dropwise, while stirring, 12 ml of a hexane solution of n-butyl lithium (1.6 mol/L) over 20 minutes. To the mixture was then added water (50 ml) and ethyl acetate (50 ml). The organic layer was washed with water and dried over anhydrous sodium sulfate. The solvent was distilled off, and the residue was purified by means of a silica gel column chromatography to give 2-amino-3'-tert-butoxycarbonylaminomethyl-5-(3-phenylpropyloxy)benzophenone as a yellow oily product (0.75 g).

NMR(CDCl$_3$) δ: 1.451(9H,s), 1.9–2.1(2H,m), 2.751(2H,t, J=8.2 Hz), 3.779(2H,t,J=6.2 Hz), 4.37(2H,d,J=6.2 Hz), 4.87 (1H,m), 5.719(2H,m), 6.7–7.6(12H,m)

(5) In methanol (20 ml) was dissolved 2-amino-3'-tert-butoxyaminomethyl-5-(3-phenylpropyloxy)benzophenone (0.75 g). To the solution was added sodium borohydride (0.15 g). The reaction mixture was concentrated, to which was added water, followed by extraction with -ethyl acetate (80 ml). The organic layer was washed with water and dried over anhydrous sodium sulfate. The solvent was distilled off to leave 2-amino-α-(3-tert-butoxycarbonylaminomethylphenyl)-5-(3-phenylpropyloxy)benzyl alcohol as a yellow oily product (0.7 g).

NMR(CDCl$_3$) δ: 1.445(9H,s), 2.05(2H,m), 2.786(2H,t, J=8 Hz), 3.883(2H,t,J=6.4 Hz), 4.30(2H,d,J=5.8 Hz), 4.85(1H, m), 5.801.(1H,s), 6.6–7.4(12H,m)

(6) In methanol (12 ml) were dissolved 2-amino-α-(3-tert-butoxycarbonylaminophenyl)-5-(3-phenylpropyloxy)benzyl alcohol (0.7 g), 4-benzyloxybenzaldehyde (0.38 g) and acetic acid (0.1 g). To the solution was added cyano sodium borohydride (0.11 g). The mixture was stirred for 30 minutes at 60° C. The reaction mixture was concentrated, to which were added ethyl acetate (50 ml) and water (100 ml). The organic layer was washed with water and dried over anhydrous sodium sulfate. The solvent was distilled off to leave 2-(4-benzyloxybenzyl)-α-3-tert-butoxycarbonylaminomethylphenyl)-5-(3-phenylpropyloxy)benzyl alcohol as a yellow oily product (0.95 g).

NMR(CDCl$_3$) δ: 1.442(9H,s), 2.05(sH,m), 2.781(2H,t, J=8.2 Hz), 3.877(2H,t,J=6.4 Hz), 4.12(2H,m), 4.28(1H,m), 5.05(2H,s), 5.817(1H,s), 6.6–7.5(21H,m)

(7) To a solution of 2-(4-benzyloxybenzyl)-α-(3-tert-butoxycarbonylaminomethylphenyl)-5-(3-phenylpropyloxy)benzyl alcohol (0.95 g), 1N sodium hydroxide (5 ml) and ethyl acetate (15 ml) was added dropwise, while stirring at room temperature, monoethyl fumaric chloride (0.25 g). The mixture was stirred for 20 minutes and, then, the organic layer was separated, which was washed with water and dried over anhydrous sodium sulfate. The solvent was distilled off, and the residue was dissolved in ethanol (20 ml). To the solution was added potassium carbonate (0.6 g). The mixture was stirred for two hours at 60° C. The reaction mixture was concentrated under reduced pressure, which was washed with water. To the concentrate were added water (50 ml) and ethyl acetate (60 ml), which was subjected to extraction. The organic layer was washed with water and dried over anhydrous sodium sulfate. The solvent was distilled off, and the residue was purified by means of a silica gel column chromatography to give 3,5-trans-1-(4-benzyloxybenzyl)-5-(3-tert-butoxycarbonylaminomethylphenyl)-2-oxo-7-(3-phenylpropyloxy)-1,2,3,5-tetrahydro-4,1-benzoxazepine-3-acetic acid ethyl ester as a colorless oily product (0.42 g), NMR(CDCl$_3$) δ: 1.246(3H,t,J=7.2 Hz), 1.437(9H,s), 2.0 (2H,m), 2.6–2.85(3H,m), 3.11(1H,dd,J=8.4,16 Hz), 3.75 (2H,m), 4.0–4.35(4H,m), 4.47(1H,dd,J=5.6,8.2 Hz), 4.73 (1H,d,J=14.6 Hz), 5.046(2H,s), 5.38(1H,d,J=14.6 Hz), 6.03 (1H, J=3 Hz), 6.8–7.5(20H,m)

(8) In a mixture of tetrahydrofuran (5 ml) and methanol (10 ml) was dissolved ethyl ester of 3.5-trans-1-(4-benzyloxybenzyl)-5-(3-tert-butoxycarbonylaminomethylphenyl)-2-oxo-7-(3-phenylpropyloxy)-1,2,3,5-tetrahydro-4,1-benzoxazepine-3-acetic acid (0.4 g). To the solution was added 1N sodium hydroxide (4 ml). The mixture was stirred for 40 minutes at 60° C. The reaction mixture was concentrated under reduced pressure, which was neutralized with a 5% aqueous solution of potassium hydrogensulfate, followed by extraction with ethyl acetate. The organic layer was washed with water and dried over anhydrous sodium sulfate. The solvent was distilled off, and the residue was dissolved in N,N-dimethylformamide (10 ml). To the solution was added 2-fluorobenzylamine (70 mg), to which were added, while stirring under ice-cooling, cyano diethyl phosphate (0.1 g) and'triethylamine (0.1 ml). The reaction mixture was stirred for 30 minutes at room temperature, to which was added water, followed by extraction with ethyl acetate (50 ml). The organic layer was washed with water and dried over anhydrous sodium sulfate. The solvent was distilled off, and the residue was purified by means of a silica gel column chromatography to give 3,5-trans-N-(2-fluorobenzyl)-1-(4-benzyloxybenzyl)-5-(3-tert-butoxycarbonylaminomethylphenyl)-2-oxo-7-(3-phenylpropyloxy)-1,2,3,5-tetrahydro-4,1-benzoxazepine-3-acetamide as a colorless oily product (0.38 g).

NMR(CDCl$_3$) δ: 1.429(9H,s), 2.00(2H,m), 2.6–2.8(3H,m), 2.93(1H,dd,J=7.2,16 Hz), 3.75(2H,m), 4.2–4.6(5H,m), 4.67 (1H,d,J=14.4 Hz), 5.04(2H,s), 5.303(1H,s), 5.40(1H,d, J=14.4 Hz), 6.02(1H,d,J=2.6 Hz), 6.38(1H,m), 6.8–7.5 (24H,m)

(9) In a mixture of ethyl acetate (10 ml) and methanol (10 ml) was dissolved 3,5-trans-N-(2-fluorobenzyl)-1-(4-benzyloxybenzyl)-5-(3-tert-butoxycarbonylaminomethylphenyl)- 2-oxo-7-(3-phenylpropyloxy)-1,2,3,5-tetrahydro-4,1-benzoxazepine-3-acetamide (0.38 g). To the solution was added 10% palladium-carbon (0.1 g). The mixture was stirred for two hours at room temperature under hydrogen atmosphere. The reaction mixture was subjected to filtration. From the filtrate, the solvent was distilled off to leave 3,5-trans-N-(2-fluorobenzyl)-5-(3-tert-butoxycarbonylaminomethylphenyl)-1-(4-hydroxybenzyl)-2-oxo-7-(3-phenylpropyloxy)-1,2,3,5-tetrahydro-4,1-benzoxazepine-3-acetamide as a colorless amorphous solid product (0.33 g).

NMR(CDCl$_3$) δ: 1.43(9H,m), 2.05(2H,m), 2.6–3.0(4H,m), 3.78(2H,m), 4.0–4.6(6H,m), 4.87(1H,s), 5.0(1H,m), 5.8(1H, m), 5.95(1H,d,J=2 Hz), 6.18(1H,m), 6.6–7.5(19H,m)

By substantially the same procedure as in Example 6, compounds in Examples 8 to 24 were produced.

EXAMPLE 8

3,5-Trans-N-(2-fluorobenzyl)-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.83(9H,s), 2.70–2.96(4H,m), 3.33(1H,d, J=13.2 Hz), 3.80–3.92(2H,m), 4.11–4.44(4H,m), 5.91(1H, s), 6.53(1H,s), 6.81–7.59(11H,m)

EXAMPLE 9

3,5-Trans-N-(2-fluorobenzyl)-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.84(9H,s), 2.70–2.90(2H,m), 3.31(1H,d, J=13.0 Hz), 3.78–3.96(2H,m), 4.08–4.15(1H,m), 4.30–4.46 (3H,m), 5.89(1H,s), 6.52(1H,s), 6.84–7.56(11H,m)

EXAMPLE 10

3,5-Trans-N-[2-(2-fluorophenyl)ethyl]-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.87(9H,s), 2.60–2.83(4H,m), 3.29–3.45 (3H,m), 4.00–4.10(2H,m), 4.35–4.46(2H,m), 5.94(3H,s), 6.54(1H,s), 6.67(1H,br), 6.29–7.59(11H,m)

EXAMPLE 11

3,5-Trans-N-(2-chlorobenzyl)-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.85(9H,s), 2.70–3.00(2H,m), 3.32(1H, d9 J=14.8 Hz), 3.90–4.00(2H,m), 4.35–4.50(4H,m), 5.92 (1H,s), 6.53(1H,s), 7.09–7.57(10H,m)

EXAMPLE 12

3,5-Trans-N-(2-methoxybenzyl)-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.87(9H,s), 2.64–2.92(2H,m), 3.32(1H,d, J=11.8 Hz), 3.76(3H,s), 3.84–4.02(2H,m), 4.24–4.50(4H,m) 5.95(1H,s), 6.53(1H,s), 6.79–7.50(10H,m)

EXAMPLE 13

3,5-Trans-N-(2,4-difluorobenzyl)-5-(3-aminomethylphenyl)-7-chloro-1-neopentyl-2-oxo-1,2,3, 5-tetrahydro-4,1-benzoxazepine-3-acetamide•monohydrochloride (non-crystalline solid)
NMR(CDCl$_3$) δ: 0.85(9H,s), 2.66–2.96(2H,m), 3.32(1H, d, J=13.8 Hz), 3.92–4.02(2H,m), 4.20–4.44(4H,m), 5.89 (4H, s), 6.52(1H,s), 6.67–7.58(9H,m)

EXAMPLE 14

3,5-Trans-N-[3,5-bis (trifluoromethyl )benzyl]-5-(3-aminomethylphenyl)-7-chloro-1-neopentyl-2-oxo-1,2,3, 5-tetrahydro-4,1-benzoxazepine-3-acetamide•monohydrochloride
NMR(CDCl$_3$) δ: 0.90(9H,s), 2.80(1H,dd,J=5.8,14.2 Hz), 2.96(1H,dd,J=7.8,14.2 Hz), 3.34(1H,d,J=13.6 Hz), 4.04(2H, s), 4.30–4.74(4H,m), 5.99(1H,s), 6.57(1H,d, J=2.0 Hz), 7.19–7.76(9H,m) m.p.: 165–170° C.

EXAMPLE 15

3,5-Trans-N-benzyl-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CDCl$_3$) δ: 0.84(9H,s), 2.7–2.9(2H,m), 3.32(1H,d, J=14.0 Hz), 4.08–4.20(2H,m), 4.32–4.50(4H,m), 5.91(1H, s), 6.52(1H,s), 7.09–7.48(11H,m)

EXAMPLE 16

3,5-Trans-N-(2-fluorobenzyl)-N-methyl-5-(3-aminomethylphenyl)-7-chloro-1-neopentyl-2-oxo-1,2,3, 5-tetrahydro-4,1-benzoxazepine-3-acetamide monohydrochloride
NMR(CDCl$_3$) δ: 0.93,0.94(total 9H, each s), 2.72–2.85(1H, m), 2.89(³⁄₁₀×3H,s), 3.03(⁶⁄₁₀×3H,s), 3.18–3.31(1H,m), 3.39 (1H,d,J=14.2 Hz), 3.85–4.05(2H,br), 4.44–4.80(4H,m), 6.00,6.02(total 1H, each s), 6.59(1H,s), 6.98–7.42(10H,m)

EXAMPLE 17

3,5-Trans-N-(pyridin-2-yl)methyl-5-(3-aminomethylphenyl)-7-chloro-1-neopentyl-2-oxo-1,2,3, 5-tetrahydro-4,1-benzoxazepine-3-acetamide•dihydrochloride (non-crystalline solid)
NMR(CD$_3$OD) δ: 0.95(9H,s), 2.86(2H,d,J=5.6,15.0 Hz), 3.02(2H,dd,J=8.2,15.0 Hz), 3.57(1H,d,J=14.2 Hz), 4.18(2H, s), 4.37–4.48(2H,m), 4.64(1H,d,J=16.4 Hz), 4.79(1H,d,J= 16.4 Hz), 6.06(1H,s), 6.51(1H,d,J=2.2 Hz), 7.44–7.61(6H, m), 7.87–8.04(2H,m), 8.53–8.77(2H,m)

EXAMPLE 18

3,5-Trans-N-(furan-2-yl)methyl-5-(3-aminomethylphenyl)-7-chloro-1-neopentyl-2-oxo-1,2,3,5-tetrahydro-4,1-benzoxazepine-3-acetamide•monohydrochloride (non-crystalline solid)
NMR(CD$_3$OD) δ: 0.94(9H,s), 2.74(2H,d,J=6.6 Hz), 3.58 (1H, d,J=14.0 Hz), 4.15(2H,s), 4.33–4.47(4H,m), 6.04(1H, s), 6.21–6.35(2H,m), 6.49(1H,d,J=2.6 Hz), 7.40–7.65(7H, m)

EXAMPLE 19

3,5-Trans-N-(thiophen-2-yl)methyl-5-(3-aminomethylphenyl)-7-chloro-1-neopentyl-2-oxo-1,2,3, 5-tetrahydro-4,1-benzoxazepine-3-acetamide•monohydrochloride (non-crystalline solid)
NMR(CDCl$_3$) δ: 0.94(9H,s), 2.74(2H,d,J=6.6 Hz), 3.58(1H, d,J=13.6 Hz), 4.13(2H,s), 4.40–4.54(4H,m), 6.04(1H,s), 6.49(1H,d,J=2.2 Hz), 6.90–6.94(2H,m), 7.21–7.65(7H,m)

EXAMPLE 20

3,5-Trans-N-(2-fluoromethylbenzyl)-5-(3-aminomethylphenyl)-7-chloro-1-neopentyl-2-oxo-1,2,3, 5-tetrahydro-4,1-benzoxazepine-3-acetamide•monohydrochloride (non-crystalline solid)
NMR(CDCl$_3$) δ: 0.94(9H,s), 2.85(2H,d,J=6.6 Hz), 3.58(1H, d,J=14.6 Hz), 4.11(2H,s), 4.42–4.57(4H,m), 6.06(1H,s), 6.50(1H,s), 7.36–7.70(10H,m)

EXAMPLE 21

3,5-Trans-N-(2,6-difluorobenzyl)-5-(3-aminomethylphenyl)-7-chloro-1-neopentyl-2-oxo-1,2,3, 5-tetrahydro-4,1-benzoxazepine-3-acetamide•monohydrochloride (non-crystalline solid)
NMR(CD$_3$OD) δ: 0.93(9H,s), 2.71(2H,d,J=6.6 Hz), 3.57 (1H,d,J=13.2 Hz), 4.17(2H,s), 4.38–4.45(4H,m), 6.02(1H, s), 6.91–7.36(9H,m)

EXAMPLE 22

3,5-Trans-N-(indol-3-yl)methyl-5-(3-aminomethylphenyl)-7-chloro-1-neopentyl-2-oxo-1,2,3,5-tetrahydro-4,1-benzoxazepine-3-acetamide•monohydrochloride (non-crystalline solid)

NMR(CD$_3$OD) δ: 0.90(9H,s), 2.72(2H,d,J=6.2 Hz), 2.93 (2H, t,J=7.3 Hz), 3.42–3.66(3H,m), 4.12(2H,s), 4.39–4.48 (2H,m), 6.05(1H, s), 6.51(1H,d,J=2.2 Hz), 6.98–7.62(11H, m)

EXAMPLE 23

3,5-Trans-N-cyclohexylmethyl-5-(3-aminomethylphenyl)-7-chloro-1-neopentyl-2-oxo-1,2,3,5-tetrahydro-4,1-benzoxazepine-3-acetamide•monohydrochloride (non-crystalline solid)

NMR(CD$_3$OD) δ: 0.94(9H,s), 1.16–1.7A(11H,m), 2.72(2H, d,J=6.8 Hz), 3.00(2H,d,J=6.6 Hz), 3.59(1H,d,J=14.0 Hz), 4.18(2H,s), 4.40–4.47(2H,m), 6.05(1H,s), 6.50(1H,d, J=2.4 Hz), 7.42–7.56(6H,m)

EXAMPLE 24

3,5-Trans-N-[2-(pyrrolidin-1-yl)ethyl]-5-(3-aminomethylphenyl)-7-chloro-1-neopentyl-2-oxo-1,2,3,5-tetrahydro-4,1-benzoxazepine-3-acetamide•dihydrochloride (non-crystalline solid)

NMR(DMSO-d$_6$) δ: 0.87(9H,s), 1.75–2.10(4H,m), 2.67(2H, m), 2.96(2H,m), 3.15(2H,m), 3.34–3.70(5H,m), 4.08(2H, m), 4.20–4.40(2H,m), 5.88(1H,s), 6.44(1H,d,J=2.4 Hz), 7.30–7.80(6H,m), 8.3–8.6(4H,m)

EXAMPLE 25

(3S,5S)-N-(2-fluorobenzyl)-5-(3-aminomethylphenyl)-7-chloro-1-neopentyl-2-oxo-1,2,3,5-tetrahydro-4,1-benzoxazepine-3-acetamide•monohydrochloride (1) In dimethylformamide (6 ml) were dissolved 3,5-trans-5-(3-tert-butoxycarbonylaminomethylphenyl)-7-chloro-1-neopentyl-2-oxo-1,2,3,5-tetrahydro-4,1-benzoxazepine-3-acetic acid (0.6 g) and L-leucine methylester-monohydrochloride (0.22 g). To the solution were added cyanophosphoric acid diethyl ester (0.20 g) and triethylamine (0.25 g). The mixture was stirred for 30 minutes at 0° C., to which was added acetic acid ethyl ester (50 ml). The mixture was washed with water. Then, the organic layer was dried over anhydrous MgSO$_4$. The solvent was distilled off, and the residue was purified by means of a silica gel column chromatography to give (3R,5R)-N-[5-(3-tert-butoxycarbonylaminomethylphenyl)-7-chloro-1-neopentyl-2-oxo-1,2,3,5-tetrahydro-4,1-benzoxazepine-3-acetyl]-L-leucine methyl ester (0.37 g) and (3S,5S)-N-[5-(3-tert-butoxycarbonylaminomethylphenyl)-7-chloro-1-neopentyl-25-oxo-1,2,3,5-tetrahydro-4,1-benzoxazepine-3-acetyl]-L-leucine methyl ester (0.40 g). (3R,5R):

NMR(CDCl$_3$) δ: 0.92(15H,s), 1.44(9H,s), 1.55–1.65(3H,m), 2.70(1H,dd,J=6.8,14.8 Hz), 2.87(1H,dd,J=6.8,14.8 Hz), 3.35(1H,d,J=13.8 Hz), 3.72(3H,s), 4.33–4.57(5H,m), 5.13–5.22(1H,br), 6.01(1H,s), 6.21(1H,d,J=7.6 Hz), 6.57 (1H,d, J=2.0 Hz), 7.18–7.64(6H,m) (3S,5S):

NMR(CDCl$_3$) δ: 0.88–0.92(15H,m), 1.45(9H,s), 1.55–1.65 (3H,m), 2.69(1H,dd,J=6.0,14.6 Hz), 2.92(1H,dd, J=6.8,14.6 Hz), 3.37(1H,d,J=14.0 Hz), 3.71(3H,s), 4.33–4.60(5H,m), 4.85–5.00(1H,br), 6.00(1H,s), 6.43(1H,d, J=8.4 Hz), 6.58 (1H,s), 7.23–7.41(6H,m)

(2) To a solution of the (3S,5S) compound produced in (1) (0.40 g) in methanol (4 ml) was added a 1N aqueous solution of sodium hydroxide (0.65 ml). The mixture was stirred for one hour at 60° C. To the reaction mixture was added water (50 m), which was neutralized with 1N hydrochloric acid, followed by extraction with acetic acid ethyl ester. The extract solution was dried over anhydrous Na$_2$SO$_4$. The solvent was distilled off to leave (3S,5S)-N-[5-(3-tert-butoxycarbonylaminomethylphenyl)-7-chloro-1-neopentyl-2-oxo-1,2,3,5-tetrahydro-4,1-benzoxazepine-3-acetyl]-L-leucine (0.25 g).

(3) To a solution of the compound produced in (2) in methanol (2 ml) was added conc. sulfuric acid (1 ml). The mixture was heated for 3 days under reflux, to which was added water (50 ml). The mixture was made alkaline with an aqueous solution of sodium hydroxide, followed by extraction with acetic acid ethyl ester. The extract solution was dried over anhydrous Na$_7$SO$_4$, and the solvent was distilled off to leave (3S,5S)-5-(3-aminomethylphenyl)-7-chloro-1-neopentyl-2-oxo-1,2,3,5-tetrahydro-4,1-benzoxazepine-3-acetic acid methyl ester (80 mg) as a colorless oily product.

NMR(CDCl$_3$) δ: 0.93(H,s), 2.79(1H,dd,J=5.8,16.4 Hz), 3.07 (1H,dd,J=8.0,16.4 Hz), 3.37(1H,d,J=14.0 Hz), 3.67(3H,s), 3.9–4.0(2H,br), 4.41(1H,dd,J=5.8,8.0 Hz), 4.50(1H,d,J= 14.0 Hz), 6.02(1H,s), 6.61(1H,d,J=1.8 Hz), 7.19–7.45(6H, m)

(4) To a solution of the compound produced in (3) (80 mg) in acetic acid ethyl ester (1 ml) were added di-tert-butyl dicarbonate (0.03 ml) and dimethyl aminopyridine (10 mg). The mixture was stirred for 30 minutes at room temperature. After completion of the reaction, acetic acid ethyl ester (50 ml) was added to the reaction mixture. The mixture was washed with water and dried over anhydrous Na$_2$SO$_4$. The solvent was distilled off, and the residue was purified by means of a silica gel column chromatography to give a colorless oily product (60 mg). To a solution of this oily product (60 mg) in methanol (1 ml) was added a iN aqueous solution of sodium hydroxide (0.25 ml). The mixture was stirred for 30 minutes at 60° C. To the reaction mixture was added water (50 ml), which was made acid with iN hydrochloric acid, followed by extraction with acetic acid ethyl ester. The extract solution was washed with water and dried over anhydrous Na,SO$^4$. The solvent was distilled off to leave a colorless oily compound (40 mg). To a solution of this compound (40 mg) in dimethylformamide (1 ml) were added 2-fluorobenzylamine (20 mg), cyanophophoric acid diethyl ester (20 mg) and triethylamine (30 mg). The mixture was stirred for 30 minutes at room temperature. To the reaction mixture was added acetic acid ethyl ester (50 ml), which was washed with water. The organic layer was dried over anhydrous Na$_2$SO$_4$. The solvent was distilled off, and the residue was purified by means of a silica gel column chromatography to give a colorless amorphous solid product (40 mg). This product (40 mg) was dissolved in a 4N acetic acid ethyl ester solution of hydrogen chloride (1 ml). The solution was left standing for 30 minutes at room temperature. The solvent was, then, distilled off to give a colorless amorphous solid product (33 mg). Optical rotation: $[α]_D^{22}$+ 165.6° (c=0.15, methanol)

EXAMPLE 26

(3R,5R)-N-(2-fluorobenzyl)-5-(3-aminomethylphenyl)-7-chloro-1-neopentyl-2-oxo-1,2,3,5-tetrahydro-4,1-benzoxazepine-3-acetamide•monohydrochloride Using the (3R,5R) compound produced in Example 25-(1) (0.37 g) as starting material, substantially the same procedure as in Example 25 was conducted to give an amorphous solid product (20 mg).

Optical rotation: $[α]_D^{22}$–166.0° (c=0.13, methanol)

Using the 3,5-trans-1-(4-biphenylmethyl)-5-(3-tert-butoxycarbonylaminomethylphenyl)-7-chloro-2-oxo-1,2,3, 5-tetrahydro-4,1-benzoxazepine-3-acetic acid as starting material, substantially the same procedures as in Example 4(3) and, then, as in Example 5 were conducted to give the compounds shown as follows.

EXAMPLE 27

3,5-Trans-N-[3,5-bis(trifluoromethyl)benzyl]-5-(3-aminomethylphenyl)-1-(4-biphenylmethyl)-7-chloro-2-oxo-1,2,3,5-tetrahydro-4,1-benzoxazepine-3-acetamide•monohydrochloride (colorless crystal)
NMR(CDCl$_3$) δ: 2.77(1H,dd), 3.04(1H,dd), 3.75(2H,br), 4.3–4.7(3H,m), 4.78(1H,d), 5.33(1H,s), 5.55(1H,d), 6.52 (1H,d), 6.8–7.8(19H,m) m.p.: 238–240° C.

EXAMPLE 28

3,5-Trans-N-(3,4,5-trimethoxybenzyl)-5-(3-aminomethylphenyl)-1-(4-biphenylmethyl)-7-chloro-2-oxo-1,2,3,5-tetrahydro-4,1-benzoxazepine-3-acetamide•monohydrochloride
NMR(CDCl$_3$) δ: 2.75(1H,dd), 2.96(1H,dd), 3.6–3.9(11H, m), 4.37(2H,dd), 4.57(1H,dd), 4.87(1H,d), 5.38(1H,s), 5.45 (1H,d), 6.32(1H,t), 6.49(2H,s), 6.52(1H,d), 6.85–7.6(15H, m)

EXAMPLE 29

3,5-Trans-N-benzhydryl-5-(3-aminomethylphenyl)-1-(4-biphenylmethyl)-7-chloro-2-oxo-1,2,3,5-tetrahydro-4,1-benzoxazepine-3-acetamide•monohydrochloride (non-crystalline solid)
NMR(CDCl$_3$) δ: 2.78(1H,dd), 3.0(1H,dd), 3.72(2H,s), 4.52 (1H,dd), 4.83(1H,d), 5.36(1H,s), 5.53(1H,d), 6.23(1H,d), 6.52(1H,d), 6.65(1H,s), 6.85–7.7(25H,m) m.p.: 200–202° C.

EXAMPLE 30

3,5-Trans-N-(2-biphenylmethyl)-5-(3-aminomethylphenyl)-1-(4-biphenylmethyl)-7-chloro-2-oxo-1,2,3,5-tetrahydro-4,1-benzoxazepine-3-acetamide•monohydrochloride (non-crystalline solid)
NMR(CDCl$_3$) δ: 2.65(1H,dd), 2.87(1H,dd), 3.73(2H,s), 4.25–4.6(3H,m), 4.85(1H,d), 5.35(1H,s), 5.48(1H,d), 6.06 (1H,t), 6.50(1H,d), 6.8–7.7(24H,m)

EXAMPLE 31

3,5-Trans-N-(4-biphenylmethyl)-5-(3-aminomethylphenyl)-1-(4-biphenylmethyl)-7-chloro-2-oxo-1,2,3,5-tetrahydro-4,1-benzoxazepine-3-acetamide•monohydrochloride (non-crystalline solid)
NMR(CDCl$_3$) δ: 2.77(1H,dd), 2.98(1H,dd), 3.75(2H,s), 4.35–4.65(3H,m), 4.87(1H,d), 5.39(1H,s), 5.50(1H,d), 6.32 (1H,t), 6.53(1H,d), 6.9–7.6(24H,m)

EXAMPLE 32

3,5-Trans-N-(4-ethoxycarbonylbenzyl)-5-(3-aminomethylphenyl)-1-(4-biphenylmethyl)-7-chloro-2-oxo-1,2,3,5-tetrahydro-4,1-benzoxazepine-3-acetamide•monohydrochloride (colorless crystal)
NMR(CDCl$_3$) δ: 1.37(3H,t), 2.77(1H,dd), 2.98(1H,dd), 3.76 (2H,br), 4.34(2H,q), 4.44–4.62(2H,m), 4.88(1H,d), 5.38 (1H,s), 5.47(1H,d), 6.34(1H,t), 6.53(1H,d), 6.9–8.0(19H,m) m.p.: 220–222° C.

EXAMPLE 33

3,5-Trans-N-(2-fluorobenzyl)-5-(3-aminomethylphenyl)-1-(4-hydroxybenzyl)-2-oxo-7-(3-phenylpropyloxy)-1,2,3,5-tetrahydro-4,1-benzoxazepine-3-acetamide•hydrochloride In ethyl acetate (5 ml) was dissolved 3,5-trans-N-(2-fluorobenzyl)-5-(3-tert-butoxycarbonylaminomethylphenyl)-1-(4-hydroxybenzyl)-2-oxo-7-(3-phenylpropyloxy)-1,2,3,5-tetrahydro-4,1-benzoxazepine-3-acetamide (0.28 g) produced in Example 7. To the solution was added 4N hydrochloric acid (ethyl acetate solution) (3 ml). The mixture was stirred for two hours. The solvent was distilled off under reduced pressure to leave the above-titled compound as an amorphous solid product (0.22 g).
NMR(CDCl$_3$) δ: 1.95(2H,m), 2.6–2.9(4H,m), 3.6–4.6(8H, m), 4.808(1H,s), 5.63(1H,d,J=13.8 Hz), 5.95(1H,d,J=2.8 Hz), 6.3–7.4(20H,m)

EXAMPLE 34

3,5-Trans-5-(3-aminomethylphenyl)-7-chloro-1-neopentyl-2-oxo-1,2,3,5-tetrahydro-4,1-benzoxazepine-3-acetic acid 2-fluorobenzylester•hydrochloride
To a solution of 3,5-trans-5-(3-tert-butoxycarbonylaminomethylphenyl)-7-chloro-1-neopentyl-2-oxo-1,2,3,5-tetrahydro-4,1-benzoxazepine-3-acetic acid (100 mg) produced in Example 6-(1) and 2-fluorobenzyl chloride (30 mg) in dimethylformamide (1 ml) was added potassium carbonate (39 mg). The mixture was stirred for one hour at 60° C., to which was added acetic acid ethyl ester (50 ml). The mixture was washed with water, and the organic layer was dried over anhydrous Na$_2$SO$_4$. The solvent was distilled off, and the residue was purified by means of a silica gel column chromatography to give a colorless oily compound. The oily compound was dissolved in 4N acetic acid ethyl ester solution of hydrogen chloride (1 ml). The solution was stirred for one hour at room temperature. The solvent was distilled off to leave a colorless amorphous solid product (58 mg).
NMR(CDCl$_3$) δ: 0.90(9H,m), 2.86(1H,dd,J=6.4,15.6 Hz), 3.10(1H,dd,J=8.0,15.6 Hz), 3.33(1H,d,J=14.0 Hz), 4.08(2H, br), 4.35–4.50(2H,m), 5.11(1H,d,J=11.6 Hz), 5.20(1H,d,J= 11.6 Hz), 5.99(1H,s), 6.55(1H,s), 6.98– 7.55(10H,m)

EXAMPLE 35

3,5-Trans-5-(3-tert-butoxycarbonylaminomethylphenyl)-7-chloro-3-(2-fluorophenylacetyl)aminomethyl-1-neopentyl-1,2,3,5-tetrahydro-4,1-benzoxazepin-2-one
(1) To a solution of 3,5-trans-5-(3-tert-butoxycarbonylaminomethylphenyl)-7-chloro-1-neopentyl-2-oxo-1,2,3,5-tetrahydro-4,1-benzoxazepine-3-acetic acid (0.2 g) produced in Example 6-(1) in dimethylformamide (2 ml) were added triethylamine (44 mg) and diphenylphosphoryl azide. The mixture was stirred for 30 minutes at room temperature. To the reaction mixture was added water, which was subjected to extraction with acetic acid ethyl ester. The extract was washed with water and dried over anhydrous Na$_2$SO$_4$. The solvent was removed, and the residue was dissolved in toluene (2 ml). The solution was heated for one hour under reflux, to which was added 9-fluorenyl methanol (89 mg). The mixture was further heated overnight under reflux. The solvent was distilled off, and the residue was purified by means of a silica gel column chromatography to give 3,5-trans-5-(3-tert-butoxycarbonylaminomethylphenyl)-7-chloro-3-(fluoren-9-yl)oxycarbonylaminomethyl-1-neopentyl-1,2,3,5-tetrahydro-4,1-benzoxazepin-2-one (0.24 g) as a colorless amorphous solid product.
(2) A solution of the compound (0.24 g) produced in Example (1) and piperidine (0.15 ml) in dimethylformamide (3 ml) was stirred for 10 minutes at room temperature. To the reaction mixture was added acetic acid ethyl ester (50 ml).

The mixture was washed with water. The organic layer was dried over anhydrous Na$_2$SO$_4$ and, then, the solvent was distilled off. The residue was purified by means of a silica gel column chromatography to give 3,5-trans-3-aminomethyl-5-(3-tert-butoxycarbonylaminomethylphenyl)-7-chloro-1-neopentyl-1,2,3,5-tetrahydro-4,1-benzoxazepin-2-one (0.17 g) as a colorless amorphous solid product.

NMR(CDCl$_3$) δ: 0.93(9H,s), 1.45(9H,s), 3.36(1H,d, J=14.0 Hz), 3.55–3.70(2H,m), 3.95(1H,t,J=5.8 Hz), 4.16–4.40(5H, m), 4.51(1H,d,J=14.0 Hz), 4.83–4.90(1H,br), 5.25–5.30(1H, br), 5.99(1H,s), 6.60(1H,s), 7.26–7.77(14H,m)

(3) To a solution of the compound (0.1 g) produced in (2) and 2-fluorophenyl acetic acid (34 mg) in dimethylformamide (1 mg) were added cyano diethyl phosphate (36 mg) and triethylamine (30 mg). The mixture was stirred for 30 minutes at room temperature. To the reaction mixture was added acetic acid ethyl ester (50 ml). The mixture was washed with water and dried over anhydrous Na$_2$SO$_4$. The solvent was distilled off, and the residue was purified by means of a silica gel column chromatography to give a colorless amorphous solid product (0.13 g).

NMR(CDCl$_3$) δ: 0.9(9H,s), 1.45(9H,s), 3.33(1H,d, J=14.2 Hz), 3.54(2H,s), 3.64–3.70(2H,m), 3.92(1H,d, J=6.1 Hz), 4.35(1H,d,J=5.6 Hz), 4.45(1H,d,J=14.2 Hz), 4.85–4.95(1H, br), 5.93(1H,s), 6.05–6.11(1H,br), 6.57(1H,d,J=2.2 Hz), 7.03–7.41(10H,m)

EXAMPLE 36

3,5-Trans-5-(3-aminomethylphenyl)-7-chloro-3-(2-fluorophenylacetyl)aminomethyl-1-neopentyl-1,2,3,5-tetrahydro-4,1-benzoxazepin-2-one•monohydrochloride The compound produced in Example 35 (0.12 g) was dissolved in 4N acetic acid ethyl ester solution of hydrogen chloride (1 ml). The solution was left standing for 30 minutes at room temperature. The solvent was then distilled off to leave a colorless amorphous solid product (69 mg).

NMR(CDCl$_3$) δ: 0.94(9H,s), 3.47–3.72(5H,m), 3.99(1H,t, J=5.8 Hz), 4.17(2H,s), 4.44(1H,d,J=14.2 Hz), 6.02(1H,s), 6.50(1H,d,J=2.2 Hz), 6.98–7.61(10H,m)

EXAMPLE 37

3,5-Trans-N-(2-fluorobenzyl)-5-(3-tert-butoxycarbonylaminomethylphenyl)-1-(4-hydroxybenzyl)-7-(isobutyloxy)-2-oxo-1,2,3,5-tetrahydro-4,1-benzoxazepine-3-acetamide (1) A solution of N-methyl-N-methyloxy-2-benzyloxycarbonylamino-5-hydroxybenzamide (3.0 g), isopropyl iodide (2.2 g) and potassium carbonate (2.0 g) in N,N-dimethylformamide (20 ml) was stirred for 15 hours at 70° C. To the reaction mixture was added water, which was subjected to extraction with ethyl acetate (80 ml). The organic layer was washed with water and dried over anhydrous sodium sulfate. The solvent was distilled off, and the residue was purified by means of a silica gel column chromatography to give N-methyl-N-methyloxy-2-benzyloxycarbonylamino-5-isobutyloxybenzamide.as an orange oily product (1.0 g).

NMR(CDCl$_3$) δ: 1.01(6H,d,J=6.8 Hz), 2.05(1H,m), 3.345 (3H,s), 3.542(3H,s), 3.69(2H,d,J=6.6 Hz), 5.175(2H,s), 6.9–7.5(7H,m), 7.8–8.3(2H,m)

(2) N-Methyl-N-methyloxy-2-benzyloxycarbonylamino-5-isobutyloxybenzamide (1.0 g) was dissolved in a mixture of ethyl acetate (10 ml) and methanol (10 ml). To the solution was added 10% palladium-carbon (0.2 g). The mixture was stirred for two hours at room temperature under hydrogen atmosphere. The reaction mixture was subjected to filtration. From the filtrate, the solvent was distilled off to leave N-methyl-N-methyloxy-2-amino-5-isobutyloxybenzamide as a yellow oily product (0.6 g).

NMR(CDCl$_3$) δ: 1.03(6H,d,J=6.8 Hz), 2.05(1H,m), 3.35 (3H,s), 3.614(3H,s), 3.64(2H,d,J=6.6 Hz), 6.65–6.95(3H,m)

(3) N-Methyl-N-methyloxy-2-amino-5-isobutyloxybenzamide (0.6 g) and N-tert-butoxycarbonyl 3-bromobenzylamine (0.76 g) were dissolved in tetrahydrofuran (18 ml). The solution was cooled to −78° C., to which was added dropwise, while stirring, 9 ml of a hexanoic solution of n-butyl lithium (1.6 mol./L) over 20 minutes. To the reaction mixture were added water (50 ml) and ethyl acetate (50 ml). The organic layer was washed with water and dried over anhydrous sodium sulfate. The solvent was distilled off. The residue was purified by means of a silica gel column chromatography to give 2-amino-3'-tert-butoxycarbonylaminomethyl-5-isobutyloxy-benzophenone as a yellow oily product (0.38 g).

NMR(CDCl$_3$) δ: 0.95(6H,d,J=6.6 Hz), 1.455(9H,s), 2.0(1H, m), 3.56(2H,d,J=6.6 Hz), 4.41(2H,d,J=6.2 Hz), 4.90(1H,m), 5.70(2H,m), 6.65–7.6(7H,m)

(4) In methanol (12 ml) was dissolved 2-amino-3'-tert-butoxycarbonylaminomethyl-5-isobutyloxy-benzophenone (0.38 g). To the solution was added, while stirring at room temperature, sodium borohydride (50 mg). The reaction mixture was concentrated, to which was added water, followed by extraction with ethyl acetate (50 ml). The organic layer was washed with water and dried over anhydrous sodium sulfate. The solvent was distilled off to leave 2-amino-α-(3-tert-butoxycarbonylaminomethylphenyl)-5-isobutyloxy-benzyl alcohol as a yellow oily product (0.36 g).

NMR(CDCl$_3$) δ: 1.02(6H,d,J=6.6 Hz), 1.449(9H,s), 2.05 (1H,m), 3.64(2H,d,J=6.6 Hz), 4.31(2H,d,J=5.6 Hz), 4.85 (1H,m), 6.797(1H,s), 6.6–7.5(7H,m) (5) In methanol (12 ml) were dissolved 2-amino-α-(3-tert-butoxycarbonylaminomethylphenyl)-5-isobutyloxybenzyl alcohol (0.36 g), 4-benzyloxy-benzaldehyde (0.2 g) and acetic acid (0.05 g). To the solution was added cyano sodium borohydride (0.065 g). The mixture was stirred for 20 minutes at 60° C. To the reaction mixture was added water (6 ml), which was subjected to extraction with ethyl acetate (60 ml). The organic layer was washed with water and dried over anhydrous sodium sulfate. The solvent was distilled off to leave 2-(4-benzyloxybenzylamino)-α-(3-tert-butoxycarbonylaminomethylphenyl)-5-isobutyloxybenzyl alcohol as a yellow oily product (0.45 g).

NMR(CDCl$_3$) δ: 0.99(6H,d,J=6.8 Hz), 1.443(9H,s), 2.05 (1H,m), 3.63(2H,d,J=6.4 Hz), 4.11(2H,s), 4.28(2H,m), 5.094(2H,s), 5.815(1H,s), 6.6–7.5(16H,m)

(6) In ethyl acetate (20 ml) was dissolved 2-(4-benzyloxybenzyl)-α-(3-tert-butoxycarbonylaminomethylphenyl)-5-isobutyloxy-benzyl alcohol (0.45 g). To the solution was added 1N sodium hydroxide (3 ml). To the mixture was added, while stirring at room temperature, monoethyl fumarate chloride (0.13 g). The organic layer was separated and washed with water, which was dried over anhydrous sodium sulfate. The solvent was distilled off, and the residue was dissolved in ethanol. To the solution was added potassium carbonate (0.3 g). The mixture was stirred for two hours at 60° C. The solvent was distilled off. To the residue were added ethyl acetate (50 ml) and water (60 ml). The organic layer was washed with water and dried over anhydrous sodium sulfate. The solvent was distilled off, and the residue was purified by means of a silica gel column chromatography to give 3,5-trans-1-(4-benzyloxybenzyl)-5-(3-tertbutoxycarbonylaminomethylphenyl)-7-isobutyloxy-2-oxo-1,2,3,5-tetrahydro-4,1-benzoxazepine-3-acetic acid ethyl ester as a colorless oily product (0.2 g) and 3,5-cis compound (60 mg).
NMR(CDCl$_3$) δ: 0.93(6H,d,J=6.6 Hz), 1.27(3H,t,J=7 Hz), 1.95(1H,m), 2.75(1H,dd,J=5.2,16.6 Hz), 3.10(1H,dd, J=8, 16.6 Hz), 3.53(2H,dd,J=2,6.7 Hz), 4.13(2H,q,J=7 Hz), 4.2–4.5(3H,m), 4.73(1H,d,J=14.4 Hz), 5.043(2H,s), 5.319 (1H,s), 5.40(1H,d,J=14.4 Hz), 6.02(1H,d,J=2.8 Hz), 6.8–7.5 (15H,m)

(7) In a mixture of tetrahydrofuran (5 ml) and methanol (10 ml) was dissolved 3,5-trans-1-(4-benzyloxybenzyl)-5-(3-tert-butoxycarbonylaminomethylphenyl)-7-isobutyloxy-2-oxo-1,2,3,5-tetrahydro-4,1-benzoxazepine-3-acetic acid ethyl ester (0.4 g). To the solution was added 3 ml of 1N sodium hydroxide, which was stirred for 40 minutes at 60° C. The reaction mixture was concentrated, to which was added water (20 ml), followed by neutralization with 5% potassium hydrogensulfate. The resultant was subjected to extraction with ethyl acetate (50 ml). The organic layer was washed with water and, then, dried over anhydrous sodium sulfate. The solvent was distilled off. The residue was dissolved in N,N-dimethylformamide (6 ml), to which was added 2-fluorobenzylamine (73 mg). To the mixture were added, while stirring at 0° C., cyano diethyl phosphate (95 mg) and triethylamine (0.1 ml). The reaction nmixture was stirred for 30 minutes at room temperature, to which was then added ice-water, followed by extraction with ethyl acetate (60 ml). The organic layer was washed with water and dried over anhydrous sodium sulfate. The solvent was distilled off, and the residue was purified by means of a silica gel column chromatography to give 3,5-trans-N-(2-fluorobenzyl)-1-(4-benzyloxybenzyl)-5-(3-tert-butoxycarbonylaminomethylphenyl)-7-isobutyloxy-2-oxo-1,2,3,5-tetrahydro-4,1-benzoxazepine-3-acetamide as a colorless oily product (0.21 g).
NMR(CDCl$_3$) δ: 0.94(6H,d,J=6.6 Hz), 1.432(9H,s), 1.95 (1H,m), 2.70(1H,dd,J=5.9,15.8 Hz), 2.93(1H,dd,J=7.2, 15.8 Hz), 3.53(2H,dd,J=2.2,6.4 Hz), 4.25(2H,d,J=5.9 Hz), 4.3–4.6(3H,m), 4.67(1H,d,J=14.3 Hz), 4.83(1H,m), 5.04 (2H,s), 5.29(1H,s), 5.41(1H,d,J=14.3 Hz), 6.00(1H,d, J=2.8 Hz), 6.37(1H,m), 6.8–7.5(19H,m)

(8) In a mixture of ethyl acetate (6 ml) and methanol (10 ml) was dissolved 3,5-trans-N-(2-fluorobenzyl)-1-(4-benzyloxybenzyl)-5-(3-tert-butoxycarbonylaminomethylphenyl)-7-isobutyloxy-2-oxo-1,2,3,5-tetrahydro-4,1-benzoxazepine-3-acetamide (0.21 g). To the solution was added 10% palladium-carbon (0.06 g). The mixture was stirred for 3 hours under hydrogen gas atmosphere. The reaction mixture was subjected to filtration. From the filtrate, the solvent was distilled off. To the residue was added water, which was subjected to extraction with ethyl acetate (50 ml). The organic layer was washed with water and dried over anhydrous sodium sulfate. The solvent was distilled off to leave 3,5-trans-N-(2-fluorobenzyl)-5-(3-tert-butoxycarbonylaminomethylphenyl)-1-(4-hydroxybenzyl)-7-isobutyloxy-2-oxo-1,2,3,5-tetrahydro-4,1-benzoxazepine-3-acetamide as a colorless oily product (0.16 g).
NMR(CDCl$_3$) δ: 0.95(6H,d,J=6.6 Hz), 1.45(9H,s), 2.0(1H, m), 2.67(1H,dd,J=6.2,16 Hz), 2.86(1H,dd,J=7.2,16 Hz), 3.56(1H,dd,J=3.8,6.4 Hz), 4.0–4.7(6H,m), 4.87(1H,s), 5.02 (1H,m), 5.7–7.5(14H,m)

EXAMPLE 38

3,5-Trans-5-(3-tert-butoxycarbonylaminomethylphenyl)-7-chloro-3-[3-(2-fluorobenzyl)ureido]methyl-1-neopentyl-1,2,3,5-tetrahydro-4,1-benzoxazepin-2-one Employing 2-fluorobenzylamine in place of 9-fluorenyl methanol in Example 35, a colorless amorphous solid product (0.26 g) was produced by substantially the same procedure as in Example 37.
NMR(CDCl$_3$) δ: 0.91(9H,s), 1.40(9H,s), 3.32(1H,d, J=13.6 Hz), 3.45–3.65(1H,m), 3.71–3.85(1H,m), 3.96(1H,t, J=6.1 Hz), 4.10–4.22(1H,m), 4.30–4.51(4H,m), 4.95–5.05 (1H, br), 5.35–5.45(1H,br), 5.98(1H,s), 6.55(1H,d, J=2.0 Hz), 6.95–7.48(11H,m)

EXAMPLE 39

3,5-Trans-N-(2-fluorobenzyl)-5-(3-aminomethylphenyl)-1-(4-hydroxybenzyl)-7-isobutyloxy-2-oxo-1,2,3,5-tetrahydro-4,1-benzoxazepine-3-acetamide•hydrochloride In ethyl acetate (2 ml) was dissolved 3,5-trans-N-(2-fluorobenzyl)-5-(3-tert-butoxycarbonylaminomethylphenyl)-1-(4-hydroxybenzyl)-7-isobutyloxy-2-oxo-1,2,3,5-tetrahydro-2-oxo-4,1-benzoxazepine-3-acetamide (0.16 g). To the solution was added 4N hydrochloric acid (ethyl acetate solution) (2 ml). The mixture was stirred for two hours. The solvent was distilled off to leave the above-titled compound as a colorless amorphous solid product (0.11 g).
NMR(CDCl$_3$) δ: 0.93(6H,d,J=6.6 Hz), 1.95(1H,m), 2.6–2.9 (2H,m), 3.4–3.6(2H,m), 3.80(2H,br), 4.0–4.65(6H,m), 4.795(1H,s), 5.63(1H,d,J=13.8 Hz), 5.95(1H,d,J=2.8 Hz), 6.39(1H,br), 6.5–7.4(14H,m)

EXAMPLE 40

3,5-Trans-5-(3-aminomethylphenyl)-7-chloro-3-[3-(2-fluorobenzyl)ureido]methyl-1-neopentyl-1,2,3,5-tetrahydro-4,1-benzoxazepin-2-one.monohydrochloride Employing the compound produced in Example 38 (0.20 g), a colorless amorphous solid product (0.15 g) was produced by substantially the same procedure as in Example 36.
NMR(CD$_3$OD) δ: 0.94(9H,s), 3.56(1H,d,J=13.8 Hz), 3.57 (1H,d,J=6.0 Hz), 3.95(1H,t,J=6.0 Hz), 4.18(2H,s), 4.32 (2H, s), 4.47(1H,d,J=13.8 Hz), 6.05(1H,s), 6.51(1H,d, J=2.4 Hz), 7.00–7.64(10H,m)

EXAMPLE 41

3,5-Trans-N-(2-fluorobenzyl)-5-(3-benzylaminomethylphenyl)-7-chloro-1-neopentyl-2-oxo-1,2,3,5-tetrahydro-4,1-benzoxazepine-3-acetamide•monohydrochloride (1) A solution of N-methyl-N-methyloxy-2-amino-5-chlorobenzamide (2 g) and 2-(3-bromophenyl)-1,3-dioxolane (2.1 g) in tetrahydrofuran (65 ml) was cooled to −78° C. To the solution was added dropwise gradually a hexane solution of n-butyl lithium (1.6 mol/L)(11.6 ml). To the mixture were added water (300 ml) and acetic acid ethyl ester (50 ml). The organic layer was washed with water and dried over anhydrous Na$_2$SO$_4$, then the solvent was distilled off. The residue was purified by means of a silica gel column chromatography to give 2-[3-(2-amino-5-chlorobenzoyl) phenyl-1,3-dioxolane (1.6 g) as a colorless oily compound.
NMR(CDCl$_3$) δ: 4.00–4.18(4H,m), 6.08(2H,br), 6.69(1H,d, J=8.8 Hz), 7.21–7.76(6H,m)

(2) The compound produced by repeating the reaction step of (1) several times (15.8 g) was dissolved in methanol (100 ml). To the solution was added sodium borohydride (2.5 g). The mixture was stirred for 30 minutes at 0° C., to which was added acetic acid ethyl ester (200 ml). The mixture was washed with water and dried over anhydrous Na$_2$SO$_4$. The solvent was distilled off, and the residue was purified by means of a silica gel column chromatography to give the object 2-[3-(2-amino-5-chloro-α-hydroxybenzyl)phenyl]-1,3-dioxolane (0.95 g) as a colorless oily product.

(3) To a methanol (10 ml) solution of the compound produced in (2) (0.6 g) were added pivalic aldehyde (190 mg) and acetic acid (150 mg). The mixture was stirred for 10 minutes at room temperature. To the reaction mixture was added cyano sodium borohydride (150 mg). The mixture was stirred for 30 minutes at 60° C., to which was added acetic acid ethyl ester (50 ml). The mixture was washed with water and dried over anhydrous $Na_2SO_4$. The solvent was then distilled off, and the residue was purified by means of a silica gel column chromatography to give the object 2-[3-(5-chloro-α-hydroxy-2-neopentylaminobenzylphenyl]-1,3-dioxolane (0.86 g) as a colorless oily product.
NMR($CDCl_3$) δ: 0.82(9H,s), 2.73(2H,s), 3.97–4.15(4H,m), 5.76(1H,s), 5.78(1H,s), 6.55(1H,d,J=9.8 Hz), 7.04(1H,d, J=2.6 Hz), 7.14(1H,dd,J=2.6,8.4 Hz), 7.35–7.53(4H,m)

(4) To an acetic acid ethyl ester (10 ml) solution of the compound (0.86 g) produced in (3) were added sodium hydrogencarbonate (0.29 g) and fumaric chloride monoethyl ester (370 mg). The mixture was stirred for 10 minutes at room temperature. To the reaction mixture was added acetic acid ethyl ester (30 ml). The organic layer was washed with water and dried over anhydrous $Na_2SO_4$. The solvent was distilled off, and the residue was dissolved in ethanol (10 ml). To the solution was added potassium carbonate (270 mg). The mixture was stirred overnight at room temperature. Insolubles were filtered off, and the solvent was distilled off. The residue was recrystallized from acetic acid ethyl ester-n-hexane to give 3,5-trans-7-chloro-5-(3-(1,3-dioxolan-2-yl)phenyl]-1-neopentyl-2-oxo-1,2,3,5-tetrahydro-4,1-benzoxazepine-3-acetic acid ethyl ester (0.62 g) as colorless crystals, m.p.162–164° C.

(5) To an ethanol (20 ml) solution of the compound (2 g) produced by repeating the procedure of (4) was added a 1N aqueous solution of sodium hydroxide (4 ml). The mixture was stirred for 3 hours at 60° C. The reaction mixture was neutralized, to which was added acetic acid ethyl ester (100 ml). The mixture was washed with water and dried over anhydrous $MgSO_4$. The solvent was distilled off, and the residue was purified by means of a silica gel column chromatography to give 3,5-trans-7-chloro-5-[3-(1,3-dioxolan-1-yl)phenyl]-1-neopentyl-2-oxo-1,2,3,5-tetrahydro-4,1-benzoxazepine-3-acetic acid (1.7 g) as a colorless amorphous solid product.
NMR($CDCl_3$) δ: 0.93(9H,s), 2.83(1H,dd,J=5.2,16.4 Hz), 3.09(1H,dd,J=7.6,16.4 Hz), 3.38(1H,d,J=14.4 Hz), 4.00–4.19(4H,m), 4.35(1H,dd,J=5.2,7.6 Hz), 4.50(1H,d,J=14.4 Hz), 5.86(1H,s), 6.03(1H,s), 6.61(1H,d,J=2.0 Hz), 7.17–7.53(6H,m)

(6) To a dimethylformamide (20 ml) solution of the compound produced in (5) (1.7 g) and 2-fluorobenzylamine (0.52 f) were added cyano diethyl phosphate (0.73 g) and triethylamine (0.5 g). The mixture was stirred for 30 minutes at room temperature. To the reaction mixture was added acetic acid ethyl ester (100 ml). The mixture was washed with water and dried over anhydrous $Na_2SO_4$. The solvent was distilled off, and the residue was purified by means of a silica gel column chromatography to give 3,5-trans-N-(2-fluorobenzyl)-7-chloro-5-[3-(1,3-dioxolan-2-yl)phenyl]-1-neopentyl-2-oxo-1,2,3,5-tetrahydro-4,1-benzoxazepine-3-acetamide (2.0 g).
NMR($CDCl_3$) δ: 0.92(9H,s), 2.69(1H,d,J=6.2,14.8 Hz), 2.88 (1H,dd,J=7.0,14.8 Hz), 3.35(1H,d,J=14.0 Hz), 4.00–4.18 (4H,m), 4.38–4.50(4H,m), 5.83(1H,s), 6.11(1H,s), 6.30(1H, br), 6.58(1H,d,J=2.2 Hz), 6.98–7.55(10H,m)

(7) To an acetone (8 ml) solution of the compound produced in (6) (2.0 g) were added p-toluenesulfonic acid/monhydrate (0.2 g) and water (1 ml). The mixture was stirred for 4 hours at room temperature, to which was added acetic acid ethyl ester (50 ml). The mixture was washed with water. Then, the organic layer was dried over anhydrous $Na_2SO_4$. The solvent was distilled off to leave 3,5-trans-N-(2-fluorobenzyl)-7-chloro-5-(3-formylphenyl)-1-neopentyl-2-oxo-1,2,3,5-tetrahydro-4,1-benzoxazepine-3-acetamide (1.76 g) as a colorless amorphous solid product.
NMR($CDCl_3$) δ: 0.93(9H,s), 2.71(1H,dd,J=6.4,14.8 Hz), 2.90(1H,dd,J=7.2,14.8 Hz), 3.37(1H,d,J=14.8 Hz), 4.37–4.62(4H,m), 6.08(1H,s), 6.24–6.30(1H,br), 6.49(1H,d, J=2.0 Hz), 6.98–7.96(10H,m), 10.04(1H,s)

(8) To a methanol (1 ml) solution of the compound produced in (7) (0.1 g) were added benzylamine (22 mg) and acetic acid (13 mg). The mixture was stirred for 10 minutes at room temperature. To the reaction mixture was added cyano sodium borohydride (14 mg). The mixture was stirred for one hour at room temperature, to which was added water (10 ml), followed by extraction with acetic acid ethyl ester (50 ml). The extract solution was washed with water and dried over anhydrous $Na_2SO_4$. The solvent was, then, distilled off. The residue was purified by means of a silica gel column chromatography to give a colorless oily compound. This compound was dissolved in a 4N acetic acid ethyl ester solution of hydrogen chloride (0.2 ml). The solvent was distilled off to leave a colorless amorphous solid product (83 mg). NMR($CDCl_3$) δ: 0.92(9H,s), 2.69(1H,dd,J=5.8,14.8 Hz), 2.89(1H,dd,J=7.4,14.8 Hz), 3.35(1H,d,J=13.6 Hz), 3.73–3.83(4H,m), 4.39–4.51(4H,m), 6.00(1H,s), 6.26–6.36 (1H,br), 6.58(1H,d,J=2.2 Hz), 6.97–7.39(15H,m)

Employing 3,5-trans-N-(2-fluorobenzyl)-7-chloro-5-(3-formylphenyl)-1-neopentyl-2-oxo-1,2,3,5-tetrahydro-4,1-benzoxazepine-3-acetamide, reductive amination reaction with various amines was conducted in substantially the same procedure as in Example 41-(8) to synthesize the compounds of Examples 42–44 shown as follows.

EXAMPLE 42

3,5-Trans-N-(2-fluorobenzyl)-7-chloro-1-neopentyl-2-oxo-5-[3-(piperidin-1-yl)methylphenyl]-1,2,3,5-tetrahydro-4,1-benzoxazepine-3-acetamide•monohydrochloride (non-crystalline solid)
NMR($CDCl_3$) δ: 0.92(9H,s), 1.40–1.63(6H,m), 2.35–2.45 (4H,m), 2.70(1H,dd,J=5.8,14.2 Hz), 2.89(1H,dd,J=7.0, 14.2 Hz), 3.35(1H,d,J=13.6 Hz), 3.51(2H,s), 4.39–4.51 (4H,m), 5.99(1H,s), 6.30–6.40(1H,br), 6.60(1H,d, J=2.0 Hz), 6.95–7.39(10H,m)

EXAMPLE 43

3,5-Trans-N-(2-fluorobenzyl)-7-chloro-5-(3-methylaminomethylphenyl)-1-neopentyl-2-oxo-1,2,3,5-tetrahydro-4,1-benzoxazepine-3-acetamide•monohydrochloride (non-crystalline solid)
NMR($CDCl_3$) δ: 0.92(9H,s), 2.47(3H,s), 2.70(1H,dd,J=5.4, 13.6 Hz), 2.88(1H,dd,J=7.4,13.8 Hz), 3.35(1H,d,J=14.4 Hz), 3.77(2H,s), 4.39–4.51(4H,m), 5.99(1H,s), 6.30–6.40 (1H, br), 6.58(1H,d,J=2.2 Hz), 6.98–7.39(10H,m)

EXAMPLE 44

3,5-Trans-N-(2-fluorobenzyl)-7-chloro-5-(3-dimethylaminomethylphenyl)-1-neopentyl-2-oxo-1,2,3,5-tetrahydro-4,1-benzoxazepine-3-acetamide•monohydrochloride
NMR($CDCl_3$) δ: 0.92(9H,s), 2.25(6H,s), 2.70(1H,dd,J=6.0, 14.4 Hz), 2.89(1H,dd,J=7.4,14.4 Hz), 3.35(1H,d,J=13.8 Hz), 3.46(2H,s), 4.38–4.50(4H,m), 6.00(1H,s), 6.30–6.40(1H, br), 6.58(1H,d,J=1.8 Hz), 7.02–7.42(10H,m)

By substantially the same procedure as in Example 1, compounds in Table 1 to 4 were produced.

TABLE 1

[Structure: benzoxazepine core with Cl, NHBoc-CH2-phenyl, fluorobenzyl amide, and N-R substituent]

| Compound No. | R | forms | NMR (solvents) |
|---|---|---|---|
| 45 | phenyl-(CH₂)₃— | oily product | (CDCl₃)δ: 1.43(9H, s), 1.9–2.1(2H, m), 2.6–3.0(4H, m), 3.65(1H, m), 4.1–4.6(6H, m), 4.9(1H, m), 5.73(1H, s), 6.565(1H, d, J=2.2Hz), 6.9–7.5(15H, m). |
| 46 | cyclohexyl-CH₂— | oily product | (CDCl₃)δ: 0.8–1.9(11H, m), 1.445(9H, s), 1.68(1H, dd, J=5.8, 16Hz), 2.93(1H, dd, J=7.4, 16Hz), 3.43(1H, dd, J=8, 16Hz), 4.1–4.6(6H, m), 4.85(1H, m), 5.813(1H, s), 6.23(1H, m), 6.48(1H, d, J=2.4Hz), 6.95–7.5(10H, m). |
| 47 | phenyl-(CH₂)₂— | noncrystalline solid | (CDCl₃)δ: 1.448(9H, s), 2.669(1H, dd, J=6.0, 14.2Hz), 2.882(1H, dd, J=7.0, 14.2Hz), 2.97–3.05(2H, m), 3.85–4.00(1H, m), 4.20–4.51(5H, m), 4.61–4.72(1H, m), 4.80–4.86(1H, br), 5.306(1H, s), 6.27–6.31(1H, br), 6.49(1H, d, J=2.4Hz), 7.01–7.56(15H, m). |
| 48 | 3-thienyl-CH₂— | oily product | (CDCl₃)δ: 1.453(9H, s), 2.69(1H, dd, J=6, 14Hz), 2.93(1H, dd, J=7.2, 15.6Hz), 4.(2H, d, J=5.8Hz) 4.35–4.6(3H, m), 4.77(1H, J= , 14.6Hz) 4.83(1H, m), 5.27(1H, s), 5.44(1H, d, J=14.Hz), 6.33(1H, m), 6.49(1H, d, J=2Hz), 6.9–7.5( , m). |
| 49 | 4-phenoxyphenyl-CH₂— | oily product | (CDCl₃)δ: 1.433(9H, s), 2.72(1H, dd, J= , 15Hz), 2.94(1H, dd, J=7.4, 15.6Hz), 4.(2H, d, J=6Hz), 4.33–4.6(3H, m), 4.77(1H, J= , 14.6Hz), 4.9(1H, m), 5.34(1H, s), 5.42(1H, , J=4.6Hz), 6.36(1H, m), 6.50(1H, d, J=2Hz), 6.9–7.4(19H, m). |
| 50 | 3-methoxybenzyl (CH₃O-phenyl-CH₂—) | oily product | (CDCl₃)δ: 1.45(9H, s), 2.72(1H, dd, J=5.8, 16Hz), 2.95(1H, dd, J=9, 15.5Hz), 3.73(3H, s), 4.2–4.6(5H, m), 4.85(1H, d, J=14.8Hz), 4.96(1H, m), 5.33(1H, d, J=14.8Hz), 5.43(1H, s), 6.49(1H, d, J=2.2Hz), 6.55(1H, m), 6.85–7.4(14H, m). |
| 51 | (CH₃CH₂)₂CHCH₂— | oily product | (CDCl₃)δ: 0.8–1.0(6H, m), 1.2–1.7(5H, m), 1.44(9H, s), 2.68(1H, dd, J=6, 17.5Hz), 2.91(1H, dd, J=7, 16Hz), 3.43(1H, dd, J=15, 4.5Hz), 4.2–4.6 (6H, m), 4.85(1H, m), 5.80(1H, s), 6.29(1H, m), 6.576(1H, d, J=2.4Hz), 6.9–7.5(10H, m). |

TABLE 2

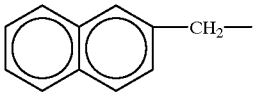

| Compound No. | R | forms | NMR (solvents) |
|---|---|---|---|
| 52 | CH₃(CH₂)₄— | oily product | (CDCl₃)δ: 0.897(3H, t, J=6.8Hz), 1.2–1.9(6H, m), 1.44(9H, s), 2.69(1H, dd, J=6, 16Hz), 2.91(1H, dd, J=7.2, 15Hz), 3.6(1H, m), 4.2–4.6(6H, m), 4.9(1H, m), 5.73(1H, s), 6.41(1H, m), 6.57(1H, d, J=2.4Hz), 6.9–7.5(10H, m). |
| 53 | 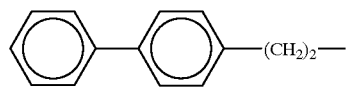 | oily product | (CDCl₃)δ: 1.45(9H, s), 2.73(1H, dd, J=5.8, 16Hz), 2.95(1H, dd, J=7.4, 16Hz), 4.16(2H, d, J=6.4Hz), 4.35–4.8(4H, m), 5.03(1H, d, J=14.8Hz), 5.39(1H, s), 5.59(1H, d, J=14.6Hz), 6.23(1H, m), 6.46(1H, s) 6.7–7.9(17H, m). |
| 54 | 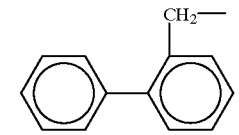 | oily product | (CDCl₃)δ: 1.43(9H, s), 2.67(1H, dd, J=6, 15.8Hz), 2.90(1H, dd, J=7.6, 16Hz), 3.05(2H, m), 3.8–4.2(3H, m), 4.35–4.85(5H, m), 5.27(1H, s), 6.37(1H, m), 6.49(1H, d, J=2.2Hz), 6.9–7.6(19H, m). |
| 55 | 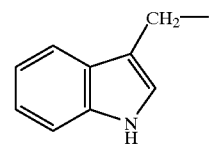 | oily product | (CDCl₃)δ: 1.45(9H, s), 2.69(1H, dd, J=6, 16Hz), 2.93(1H, dd, J=7.4, 15.8Hz), 4.2–4.6(5H, m), 4.85(1H, m), 5.12(1H, d, J=15.2Hz), 5.32(1H, d, J=15.4Hz), 5.45(1H, s), 6.38(1H, m), 6.42(1H, d, J=2.4Hz), 6.65(1H, d, J=8.6Hz), 6.9–7.7(18H, m). |
| 56 | 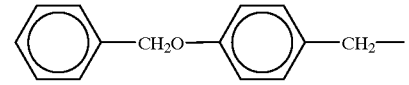 | oily product | (CDCl₃)δ: 1.46(9H, s), 2.68(1H, dd, J=6.2, 16Hz), 2.90(1H, dd, J=7, 15Hz), 4.1(2H, m), 4.3–4.6(3H, m), 4.67(1H, d, J=14.4Hz), 4.8(1H, m), 5.02(1H, s), 5.83(1H, d, J=14.6Hz), 6.35(1H, s), 6.45–7.6(14H, m), 8.6(1H, m). |
| 57 | 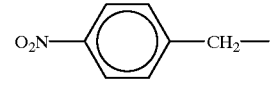 | oily product | (CDCl₃)δ: 1.44(9H, s), 2.70(1H, dd, J=5.8, 15Hz), 2.93(1H, dd, J=7.2, 15Hz), 4.27(2H, d, J=5.6Hz), 4.35–4.65(3H, m), 4.73(1H, d, J=14.6Hz), 4.85(1H, m), 5.05 (2H, s), 5.34(1H, s), 5.40(1H, d, J=14.8Hz), 6.26(1H, m). |
| 58 | O₂N—⟨phenyl⟩—CH₂— | oily product | (CDCl₃)δ: 1.44(9H, s), 2.73(1H, dd, J=5.4, 15.6Hz), 2.98(1H, dd, J=8, 15.8Hz), 4.31(2H, d, J=6Hz), 4.48 (2H, m), 4.63(1H, dd, J=10, 5.2Hz), 5.22(2H, s), 5.51 (1H, s), 6.23(1H, m), 6.56(1H, d, J=2.4Hz), 6.9–7.6(12H, m), 8.2(2H, m). |
| 59 | 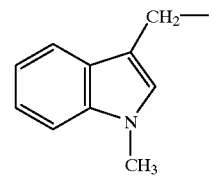 | oily product | (CDCl₃)δ: 1.46(9H, s), 2.68(1H, dd, J=6.4, 15.8Hz), 2.92(1H, dd, J=7.2, 16Hz), 3.68(3H, s), 4.0–4.2(2H, m), 4.3–4.6(3H, m), 4.77(1H, d, J=14.6Hz), 5.09(1H, s), 5.77(1H, d, J=1.48Hz), 6.39(1H, s), 6.6–7.5(15H, m). |

TABLE 3

[Structure: benzothiazepine core with Cl, 3-(aminomethyl)phenyl substituent, CH₂CONH-(2-fluorobenzyl) side chain, N-R group, and C=O]

| Compound No. | R | forms | NMR (solvents) |
|---|---|---|---|
| 60 | C₆H₅-(CH₂)₃— | hydrochloride noncrystalline solid | (CDCl₃)δ: 1.8–2.1(2H, m), 2.5–3.0(4H, m), 3.65 (1H, m), 3.88(2H, brs), 4.1–4.5(4H, m), 5.66(1H, s), 6.52(1H, d, J=24Hz), 6.8–7.6(15H, m). |
| 61 | cyclohexyl-CH₂— | hydrochloride noncrystalline solid | (CDCl₃)δ: 0.8–1.9(11H, m), 2.6–3.0(2H, m), 3.4 (1H, m), 3.98(2H, brs), 4.05–4.5(4H, m), 5.73(1H, s), 6.54(1H, d, J=1.4Hz), 6.8–7.7(10H, m). |
| 62 | C₆H₅-(CH₂)₂— | hydrochloride noncrystalline solid | (CDCl₃)δ: 2.732(1H, dd, J=7.4, 15.0Hz), 2.840 (1H, dd, J=6.6, 15.0Hz), 3.01–3.09(2H, m), 4.077 (2H, s), 4.12–4.23(1H, m), 4.38–4.45(3H, m), 4.61–4.80 (1H, m), 5.319(1H, s), 6.379(1H, d, J=2.0Hz), 7.05–7.43(15H, m). |
| 63 | 3-thienyl-CH₂— | hydrochloride noncrystalline solid | (CDCl₃)δ: 1.88(2H, m), 2.72(1H, dd, J=6, 16Hz), 2.93(1H, dd, J=7.4, 15.8Hz), 3.85(2H, s), 4.3–4.6(3H, m), 4.78(1H, d, J=14.6Hz), 5.31(1H, s), 5.43(1H, d, J=14.6Hz), 6.58(1H, m), 6.51(1H, d, J=2.2Hz), 6.9–7.5(13H, m). |
| 64 | C₆H₅-O-C₆H₄-CH₂— | hydrochloride mp 196–200° C. | (CDCl₃)δ: 1.74(2H, m), 2.72(1H, dd, J=6, 14Hz), 2.93(1H, dd, J=7.4, 14Hz), 3.85(2H, brs), 4.3–4.6 (3H, m), 4.77(1H, d, J=14.4Hz), 5.36(1H, s), 5.43(1H, d, J=14.6Hz), 6.49(1H, m), 6.52(1H, d, J=2Hz), 6.9–7.5(19H, m). |
| 65 | 3-CH₃O-C₆H₄-CH₂— | hydrochloride noncrystalline solid | (CDCl₃)δ: 2.17(2H, m), 2.73(1H, dd, J=5.8, 16Hz), 2.95(1H, dd, J=7.2, 15.8Hz), 3.74(3H, s), 3.84 (2H, brs), 4.3–4.6(3H, m), 4.86(1H, d, J=14.6Hz), 5.13(1H, d, J=14.8Hz), 5.46(1H, s), 6.47(1H, m), 6.52(1H, d, J=2.2Hz), 6.75–7.4(14H, m). |
| 66 | (CH₃CH₂)₂CHCH₂— | hydrochloride noncrystalline solid | (CDCl₃)δ: 0.8–1.0(6H, m), 1.2–1.7(5H, m), 1.89 (2H, m), 2.72(1H, dd, J=6, 16Hz), 2.89(1H, dd, J=7.2, 15.8Hz), 3.43(1H, dd, J=6, 16Hz), 3.89(2H, s), 4.3–4.6(4H, m), 5.81(1H, s), 6.39 (1H, m), 6.60(1H, d, J=2.4Hz), 6.9–7.5(10H, m). |

TABLE 4

[Structure: benzoxazepine core with Cl, NH2-benzyl, 2-fluorobenzyl CONH side chain, and N-R group]

| Compound No. | R | forms | NMR (solvents) |
|---|---|---|---|
| 67 | CH₃(CH₂)₄— | hydrochloride noncrystalline solid | (CDCl₃)δ: 0.90(3H, t, J=7Hz), 1.2–2.0(8H, m), 2.70(1H, dd, J=7, 16.2Hz), 2.89(1H, dd, J=7.2, 16Hz), 3.6(1H, m), 3.89(2H, m), 4.2–4.6(4H, m), 5.75(1H, s), 6.43(1H, m), 8.60(1H, d, J=2.4Hz), 6.9–7.5(10H, m). |
| 68 | 2-naphthyl-CH₂— | hydrochloride noncrystalline solid | (CDCl₃)δ: 1.91(2H, brs), 2.73(1H, dd, J=6, 16Hz), 2.97(1H, dd, J=7.4, 15.8Hz), 3.72(2H, s), 4.3–4.65(3H, m), 4.98(1H, d, J=14.8Hz), 5.37(1H, s), 5.63(1H, d, J=14.8Hz), 6.37(1H, m), 6.47(1H, s), 6.7–7.9(17H, m). |
| 69 | 4-biphenyl-(CH₂)₂— | hydrochloride noncrystalline solid | (CDCl₃)δ: 2.6–3.1(4H, m), 3.7–4.0(3H, m), 4.2–4.7(4H, m), 5.33(1H, s), 6.46(1H, s), 6.8–7.7(19H, m). |
| 70 | 2-biphenyl-CH₂— | hydrochloride mp 243–245° C. | (CDCl₃)δ: 2.6–3.0(2H, m), 3.87(2H, brs), 4.3–4.6(3H, m), 5.07(1H, d, J=14.6Hz), 5.27(1H, d, J=14.8Hz), 5.43(1H, s), 6.37(1H, d, J=2.2Hz), 6.6–7.6(19H, m). |
| 71 | indol-3-yl-CH₂— | hydrochloride noncrystalline solid | (CDCl₃)δ: 2.67(1H, dd, J=6.2, 16Hz), 2.89(1H, dd, J=7.2, 16Hz), 3.64(2H, s), 4.3–4.6(3H, m), 4.67(1H, d, J=14.6Hz), 5.07(1H, s), 5.83(1H, d, J=14.6Hz), 6.38(1H, m), 6.6–7.5(16H, m), 8.6(1H, m). |
| 72 | 4-(PhCH₂O)-C₆H₄-CH₂— | hydrochloride noncrystalline solid | (CDCl₃)δ: 2.72(1H, dd, J=6, 15.8Hz), 2.93(1H, dd, J=7.2, 16Hz), 3.83(2H, s), 4.3–4.6(3H, m), 4.72(1H, d, J=14.2Hz), 5.03(2H, s), 5.35(1H, s), 5.43(1H, d, J=14.4Hz), 6.37(1H, m), 6.50(1H, d, J=2.2Hz), 6.8–7.5(19H, m). |
| 73 | 4-O₂N-C₆H₄-CH₂— | hydrochloride noncrystalline solid | (CDCl₃)δ: 2.76(1H, dd, J=5.8, 15.8Hz), 2.95(1H, dd, J=7.4, 16Hz), 4.40(2H, brs), 4.4–4.7(3H, m), 5.25(2H, s), 5.53(1H, s), 6.23(1H, m), 6.58(1H, d, J=2.2Hz), 6.9–7.6(12H, m), 8.1(2H, m). |
| 74 | 1-methylindol-3-yl-CH₂— | hydrochloride noncrystalline solid | (CDCl₃)δ: 2.70(1H, dd, J=5.6, 16Hz), 2.96(1H, dd, J=7.2, 16Hz), 3.72(3H, s), 4.1–4.25(2H, m), 4.3–4.6(3H, m), 4.80(1H, d, J=14.8Hz), 5.06(1H, s), 5.79(1H, d, J=15Hz), 6.36(1H, brs), 6.6–7.5(15H, m). |

EXAMPLE 75

3,5-Trans-N-(2-fluorobenzyl)-5-(2-tert-butoxycarbonylaminomethylphenyl)-7-chloro-1-neopentyl-2-oxo-1,2,3,5-tetrahydro-4,1-benzoxazepine-3-acetamide (1) A tetrahydrofuran (30 ml) solution of N-methyl-N-methyloxy-2-amino-5-chlorobenzamide (4.3 g) and N-tert-butoxycarbonyl-2-bromobenzylamine (3.82 g) was cooled to −78° C. To the solution was gradually added dropwise a hexane solution of n-butyl lithium (1.6 mol/L) (42 ml). To the mixture were then added water (100 ml) and acetic acid ethyl ester (100 ml). The organic layer was washed with water and dried over anhydrous $MgSO_4$. The solvent was then distilled off. The residual oily compound was purified by means of a silica gel column chromatography to give a yellow solid product, which was recrystallized from n-hexane-isopropyl ether. The crystals were collected by filtration to afford 2-amino-2'-tert-butoxycarbonylaminomethyl-5-chlorobenzophenone (1.3 g) as a pale yellow crystalline product.

(2) To a methanol (5 ml) solution of 2-amino-2'-tert-butoxycarbonylaminomethyl-5-chlorobenzophenone (0.5 g) was added sodium borohydride (79 mg). The mixture was stirred for 3 hours at room temperature. To the reaction mixture was added acetic acid ethyl ester (100 ml), which was washed with water and, then, dried over anhydrous $MgSO_4$. The solvent was distilled off, and the residue was purified by means of a silica gel column chromatography to give the object 2-amino-5-chloro-α-(2-tert-butoxycarbonylaminomethylphenyl)benzyl alcohol (0.5 g) as a colorless oily product.

NMR($CDCl_3$) δ: 1.40(9H,s), 3.95–4.10(2H,br), 4.30(1H, dd,J=6.6,15.0 Hz), 4.41(1H,dd,J=5.8,15.0 Hz), 5.0–5.10 (1H,br), 6.10(1H,s), 6.62(1H,d,J=8.4 Hz), 6.95(1H,d, J=2.2 Hz), 7.07(1H,dd,J=2.6,8.4 Hz), 7.26–7.38(5H,m)

(3) To a methanol (5 ml) solution of 2-amino-5-chloro-α-(2-tert-butoxycarbonylaminomethylphenyl)benzyl alcohol (0.5 g) were added trimethyl acetaldehyde (132 mg) and acetic acid (92 mg). The mixture was stirred for 10 minutes at room temperature, to which was added sodium cyano borohydride (97 mg), followed by stirring for one hour at room temperature. To the reaction mixture was added acetic acid ethyl ester (50 ml). The mixture was washed with water and dried over anhydrous $Na_2SO_4$. The solvent was then distilled off. The residue was purified by means of a silica gel column chromatography to give the object 5-chloro-α-(2-tert-butoxycarbonylaminomethylphenyl)-2-neopentylaminobenzyl alcohol (0.61 g) as a colorless oily product.

NMR($CDCl_3$) δ: 0.85(9H,s), 1.40(9H,s), 1.59–1.70(1H,br), 2.79(2H,s), 4.29(1H,dd,J=6.0,14.8 Hz), 4.45(1H,dd,J=6.2, 14.8 Hz), 4.98–5.09(1H,br), 6.05(1H,s), 6.59(1H,d, J=8.8 Hz), 6.97–7.39(6H,m)

(4) To an acetic acid ethyl ester (6 ml) solution of 5-chloro-α-(2-tert-butoxycarbonylaminomethylphenyl)-2-neopentylaminobenzyl alcohol (0.61 g) were added water (3 ml) and iN aqueous solution of sodium hydroxide (1.5 ml). To the mixture was added fumaric chloride monoethyl ester (236 mg). The mixture was stirred for one hour under ice-cooling, to which was added acetic acid ethyl ester (30 ml). The organic layer was washed with water and dried over anhydrous $MgSO_4$. The solvent was distilled off. The residue was dissolved in ethanol (10 ml), to which was added potassium carbonate (360 mg). The mixture was stirred overnight at room temperature. Insolubles were filtered off. From the filtrate, the solvent was distilled off. The residue was purified by means of a silica gel column chromatography, followed by recrystallization from hexane to afford 3,5-trans-5-(2-tert-butoxycarbonylaminomethylphenyl)-7-chloro-1-neopentyl-2-oxo-1,2,3,5-tetrahydro-4,1-benzoxazepine-3-acetic acid ethyl ester (0.75 g) as a colorless crystalline product, m.p.153–156° C.

NMR($CDCl_3$) δ: 0.93(9H,s), 1.24(3H,t,J=7.2 Hz), 1.40 (9H, s), 2.78(1H,dd,J=6.2,16.4 Hz), 3.04(1H,dd,J=7.4, 16.4 Hz), 3.40(1H,d,J=13.8 Hz), 4.01–4.21(4H,m), 4.43–4.60(3H,m), 6.14(1H,s), 6.57(1H,s), 7.34–7.57(6H,m)

(5) To an ethanol (8 ml) solution of the compound produced in (4) (0.75 g) was added a 1N aqueous solution of sodium hydroxide. The mixture was stirred for one hour at 60° C. The reaction mixture was neutralized, to which was then added acetic acid ethyl ester (50 ml). The organic layer was washed with water and dried over anhydrous $Na_2SO_4$. The solvent was then distilled off, and the residue was recrystallized from ethyl ether-n-hexane to give a colorless crystalline compound (0.23 g), m.p.149–152° C.

(6) To a dimethylformamide (1 ml) solution of the compound produced in (5) (0.1 g) and 2-fluorobenzylamine (26 mg) were added diethyl cyano phosphate (37 mg) and triethylamine (28 mg). The mixture was stirred for 30 minutes at room temperature, to which was added acetic acid ethyl ester (50 ml). The mixture was washed with water and dried over anhydrous $Na_2SO_4$. The solvent was distilled off, and the residue was purified by means of a silica gel column chromatography to give a colorless amorphous solid product (0.12 g).

NMR($CDCl_3$) δ: 0.92(9H,s), 1.40(9H,s), 2.69(1H,dd,J=6.2, 14.6 Hz), 2.87(1H,dd,J=6.6,14.6 Hz), 3.39(1H,d,J=14.0 Hz), 3.90–4.15(2H,m), 4.37–4.65(5H,m), 6.11(1H,s), 6.28 (1H, br), 6.54(1H,s), 6.98–7.50(10H,m)

EXAMPLE 76

3,5-Trans-N-(2-fluorobenzyl)-5-(2-aminomethylphenyl)-7-chloro-1-neopentyl-2-oxo-1,2,3,5-tetrahydro-4,1-benzoxazepine-3-acetamide•monohydrochloride The compound produced in Example 75 (0.12 g) was dissolved in a 4N acetic acid ethyl ester solution of hydrogen chloride (2 ml). The solution was left standing for 30 minutes at room temperature. The solvent was distilled off to give a colorless amorphous solid product (80 mg).

NMR($CDCl_3$) δ: 0.93(9H,s), 2.81(2H,d,J=6.2 Hz), 3.60 (1H, d,J=14.4 Hz), 3.97(1H,d,J=13.6 Hz), 4.13(1H,d, J=13.6 Hz), 4.41(2H,s), 4.52(1H,t,J=6.2 Hz), 6.15(1H,s), 6.47(1H,s), 6.99–7.68(10H,m)

EXAMPLE 77

3,5-Trans-N-(2-fluorobenzyl)-1-(4-biphenylmethyl)-5-(2-tert-butoxycarbonylaminomethylphenyl)-7-chloro-2-oxo-1,2,3,5-tetrahydro-4,1-benzoxazepine-3-acetamide Employing 2-amino-5-chloro-α-(2-tert-butoxycarbonylaminomethylphenyl)benzyl alcohol produced in Example 75-(2), a colorless oily compound was produced by substantially the same procedure as in Example 4.

NMR($CDCl_3$) δ: 1.30(9H,s), 2.76(1H,dd,J=5.2,14.8 Hz), 2.95(1H,dd,J=7.0,15.0 Hz), 3.55(2H,m), 4.3–4.65(3H,m), 4.92(1H,d,J=17.0 Hz), 5.53(1H,d,J=16.8 Hz), 6.3–6.5(2H, m), 6.9–7.6(19H,m)

EXAMPLE 78

3,5-Trans-N-(2-fluorobenzyl)-5-(2-aminomethylphenyl)-1-(4-biphenylmethyl)-7-chloro-2-oxo-1,2,3,5-tetrahydro-4, 1-benzoxazepine-3-acetamide•monohydrochloride Employing the compound (0.18 g) produced in Example 77, a colorless amorphous solid compound was produced by substantially the same procedure as in Example 2.

NMR($CDCl_3$) δ: 2.8–3.2(2H,m), 3.9–4.6(5H,m), 4.73(1H, d), 5.37(1H,s), 5.57(1H,d), 6.38(1H,d), 6.47(1H,d), 6.8–7.8 (19H,m)

EXAMPLE 79

3,5-Trans-N-(2-fluorobenzyl)-5-(3-tert-butoxycarbonylaminophenyl)-7-chloro-1-neopentyl-2-oxo-1,2,3,5-tetrahydro-4,1-benzoxazepine-3-acetamide (1) A tetrahydrofuran (30 ml) solution of N-methyl-N-methyloxy-2-amino-5-chlorobenzamide (4.3 g) and N-tert-butoxycarbonyl-3-bromoaniline (3.79 g) was cooled to −78° C. To the solution was gradually added dropwise a hexane solution of n-butyl lithium (1.6 mol/L) (42 ml). To the mixture were added water (100 ml) and acetic acid ethyl ester (300 ml). The organic layer was washed with water and dried over anhydrous $MgSO_4$. The solvent was then distilled off, and the residue was purified by means of a silica gel column chromatography to give 2-amino-3'-tert-butoxycarbonylamino-5-chlorobenzophenone (0.7 g) as a yellow oily product.

(2) To a methanol (5 ml) solution of 2-amino-3'-tert-butoxycarbonylamino-5-chlorobenzophenone (0.4 g) was added sodium borohydride (66 mg). The mixture was stirred for one hour at room temperature, to which was added acetic acid ethyl ester (l00.ml). The mixture was washed with water and dried over anhydrous $MgSO_4$. The solvent was then distilled off, and the residue was purified by means of a silica gel column chromatography to afford the object 2-amino-5-chloro-α-(3-tert-butoxycarbonylaminophenyl) benzyl alcohol (0.4 g) as a colorless oily product.

NMR($CDCl_3$) δ: 1.50(9H,s), 3.91–3.99(2H,br), 5.74(1H,s), 6.52(1H,br), 6.58(1H,d,J=8.8 Hz), 7.00–7.40(6H,m)

(3) To a methanol (4 ml) solution of 2-amino-5-chloro-α-(3-tert-butoxycarbonylaminophenyl) benzyl alcohol (0.4 g) were added trimethyl acetaldehyde (109 mg) and acetic acid (76 mg). The mixture was stirred for 10 minutes at room temperature, to which was added sodium cyano borohydride (79 mg). The mixture was stirred for one hour at room temperature, to which was added acetic acid ethyl ester (50 ml). The mixture was washed with water and dried over anhydrous $MgSO_4$. The solvent was then distilled off, and the residue was purified by means of a silica gel column chromatography to give the object 5-chloro-α-(3-tert-butoxycarbonylaminophenyl)-2-neopentylaminobenzyl alcohol (0.43 g) as a colorless amorphous solid product.

NMR($CDCl_3$) δ: 0.84(9H,s), 1.50(9H,s), 2.74(2H,s), 4.11 (1H,br), 5.74(1H,s), 6.47(1H,br), 6.55(1H,d, J=8.8 Hz), 7.04–7.36(6H,m)

(4) To an acetic acid ethyl ester (5 ml) solution of 5-chloro-α-(3-tert-butoxycarbonylaminophenyl)-2-neopentylaminobenzyl alcohol (0.48 g) were added water (2 ml) and a 1N aqueous solution of sodium hydroxide (1.5 ml). To the mixture was added monoethyl ester of fumaric chloride (195 mg), which was stirred for 10 minutes under ice-cooling. To the reaction mixture was added acetic acid ethyl ester (100 ml). The organic layer was washed with water and dried over anhydrous $Na_2SO_4$. The solvent was then distilled off, and the residue was dissolved in ethanol (10 ml). To the solution was added potassium carbonate (200 mg). The mixture was stirred overnight at room temperature. Insolubles were filtered off, and the solvent was distilled off. The residue was purified by means of a silica gel column chromatography to give 3,5-trans-5-(3-tert-butoxycarbonylaminophenyl)-7-chloro-1-neopentyl-2-oxo-1,2,3,5-tetrahydro-4,1-benzoxazepine-3-acetic acid ethyl ester (0.55 g) as an amorphous solid product.

NMR($CDCl_3$) δ: 0.92(9H,s), 1.24(3H,t,J=7.0 Hz), 1.52(9H, s), 2.76(1H,dd,J=5.6,16.6 Hz), 3.05(1H,dd, J=7.8,16.6 Hz), 3.36(1H,d,J=14.0 Hz), 4.12(2H,dq, J=1.0,7.0 Hz), 4.38(1H, dd,J=5.6,7.8 Hz), 4.50(1H,d, J=14.0 Hz), 5.97(1H,s), 6.55 (1H,s), 6.65(1H,d,J=1.8 Hz), 6.14–7.60(6H,m)

(5) To an ethanol (5 ml) solution of the compound produced in (4) (0.55 g) was added a 1N aqueous solution of sodium hydroxide (1.2 ml). The mixture was stirred for one hour at 60° C., which was neutralized, followed by addition of acetic acid ethyl ester (50 ml). The organic layer was washed with water and dried over anhydrous $Na_2SO_4$. The solvent was then distilled off, and the residue was purified by means of a silica gel column chromatography to give a colorless amorphous solid product (0.53 g).

NMR($CDCl_3$) δ: 0.92(9H,s), 1.52(9H,s), 2.86(1H,dd,J=6.2, 16.4 Hz), 3.04(1H,dd,J=7.2,16.4 Hz), 3.36(1H,d,J=14.0 Hz), 4.35(1H,dd,J=6.2,7.2 Hz), 4.50(1H,d,J=14.0 Hz), 5.99 (1H, s), 6.65(1H,d,J=1.8 Hz), 6.75–6.80(1H,br), 6.93(1H, d,J=7.8 Hz), 7.27–7.60(5H,m)

(6) To a dimethylformamide (1 ml) solution of the compound produced in (5) (0.1 g) and 2-fluorobenzylamine (27 mg) were added diethyl cyano phosphate (35 mg) and triethylamine (29 mg). The mixture was stirred for 30 minutes at room temperature, to which was added acetic acid ethyl ester (50 ml). The mixture was washed with water and dried over anhydrous $Na_2SO_4$. The solvent was then distilled off, and the residue was purified by means of a silica gel column chromatography to give 3,5-trans-N-(2-fluorobenzyl)-5-(3-tert-butoxycarbonylaminophenyl)-7-chloro-1-neopentyl-2-oxo-1,2,3,5-tetrahydro-4,1-benzoxazepine-3-acetamide (0.12 g) as a colorless amorphous solid product.

NMR($CDCl_3$) δ: 0.91(9H,s), 1.51(9H,s), 2.70(1H,dd,J=6.4, 14.6 Hz), 2.86(1H,dd,J=6.8,14.6 Hz), 3.35(1H,d,J=14.0 Hz), 4.37–4.55(4H,m), 5.96(1H,s), 6.31–6.39(1H,br), 6.53–6.57 (1H,br), 6.63(1H,d,J=2.4 Hz), 6.88–7.61(10H,m)

EXAMPLE 80

3,5-Trans-N-(2-fluorobenzyl)-5-(3-aminophenyl)-7 -chloro-1-ndopentyl-2-oxo-1,2,3,5-tetrahydro-4,1-benzoxazepine-3-acetamide•monohydrochloride The compound produced in Example 79 (0.12 g) was dissolved in a 4N acetic acid ethyl ester solution of hydrogen chloride (2 ml). The solution was left standing for 30 minutes at room temperature. The solvent was distilled off to leave a colorless amorphous solid product (0.09 g), NMR($CDCl_3$) δ: 0.94(9H,s), 2.74(1H,d,J=4.6,15 Hz), 2.85 (1H,dd,J=4.2,15.4 Hz), 3.58(1H,d,J=14.2 Hz), 4.41–4.94 (3H,m), 6.07(1H,s), 6.46(1H,d,J=2.4 Hz), 7.05–7.68(10H, m)

EXAMPLE 81

3,5-Trans-N-(2-fluorobenzyl)-5-(4-tert-butoxycarbonylaminomethylphenyl)-7-chloro-1-neopentyl-2-oxo-1,2,3,5-tetrahydro-4,1-benzoxazepine-3-acetamide (1) A tetrahydrofuran (30 ml) solution of N-methyl-N-methyloxy-2-amino-5-chlorobenzamide (3.21 g) and N-tert-butoxycarbonyl-4-bromobenzylamine (2.86 g) was cooled to −78° C. To the solution kas gradually added dropwise a hexane solution of n-butyl lithium (1.6 mol/L) (31 ml). To the mixture were then added water (100 ml) and acetic acid ethyl ester (100 ml). The organic layer was washed with water and dried over anhydrous $MgSO_4$. The solvent was then distilled off, and the residue was purified by means of a silica gel column chromatography. followed by crystallization. The crystals were collected to give 2-amino-4'-tert-butoxycarbonylaminomethyl-5-chlorobenzophenone (0.9 g) as a pale yellow crystalline product.

(2) To a methanol (10 ml) solution of 2-amino-4'-tert-butoxycarbonylaminomethyl-5-chlorobenzophenone (0.9 g) was added sodium borohydride (0.28 g). The mixture was stirred for 30 minutes at room temperature, to which was added acetic acid ethyl ester (100 ml). The mixture was washed with water and dried over anhydrous $Na_2SO_4$. The solvent was then distilled off, and the residue was purified by means of a silica gel column chromatography to give the object 2-amino-5-chloro-α-(4-tert-butoxycarbonylaminomethylphenyl)benzyl alcohol (0.85 g) as a colorless oily product.

NMR(CDCl$_3$) δ: 1.46(9H,s), 2.6–2.8(1H,br), 3.80–4.00(1H, br), 4.31(2H,d,J=6.0 Hz), 4.80–4.95(1H,br), 5.78(1H,s), 6.59(1H,d,J=8.8 Hz), 7.05–7.37(6H,m)

(3) To a methanol (8 ml) solution of 2-amino-5-chloro-α-(4-tert-butoxycarbonylaminomethylphenyl)benzyl alcohol (0.83 g) were added trimethyl acetaldehyde (220 mg) and acetic acid (170 mg). The mixture was stirred for 10 minutes at room temperature, to which was added sodium cyano borohydride (160 mg). The mixture was stirred overnight at room temperature, to which was added acetic acid ethyl ester (100 ml). The mixture was washed with water and dried over anhydrous Na$_2$SO$_4$. The solvent was then distilled off, and the residue was purified by means of a silica gel column chromatography to give the object 5-chloro-α-(4-tert-butoxycarbonylaminomethylphenyl)-2-neopentylaminobenzyl alcohol (0.99 g) as a colorless oily product.

NMR(CDCl$_3$) δ: 0.83(9H,s), 1.45(9H,s), 2.74(2H,s), 4.29 (2H,d,J=6.2 Hz), 4.75–4.85(1H,br), 5.77(1H,s), 6.56(1H,d, J=8.8 Hz), 7.05–7.39(6H,m)

(4) To an acetic acid ethyl ester (10 ml) solution of 5-chloro-α-(4-tert-butoxycarbonylaminomethylphenyl)-2-neopentylaminobenzyl alcohol (0.99 g) were added water (3 ml) and a 1N aqueous solution of sodium hydroxide. To the mixture was added monoethyl ester of fumaric chloride (370 mg), which was stirred for 30 minutes under ice-cooling. To the reaction mixture was added acetic acid ethyl ester (30 ml). The organic layer was washed with water and dried over anhydrous Na$_2$SO$_4$. The solvent was then distilled off, and the residue was dissolved in ethanol (20 ml). To the solution was added potassium carbonate (700 mg). The mixture was stirred overnight at room temperature. Insolubles were filtered off. From the filtrate, the solvent was distilled off, and the residue was purified by means of a silica gel column chromatography to give 3,5-trans-5-(4-tert-butoxycarbonylaminomethylphenyl)-7-chloro-1-neopentyl-2-oxo-1,2,3,5-tetrahydro-4,1-benzoxazepine-3-acetic acid ethyl ester (1.08 g) as a colorless oily product.

NMR(CDCl$_3$) δ: 0.92(9H,s), 1.24(3H,t,J=7.2 Hz), 1.48 (9H, s), 2.76(1H,dd,J=6.2,16.4 Hz), 3.03(1H,dd,J=7.4, 16.4 Hz), 3.36(1H,d,J=14.2 Hz), 4.12(2H,dq,J=1.6,7.2 Hz), 4.36–4.43 (3H,m), 4.50(1H,d,J=14.2 Hz), 4.85–4.95(1H,br), 6.00(1H, s), 6.60(1H,s), 7.20–7.38(6H,m)

(5) To an ethanol (10 ml) solution of the compound produced in (4) (1.08 g) was added a 1N aqueous solution of sodium hydroxide (2 ml). The mixture was stirred for two hours at 60° C., to which was added acetic acid ethyl ester (100 ml). The mixture was washed with water and dried over anhydrous NazSO$_4$. The solvent was then distilled off, and the residue was recrystallized from ethyl ether-n-hexane to give colorless crystals (0.90 g), m.p.247–238° C.

(6) To a dimethylformamide (2 ml) solution of the compound produced in (5) (0.2 g) and 2-fluorobenzylamine (52 mg) were added diethyl cyano phosphate (74 mg) and triethylamine (57 mg). The mixture was stirred for 30 30 minutes at room temperature, to which was added acetic acid ethyl ester (50 ml). The mixture was washed with water and dried over anhydrous Na$_2$SO$_4$. The solvent was then distilled off, and the residue was purified by means of a silica gel column chromatography, which was recrystallized from hexane to give colorless crystals (0.25 g), m.p.183–185° C.

EXAMPLE 82

3,5-Trans-N-(2-fluorobenzyl)-5-(4-aminomethylphenyl)-7-chloro-1-neopentyl-2-oxo-1,2,3,5-tetrahydro-4,1-benzoxazepine-3-acetamide•monohydrochloride The compound produced in Example 81 (0.15 g) was dissolved in a 4N acetic acid ethyl ester solution of hydrogen chloride (3 ml). The solution was left standing for 30 minutes at room temperature. The solvent was distilled off to give a colorless amorphous solid product (135 mg).

NMR(CDCl$_3$) δ: 0.93(9H,s), 2.77(2H,d,J=6.6 Hz), 3.56(1H, d,J=14.0 Hz), 4.19(2H,s), 4.41–4.48(4H,m), 6.04(1H,s), 6.45(1H,d,J=2.2 Hz), 7.02–7.63(10H,m)

EXAMPLE 83

3,5-Trans-N-(2-fluorobenzyl)-5-[3-(2-aminoethyl)phenyl]-7-chloro-1-neopentyl-2-oxo-1,2,3,5-tetrahydro-4,1-benzoxazepine-3-acetamide•monohydrochloride (1) To a tetrahydrofuran (5 ml) solution of 3,5-trans-N-(2-fluorobenzyl)-7-chloro-5-(3-fbrmylphenyl)-1-neopentyl-2-oxo-1,2,3,5-tetrahydro-4,1-benzoxazepine-3-acetamide (0.5 g) produced in Example 41 was added (carboethoxymethylene)triphenylphosphorane (0.35 g). The mixture was stirred for 3 hours at room temperature, to which was added acetic acid ethyl ester (50 ml). The mixture was washed with water, and the organic layer was dried over Na$_2$SO$_4$. The solvent was then distilled off, and the residue was purified by means of a silica gel column chromatography to give a colorless oily product (0.53 g).

NMR(CDCl$_3$) δ: 0.93(9H,s), 1.32(3H,t,J=7.0 Hz), 2.70(1H, dd,J=5.8,14.2 Hz), 2.90(1H,dd,J=7.0,14.2 Hz), 3.36(1H,d, J=13.8 Hz), 4.26(2H,q,J=7.0 Hz), 4.38–4.52 (4H,m), 6.00 (1H,s), 6.25–6.40(1H,br), 6.46(1H,d, J=16.2 Hz), 6.55(1H, d,J=2.2 Hz), 6.97–7.73(11H,m)

(2) An acetic acid ethyl ester (10 ml) solution of the compound (0.53 g) produced in (1) was subjected to catalytic reduction under normal pressure at ordinary temperature using a 10% palladium-carbon catalyst. The catalyst was filtered off, and, from the filtrate, the solvent was distilled off to give a colorless amorphous solid product (0.48 g).

NMR(CDCl$_3$) δ: 0.92(9H,s), 1.21(3H,t,J=7.2 Hz), 2.59–2.74 (3H,m), 2.84–3.01(3H,m), 3.35(1H,d,J=14.0 Hz), 4.11(2H, q,J=7.2 Hz), 4.38–4.55(4H,m), 5.97(1H,s), 6.25–6.35(1H, br), 6.58(1H,d,J=1.8 Hz), 6.98–7.33(10H,m)

(3) To an ethanol (5 ml)) solution of the compound (0.48 g) produced in (2) was added a 1N aqueous 7: solution of sodium hydroxide (0.8 ml). The mixture was stirred for 3 hours at 60° C., which was neutralized, followed by extraction with acetic acid ethyl ester (100 ml). The extract solution was washed with water and dried over anhydrous Na$_2$SO$_4$. The solvent was distilled off to leave a colorless amorphous solid product (0.39 g).

(4) To a dimethylformamide (2 ml) solution of the compound produced in (3) (0.2 g) were added triethylamine (40 mg) and diphenyl phosphoryl azide (104 mg). The mixture was stirred for 30 minutes at room temperature, to which was added water (50 ml), followed by extraction with acetic acid ethyl ester (50 ml). The extract solution was washed with water and dried over Na$_2$SO$_4$. The solvent was distilled off, and the residue was dissolved in toluene (2 ml). The solution was heated for one hour under reflux, to which was added 9-fluorenyl methanol (135 mg). The mixture was further heated overnight under reflux. The solvent was distilled off, and the residue was purified by means of a silica gel column chromatography to give a colorless amorphous solid product (0.12 g).

NMR(CDCl$_3$) δ: 0.91(9H,s), 2.67(1H,dd,J=5.2,14.6 Hz), 2.82–2.92(3H,m), 3.35(1H,d,J=14.2 Hz), 3.40–3.55(2H,m), 4.20(1H,t,J=7.0 Hz), 4.37–4.54(6H,m), 4.75–4.85(1H,br), 5.97(1H,s), 6.20–6.30(1H,br), 6.59(1H,d,J=1.8 Hz), 7.04–7.78(18H,m)

(5) To a dimethylformamide (1.5 ml) solution of the compound produced in (4) (0.12 g) was added piperidine (0.1 ml). The mixture was stirred for 30 minutes at room temperature, to which was added acetic acid ethyl ester (50 ml). The mixture was washed with water, and the organic layer was dried over anhydrous $Na_2SO_4$. The solvent was then distilled off, and the residue was purified by means of a silica gel column chromatography to give an oily compound. The oily compound was dissolved in a 4N acetic acid ethyl ester solution of hydrogen chloride. The solvent was then distilled off to leave a colorless amorphous solid product (53 mg).

NMR(CDCl$_3$) δ: 0.94(9H,s), 2.78(2H,d,J=7.2 Hz), 2.95–3.02 (2H,m), 3.15–3.24(2H,m), 3.57(1H,d,J=14.2 Hz), 4.41–4.48 (4H,m), 6.02(1H,s), 6.52(1H,d,J=2.2 Hz), 7.01–7.63(6H,m)

EXAMPLE 84

3,5-Trans-N-(2-fluorobenzyl)-5-[4-(2-tert-butoxycarbonylaminoethyl)phenyl]-1-(4-biphenylmethyl)-7-chloro-2-oxo-1,2,3,5-tetrahydro-4,1-benzoxazepine-3-acetamide (1) A tetrahydrofuran (70 ml) solution of N-methyl-N-methyloxy-2-amino-5-chlorobenzamide (6.4 g) and N-tert-butoxycarbonyl-3-bromophenethylamine (6.0 g) was cooled to −78° C., to which was gradually added dropwise a hexane solution of n-butyl lithium (1.6 mol/L) (67 ml). To the mixture were then added water (300 ml) and acetic acid ethyl ester (300 ml). The organic layer was washed with water and dried over anhydrous MgSO$_4$, and the solvent was distilled off. The residual oily compound was purified by means of a silica gel column chromatography, followed by recrystallization from hexane to afford 2-amino-4'-(2-tert-butoxycarbonylaminoethyl)-5-chlorobenzophenone (3.97 g) as a pale yellow crystalline product.

(2) To a methanol (40 ml) solution of 2-amino-4'-(2-tert-butoxycarbonylaminoethyl)-5-chlorobenzophenone (2.0 g) was added sodium borohydride (0.5 g). The mixture was stirred for 30 minutes at room temperature, to which was added acetic acid ethyl ester (100 ml). The mixture was washed with water and, then, dried over anhydrous MgSO$_4$, followed by distilling off the solvent. The residue was purified by means of a silica gel column chromatography to give the object 2-amino-5-chloro-α-[4-(2-tert-butoxycarbonylaminoethyl)phenyl]benzyl alcohol (2.2 g) as a colorless oily product.

(3) To a methanol (20 ml) solution of 2-amino-5-chloro-α-[4-(2-tert-butoxycarbonylaminoethyl)phenyl]benzyl alcohol (1.0 g) were added 4-biphenyl carbaldehyde (0.53 g) and acetic acid (200 mg). The mixture was stirred for 10 minutes at room temperature, to which was added sodium cyano borohydride (180 mg). The mixture was stirred for 30 minutes at room temperature, to which was added acetic acid ethyl ester (50 ml). The mixture was washed with water and dried over anhydrous MgSO$_4$. The solvent was then distilled off, and the residue was purified by means of a silica gel column chromatography to give the object 2-(4-biphenylmethylamino)-5-chloro-α-[4-(2-tert-butoxycarbonylaminoethyl)phenyl]benzyl alcohol (1.2 g) as a colorless oily product.

(4) To an acetic acid ethyl ester (20 ml) solution of 2-(4-biphenylmethylamino)-5-chloro-α-[4-(2-tert-butoxycarbonylaminoethyl)phenyl]benzyl alcohol (1.2 g) was added a 1N aqueous solution of sodium hydroxide (8 ml). To the mixture was added fumaric chloride monoethyl ester (400 mg). The mixture was stirred for one hour under ice-cooling, to which was added acetic acid ethyl ester (30 ml). The organic layer was washed with water and dried over anhydrous MgSO$_4$. The solvent was distilled off, and the residue was dissolved in ethanol (25 ml). To the solution was added potassium carbonate (800 mg). The mixture was stirred overnight at room temperature. Insolubles were filtered off, and, from the filtrate, the solvent was distilled off. The residue was purified by means of a silica gel column chromatography, which was recrystallized from hexane to give 3,5-trans-1-(4-biphenylmethyl)-5-[4-(2-tert-butoxycarbonylaminoethyl)phenyl]-7-chloro-2-oxo-1,2,3,5-tetrahydro-4,1-benzoxazepine-3-acetic acid ethyl ester (0.6 g).

NMR(CDCl$_3$) δ: 1.26(3H,t,J=7.2 Hz), 1.43(9H,s), 2.8 (3H, m), 3.13(1H,dd,J=8.2,16.2 Hz), 3.35(2H,m), 4.15(2H, q,J=7.3,12 Hz), 4.5(1H,dd,J=5.4,10 Hz), 4.92(1H,d, J=14.8 Hz), 5.40(1H,s), 5.48(1H,d,J=14.6 Hz), 6.55(1H, d,J=1.4 hz), 7.0–7.6(15H,m)

(5) To an ethanol (10 ml) solution of the compound (0.6 g) produced in (4) was added a 1N aqueous solution of sodium hydroxide (4 ml). The mixture was stirred for 2 hours at 60° C., which was neutralized, followed by addition of acetic acid ethyl ester (50 ml). The organic layer was washed with water and dried over anhydrous MgSO$_4$. The solvent was then distilled off, and the residue was purified by means of a silica gel column chromatography to give a colorless crystalline product (0.34 g), m.p.224–225° C.

(6) To a dimethylformamide (8 ml) solution of the compound produced in (5) (0.33 g) and 2-fluorobenzylamine (80 mg) were added diethyl cyano phosphate (110 mg) and triethylamine (100 mg). The mixture was stirred for 30 minutes at room temperature, to which was added acetic acid ethyl ester (50 ml). The mixture was washed with water and dried over anhydrous MgSO$_4$. The solvent was distilled off, and the residue was purified by means of a silica gel column chromatography to give a colorless oily product (0.2 g).

NMR(CDCl$_3$) δ: 1.43(9H,s), 2.1–3.0(4H,m), 3.35(2H,m), 4.3–4.7(3H,m), 4.83(1H,d,J=14.8 Hz), 5.36(1H,s), 5.49(1H, d,J=14.8 Hz), 6.40(1H,m), 6.50(1H,d,J=1.8 Hz), 6.9–7.6 (19H,m)

EXAMPLE 85

3,5-Trans-N-(2-fluorobenzyl)-5-[4-(2-aminoethyl)phenyl]-1-(4-biphenylmethyl)-7-chloro-2-oxo-1,2,3,5-tetrahydro-4,1-benzoxazepine-3-acetamide•monohydrochloride The compound (0.2 g) produced in Example 84 was dissolved in a 4N acetic acid ethyl ester solution of hydrogen chloride (2 ml). The solution was left standing for 30 minutes. The solvent was then distilled off to leave a colorless amorphous solid product (0.14 g).

NMR(CDCl$_3$) δ: 2.10(2H,m), 2.6–3.1(6H,m), 4.3–4.6(3H, m), 4.83(1H,d,J=15.0 Hz), 5.36(1H,s), 5.48(1H,d,J=14.8 Hz), 6.46(1H,m), 6.53(1H,d,J=2 Hz), 6.9–7.6(19H,m)

EXAMPLE 86

3,5-Trans-N- (2-fluorobenzyl)-1-(4-biphenylmethyl)-5-(4-tert-butoxycarbonylaminomethylphenyl)-7-chloro-2-oxo-1,2,3,5-tetrahydro-4,1-benzoxazepine-3-acetamide Employing 2-amino-5-chloro-α-(4-tert-butoxycarbonylaminomethylphenyl)benzyl alcohol produced in Example 81-(2), a colorless crystalline product, m.p.194–195° C., was produced by substantially the same procedure as in Example 4.

NMR(CDCl$_3$) δ: 1.47(9H,s), 2.73(1H,dd,J=6.2,17 Hz), 2.93 (1H,dd,J=7.0,16.8 Hz), 4.31(2H,d,J=5.4 Hz), 4.35–4.65 (3H,m), 4.65(1H,d,J=14.4 Hz), 5.36(1H,s), 5.51(1H,d, J=14.6 Hz), 6.23(1H,m), 6.50(1H,d,J=1.8 Hz), 6.9–7.6(19H, m)

EXAMPLE 87

3,5-Trans-N-(2-fluorobenzyl)-5-(4-aminomethylphenyl)-1-(4-biphenylmethyl)-7-chloro-2-oxo-1,2,3,5-tetrahydro-4,1-benzoxazepine-3-acetamide•monohydrochloride The compound (0.2 g) produced in Example 86 was dissolved in a 4N acetic acid ethyl ester solution of hydrogen chloride (3 ml). The solution was left standing for 3 hours at room temperature. The solvent was distilled off to leave a colorless amorphous solid product (0.16 g).
NMR(CDCl$_3$) δ: 2.73(1H,dd,J=6.0,16.0 Hz), 2.94(1H,dd, J=7.0,16.0 Hz), 3.87(2H,s), 4.3–4.65(3H,m), 4.85(1H,d, J=14.8 Hz), 5.38(1H,s), 5.50(1H,d,J=14.6 Hz), 6.33(1H,m), 6.53(1H,d,J=2 Hz), 6.9–7.6(19H,m)

EXAMPLE 88

3,5-Trans-N-(2-fluorobenzyl)-1-(4-biphenylmethyl)-5-(2-tert-butoxycarbonylaminomethylthiophen-5-yl)-7-chloro-2-oxo-1,2,3,5-tetrahydro-4,1-benzoxazepine-3-acetamide (A),
3,5-cis-N-(2-fluorobenzyl)-1-(4-biphenylmethyl)-5-(2-tert-butoxycarbonylaminomethylthiophen-5-yl)-7-chloro-2-oxo-1,2,3,5-tetrahydro-4,1-benzoxazepine-3-acetamide (B), A tetrahydrofuran (60 ml) solution of N-methyl-N-methyloxy-2-amino-5-chlorobenzamide (4.96 g) and 2-bromo-5-tert-butoxycarbonylaminomethylthiophene (5.45 g) was cooled to −78° C. To the solution was gradually added dropwise a hexane solution of n-butyl lithium (1.6 mol/L) (47 ml). To the mixture were further added water (200 ml) and acetic acid ethyl ester (200 ml). The organic layer was washed with water and dried over anhydrous MgSO$_4$, followed by distilling off the solvent. The residual oily compound was purified by means of a silica gel column chromatography to give 2-(2-tert-butoxycarbonylaminomethylthiophen-5-yl)carbonyl-4-chloroaniline (0.5 g) as a yellow oily product. To a methanol (8 ml) solution of this product (0.15 g) was added sodium borohydride (60 mg). The mixture was stirred for 30 minutes at room temperature, to which was added acetic acid ethyl ester (100 ml). The mixture was washed with water and dried over anhydrous MgSO$_4$. The solvent was then distilled off. To a methanol (5 ml) solution of the residue were added 4-biphenylcarbaldehyde (100 mg) and acetic acid (40 mg). The mixture was stirred for 10 minutes at room temperature, to which was added sodium cyano borohydride (40 mg). The mixture was stirred for 30 minutes at 60° C., to which was added acetic acid ethyl ester (50 ml). The mixture was washed with water and dried over anhydrous MgSO$_4$. The solvent was then distilled off to leave 0.2 g of a residual compound.

This compound was dissolved in acetic acid ethyl ester (8 ml), to which was added a 1N aqueous solution of sodium hydroxide. To the mixture was added fumaric chloride monoethyl ester (40 mg). The mixture was stirred for 20 minutes under ice-cooling, to which was added acetic acid ethyl ester (30 ml). The organic layer was washed with water and dried over anhydrous MgSO$_4$. The solvent was distilled off, and the residue was dissolved in ethanol (6 ml), to which was added potassium carbonate (100 mg). The mixture was stirred for 30 minutes at 60° C. Insolubles were filtered off, and, from the filtrate, the solvent was distilled off. The residue was purified by means of a silica gel column chromatography to give a colorless oily compound (0.4 g). This compound (0.2 g) was dissolved in ethanol (10 ml), to which was added a 1N aqueous solution of sodium hydroxide (2 ml). The mixture was stirred for one hour at 60° C., which was neutralized, followed by addition of acetic acid ethyl ester (50 ml). The organic layer was washed with water and dried over anhydrous MgSO$_4$. The solvent was distilled off, and the residue was dissolved in dimethylformamide (4 ml). To the solution were added 2-fluorobenzylamine (40 mg), diethyl cyano phosphate (80 mg) and triethylamine (60 mg). The mixture was stirred for 30 minutes at room temperature, to which was added acetic acid ethyl ester (50 ml). The mixture was washed with water and dried over anhydrous MgSO$_4$. The solvent was distilled off. The residue was purified by means of a silica gelcolumn chromatography to give 3,5-cis compound (20 mg) and 3,5-trans compound (50 mg) as colorless oily products.

3,5-cis(B)
NMR(CDCl$_3$) δ: 1.44(9H,s), 2.78(1H,dd), 3.0(1H,dd), 4.05 (1H,d), 4.35(2H,d), 4.48(2H,d), 4.77(1H,dd), 4.86(1H,m), 5.03(1H,d), 6.01(1H,s), 6.40(1H,t), 6.52(1H,m), 6.73(1H,d), 6.9–7.76(16H,m)

3,5-trans(A)
NMR(CDCl$_3$) δ: 1.45(9H,s), 2.70(1H,dd), 2.93(1H,dd), 4.3–4.6(5H,m), 4.95(1H,d), 5.36(1H,d), 5.64(1H,s), 6.35 (1H,t), 6.57(1H,d), 6.8–7.6(17H,m)

EXAMPLE 89

3,5-Trans-N-(2-fluorobenzyl)-5-(2-aminomethylthiophen-5-yl)-1-(4-biphenylmethyl)-7-chloro-2-oxo-1,2,3,5-tetrahydro-4,1-benzoxazepine-3-acetamide•monohydrochloride The 3,5-trans compound (A) produced in Example 88 (50 mg) was dissolved in a 4N acetic acid ethyl ester solution of hydrogen chloride, which was left standing for 30 minutes at room temperature. The solvent was then distilled off to give a colorless amorphous solid product (30 mg).
NMR(CDCl$_3$) δ: 2.72(1H,dd), 2.93(1H,dd), 4.00(2H,s), 4.3–4.65(3H,m), 4.93(1H,d), 5.4(1H,d), 5.63(1H,s), 6.27 (1H,t), 6.57(1H,d), 6.75–7.7(17H,m)

EXAMPLE 90

3,5-Trans-N-(2-fluorobenzyl)-5-(2-tert-butoxycarbonylaminomethylthiophen-5-yl)-7-chloro-1-(4-methoxybenzyl)-2-oxo-1,2,3,5-tetrahydro-4,1-benzoxazepine-3-acetamide By substantially the same procedure as in Example 88, a colorless oily compound was produced.
NMR(CDCl$_3$) δ: 1.46(9H,s), 2.68(1H,dd,J=6.2,16.0 Hz), 2.88(1H,dd,J=7.2,15.8 Hz), 3.77(3H,s), 4.3–4.6(5H,m), 4.73 (1H,d,J=14.6 Hz), 4.9(1H,m), 5.33(1H,d,J=14.6 Hz), 5.55 (1H,s), 6.33(1H,m), 6.55(1H,d,J=3.8 Hz), 6.7–7.5(12H,m)

EXAMPLE 91

3,5-Trans-N-(2-fluorobenzyl)-5-(2-aminomethylthiophen-5-yl)-7-chloro-1-(4-methoxybenzyl)-2-oxo-1,2,3,5-tetrahydro-4,1-benzoxazepine-3-acetamide•monohydrochloride The compound produced in Example 90 (0.1 g) was dissolved in a 4N acetic acid ethyl ester solution of hydrogen chloride (1 ml). The solution was left standing for 30 minutes, followed by distilling off the solvent to give a colorless amorphous solid product (70 mg).
NMR(CDCl$_3$) δ: 2.1–3.0(2H,m), 3.71(3H,s), 4.0–4.6(5H, m), 4.8(1H,d,J=15 Hz), 5.11(1H,d,J=14.8 Hz), 5.62(1H,s), 6.55(1H,br), 6.7–7.5(12H,m)

EXAMPLE 92

3,5-Trans-N-(2-fluorobenzyl)-5-[3-[(1-tert-butoxycarbonylamino-1-methyl)ethyl]phenyl]-1-(4-biphenylmethyl)-7-chloro-2-oxo-1,2,3,5-tetrahydro-4,1-benzoxazepine-3-acetamide (A), 3,5-cis-N-(2-fluorobenzyl)-5-[3-[(1-tert-butoxycarbonylamino-1-methyl)ethyl]phenyl]-1-(4-biphenylmethyl)-7-chloro-2-oxo-1,2,3,5-tetrahydro-4,1-benzoxazepine-3-acetamide (B)

(1) To a toluene (200 ml) solution of 3-bromobenzonitrile (18 g) was added methyl magnesium bromide (3 mol/L ethyl ether solution) (120 ml). After distilling off ethyl ether under ordinary pressure, the mixture was heated for 6 hours under reflux. To the reaction mixture was added a saturated aqueous solution of ammonium chloride, which was subjected to extraction with acetic acid ethyl ester:(200 ml). The extract solution was washed with 1N hydrochloric acid (150 ml). Then, the aqueous layer was made alkaline with a 1N aqueous solution of sodium hydroxide (200 ml), which was then subjected to extraction with acetic acid ethyl ester (200 ml). The extract solution was dried over anhydrous $MgSO_4$, and the solvent was distilled off. The residue was dissolved in ethyl ether (100 ml), to which was added a 1N aqueous solution of sodium hydroxide. To the mixture was added di-t-butyl dicarbonate (15 g), which was stirred for 5 hours at room temperature. To the reaction mixture was further added ethyl ether (100 ml). The organic layer was washed with water and dried over anhydrous $MgSO_4$. The solvent was then distilled off, and the residue was purified by means of a silica gel column chromatography to give 1-[(1-tert-butoxycarbonylamino-1-methyl)ethyl]-3-bromobenzene (7.0 g) as a colorless oily product.
NMR($CDCl_3$) δ: 1.37(9H,s,br), 1.59(6H,s), 4.95(1H,s,br), 7.15–7.38(3H,m), 7.50–7.55(1H,m)

(2) A tetrahydrofuran (50 ml) solution of N-methyl-N-methyloxy-2-amino-5-chlorobenzamide (3.21 g) and the compound (3.14 g) produced in (1) was cooled to −78° C. To the solution was gradually added dropwise a hexane solution of n-butyl lithium (1.6 mol/L) (32 ml). To the mixture were then added water (100 ml) and acetic acid ethyl ester (100 ml). The organic layer was washed with water and dried over anhydrous $MgSO_4$, followed by distilling off the solvent. The residual oily compound was purified by a silica gel column chromatography to give 2-amino-3'-(1-tert-butoxycarbonylamino-1-methyl)ethyl-5-chlorobenzophenone (1.5 g) as a pale yellow oily product.

(3) To a methanol (20 ml) solution of 2-amino-3'-(1-tert-butoxycarbonylamino-1-methyl)ethyl-5-chlorobenzophenone (1.2 g) was added sodium borohydride (0.3 g). The mixture was stirred for 30 minutes at room temperature. To the reaction mixture was added acetic acid ethyl ester (100 ml), which was washed with water and dried over anhydrous $MgSO_4$. The solvent was then distilled off, and the residue was dissolved in methanol (20 ml). To the solution were added 4-biphenylcarbaldehyde (0.73 g) and acetic acid (0.25 g). The mixture was stirred for 10 minutes at room temperature, to which was added sodium cyano borohydride (0.25 g). The mixture was stirred for 40 minutes at 60° C. To the reaction mixture was added acetic acid ethyl ester (50 ml), which was washed with water and dried over anhydrous $MgSO_4$. The solvent was then distilled off. The residue was purified by means of a silica gel column chromatography to give the object 2-(4-biphenylmethylamino)-5-chloro-α-[3-[(1-tert-butoxycarbonylamino-1-methyl)ethyl]phenyl]benzyl alcohol (1.5 g) as a colorless oily product. To an acetic acid ethyl ester (20 ml) solution of this compound (15 g) was added a 1N aqueous solution of sodium hydroxide. The mixture was stirred for one hour under ice-cooling, to which was added acetic acid ethyl ester (30 ml). The organic layer was washed with water and dried over anhydrous $MgSO_4$. The solvent was distilled off, and the residue was dissolved in ethanol (25 ml). To the solution was added potassium carbonate (1 g). The mixture was stirred for 2 hours at 60° C. Insolubles were filtered off and, from the filtrate, the solvent was distilled off. The residue was purified by means of a silica gel column chromatography to give 3,5-trans-5-[3-[(1-tert-butoxycarbonylamino-1-methyl)ethyl]phenyl]-1-(4-biphenylmethyl)-7-chloro-oxo-1,2,3,5-tetrahydro-4,1-benzoxazepine-3-acetic acid ethyl ester (0.16 g) and 3,5-cis-5-[3-[(1-tert-butoxycarbonylamino-1-methyl)ethyl]phenyl]-1-(4-biphenylmethyl)-7-chloro-2-oxo-1,2,3,5-tetrahydro-4,1-benzoxazepine-3-acetic acid ethyl ester (0.25 g) and a mixture of them (1.1 g) as colorless oily products, respectively.

3,5-Trans
NMR($CDCl_3$) δ: 1.1–1.5(18H,m), 2.90(1H,dd), 3.28(1H, dd), 3.63(1H,d), 4.15(2H,q), 4.6–4.75(2H,m), 5.00(1H,m), 5.91(1H,s), 6.8–7.7(16H,m)

3,5-Cis
NMR($CDCl_3$) δ: 1.1–1.5(18H,m), 2.77(1H,dd), 3.13(1H,d), 4.13(2H,q), 3.47(1H,dd), 4.84(1H,d), 5.28(1H,s), 5.53(1H, d), 6.56(1H,s), 6.9–7.7(15H,m)

(4) The mixture of 3,5-trans compound and 3,5-cis compound produced in (3) (1.1 g) was dissolved in a mixture of tetrahydrofuran (6 ml) and methanol (15 ml). To the solution was added a 1N aqueous solution of sodium hydroxide (8 ml), which was stirred for 40 minutes at 60° C. The reaction mixture was neutralized, to which was then added acetic acid ethyl ester (50 ml). The mixture was washed with water and dried over anhydrous $MgSO_4$. The solvent was distilled off, and the residue was purified by a silica gel column chromatography to give a colorless amorphous solid product (0.65 g). To a dimethylformamide (6 ml) solution of this compound (0.25 g) and 2-fluorobenzylamine (60 mg) were added diethyl cyano phosphate (75 ml) and triethylamine (60 mg). The mixture was stirred for 30 minutes at room temperature, to which was added acetic acid ethyl ester (50 ml). The mixture was washed with water and dried over anhydrous $MgSO_4$. The solvent was distilled off, and the residue was purified by means of a silica gel column chromatography to give two species of colorless oily compounds, i.e. 3,5-trans-N-(2-fluorobenzyl)-5-[3-[(1-tert-butoxycarbonylamino-1-methyl)ethyl]phenyl]-1-(4-biphenylmethyl)-7-chloro-2-oxo-1,2,3,5-tetrahydro-4,1-benzoxazepine-3-acetamide (A) (0.2 g) and 3,5-cis-N-(2-fluorobenzyl)-5-[3-[(1-tert-butoxycarbonylamino-1-methyl)ethyl]phenyl]-1-(4-biphenylmethyl)-7-chloro-2-oxo-1,2,3,5-tetrahydro-4,1-benzoxazepine-3-acetamide (B) (60 mg).

3,5-Trans(A)
NMR($CDCl_3$) δ: 1.0–1.6(15H,m), 2.72(1H,dd), 2.94(1H, dd), 4.5(3H,m), 4.78(1H,d), 5.24(1H,s), 5.54(1H,d), 6.33 (1H, t), 6.55(1H,m), 6.8–7.7(19H,m)

3,5-Cis(B)
NMR($CDCl_3$) δ: 1.34(9H,brs), 1.58,1.59(each 3H,s), 2.87 (1H,dd), 3.08(1H,dd), 3.64(1H,d), 4.35–4.8(4H,m), 4.98 (1H,s), 5.91(1H,s), 6.5(1H,m), 5.8–7.6(20H,m)

EXAMPLE 93

3,5-Trans-N-(2-fluorobenzyl)-5-[3-[(1-amino-1-methyl)ethyl]phenyl]-1-(4-biphenylmethyl)-7-chloro-2-oxo-1,2,3,5-tetrahydro-4,1-benzoxazepine-3-acetamide•monohydrochloride The compound A produced in Example 92 (0.2 g) was dissolved in a 4N acetic acid ethyl ester (3 ml) solution of hydrogen chloride. The solution was left standing for 30 minutes at room temperature. The solvent was then distilled off to leave a colorless amorphous solid product (100 mg).
NMR($CDCl_3$) δ: 1.36,1.37(each 3H,s), 2.73(1H,dd), 3.97 (1H,dd), 4.35–4.6(3H,m), 4.9(1H,d), 5.41(1H,s), 5.46(1H, d), 6.33(1H,t), 6.54(1H,d), 6.9–7.6(19H,m)

EXAMPLE 94

3,5-Cis-N-(2-fluorobenzyl)-5-[3-[(1-amino-1-methyl)ethyl]phenyl]-1-(4-biphenylmethyl)-7-chloro-2-oxo-1,2,3,5-tetrahydro-4,1-benzoxazepine-3-acetamide•monohydrochloride The compound B produced in Example 92 (60 mg) was subjected to substantially the same procedure as in Example 93 to give a colorless amorphous solid product (45 mg).
NMR(CDCl$_3$) δ: 1.51(6H,s), 2.7–3.2(4H,m), 3.63(1H,d), 4.48(2H,d), 4.62(1H,d), 4.72(1H,t), 5.92(1H,s), 6.65–7.7 (20H,m)

EXAMPLE 95

3,5-Trans-N-(4-fluorobenzyl)-1-(4-biphenylmethyl)-5-(3-tert-butoxycarbonylaminomethylphenyl)-7-chloro-2-oxo-1,2,3,5-tetrahydro-4,1-benzoxazepine-3-acetamide In substantially the same manner as in Example 4-(3), 3,5-trans-1-(4-biphenylmethyl)-5-(3-tert-butoxycarbonylaminomethylphenyl)-7-chloro-2-oxo-1,2,3,5-tetrahydro-4,1-benzoxazepine-3-acetic acid produced in Example 4-(2) (0.2 g) was allowed to react with 4-fluorobenzylamine (0.05 g) to give the titled compound (0.22 g) as a colorless oily product.
NMR(CDCl$_3$) δ: 1.433(9H,s), 2.73(1H,dd,J=5.6,15.8 Hz), 2.95(1H,dd,J=7.6,15.8 Hz), 4.0–4.6(5H,m), 4.73(1H,m), 4.90(1H,d,J=14.4 Hz), 5.362(1H,s), 5.45(1H,d,J=14.8 Hz), 6.24(1H,m), 6.50(1H,d,J=2 Hz), 6.8–7.7(19H,m)

EXAMPLE 96

3,5-Trans-N-(4-fluorobenzyl)-1-(4-biphenylmethyl)-5-(3-aminomethylphenyl)-7-chloro-2-oxo-1,2,3,5-tetrahydro-4,1-benzoxazepine-3-acetamide•hydrochloride The compound produced in Example 95 (0.22 g) was dissolved in ethyl acetate (3 ml). To the solution was added 4N hydrochloric acid (ethyl acetate solution) (2 ml), and the mixture was stirred for one hour. The reaction mixture was concentrated to give a crystalline product, which was recrystallized from a mixture of ethanol and ethyl acetate to give the titled compound (0.18 g). m.p.: 268–270° C.
NMR(CDCl$_3$) δ: 2.67(1H,dd,J=6.4,18 Hz), 2.92(1H,dd,J=8.6, 15.8 Hz), 4.04(2H,s), 4.27(2H,d,J=5.2 Hz), 4.49(1H,m), 5.18(1H,d,J=15.8 Hz), 5.40(1H,d,J=15.8 Hz), 5.568(1H,s), 6.40(1H,d,J=2 Hz), 7.0–7.7(19H,m), 8.32(2H,m), 8.58(1H,m)

EXAMPLE 97

N-(2-Fluorobenzyl)-1-(4-biphenylmethyl)-5-(3-tertbutoxycarbonylaminomethylphenyl)-7-chloro-2,3-dihydro-2-oxo-1,2,3,5-tetrahydro-4,1-benzoxazepine-3-acetamide (1) A tetrahydrofuran (25 ml) solution of N-(9-fluorenylmethyl)oxycarbonyl-D,L-aspartic acid 5-methyl ester (0.5 g) was cooled with ice, to which were added N-methyl morpholine (0.2 g) and ethyl chloroformate (0.2 g). The mixture was stirred for 20 minutes at 0° C. To the reaction mixture was then added a tetrahydrofuran (3 ml) solution of 2-amino-3'-tert-butoxycarbonylaminomethyl-5-chlorobenzophenone (0.4 g). The mixture was stirred overnight at room temperature, to which was added water (100 ml). The mixture was subjected to extraction with acetic acid ethyl ester. The extract solution was washed with water and dried over anhydrous Na$_2$SO$_4$. The solvent was distilled off, and the residue was purified by means of a silica gel column chromatography to give a colorless oily product (0.27 g). A dimethylformamide (3 ml) solution of this compound (0.27 g) and piperidine (0.15 ml) was stirred for 10 minutes at room temperature, to which was added acetic acid ethyl ester (50 ml). The mixture was washed with water, and the organic layer was dried over anhydrous Na$_2$SO$_4$. The solvent was then distilled off, and the residue was dissolved in dimethylformamide (3 ml). To the solution was added acetic acid (0.15 ml), and the mixture was stirred for one hour at 60° C. To the reaction mixture was added acetic acid ethyl ester (100 ml). The mixture was washed with water and dried over anhydrous Na$_2$SO$_4$. The solvent was then distilled off, and the residue was purified by means of a silica gel column chromatography to give 5-(3-tert-butoxycarbonylaminomethylphenyl)-7-chloro-2,3-dihydro-2-oxo-1H-1,4-benzodiazepine-3-acetic acid methyl ester (90 mg) as a colorless amorphous solid product.
NMR(CDCl$_3$) δ: 1.45(9H,s), 3.19(1H,dd,J=6.4,17.0 Hz), 3.45(1H,dd,J=7.6,17.0 Hz), 3.74(3H,s), 4.16(1H,dd,J=6.4, 7.6 Hz), 4.34(2H,d,J=6.0 Hz), 4.85–5.00(1H,br), 7.12(1H, d,J=8.6 Hz), 7.27–7.52(5H,m), 8.01(1H,s), 8.7–8.9(1H,br)

(2) To a dimethylformamide (1 ml) solution of the compound produced in (1) (120 mg) were added 4-chloromethyl biphenyl (57 mg), sodium iodide (8 mg) and potassium carbonate (53 mg). The mixture was stirred for one hour at 60° C., to which was added acetic acid ethyl ester (50 ml). The mixture was washed with water, and the organic layer was dried over anhydrous Na$_2$SO$_4$. The solvent was then distilled off, and the residue was purified by means of a silica gel column chromatography to give a colorless oily product (0.10 g).
NMR(CDCl$_3$) δ: 1.45(9H,s), 3.21(1H,dd,J=6.0,17.0 Hz), 3.59(1H,dd,J=8.2,17.0 Hz), 3.75(3H,s), 4.21–4.28(3H,m), 4.72–4.83(1H,br), 4.81(1H,d,J=15.6 Hz), 5.62(1H,d, J=15.6 Hz), 6.98–7.51(16H,m)

(3) To a methanol (1 ml) solution of the compound (0.1 g) produced in (2) was added a iN aqueous solution of sodium hydroxide (0.2 ml). The mixture was stirred for one hour at 60° C. The reaction mixture was neutralized, to which was then added acetic acid ethyl ester (50 ml). The mixture was washed with water and dried over anhydrous MgSO$_4$. The solvent was distilled off, and the residue was purified by means of a silica gel column chromatography to give a colorless amorphous solid product (0.10 g). To a dimethylformamide (1 ml) solution of this compound (0.1 g) and 2-fluorobenzylamine (22 mg) were added diethyl cyano phosphate (29 mg) and triethylamine (24 mg). The mixture was stirred for 30 minutes at room temperature, to which was added acetic acid ethyl ester (50 ml). The mixture was washed with water and dried over anhydrous MgSO$_4$. The solvent was distilled off, and the residue was purified by means of a silica gel column chromatography to give an amorphous solid product (0.12 g).
NMR(CDCl$_3$) δ: 1.44(9H,s), 3.12(1H,dd,J=6.6,14.8 Hz), 3.31(1H,dd,J=7.0,14.8 Hz), 4.11–4.30(3H,m), 4.47(1H,dd, J=5.0,15.0 Hz), 4.63(1H,dd,J=5.8,15.0 Hz), 4.65–4.75 (1H, br), 4.76(1H,d,15.4 Hz), 5.62(1H,d,J=15.4 Hz), 6.55–6.65 (1H,br), 6.97–7.44(20H,m)

EXAMPLE 98

N-(2-Fluorobenzyl)-5-(3-aminomethylphenyl)-1-(4-biphenylmethyl)-7-chloro-2,3-dihydro-2-oxo-1H-1,4-benzodiazepine-3-acetamide•monohydrochloride The compound produced in Example 97 (0.12 g) was dissolved in a 4N acetic acid ethyl ester solution of hydrogen chloride. The solution was left standing for 30 minutes. The solvent was then distilled off to give a colorless amorphous solid product (84 mg).
NMR(CDCl$_3$) δ: 3.18–3.32(2H,m), 4.04(2H,s), 4.42(1H,t, J=7.0 Hz), 4.47(2H,s), 4.93(1H,d,J=15.4 Hz), 5.68(1H,d, J=15.4 Hz), 7.03–7.77(20H,m)

EXAMPLE 99

3,5-Trans-5-(3-tert-butoxycarbonylaminomethylphenyl)-7-chloro-3-(2-fluorobenzyl)aminomethyl-1-neopentyl-1,2,3,5-tetrahydro-4,1-benzoxazepin-2-one Acetic acid (27 mg) and 2-fluorobenzaldehyde (80 mg) were added to a methanol (2 ml) solution of 3,5-trans-3-aminomethyl-5-(3-tert-butoxycarbonylaminomethylphenyl)-7-chloro-1-neopentyl-1,2,3,5-tetrahydro-4,1-benzoxazepin-2-one (0.11 g). To the mixture was added sodium cyano borohydride (29 mg), which was stirred for 30 minutes at room temperature. To the reaction mixture was added acetic acid ethyl ester (50 ml), which was washed with water. The organic layer was dried over anhydrous $Na_2SO_4$. The solvent was distilled off, and the residue was purified by means of a silica gel column chromatography to give a colorless oily product (40 mg).

NMR($CDCl_3$) δ: 0.91(9H,s), 1.45(9H,s), 2.97(1H,dd,J=6.2, 12.0 Hz), 3.10(1H,dd,J=6.0,12.0 Hz), 3.32(1H,d,J=14.0 Hz), 3.85(2H,s), 4.01(1H,t,J=6.2 Hz), 4.36(2H,d,J=6.2 Hz), 4.49 (1H,d,J=14.0 Hz), 4.87–4.95(1H,br), 5.99(1H,s), 6.57(1H, d,J=2.2 Hz), 6.96–7.41(10H,m)

EXAMPLE 100

3,5-Trans-5-(3-aminomethylphenyl)-7-chloro-3-(2-fluorobenzyl)aminomethyl-1-neopentyl-1,2,3,5-tetrahydro-4,1-benzoxazepin-2-one-dihydrochloride The compound produced in Example 99 (40 mg) was dissolved in a 4N acetic acid ethyl ester solution of hydrogen chloride. The solution was left standing for 30 minutes. The solvent was then distilled off to leave a colorless amorphous solid product (35 mg).

NMR($CDCl_3$) δ: 0.95(9H,s), 3.42–3.62(3H,m), 4.20(2H,s), 4.28–4.33(1H,m), 4.37(2H,s), 4.38–4.49(1H,m), 6.13(1H,s), 6.57(1H,s), 7.23–7.63(10H,m)

EXAMPLE 101

3,5-Trans-N-(2-fluorobenzyl)-5-(3-tert-butoxycarbonylaminomethylphenyl)-7-chloro-1-(4-hydroxybenzyl)-2-oxo-1,2,3,5-tetrahydro-4,1-benzoxazepine-3-acetamide p The compound (0.65 g) produced in Example 57 was dissolved in a mixture of acetic acid ethyl ester (20 ml) and methanol (10 ml). The solution was subjected to catalytic reduction in the presence of 10% palladium-carbon (0.1 g) as catalyst at ordinary temperature under atmospheric pressure. The catalyst was filtered off, and the filtrate was washed with water. The organic layer was dried over anhydrous $Na_2SO_4$. The solvent was then distilled off to give a colorless amorphous solid product (0.48 g).

NMR($CDCl_3$) δ: 1.4(9H,m), 2.68(1H,dd), 2.88(1H,dd), 4.0–4.65(5H,m), 4.81(1H,s), 4.9–5.1(2H,m), 5.7–6.5(4H, m), 6.65–7.6(14H,m)

EXAMPLE 102

3,5-Trans-N-(2-fluorobenzyl)-5-(3-aminomethylphenyl)-7-chloro-1-(4-hydroxybenzyl)-2-oxo-1,2,3,5-tetrahydro-4,1-benzoxazepine-3-acetamide•monohydrochloride The compound produced in Example 101 (0.22 g) was dissolved in a 4N acetic acid ethyl ester solution of hydrogen chloride (5 ml). The solution was left standing for 30 minutes. The solvent was then distilled off to leave a colorless amorphous solid product (0.21 g).

NMR($CDCl_3$) δ: 2.8(2H,m), 3.7–4.1(4H,m), 4.3–4.65(4H, m), 4.85(1H,s), 4.91(1H,d), 5.63(1H,d), 6.41(1H,d), 6.5–7.5 (14H,m)

EXAMPLE 103

3,5-Trans-N-(2-fluorobenzyl)-1-(4-acetyloxybenzyl)-5-(3-aminomethylphenyl)-7-chloro-2-oxo-1,2,3,5-tetrahydro-4,1-benzoxazepine-3-acetamide•monohydrochloride To a dichloromethane (8 ml) solution of the compound (100 mg) produced in Example 101 were added acetic anhydride (0.2 ml) and triethylamine (0.2 ml). The mixture was stirred for 40 minutes at room temperature. The solvent was distilled off, and the residue was purified by means of a silica gel column chromatography to give an oily product (80 mg). This product was dissolved in a 4N acetic acid ethyl ester solution of hydrogen chloride (2 ml), which was left standing for 30 minutes. The solvent was then distilled off to leave a colorless amorphous solid product (70 mg).

NMR($CDCl_3$) δ: 2.30,2.29(3H,each s), 2.5–3.0(2H,m), 3.83 (2H,m), 4.2–4.6(3H,m), 4.73,4.92(1H,each d, J=15.0 Hz), 5.23,5.29(1H,each s), 5.47,5.68(1H, each d,J=15.0 Hz), 6.3–7.5(15H,m)

EXAMPLE 104

3,5-Trans-N-(2-fluorobenzyl)-5-(3-aminomethylphenyl)-7-chloro-2-oxo-1-[4-[(3-phenoxypropyl)oxy]benzyl]-1,2,3,5-tetrahydro-4,1-benzoxazepine-3-acetamide•monohydrochloride To a dimethylformamide (4 ml) solution of the compound produced in Example 101 (100 mg) were added 3-phenoxypropyl bromide (40 mg) and potassium carbonate (50 mg). The mixture was stirred for one hour at 70–80° C., to which was added acetic acid ethyl ester (50 ml). The mixture was washed with water and dried over anhydrous $Na_2SO_4$. The solvent was distilled off, and the residue was purified by means of a silica gel column chromatography to give a colorless oily product (0.08 g). This product was dissolved in a 4N acetic acid ethyl ester solution of hydrogen chloride (2 ml). The solution was left standing for 30 minutes at room temperature. The solvent was then distilled off to leave a colorless amorphous solid product (65 mg).

NMR($CDCl_3$) δ: 1.82(2H,br), 1.97(4H,m), 2.72(1H,dd), 2.92(1H,dd), 3.83(2H,s), 4.02(4H,m), 4.35–4.6(3H,m), 4.7 (1H,d), 5.33(1H,s), 5.43(1H,d), 6.33(1H,t), 6.49(1H,d), 6.75–7.4(19H,m)

EXAMPLE 105

3,5-Trans-N-(2-fluorobenzyl)-5-(3-aminomethylphenyl)-7-chloro-2-oxo-1-(4-pivaloyloxybenzyl)-1,2,3,5-tetrahydro-4,1-benzoxazepine-3-acetamide•monohydrochloride To a dichloromethane (10 ml) solution of the compound produced in Example 101 (110 mg) were added pivaloyl chloride (30 mg) and triethylamine (30 mg). The mixture was stirred for 20 minutes at room temperature. The reaction mixture was then subjected to substantially the same procedure as in Example 104 to give a colorless amorphous solid product (78 mg).

NMR($CDCl_3$) δ: 1.30(9H,s), 2.63(1H,dd), 2.87(1H,dd), 4.03 (2H,s), 4.30(2H,d), 4.44(1H,t), 4.98(1H,d), 5.43(1H,d), 5.44 (1H,s), 6.36(1H,d), 7.0–7.7(14H,m), 8.2–8.7(3H,m)

EXAMPLE 106

3,5-Trans-N-(2-fluorobenzyl)-5-(3-aminomethylphenyl)-7-chloro-1-(4-ethoxycarbonylmethyloxybenzyl)-2-oxo-1,2,3,5-tetrahydro-4,1-benzoxazepine-3-acetamide•monohydrochloride To an acetonitrile (5 ml) solution of the compound produced in Example 101 (100 mg) were added ethyl bromoacetate (30 mg) and potassium carbonate (35 mg). The mixture was heated for 1.5 hour under reflux, The reaction mixture was then subjected to substantially the same procedure as in Example 104 to give a colorless amorphous solid product (55 mg).

NMR($CDCl_3$) δ: 1.27(3H,s), 2.5–3.0(4H,m), 3.85(2H,s), 4.25(2H,q), 4.5(3H,m), 4.59(2H,s), 4.72(1H,d), 5.31(1H,s), 5.42(1H,d), 6.49(1H,d), 6.75–7.5(14H,m)

EXAMPLE 107

3,5-Trans-N-(2-fluorobenzyl)-5-(3-aminomethylphenyl)-7-chloro-1-[4-(N,N-dimethylcarbamoylmethyloxy)benzyl)-2-oxo-1,2,3,5-tetrahydro-4,1-benzoxazepine-2-acetamide•monohydrochloride To an acetonitrile (10 ml) solution of the compound produced in Example 101 (130 mg) were added dimethyl carbamoyl chloride (30 mg) and potassium carbonate (50 mg). The mixture was stirred for 3 hours at 50–70° C., which was then subjected to substantially the same procedure as in Example 104 to give a colorless amorphous solid product. NMR(CDCl$_3$) δ: 2.3(2H,br), 2.72(1H,dd), 2.93(1H,dd), 3.00 (3H,s), 3.08(3H,s), 3.83(2H,br), 4.3–4.6(3H,m), 4.67(1H,d), 5.29(1H,s), 5.52(1H,d), 6.5(2H,m), 6.9–7.4(14H,m)

EXAMPLE 108

3,5-Trans-N-(2-fluorobenzyl)-1-[4-(2-acetoxyethyloxy)benzyl]-5-(3-aminomethylphenyl)-7-chloro-2-oxo-1,2,3,5-tetrahydro-4,1-benzoxazepine-3-acetamide•monohydrochloride To a dimethylformamide (8 ml) solution of the compound produced in Example 101 (100 mg) and acetic acid 2-bromoethyl ester (30 mg) was added sodium hydride (60% in oil, 8 mg). The mixture was stirred for 30 minutes at 70° C., which was then subjected to substantially the same procedure as in Example 10 to give a colorless amorphous solid product (18 mg). NMR(CDCl$_3$) δ: 2.09(3H,s), 2.73(1H,dd), 2.93(1H,dd), 4.1–4.6(9H,m), 4.73(1H,d), 5.36(1H,s), 5.40(1H,d), 6.48 (1H,t), 6.5(1H,d), 6.8–7.5(14H,m)

EXAMPLE 109

3,5-Trans-N-(2-fluorobenzyl)-5-(3-aminomethylphenyl)-7-chloro-1-[4-(2-hydroxyethyloxy)benzyl]-2-oxo-1,2,3,5-tetrahydro-4,1-benzoxazepine-3-acetamide•monohydrochloride In a mixture of tetrahydrofuran (1 ml) and methanol (4 ml) was dissolved the intermediate 3,5-trans-N-(2-fluorobenzyl)-1-[4-(2-(acetoxyethyloxy)benzyl]-5-(3-tert-butoxycarbonylaminomethylphenyl)-7-chloro-2-oxo-1,2,3,5-tetrahydro-4,1-benzoxazepine-3-acetamide (70 mg) produced in Example 108. To the solution was added a 1N aqueous solution of sodium hydroxide. The mixture was stirred for 30 minutes at 60° C., to which was added acetic acid ethyl ester. The mixture was washed with water and dried over anhydrous Na$_2$SO$_4$. The solvent was then distilled off to leave a crystalline product (52 mg), m.p.170–172° C. This product was subjected to substantially the same procedure as in Example 104 to give a colorless amorphous solid product (36 mg). NMR(CDCl$_3$) δ: 2.24(2H,m), 2.73(1H,dd), 2.93(1H,dd), 3.7–4.6(9H,m), 4.73(1H,d), 5.35(1H,s), 5.40(1H,d), 6.38 (1H,t), 6.5(1H,d), 6.7–7.5(14H,m)

EXAMPLE 110

3,5-Trans-N-(2-fluorobenzyl)-5-(3-aminomethylphenyl)-1-(4-carbonylmethyloxybenzyl)-7-chloro-2-oxo-1,2,3,5-tetrahydro-4,1-benzoxazepine-3-acetamide•monohydrochloride In a mixture of tetrahydrofuran (2 ml) and methanol (5 ml) was dissolved the intermediate 3,5-trans-N-(2-fluorobenzyl)-5-(3-tert-butoxycarbonylaminomethylphenyl)- 7-chloro-1-(4-ethoxycarbonylmethyloxybenzyl)-2-oxo-1,2,3,5-tetrahydro-4,1-benzoxazepine-3-acetamide (0.12 g). To the solution was added a 1N aqueous solution of sodium hydroxide (2 ml). The mixture was stirred for 40 minutes at 60° C., which was neutralized, followed by extraction with acetic acid ethyl ester. The extract was dried over anhydrous Na$_2$SO$_4$. The solvent was distilled off, and the residue was subjected to substantially the same procedure as in Example 104 to give a colorless amorphous solid product (58 mg). NMR(CDCl$_3$) δ: 2.4–3.0(2H,m), 3.70(2H,m), 4.0–4.6(4H, m), 4.77(2H,s), 5.72(1H,d,J=15 Hz), 6.2–7.6(15H,m)

EXAMPLE 111

3,5-Trans-N-(2-fluorobenzyl)-5-(3-aminomethylphenyl)-7-chloro-1-(4-methoxycarbonylmethyloxybenzyl)-2-oxo-1,2,3,5-tetrahydro-4,1-benzoxazepine-3-acetamide•monohydrochloride To an acetonitrile (8 ml) solution of the compound produced in Example 101 (200 mg) were added methyl bromoacetate (55 mg) and potassium carbonate (100 mg). The mixture was stirred for 1.5 hour at 70° C., followed by substantially the same procedure as in Example 104 to give a colorless amorphous solid product (43 mg). NMR(CDCl$_3$) δ: 2.72(1H,dd), 2.92(1H,dd), 3.78(3H,s), 3.85 (2H,br), 4.3–4.55(3H,m), 4.61(2H,s), 4.7(1H,d), 5.31(1H,s), 5.43(1H,d), 6.4(1H,t), 6.5(1H,d), 6.75–7.4(14H,m)

EXAMPLE 112

3,5-Trans-N-(2-fluorobenzyl)-5-(3-acetylaminomethylphenyl)-7-chloro-1-neopentyl-2-oxo-1,2,3,5-tetrahydro-4,1-benzoxazepine-3-acetamide To a pyridine (1 ml) solution of the compound (0.1 g) produced in Example 6 were added acetic anhydride (20 mg) and dimethylaminopyridine (5 mg). The mixture was stirred for 30 minutes at room temperature, to which was added acetic acid ethyl ester (50 ml). The mixture was washed with water and dried over anhydrous Na$_2$SO$_4$. The solvent was distilled off, and the residue was purified by means of a silica gel column chromatography to give a colorless amorphous solid product (72 mg). NMR(CDCl$_3$) δ: 0.91(9H,s), 2.04(3H,s), 2.69(1H,dd,J=6.0, 14.8 Hz), 2.88(1H,dd,J=7.2,14.8 Hz), 3.35(1H,d,J=14.0 Hz), 4.35–4.59(6H,m), 5.75–5.88(1H,br), 5.98(1H,s), 6.27–6.39 (1H,br), 6.57(1H,d,J=2.2 Hz), 6.97–7.40(10H,m)

EXAMPLE 113

3,5-Trans-N-(2-fluorobenzyl)-7-chloro-5-(3-methanesulfonylaminomethylphenyl)-1-neopentyl-2-oxo-1,2,3,5-tetrahydro-4,1-benzoxazepine-3-acetamide To an acetic acid ethyl ester (1 ml) solution of the compound produced in Example 6 (0.1 g) were added triethylamine (44 mg) and methanesulfonyl chloride (22 mg). The mixture was stirred for J0 minutes at room temperature, followed by substantially the same procedure as in Example 112 to give a colorless amorphous solid product (75 mg). NMR(CDCl$_3$) δ: 0.92(9H,s), 2.70(1H,dd,J=5.4,14.6 Hz), 2.88(3H,s), 2.88(1H,dd,J=7.0,14.6 Hz), 3.36(1H,d, J=14.0 Hz), 4.33–4.59(6H,m), 4.75–4.85(1H,br), 6.00(1H,s), 6.28–6.38(1H,br), 6.51(1H,d,J=1.8 Hz), 7.03–7.40(10H,m)

EXAMPLE 114

3,5-Trans-N-(2-fluorobenzyl)-7-chloro-1-neopentyl-2-oxo-5-(3-trifluoroacetylaminomethylphenyl)-1,2,3,5-tetrahydro-4,1-benzoxazepine-3-acetamide Employing the compound produced in Example 6 (100 mg) and trifluoroacetic anhydride (40 mg), substantially the same procedure as in Example 112 was conducted to give a colorless amorphous solid product (64 mg).

NMR(CDCl₃) δ: 0.91(9H,s), 2.69(1H,d,J=6.0,14.4 Hz), 2.88 (1H,dd,J=7.2,14.4 Hz), 3.35(1H,d,J=13.6 Hz), 4.38–4.57 (6H,m), 5.98(1H,s), 6.28–6.38(1H,br), 6.54(1H,d, J=2.2 Hz), 6.65–6.75(1H,br), 6.96–7.41(10H,m)

EXAMPLE 115

3,5-Trans-N-(2-fluorobenzyl)-7-chloro-5-(3-methoxycarbonylaminomethylphenyl)-1-neopentyl-2-oxo-1,2,3,5-tetrahydro-4,1-benzoxazepine-3-acetamide To a tetrahydrofuran (1 ml) solution of the compound produced in Example 6 (100 mg) were added triethylamine (44 mg) and methoxycarbonyl (18 mg). The -mixture was stirred for 30 minutes at 0C, followed by substantially the same procedure as in Example 112 to give a colorless amorphous solid product (67 mg).

NMR(CDCl₃) δ: 0.92(9H,s), 2.69(1H,dd,J=5.8,14.2 Hz), 2.88(1H,d,J=7.2,14.2 Hz), 3.35(1H,d,J=14.0 Hz), 3.70 (3H, s), 4.37–4.51(6H,m), 4.95–5.05(1H,br), 5.98(1H,s), 6.25–6.35(1H,br), 6.56(1H,d,J=2.2 Hz), 6.98–7.39(10H,m)

EXAMPLE 116

3,5-Trans-N-(2-fluorobenzyl)-7-chloro-5-(3-methylureidomethylphenyl)-1-neopentyl-2-oxo-1,2,3,5-tetrahydro-4,1-benzoxazepine-2-acetamide To a tetrahydrofuran (3 ml) solution of the compound produced in Example 6 (100 mg) was added triethylamine (44 mg). To the mixture was added, while stirring at 0° C., triphosgene (28 mg). The mixture was stirred for further 30 minutes at 0° C., to which was added a 30% aqueous solution of methylamine (0.038 ml). The mixture was stirred for further 30 minutes at 0° C., followed by substantially the same procedure as in Example 112 to give a colorless amorphous solid product (80 mg).

NMR(CDCl₃) δ: 0.91(9H,s), 2.70(1H,dd,J=5.4,13.8 Hz), 2.75,2.78(3H,each s), 2.86(1H,dd,J=7.2,13.8 Hz), 3.35 (1H, d,J=13.6 Hz), 4.38–4.50(7H,m), 4.75–4.85(l,br), 5.97(1H,s), 6.35–6.50(1H,br), 6.57(1H,d,J=2.2 Hz), 6.96–7.34(10H,m)

EXAMPLE 117

3,5-Trans-N-(2-fluorobenzyl)-5-(3-acetylaminomethylphenyl)-1-(4-biphenylmethyl)-7-chloro-2-oxo-1,2,3,5-tetrahydro-4,1-benzoxazepine-3-acetamide Employing the compound produced in Example 5 (40 mg) and acetic anhydride (0.1 ml), substantially the same procedure as in Example 112 was taken to give a colorless crystalline product, m.p.168–170° C. (38 mg).

NMR(CDCl₃) δ: 1.95(3H,s), 2.73(1H,dd,J=5.8,16 Hz), 2.95 (1H,dd,J=7.4,15.8 Hz), 4.34(2H,d,J=5.8 Hz), 4.35–4.65(3H, m), 4.87(1H,d,J=14.6 Hz), 5.37(1H,s), 5.47(1H,d, J=14.6 Hz), 5.63(1H,m), 6.38(1H,m), 6.50(1H,d,J=2.2 Hz), 6.9–7.7 (21H,m)

EXAMPLE 118

3,5-Trans-N-(2-fluorobenzyl)-1-(4-aminobenzyl)-5-(3-N-tert-butoxycarbonylaminomethylphenyl)-7-chloro-2-oxo-1,2,3,5-tetrahydro-4,1-benzoxazepine-2-acetamide An acetic acid ethyl ester (20 ml) solution of the compound produced in Example 58 (1 g) was subjected to catalytic hydrogenation in the presence of a 10% palladium-carbon (0.1 g). The catalyst was filtered off. The solvent was distilled off, and the residue was purified by means of a silica gel column chromatography to give a colorless oily product (0.7 g).

NMR(CDCl₃) δ: 1.28(9H,s), 2.69(1H,dd), 2.89(1H,dd), 3.7–4.6(6H,m), 5.13(1H,s), 5.27(1H,m), 5.60(1H,d), 6.34 (1H,m), 6.47(1H,d), 6.5–7.5(14H,m)

EXAMPLE 119

3,5-Trans-N-(2-fluorobenzyl)-1-(4-acetylaminobenzyl)-5-(3-aminomethylphenyl)-7-chloro-2-oxo-1,2,3,5-tetrahydro-4,1-benzoxazepine-3-acetamide•monohydrochloride To a dichloromethane (5 ml) solution of the compound produced in Example 118 (0.15 g) were added acetic anhydride (0.1 ml) and triethylamine (0.1 ml). The mixture was stirred for one hour at room temperature. The solvent was then distilled off, and the residue was purified by means of a silica gel column chromatography to give a colorless oily product (0.12 g). To this compound was added a 4N acetic acid ethyl ester solution of hydrogen chloride (1 ml). The mixture was left standing for 40 minutes at room temperature. The solvent was distilled off to leave a colorless amorphous solid product (54 mg).

NMR(CDCl₃) δ: 2.14(3H,s), 2.72(1H,dd), 2.90(1H,dd), 3.85 (2H,br), 4.3–4.6(3H,m), 4.67(1H,d), 5.25(1H,s), 5.48(1H,d), 6.41(1H,t), 6.48(1H,d), 6.8–7.9(15H,m)

EXAMPLE 120

3,5-Trans-N-(2-fluorobenzyl)-5-(3-aminomethylphenyl)-7-chloro-1-(4-methanesulfonylaminobenzyl)-2-oxo-1,2,3,5-tetrahydro-4,1-benzoxazepine-3-acetamide•monohydrochloride To a dichloromethane (5 ml) solution of the compound produced in Example 118 (0.15 g) were added methanesulfonyl chloride (0.05 g) and triethylamine (0.04 g). The mixture was stirred for 30 minutes at room temperature, followed by substantially the same procedure as in Example 119 to give a colorless amorphous product (70 mg).

NMR(CDCl₃) δ: 2.72(1H,dd), 2.94(1H,dd), 3.39(3H,s), 3.83 (2H,br), 4.3–4.6(3H,m), 4.85(1H,d), 5.34(1H,s), 5.47(1H,d), 6.33(1H,t), 6.53(1H,t), 6.9–7.5(14H,m)

EXAMPLE 121

3,5-Trans-N-(2-fluorobenzyl)-5-(3-N-tert-butoxycarbonylaminomethylphenyl)-7-chloro-1-(4-dimethylaminobenzyl)-2-oxo-1,2,3,5-tetrahydro-4,1-benzoxazepine-3-acetamide Employing 2-amino-5-chloro-α-(3-tert-butoxycarbonylaminomethylphenyl)benzyl alcohol (0.5 g) and 4-dimethylaminobenzaldehyde (0.23 g), substantially the same procedures as in Example 1 was taken to produce a colorless oily compound (0.2 g).

NMR(CDCl₃) δ: 1.44(9H,s), 2.6–3.0(2H,m), 2.93(6H,s), 4.23(2H,d,J=5.8 Hz), 4.35–4.7(4H,m), 4.95(1H,m), 5.25 (1H,s), 5.47(1H,d,J=14.2 Hz), 6.40(1H,t), 6.45(1H,d,J=1.6 Hz), 6.6–7.4(14H,m)

EXAMPLE 122

3,5-Trans-N-(2-fluorobenzyl)-5-(3-aminomethylphenyl)-7-chloro-1-(4-dimethylaminobenzyl)-2-oxo-1,2,3,5-tetrahydro-4,1-benzoxazepine-3-acetamide•dihydrochloride NMR(CDCl₃) δ: 2.72(1H,dd), 2.93(6H,s), 3.82(2H,m), 4.35–4.7(4H,m), 5.28(1H,s), 5.47(1H,d,J=14.4 Hz), 6.42 (1H,t), 6.47(1H,d,J=2 Hz), 6.55–7.5(14H,m)

EXAMPLE 123

3,5-Trans-N-(2-fluorobenzyl)-5-[3-(3-tert-butoxyxcarbonylaminopropyl)aminomethylphenyl]-7-chloro-1-neopentyl-2-oxo-1,2,3,5-tetrahydro-4,1-benzoxazepine-2-acetamide Employing 3,5-trans-N-(2-fluorobenzyl)-7-chloro-5-(3-formylphenyl)-1-neopentyl-2-oxo-1,2,3,5-tetrahydro-4,1- benzoxazepine-3-acetamide produced in Example 41-(7) (0.2 g) and N-Boc-1,3-diaminopropane (71 mg), substantially the same procedure as in Example 41-(8) was taken to give a colorless amorphous solid product (0.28 g).
NMR(CDCl$_3$) δ: 0.92(9H,s), 1.43(9H,s), 1.61–1.70(2H,m), 2.66–2.75(3H,m), 2.89(1H,dd,J=7.0,14.2 Hz), 3.18–3.26 (2H,m), 3.35(1H,d,J=13.8 Hz), 3.79(2H,s), 4.38–4.51(4H, m), 5.10–5.15(1H,br), 5.99(1H,s), 6.30–6.45(1H,br), 6.59 (1H,d,J=2.2 Hz), 7.02–7.38(10H,m)

EXAMPLE 124

3,5-Trans-N-(2-fluorobenzyl)-5-[3-(3-aminopropyl) aminomethylphenyl]-7-chloro-1-neopentyl-2-oxo-1,2,3, 5-tetrahydro-4,1-benzoxazepine-3-acetamide•dihydrochloride The compound produced in Example 123 (0.20 g) was dissolved in a 4N acetic acid ethyl ester solution of hydrogen chloride (3 ml). The solution was left standing for 30 minutes at room temperature, followed by distilling off the solvent to leave a colorless amorphous solid product (0.16 g).
NMR(CDCl$_3$) δ: 0.95(9H,s), 2.01–2.20(2H,m), 2.77–2.85 (2H,m), 3.20–3.22(4H,m), 3.75(1H,d,J=14.6 Hz), 4.24(2H, s), 4.42–4.48(4H,m), 6.06(1H,s), 6.49(1H,d,J=2.2 Hz), 7.01–7.59(10H,m)

EXAMPLE 125

3,5-Trans-N-(2-fluorobenzyl)-5-(3-aminoacetylaminomethylphenyl)-1-benzyl-7-chloro-2-oxo-1,2,3,5-tetrahydro-4,1-benzoxazepine-3-acetamide•monohydrochloride To a dimethylformamide (3 ml) solution of the compound produced in Example 2 (80 mg) and N-Boc-glycine (40 mg) were added diethyl cyano phosphate (50 mg) and triethylamine (0.05 ml). The mixture was stirred for 20 minutes at room temperature, to which was added acetic acid ethyl ester (50 ml). The mixture was washed with water and dried over Na$_2$SO$_4$. The solvent was distilled off to leave an oily compound (70 mg), which was dissolved in a 4N acetic acid ethyl ester solution of hydrogen chloride (2 ml). The solution was left standing for 30 minutes at room temperature to give a colorless amorphous solid product (47 mg).
NMR(CDCl$_3$) δ: 2.72(1H,dd), 2.93(1H,dd), 3.41(2H,s), 4.3–4.6(5H,m), 4.85(1H,d), 5.37(1H,s), 5.93(1H,d), 6.41 (1H,t), 6.50(1H,d), 6.9–7.7(16H,m)

EXAMPLE 126

3,5-Trans-N-(2-fluorobenzyl)-1-(4-biphenylmethyl)-7-chloro-2-oxo-5-[3-[piperidin-4-yl]carbonylaminomethyl] phenyl]-1,2,3,5-tetrahydro-4,1-benzoxazepine-3-acetamide•monohydrochloride To a dimethylformamide (5 ml) solution of the compound produced in Example 5 (0.1 g) and N-Boc-piperidine-4-carboxylic acid (42 mg) were added diethyl cyano phosphate (30 mg) and triethylamine (0.03 ml). The mixture was stirred for 20 minutes at room temperature, followed by substantially the same procedure as in Example 125 to give a colorless amorphous solid product (70 mg).
NMR(CDCl$_3$) δ: 1.4–2.3(5H,m), 2.5–3.2(6H,m), 4.2–4.6 (5H,m), 4.88(1H,d,J=14.6 Hz), 5.37(1H,s), 5.45(1H,d, J=14.6 hz), 5.86(1H,m), 6.48(1H,d,J=1.8 Hz), 6.55(1H,m), 6.8–7.7(19H,m)

EXAMPLE 127

3,5-Trans-N-(2-fluorobenzyl)-5-[2-(3-aminopropyloxy) phenyl]-7-chloro-1-isobutyl-2-oxo-1,2,3,5-tetrahydro-4, 1-benzoxazepine-3-acetamide•monohydrochloride (1) To a dimethylformamide (15 ml) solution of 3,5-trans-7-chloro-5-(2-hydroxyphenyl)-1-isobutyl-2-oxo-1,2,3,5-tetrahydro-4,1-benzoxazepine-3-acetic acid ethyl ester (0.8 g) were added bromopropyl phthalimide (0.6 g) and potassium carbonate (0.38 g). The mixture was stirred for 4 hours at 60° C., to which was added acetic acid ethyl ester (50 ml). The mixture was washed with water and dried over anhydrous Na$_2$SO$_4$. The solvent was then distilled off, and the residue (1.1 g) was dissolved in ethanol (20 ml). To the solution was added hydrazine.monohydrate (0.2 ml), and the mixture was stirred for 3 hours at 60–70° C. Insolubles were filtered off, and, from the filtrate, the solvent was distilled off. The residue was dissolved in tetrahydrofuran (20 ml), to which was added di-t-butyl dicarboxylate (0.46 g). The mixture was stirred for 20 minutes at room temperature. The reaction mixture was concentrated under reduced pressure. The concentrate was purified by means of a silica gel column chromatography to give 3,5-trans-5-[2-(3-tert-butoxycarbonylaminopropyloxy)phenyl]-1-isobutyl-2-oxo-1,2,3,5-tetrahydro-4,1-benzoxazepine-3-acetic acid ethyl ester as a colorless oily product (1.0 g).
NMR(CDCl$_3$) δ: 0.92(3H,d), 0.99(3H,d), 1.26(3H,t), 1.42 (9H,s), 1.66(2H,m), 2.0(1H,m), 2.5–3.0(3H,m), 3.45(1H, dd), 3.7–4.0(2H,m), 4.15(2H,dq), 4.28(1H,m), 4.42(1H,dd), 6.09(1H,s), 6.65(1H,d), 6.8–7.7(6H,m) (2) The compound produced in (1) (0.8 g) was dissolved in a mixture of tetrahydrofuran (8 ml) and methanol (10 ml). To the solution was added a 1N aqueous solution of sodium hydroxide (4 ml). The mixture was stirred for one hour at 60–70° C. The reaction mixture was neutralized, which was subjected to extraction with acetic acid ethyl ester (30 ml). The extract solution was dried over anhydrous Na$_2$SO$_4$. The solvent was then distilled off to leave an amorphous solid product (0.15 g), which was dissolved in dimethylformamide (6 ml). To the solution were added 2-fluorobenzylamine (40 mg), triethylamine (0.05 ml) and diethyl cyano phosphate (60 mg). The mixture was stirred for 30 minutes at room temperature. To the reaction mixture was added acetic acid ethyl ester (30 ml), which was washed with water. The organic layer was dried over anhydrous Na$_2$SO$_4$. The solvent was distilled off, and the residue was purified by means of a silica gel column chromatography to give a colorless oily product (0.18 g). This compound (0.18 g) was dissolved in a 4N acetic acid ethyl ester solution of hydrogen chloride. The solution was left standing for 30 minutes, followed by distilling off the solvent to give a colorless amorphous solid product (0.1 g).
NMR(CDCl$_3$) δ: 0.92(3H,d), 0.98(3H,d), 1.5–2.5(5H,m), 2.72(1H,dd), 2.87(1H,dd), 3.42(1H,m), 3.8–4.7(8H,m), 6.07 (1H,s), 6.57(1H,m), 6.62(1H,d), 6.8–7.6(10H,m)

EXAMPLE 128

3,5-Trans-N-(2-fluorobenzyl)-5-[4-(3-aminopropyloxy)-2-methoxyphenyl]-7-chloro-1-neopentyl-2-oxo-1,2,3,5-tetrahydro-4,1-benzoxazepine-3-acetamide•monohydrochloride (1) Employing 3,5-trans-7-chloro-5-(4-hydroxy-2-methoxyphenyl)-1-neopentyl-2-oxo-1,2,3,5-tetrahydro-4,1-benzoxazepine-3-acetic acid ethyl ester (3.0 g) and bromopropyl phthalimide (1.8 g), substantially the same procedure as in Example 127-(1) was taken to give 3,5-trans-5-[4-(3-tert-butoxycarbonylaminopropyloxy)-2-methoxyphenyl]-1-neopentyl-2-oxo-1,2,3,5-tetrahydro-4,1-benzoxazepine-3-acetic acid ethyl ester (1.7 g).
(2) The compound produced in (1) (1.0 g) was subjected to hydrolysis by substantially the same procedure as in Example 127-(2) to give a compound (0.15 g), m.p.158–160° C. Employing this compound and 2-fluorobenzylamine (40 mg), substantially the same procedure as in Example 127-(2) was taken to give a colorless amorphous solid product (0.125 g).
NMR(CDCl$_3$) δ: 0.91(9H,s), 1.8–2.2(4H,m), 2.6–3.1(4H,m), 3.33(1H,d), 3.59(3H,s), 4.3–4.6(4H,m), 6.18(1H,s), 6.4–7.5 (10H,m) m.p.: 90–95° C.

EXAMPLE 129

3,5-Trans-1-(4-biphenylmethyl)-5-(3-tert-butoxycarbonylaminomethylphenyl)-7-chloro-3-[1-(4-fluorophenyl)piperazin-4-yl-carbonylmethyl]-1,2,3,5-tetrahydro-4,1-benzoxazepin-2-one To a dimethylformamide (6 ml) solution of the compound produced in Example 4-(2) were added 1-(4-fluorophenyl) piperazine (52 mg), triethylamine (0.04 g) and diethyl cyano phosphate (50 mg). The mixture was stirred for 20 minutes at room temperature. To the reaction mixture was added acetic acid ethyl ester (50 ml). The mixture was washed with water and dried over anhydrous Na$_2$SO$_4$. The solvent was then distilled off. The residue was purified by means of a silica gel column chromatography to give a colorless amorphous solid product (0.13 g).
NMR(CDCl$_3$) δ: 1.44(9H,s), 2.80(1H,dd), 2.9–3.4(5H,m), 3.6–3.9(4H,m), 4.22(2H,d), 4.63(1H,dd), 4.90(1H,d, J=Hz), 5.36(1H,s), 5.50(1H,d,J=14.8 Hz), 6.49(1H,s), 6.8–7.7(19H,m)

EXAMPLE 130

3,5-Trans-5-(3-aminomethylphenyl)-1-(4-biphenylmethyl)-7-chloro-3-[1-(4-fluorophenyl)piperazin-4-yl-carbonylmethyl]-1,2,3,5-tetrahydro-4,1-benzoxazepin-2-one monohydrochloride The compound produced in Example 129 (0.12 g) was dissolved in a 4N acetic acid ethyl ester solution of hydrogen chloride (2 ml). The solution was left standing for 30 minutes at room temperature. The solvent was then distilled off to leave a colorless amorphous solid product (0.11 g).
NMR(CDCl$_3$) δ: 2.5–3.4(8H,m), 3.6–3.9(6H,m), 4.63(1H,dd), 4.90(1H,d,J=14.8 Hz), 5.38(1H,s), 5.50(1H,d,J=14.8 Hz), 6.51(1H,s), 6.8–7.6(19H,m)

EXAMPLE 131

3,5-Trans-1-(4-biphenylmethyl)-5-(3-tert-butoxycarbonylaminomethylphenyl)-7-chloro-3-(4-phenylpiperidin-1-yl-carbonylmethyl)-1,2,3,5-tetrahydro-4,1-benzoxazepin-2-one Employing the compound produced in Example 4-(2) (0.15 g) and 4-phenylpiperidine (42 mg), a colorless amorphous solid product (0.14 g) was produced by substantially the same procedure as in Example 128.
NMR(CDCl$_3$) δ: 1.1–2.0(4H,m), 1.44(9H,s), 2.5–3.4(5H,m), 4.0–4.3(3H,m), 4.6–5.0(3H,m), 5.37(1H,s), 5.53(1H,m), 6.49(1H,s), 6.9–7.7(20H,m)

EXAMPLE 132

3,5-Trans-5-(3-aminomethylphenyl)-1-(4-biphenylmethyl)-7-chloro-3-(4-phenylpiperidin-1-yl-carbonylmethyl)-1,2,3,5-tetrahydro-4,1-benzoxazepin-2-one•monohydrochloride Employing the compound produced in Example 131 (0.1 g), a colorless amorphous solid product (0.07 g) was produced by substantially the same procedure as in Example 129.
NMR(CDCl$_3$) δ: 1.4–2.0(4H,m), 2.55–3.4(6H,m), 3.79(2H, br), 4.65(1H,m), 4.9(1H,dd), 5.40(1H,s), 5.55(1H,dd), 6.52 (1H,d,J=18 Hz), 6.9–7.65(20H,m)

EXAMPLE 133

3,5-Trans-N-(2-fluorobenzyl)-7-chloro-1-(3,3-dimethylbutyl)-2-oxo-5-(3-tritylaminomethylphenyl)-1,2,3,5-tetrahydro-4,1-benzoxazepine-3-acetamide (A),
3,5-cis-N-(2-fluorobenzyl)-7-chloro-1-(3,3-dimethylbutyl)-2-oxo-5-(3-tritylaminomethylphenyl)-1,2,3,5-tetrahydro-4,1-benzoxazepine-3-acetamide (B)

(1) A tetrahydrofuran (30 ml) solution of N-methyl-N-methyloxy-2-amino-5-chlorobenzamide (3.22 g) and N-trityl-3-bromobenzylamine (4.28 g) was cooled to −78° C. To the solution was gradually added dropwise a hexane solution of n-butyl lithium (1.6 mol/L) (31 ml). To the mixture were then added water (70 ml) and acetic acid ethyl ester (100 ml). The organic layer was washed with water and dried over anhydrous MgSO$_4$. The solvent was distilled off, and the residual yellow oily compound was purified by a silica gel column chromatography to give 2-amino-3'-tritylaminomethyl-5-chlorobenzophenone (2.2 g) as a yellow oily product.

(2) To a methanol (20 ml) solution of 2-amino-3'-tritylaminomethyl-5-chlorobenzophenone (2 g) was added sodium borohydride (227 mg). The mixture was stirred for 3 hours at room temperature, to which was added acetic acid ethyl ester (100 ml). The mixture was washed with water and then dried over anhydrous MgSO$_4$. The solvent was then distilled off, and the residue was purified by means of a silica gel column chromatography to give the-object 2-amino-5-chloro-α-(3-tritylaminomethylphenyl)benzyl alcohol (2.0 g) as a colorless oily product.
NMR(CDCl$_3$) δ: 3.34(2H,s), 5.77(1H,s), 6.58(1H,d, J=9.0 Hz), 7.05–7.55(21H,m)

(3) To an acetic acid ethyl ester (20 ml) solution of the compound produced in (2) (2 g) were added water (8 ml) and a 1N aqueous solution of sodium hydroxide (5 ml). To the mixture was added, at 0° C., an acetic acid ethyl ester (3 ml) solution of tert-butyl acetyl chloride (0.59 g). The mixture was stirred for further 30 minutes, to which was added acetic acid ethyl ester (100 ml). The mixture was washed with water and dried over anhydrous Na$_2$SO$_4$, then the solvent was distilled off. The residue was purified by means of a silica gel column chromatography to give N-[4-chloro-2-(3-tritylaminomethyl-α-hydroxybenzyl)phenyl]-3,3-dimethylbutanamide (2.2 g) as a colorless oily product. To a dichloromethane (20 ml) solution of this compound (2 g) was added tetra-n-butyl ammonium borohydride (2.6 g). The mixture was heated for 2 hours under reflux, to which was then added acetic acid ethyl ester (100 ml). The mixture was washed with water and dried over anhydrous Na$_2$SO$_4$, then the solvent was distilled off. The residue was purified by means of a silica gel column chromatography to give 5-chloro-2-(3,3-dimethylbutylamino)-α-(3-tritylaminomethylphenyl)benzyl alcohol as a colorless oily product (1.93 g).
NMR(CDCl$_3$) δ: 0.88(9H,s), 1.34–1.42(2H,m), 2.97–3.05 (2H,m), 3.34(2H,s), 5.77(1H,s), 6.58(1H,d,J=8.4 Hz), 6.99 (1H,d,J=2.6 Hz), 7.13–7.51(20H,m)

(4) To an acetic acid ethyl ester (20 ml) solution of 5-chloro-2-(3,3-dimethylbutylamino)-α-(3-tritylaminomethylphenyl) benzyl alcohol (1.97 g) were added water (7 ml) and a 1N aqueous solution of sodium hydroxide (4 ml). To the mixture was added fumaric chloride monoethyl ester (0.55 g). The mixture was stirred for one hour under ice-cooling to which was added acetic acid ethyl ester (30 ml). The organic layer was washed with water and dried over anhydrous MgSO$_4$. The solvent was distilled off, and the residue was then dissolved in ethanol (50 ml). To the solution was added potassium carbonate (500 mg). The mixture was stirred overnight at room temperature. Insolubles were filtered off, and, then the solvent was distilled off. The residue was purified by means of a silica gel column chromatography to give 7-chloro-1-(3,3-dimethylbutyl)-1,2,3,5-tetrahydro-5-(3-tritylaminomethylphenyl)-2-oxo-1,2,3,5-tetrahydro-4,1-benzoxazepine-3-acetic acid ethyl ester (2.0 g) as a colorless oily product.

NMR(CDCl$_3$) δ: 0.63(½×9H,s), 0.97(½×9H,s), 1.17– 1.29 (5H,m), 2.69–3.22(3H,m), 3.27(½×2H,s), 3.37 (½×2H,s), 3.18–3.81(½×2H,m), 4.04–4.19(2H,m), 4.41(½×1H,dd, J=5.8,8.0 HZ), 4.51(½×1H,t,J=6.8 Hz), 5.72(½×1H,s), 5.88 (½×1H,s), 6.64(½×1H,d,J=2.2 Hz), 7.00–7.57(21H+½×1H, m)

(5) To an ethanol (20 ml) solution of the compound produced in (4) (1.9 g) was added a 1N aqueous solution of sodium hydroxide (3 ml). The mixture was stirred for one hour at 60° C., which was neutralized, followed by addition of acetic acid ethyl ester (50 ml). The mixture was washed with water and dried over anhydrous MgSO$_4$. The solvent was distilled off, and the residue was purified by means of a silica gel column chromatography to give a colorless amorphous solid product (1.4 g). To a dimethylformamide (8 ml) solution of this compound (0.80 g) and 2-fluorobenzylamine (0.16 g) were added diethyl cyano phosphate (227 mg) and triethylamine (176 mg). The mixture was stirred for 30 minutes at room temperature, to which was added acetic acid ethyl ester (50 ml). The mixture was washed with water &nd dried over anhydrous MgSO$_4$. The solvent was then distilled off, and the residue was purified by means of a silica gel column chromatography to give two species of colorless oily products, i.e. 3,5-trans compound (0.22 g) and 3.5-cis compound (0.28 g).

3,5-Cis(B)

NMR(CDCl$_3$) δ: 0.10–0.25(1H,m), 0.45–0.58(1H,m), 0.62 (9H,s), 2.79(1H,dd,J=6.0,14.4 Hz), 2.95–3.12(2 H,m), 3.27 (2H,s), 3.61–3.78(1H,m), 4.45–4.54(3H,m), 5.88(1H,s), 6.34–6.40(1H,br), 6.97–7.54(26H,m)

3,5-Trans(A)

NMR(CDCl$_3$) δ: 0.97(9H,s), 1.47–1.68(2H,m), 2.66(1H,dd, J=6.2,14.6 Hz), 2.88(1H,dd,J=7.4,14.6 Hz), 3.36(2H,s), 3.62–3.78(1H,m), 4.18–4.33(1H,m), 4.39–4.45(3H,m), 5.70 (1H,s), 6.23–6.29(1H,br), 6.62(1H,d,J=2.2 Hz), 6.95– 7.58 (25H,m)

EXAMPLE 134

3,5-Trans-N-(2-fluorobenzyl)-5-(3-aminomethylphenyl)-7-chloro-1-(3,3-dimethylbutyl)-2-oxo-1,2,3,5-tetrahydro-4,1-benzoxazepine-3-acetamide•monohydrochloride To an acetone (1.8 ml) solution of the 3,5-trans compound (B) produced in Example 133 (0.15 g) was added conc. hydrochloric acid (0.2 ml). The mixture was stirred for one hour at 60° C. The reaction mixture was made alkaline with a 1N aqueous solution of sodium hydroxide, to which was added acetic acid ethyl ester (50 ml). The organic layer was washed with water and dried over anhydrous Na7SO$_4$. The solvent was then distilled off. The residue was purified by means of a silica gel column chromatography to give an oily compound. The compound was dissolved in a 4N acetic acid ethyl ester solution of hydrogen chloride (0.1 ml). The solvent was distilled off to leave a colorless amorphous solid product (83 mg).

NMR(CDCl$_3$) δ: 0.99(9H,s), 1.45–1.79.(2H,m), 2.77–2.82 (2H,m), 3.73–3.88(1H,m), 4.12(2H,s), 4.22–4.35(1H,m), 4.42–4.49(3H,m), 5.79(1H,s), 6.49(1H,s), 7.01–7.51 (10H, m)

EXAMPLE 135

3,5-Trans-N-(2-fluorobenzyl)-1-[4-(acetyloxymethyl) benzyl]-5-(3-tert-butoxycarbonylaminomethylphenyl)-7-chloro-2-oxo-1,2,3,5-tetrahydro-4,1-benzoxazepine-3-acetamide (1) To a methanol (12 ml) solution of 2-amino-5-chloro-α-(3-tert-butoxycarbonylaminomethylphenyl)benzyl alcohol (0.45 g) and 4-formyl benzoic acid methyl ester (0.24 g) was added acetic acid )0.1 g). The mixture was stirred for 10 minutes at room temperature.

To the reaction mixture was added sodium cyano borohydride, which was stirred for 2 hours at 60° C. To the reaction mixture was added acetic acid ethyl ester (50 ml), which was washed with water and dried over anhydrous MgSO$_{41}$ then the solvent was distilled off. The residue was purified by means of a silica gel column chromatography to give the objective 5-chloro-2-(4-methoxycarbonylbenzyl)-α-(tert-butoxycarbonylaminomethylphenyl)benzyl alcohol as a colorless oily product (0.7 g). A tetrahydrofuran (8 ml) solution of this product (0.7 g) was added dropwise to a tetrahydrofuran (20 ml) suspension of lithium aluminum hydride (0.14 g). The mixture was stirred for 30 minutes at room temperature, to which were added water (0.15 ml) and a 1N aqueous solution of sodium hydroxide. Insolubles were filtered off, and the filtrate was concentrated to give 5-chloro-2-(4-hydroxymethylbenzylamino)-α-(3-tert-butoxycarbonylaminomethylphenyl)benzyl alcohol as a colorless oily product (0.6 g).

NMR(CDCl$_3$) δ: 1.45(9H,s), 4.0–4.4(4H,m), 4.69(2H,d, J=8.8 Hz), 4.8(1H,m), 5.78(1H,s), 6.55(1H,m), 6.9–7.5 (11H,m)

(2) To an acetic acid ethyl ester (15 ml) solution of the product (0.6 g) produced in (1) were added a 1N aqueous solution of sodium hydroxide (5 ml) and fumaric chloride monoethyl ester (300 mg). The mixture was stirred for one hour under ice-cooling, to which was added acetic acid ethyl ester (30 ml). The organic layer was washed with water and dried over anhydrous MgSO$_4$. The solvent was distilled off, and the residue was dissolved in ethanol (15 ml). To the solution was added potassium carbonate (400 mg), which was stirred for 5 hours at 50–60° C. Insolubles were filtered off, and, from the filtrate, the solvent was distilled off. The residue was purified by means of a silica gel column chromatography to give a colorless oily product.

NMR(CDCl$_3$) δ: 1.25(3H,dt), 2.6–3.3(2H,m), 4.0–4.3 (4H, m), 4.44(⅔×1H,dt), 4.6–4.8(3H,m), 5.0(1H,m), 5.24(⅔×1H, s), 5.63(⅔×1H,d), 5.90(⅔×1H,s), 6.46(⅔×1H,s), 6.6–7.5 (10H,m)

(3) To an ethanol (10 ml) solution of the compound (0.4 g) produced in (2) was added a 1N aqueous solution of sodium hydroxide. The mixture was stirred for 0.5 hour at 60° C. The reaction mixture was neutralized, to which was then added acetic acid ethyl ester (50 ml). The organic layer was washed with water and dried over anhydrous MgSO$_4$. The solvent was distilled off,and the residue was purified by means of a silica gel column Xr, chromatography to give a colorless amorphous solid product (0.3 g). To a dimethyl-formamide (8 ml) solution of this product (0.3 g) and 2-fluorobenzylamine (80 mg) were added diethyl cyano phosphate (100 mg) and triethylamine (100 mg). The mixture was stirred for 20 minutes at room temperature, to which was added acetic acid ethyl ester (50 ml). The mixture was washed with water and, then, dried over anhydrous MgSO$_4$. The solvent was distilled off, and the residue was dissolved in pyridine (2 ml), to which was added acetic anhydride (2 ml). The mixture was stirred for 1.5 hour at room temperature, to which was added acetic acid ethyl ester (50 ml). The mixture was washed with water and dried over anhydrous Na$_2$SO$_4$. The solvent was distilled off, and the residue was purified by means of a silica gel column chromatography to give a colorless oily product (0.18 g).

NMR(CDCl$_3$) δ: 1.44(9H,s), 2.09(3H,s), 2.70(1H,dd), 2.93 (1H,dd), 4.27(2H,d,J=6 hz), 4.35–4.6(3H,m), 4.27(1H,d,J=

14.8 Hz), 5.09(2H,s), 5.3–5.5(2H,m), 6.32(1H,t), 6.5(1H,d, J=2.2 Hz), 6.9–7.4(14H,m)

EXAMPLE 136

3,5-Trans-N-(2-fluorobenzyl)-1-[4 -(acetyloxymethyl) benzyl]-5-(3-aminomethylphenyl)-7-chloro-2-oxo-1,2,3, 5-tetrahydro-4,1-benzoxazepine-3-acetamide•monohydrochloride The compound produced in Example 125 (0.16 g) was dissolved in a 4N acetic acid ethyl ester solution of hydrogen chloride (2 ml), which was left standing for 30 minutes. The solvent was distilled off to leave a colorless amorphous solid product (80 mg).
NMR(CDCl$_3$) δ: 2.08(3H,s), 2.73(1H,dd), 2.93(1H,dd), 3.6 (2H,m), 3.85(2H,m), 4.3–4.6(3H,m), 4.88(1H,d, J=15 Hz), 5.07(2H,s), 5.33(1H,d,J=14.6 hz), 5.39(1H,s), 6.49(1H,d,J= 2.2 Hz), 6.62(1H,t), 6.8–7.5(14H,m)

EXAMPLE 137

3,5-Trans-N-(2-fluorobenzyl)-5-(3-aminomethylphenyl)-7-chloro-1-[4-(hydroxymethyl)benzyl]-2-oxo-1,2,3,5-tetrahydro-4,1-benzoxazepine-3-acetamide To a methanol (2 ml) solution of the compound produced in Example 136 (40 mg) was added a 1N aqueous solution of sodium hydroxide (0.5 ml), which was stirred for 30 minutes at 60° C. Tb the reaction mixture was added acetic acid ethyl ester (20 ml), which was washed with water and dried over anhydrous Na$_2$SO$_4$. The solvent was distilled off to leave a colorless amorphous solid product (20 mg).
NMR(CDCl$_3$) δ: 2.37(2H,m), 2.68(1H,dd), 2.88(1H,dd), 3.83(2H,s), 4.3–4.55(3H,m), 4.61(2H,s), 4.95(1H,s), 5.72 (1H,d,J=14 Hz), 6.2–6.6(3H,m), 6.8–7.5(14H,m)

EXAMPLE 138

3,5-Trans-N-(2-fluorobenzyl)-1-(4-biphenylmethyl)-5-(3-tert-butoxycarbonylaminomethylphenyl)-2-oxo-1,2,3,5-tetrahydro-4,1-benzoxazepine-3-acetamide (1) A tetrahydrofuran (30 ml) solution of N-methyl-N-methyloxy-2-aminobenzamide (2.70 g) and N-tert-butoxycarbonyl-3-bromobenzylamine (2.86 g) was cooled to −78° C. To the solution was gradually added dropwise a hexane solution of n-butyl lithium (1.6 mol/L) (31 ml). To the mixture were then added water (70 ml) and acetic acid ethyl ester (70 ml). The organic layer was washed with water and dried over anhydrous MgSO$_4$. The solvent was then distilled off. The residual oily compound was purified by means of a silica gel column chromatography to give 2-amino-3'-(tert-butoxycarbonylaminomethyl) benzophenone as a yellow oily product (1.2 g).
(2) To a methanol (20 ml) solution of 2-amino-3-(tert-butoxycarbonylaminomethyl)benzophenone (1 g) was added sodium borohydride (0.3 g), which was stirred for 30 minutes at room temperature. To the reaction mixture was added acetic acid ethyl ester (100 ml). The mixture was washed with water and dried over anhydrous MgSO$_4$. The solvent was then distilled off, and the residue was purified by means of a silica gel column chromatography to give the object 2-amino-α-(3-tert-butoxycarbonylaminomethylphenyl)benzyl alcohol as a colorless oily product.
(3) Substantially the same procedure as in Example 4 was followed to give a colorless oily product (0.12 g).
NMR(CDCl$_3$) δ: 1.43(9H,s), 2.75(1H,dd,J=5.8,16 Hz), 2.95 (1H,dd,J=7.2,16 Hz), 4.1–4.8(5H,m), 4.97(1H,d, J=14.6 Hz), 5.43(1H,s), 5.46(1H,d,J=14.6 Hz), 6.54(1H,d,J=7.6 Hz), 6.9–7.7(20H,m)

EXAMPLE 139

3,5-Trans-N-(2-fluorobenzyl)-5-(3-aminomethylphenyl)-1-(4-biphenylmethyl)-2-oxo-1,2,3,5-tetrahydro-4,1-benzoxazepine-3-acetamide•monohydrochloride The compound (0.12 g) produced in Example 138 was dissolved in a 4N acetic acid ethyl ester solution of hydrogen chloride (2 ml). The solution was left standing for 30 minutes at room temperature. The solvent was then distilled off to leave a colorless amorphous solid product (45 mg).
NMR(CDCl$_3$) δ: 2.74(1H,dd,J=5.8,16 Hz), 2.97(1H,dd,J= 7.2, 16 Hz), 3.76(2H,s), 4.3–4.7(3H,m), 4.94(1H,d,J=14.6 Hz), 5.44(1H,s), 5.48(1H,d,J=14.6 Hz), 6.43(1H,m), 6.57 (1H,d, J=7.8 Hz), 6.9–7.7(20H,m)

EXAMPLE 140

3,5-Trans-N-(2-fluorobenzyl)-5-(3-aminomethylphenyl)-1-neopentyl-2-oxo-1,2,3,5-tetrahydro-4,1-benzoxazepine-3-acetamide•monohydrochloride Employing, as starting material, 2-amino-α-(3-tert-butoxycarbonylaminomethylphenyl)benzyl alcohol, a colorless amorphous solid compound (0.13 g) was produced by substantially the same procedure as in Example 8.
NMR(CDCl$_3$) δ: 0.92(9H,s), 2.72(1H,dd,J=5.8,15.8 Hz), 2.91(1H,dd,J=7.2,15.8 Hz), 3.44(1H,d,J=13.8 Hz), 3.88(2H, s), 4.3–4.6(4H,m), 6.05(1H,s), 6.56(1H,m), 6.63(1H,d,J=7.8 Hz), 6.9–7.5(11H,m)

EXAMPLE 141

3,5-Trans-N-(2-fluorobenzyl)-5-(3-tert-butoxycarbonylaminomethylphenyl)-1-(4-hydroxybenzyl)-7-methyloxy-2-oxo-1,2,3,5-tetrahydro-4,1-benzoxazepine-3-acetamide•monohydrochloride (1) An N,N-dimethylformamide (8 ml) solution of N-methyl-N-methyloxy-2-benzyloxycarbonylamino-5-hydroxybenzamide (0.8 g), methyl iodide (0.2 g) and potassium carbonate (0.5 g) was stirred for 3 hours at 60° C. The reaction mixture was poured into ice-water, which was subjected to extraction with ethyl acetate. The organic layer was washed with water, which was dried over anhydrous sodium sulfate. The solvent was distilled off, and the residue was purified by means of a silica gel column chromatography to give N-methyl-N-methyloxy 2-benzyloxycarbonylamino-5-methyloxy-benzamide as a yellow oily product (0.55 g).
NMR(CDCl$_3$) δ: 3.349(3H,s), 3.537(3H,s), 3.798(3H,s), 5.178(2H,s), 6.9–8.3(9H,m)
(2) In a mixture of ethyl acetate (8 ml) and methanol (10 ml) was dissolved N-methyl-N-methyloxy-2-benzyloxycarbonylamino-5-methyloxy-benzamide (0.55 g). To the solution was added 10% palladium-carbon (0.1 g). The mixture was stirred for 40 minutes at ordinary temperature under atmospheric pressure in hydrogen streams. The reaction mixture was subjected to filtration, and the filtrate was concentrated under reduced pressure. From the concentrate, N-methyl-N-methyloxy 2-amino-5-methyloxy-benzamide (0.35 g) was obtained.
NMR(CDCl$_3$) δ: 3.354(3H,s), 3.610(3H,s), 3.753(3H,s), 6.65–7.0(3H,s)
(3) A tetrahydrofuran (15 ml) solution of N-methyl-N-methyloxy-2-amino-5-methyloxy-benzamide (0.35 g) and N-tert-butoxycarbonyl-3-bromobenzylamine (0.48 g) was cooled to −70° C. To the solution was added dropwise, while stirring, a hexane solution of n-butyl lithium (1.6 mol/L) (6.2 ml) over 20 minutes. To the mixture were then added water (40 ml) and ethyl acetate (40 ml). The organic layer was washed with water and dried over anhydrous sodium sulfate.

The solvent was distilled off under reduced pressure. The residue was purified by means of a silica gel column chromatography to give 2-amino-3-tert-butoxycarbonylaminomethyl-5-methyloxy-benzophenone as a yellow oily product (0.18 g).
NMR(CDCl$_3$) δ: 1.453(9H,s), 3.66(3H,s), 4.38(2H,d, J=6.2 Hz), 4.92(1H,m), 5.33(2H,m), 6.7–7.65(7H,m)

(4) In methanol (10 ml) was dissolved 2-amino-3-tert-butoxycarbonylaminomethyl-5-methyloxy-benzophenone (0.18 g). To the solution was added sodium borohydride (0.08 g). The reaction mixture was concentrated, to which was added water, followed by extraction with ethyl acetate (50 ml). The organic layer was washed with water and dried over anhydrous sodium sulfate. From the residue, was obtained 2-amino-α-(3-tert-butoxycarbonylaminomethylphenyl)-5-methyloxybenzyl alcohol as an oily product (0.18 g).
NMR(CDCl$_3$) δ: 1.450(9H,s), 3.739(3H,s), 4.31(2H,d, J=6 Hz), 4.83(1H,m), 5.815(1H,s), 6.6–7.4(7H,s)

(5) In methanol (6 ml) were dissolved 2-amino-α-(3-tert-butoxycarbonylaminomethylphenyl)-5-methyloxybenzyl alcohol (0.18 g), 4-benzyloxy-benzaldehyde (0.12 g) and acetic acid (0.02 g). To the solution was added sodium cyano borohydride (0.02 mg). The mixture was stirred for 30 minutes at 60° C. The reaction mixture was concentrated, to which were added ethyl acetate (30 ml) and water (50 ml). The mixture was shaken. The organic layer was washed with water and dried over anhydrous sodium sulfate. The solvent was distilled off, and the residue was purified by means of a silica gel column chromatography to give 2-(4-benzyloxybenzyl)-α-(3-tert-butoxycarbonylaminomethylphenyl)-5-methyloxybenzyl alcohol as a colorless crystalline product (0.17 g). m.p.:86–87° C.
NMR(CDCl$_3$) δ: 1.433(9H,s), 3.721(3H,s), 4.132(2H,s), 4.28(2H,d,J=6.2 Hz), 4.78(1H,m), 5.05(2H,s), 5.826(1H, s), 6.6–7.5(16H,m)

(6) To a mixture of 2-(4-benzyloxybenzyl)-α-(3-tert-butoxycarbonylmethylphenyl)-5-methyloxybenzyl alcohol (0.17 g), 1N sodium hydroxide (2 ml) and ethyl acetate (6 ml) was added, while stirring, monoethyl fumarate chloride (53 mg). The mixture was stirred fori 20 minutes. The organic layer was separated and washed with water, which was dried over anhydrous sodium sulfate. The solvent was distilled off under reduced pressure. and the residue was dissolved in ethanol (6 ml). To the solution was added potassium carbonate (50 mg), and the mixture was stirred for 2 hours at 60° C. The reaction mixture was concentrated under reduced pressure. To the concentrate were added water (30 ml) and ethyl acetate (20 ml). The mixture was shaken, and the organic layer was separated, which was washed with water and dried over anhydrous sodium sulfate. The organic layer was dissolved in a mixture of tetrahydrofuran (3 ml) and methanol (5 ml). To the solution was added lN sodium hydroxide (2 ml), which was stirred for 30 minutes at 60° C. The reaction mixture was concentrated under reduced pressure, to which was added a 5% aqueous solution of potassium hydrogensulfate to adjust the pH to 3, followed by extraction with ethyl acetate (30 ml). The organic layer was washed with water and dried over anhydrous sodium sulfate. The solvent was distilled off, and the residue was dissolved in N,N-dimethylformamide (4 ml). To the solution was added 2-fluorobenzylamine (32 mg). To the mixture were added, while stirring at 0° C., diethyl cyano phosphate (40 mg) and triethylamine (35 mg). The reaction mixture was stirred for 20 minutes at room temperature, to which was added water, followed by extraction with ethyl acetate (20 ml). The organic layer was washed with water and dried over anhydrous sodium sulfate. The solvent was then distilled off, and the residue was purified by means of a silica gel column chromatography to give 3,5-trans-N-(2-fluorobenzyl) 1-(4-benzyloxybenzyl)-5-(3-tert-butoxycarbonylaminomethylphenyl)-5-methyloxy-2-oxo-1,2,3,5-tetrahydro-4,1-benzoxazepine-3-acetamide as a colorless oily product (0.1 g).
NMR(CDCl$_3$) δ: 1.431(9H,s), 2.68(1H,dd,J=6.2,15.8 Hz), 2.93(1H,dd,J=7.2,15.8 Hz), 3.621(3H,s), 4.24(2H,d,J=6.4 Hz), 4.30–4.60(3H,m), 4.68(1H,d,J=14.2 Hz), 4.83(1H, m), 5.043(2H,s), 5.308(1H,s), 5.40(1H,d,J=14.2 Hz), 6.02(1H, d,J=2.8 Hz), 6.35(1H,m), 6.80–7.50(19H,m)

(7) In a mixture of ethyl acetate (5 ml) and methanol (54 ml) was dissolved 3,5-trans-N-(2-fluorobenzyl) 1-(4-benzyloxybenzyl)-5-(3-tert-butoxycarbonylaminomethyloxyphenyl)-7-methyloxy-2-oxo-1,2,3,5-tetrahydro-4,1-benzoxazepine-3-acetamide (0.1 g). To the solution was added 10% palladium-carbon (30 mg). The mixture was stirred for 3 hours at room temperature under hydrogen atmosphere. The reaction mixture was subjected to filtration. From the filtrate, the solvent was distilled off under reduced pressure. From the residue, 3,5-trans-N-(2-fluorobenzyl)-5-(3-tert-butoxycarbonylaminomethylphenyl)-1-(4-hydroxybenzyl)-7-methylxoy-2-oxo-1,2,3,5-tetrahydro-4,1-benzoxazepine-3-acetamide as a colorless oily product (70 mg) was obtained.
NMR(CDCl$_3$) δ: 1.448(9H,br), 2.69(1H,dd,J=6.4,16 Hz), 2.87(1H,dd,J=7.16 Hz), 3.627(3H,s), 4.0–4.60(5H,m), 4.85–5.20(2H,m), 5.50–5.90(1H,m), 5.96(1H,br), 6.40–7.40 (15H,m)

EXAMPLE 142

3,5-Trans-N-(2-fluorobenzyl)-5-(3-aminomethylphenyl)-1-(4-hydroxybenzyl)-7-methyloxy-2-oxo-1,2,3,5-tetrahydro-4,1-benzoxazepine-3-acetamide•hydrochloride In ethyl acetate (2 ml) was dissolved 3,5-trans-N-(2-fluorobenzyl)-5-(3-tert-butoxycarbonylaminomethylphenyl)-1-(4-hydroxybenzyl-7-methyloxy-2-oxo-1,2,3,5-tetrahydro-4,1-benzoxazepine-3-acetamide (70 mg). To the solution was added 4N hydrochloric acid (ethyl acetate solution, 1 ml), and the mixture was stirred for one hour. From the reaction mixture, the solvent was distilled off to leave the titled compound as a colorless amorphous solid product (52 mg)
NMR(CDCl$_3$) δ: 2.60–2.90(2H,m), 3.617(3H,s), 3.775(2H, br), 4.10–4.70(4H,m), 4.831(1H,s), 5.63(1H,d,J=14 Hz), 5.96(1H,d,J=3 Hz), 6.424(1H,br), 6.50–7.40(15H,m)

EXAMPLE 143

3,5-Trans-N-(2-fluorobenzyl)-1-(4-biphenylmethyl)-5-(3-tert-butoxycarbonylaminomethylphenyl)-8-chloro-2-oxo-1,2,3,5-tetrahydro-4,1-benzoxazepine-3-acetamide (1) 2-Amino-4-chlorobenzoic acid (3 g) and N,O-dimethylhydroxylamine hydrochloride (1.9 g) were dissolved in a mixture of methylene chloride (40 ml) and N,N-dimethylformamide (4 ml). To the solution were added, while stirring at room temperature, 1-ethyl-3-(3-dimethylaminopropyl)-carbodiimide-hydrochloride (3.6 g) and triethylamine (1.4 g). The mixture was stirred for 90 minutes, which was then concentrated under reduced pressure. To the concentrate were added ethyl acetate (100 ml) and water (100 ml). The mixture was shaken, The organic layer was washed with water and dried over anhydrous sodium sulfate. The solvent was then distilled off, and the residue was purified by means of a silica gel chromatography to give N-methyl-N-methyloxy-2-amino-4-chlorobenzamide as a yellow oily product (3.0 g).
NMR(CDCl₃) δ: 3.343(3H,s), 3.571(3H,s), 4.83(1H,m), 6.67(2H,m), 7.36(1H,d,J=8.4 Hz)

(2) N-methyl-N-methyloxy-2-amino-4-chlorobenzamide (3.6 g) and N-tert-butoxycarbonyl-3-bromobenzylamine (5.5 g) were dissolved in tetrahydrofuran (50 ml). The solution was cooled to −78° C., to which was added dropwise, while stirring, a hexane solution of n-butyl lithium (1.6 mol/L, 60 ml) over 40 minutes. To the reaction mixture was added water, which was subjected to extraction with ethyl acetate (150 ml). The organic layer was washed with water and dried over anhydrous sodium sulfate. The solvent was distilled off. The residue was purified by means of a silica gel column chromatography to give 2-amino-3-tert-butoxycarbonylaminomethyl-4-chlorobenzophenone as a yellow oily product (2.3 g).
NMR(CDCL₃) δ: 1.456(9H,s), 4.37(2H,d,J=5.8 Hz), 4.92 (1H, m), 6.197(2H,br), 6.50–6.80(2H,m), 7.30–7.60(5H,m)

(3) In methanol (30 ml) was dissolved 2-amino-3-tert-butoxycarbonylaminomethyl-4-chlorobenzophenone (2.3 g). To the solution was added, while stirring, sodium borohydride. The mixture was stirred for 30 minutes, which was concentrated under reduced pressure. To the concentrate were added water (100 ml) and ethyl acetate (80 ml). The organic layer was washed with water and dried over anhydrous sodium sulfate. The solvent was distilled off to leave 2-amino-α-(tert-butoxycarbonylaminomethylphenyl)-4-chlorobenzyl alcohol as a colorless crystalline product (1.9 g). m.p.: 88–89° C.
NMR(CDCl₃) δ: 1.463(9H,s), 2.43(1H,d,J=4.2 Hz), 4.10 (2H, br), 4.30(2H,d,J=6.4 Hz), 4.83(1H,m), 5.82(1H,d, J=3.6 Hz), 6.60–7.40(7H,m)

(4) In methanol (20 ml) were added 2-amino-α-(3-tert-butoxycarbonylaminomethylphenyl)-4-chlorobenzyl alcohol (1.0 g) and 4-phenylbenzaldehyde (0.55 g). To the solution was added acetic acid (0.2 g), to which was added, while stirring at room temperature, sodium cyano borohydride (0.21 g). The reaction mixture was stirred for 40 minutes at 60° C., which was then concentrated. To the concentrate were added ethyl acetate (50 ml) and water (80 ml). The mixture was subjected to extraction. The organic layer was washed with water and dried over anhydrous sodium sulfate. The solvent was distilled off, and the residue was purified by means of a silica gel column chromatography to give 2-(4-biphenylmethyl)amino-α-(3-tert-butoxycarbonylaminomethylphenyl)- 4-chlorobenzyl alcohol as an oily product (1.1 g).
NMR(CDCl₃) δ: 1,428(9H,s), 2.38(1H,d,J=3.8 Hz), 4.20–4.40(4H,m), 4.76(1H,m), 5.86(1H,d,J=3.6 Hz), 6.60–7.70(16H,m)

(5) In ethyl acetate (15 ml) was dissolved 2-(4-biphenylmethyl)amino-α-(3-tert-butoxycarbonylaminomethylphenyl)-4-chlorobenzyl alcohol (1.1 g). To the solution was added iN sodium hydroxide (5 ml). To the solution was added dropwise, while stirring at room temperature, monoethyl fumarate chloride (0.35 g). The reaction mixture was separated into two layers, and the organic layer was washed with water, which was dried over anhydrous sodium sulfate. The solvent was distilled off. The residue was dissolved in ethanol (25 ml), to which was added potassium carbonate (0.8 g). The mixture was stirred for 2 hours at 60° C. The reaction mixture was concentrated, to which was added ethyl acetate (60 ml) and water (100 ml). The mixture was subjected to extraction. The organic layer was washed with water and dried over anhydrous sodium sulfate. The solvent was then distilled off. The residue was purified by means of a silica gel column chromatography to give 1-(4-biphenylmethyl)-5-(3-tert-butoxycarbonylaminomethylphenyl)-8-chloro-2-oxo-1,2,3,5-tetrahydro-4,1-benzoxazepine-3-acetic acid ethyl ester as a colorless oily product (0.7 g).
NMR(CDCL₃) δ: 1.432(7.2H,s), 1.432(1.8H,s), 2.70–3.30 (2H,m), 4.0–4.40(5.4H,m), 4.48(⅕H,dd,J=5.2 Hz,8.6 Hz), 4.95(⅕H,d,J=14.6 Hz), 5.348(⅕,s), 5.46(4/5H,d, J=14.6 Hz), 5.93(⅕H,s), 6.48(⅕H,d,J=8.4 Hz), 6.60–7.60(15.2H, m)

(6) In a mixture of tetrahydrofuran (5 ml) and methanol (20 ml) was dissolved 1-(4-biphenylmethyl)-5-(3-tert-butoxycarbonylaminomethylphenyl)-8-chloro-2 -oxo-1,2,3,5-tetrahydro-4,1-benzoxazepine-3-acetic acid ethyl ester (0.65 g). To the solution was added IN sodium hydroxide (5 ml), and the mixture was stirred for 40 minutes at 60° C. The reaction mixture was concentrated, which was neutralized with 5% potassium hydrogensulfate, followed by extraction with ethyl acetate (30 ml). The organic layer was washed with water and dried over anhydrous sodium sulfate. The solvent was then distilled off. The residue was purified by means of a silica gel column chromatography to give 1-(4-biphenylmethyl)-5-(3-tert-butoxycarbonylaminomethylphenyl)-8-chloro-2-oxo-1,2,3,5-tetrahydro-4,1-benzoxazepine-3-acetic acid as an amorphous solid product (0.45 g).
NMR(CDCl₃) δ: 1.423(9H,s), 2.80–3.40(2H,m), 3.83(⅓H, d,J=15.2 Hz), 4.10–4.70(10/3H,m), 4.95(⅓H,d,J=14.6 Hz), J 5.416(⅔H,s), 5.47(⅔H,d,J=14.6 Hz), 5.947(⅓H,s), 6.49 (⅔H,d,J=8 Hz), 6.80–7.70(15 ⅓H,m)

(7) In N,N-dimethylformamide (8 ml) were dissolved 1-(4-biphenylmethyl)-5-(3-tert-butoxycarbonylaminomethylphenyl)-8-chloro-4,1-benzoxazepine-3-acetic acid (0.3 g) and 2-fluorobenzylamine (70 mg). To the solution were added, while stirring at 0° C., diethyl cyanophosphate (0.1 g) and triethylamine (80 mg). The mixture was stirred for 20 minutes at room temperature, to which was added water (50 ml) and ethyl acetate (80 ml). The mixture was subjected to extraction. The organic layer was washed with water and dried over anhydrous sodium sulfate. The solvent was distilled off, and the residue was purified by means of a silica gel column chromatography to give N-(2-fluorobenzyl)-1-(4-biphenylmethyl)-5-(3-tert-butoxycarbonylaminomethylphenyl)-8-chloro-2-oxo-1,2,3,5-tetrahydro-4,1-benzoxazepine-2-acetamide as an amorphous solid product (0.35 g).
NMR(CDCl₃) δ: 1.416(3H,s), 1.428(6H,s), 2.60–3.20 (2H, m), 3.87(⅓H,d,J=16.0 Hz), 4.0–4.78(6⅓H,m), 4.88(⅔H,d, J=14.6 Hz), 5.366(⅓H,s), 5.48(⅔H,d, J=14.6 Hz), 5.943 (⅓H,s), 6.20–6.40(1H,m), 6.47(⅔H, d,J=8.4 Hz), 6.90–7.70 (19⅓H,m)

EXAMPLE 144

N-(2-fluorobenzyl)-5-(3-aminomethylphenyl)-1-(4-biphenylmethyl)-8-chloro-2-oxo-1,2,3,5-tetrahydro-4,1-benzoxazepine-3-acetamide•hydrochloride In ethyl acetate (3 ml) was dissolved N-(2-fluorobenzyl)-1-(4-biphenylmethyl)-5-(3-tert-butoxycarbonylaminomethylphenyl)-8-chloro-2-oxo-1,2,3,5-tetrahydro-4,1-benzoxazepine-3-acetamide (0.35 g). To the solution was added 4N hydrochloric acid (ethyl acetate solution, 3 ml). The mixture was stirred for 30 minutes at room temperature. The reaction mixture was concentrated to leave the titled compound as an amorphous solid product. (0.24 g).
NMR(CDCl₃) δ: 2.60–3.20(2H,m), 3.75(2H,br), 3.87(⅓H, d,J=15.8 Hz), 4.30–4.80(3⅓H,m), 4.86(⅔H,d,J=14.8 Hz), 5.380(⅔H,s), 5.52(⅔H,d,J=14.8 Hz), 5.958(⅓H, s), 6.48 (⅔H,d,J=8.2 Hz), 6.80–7.70(19⅓H,m)

EXAMPLE 145

3,5-Trans-N-(2-fluorobenzyl)-5-[4-[(1-tert-butoxycarbonylaminomethyl-1-methyl)ethyl]phenyl]-1-(4-biphenylmethyl)-7-chloro-2-oxo-1,2,3,5-tetrahydro-4,1-benzoxazepine-3-acetamide (1) 3-Bromobenzoic acid ethyl ester (10 g) was added dropwise to a Grignard reagent (ethyl ether 100 ml solution) prepared from metallic magnesium (2.3 g) and methyl iodide (15 g). The mixture was heated for one hour under reflux, followed by addition of a saturated ammonium chloride under ice-cooling to decompose the reaction mixture. The organic layer was washed with water and dried over anhydrous sodium sulfate. The solvent was distilled off. The residue (3 g) was dissolved in toluene (20 ml), to which was added trimethylsyl azide (1.6 g). To the mixture was added dropwise, while stirring at room temperature, boron trifluoride ethyl ether (2.4 g) over 10 minutes. The reaction mixture was stirred for 24 hours at room temperature, to which was added water. The organic layer was separated and washed with water, followed by drying over anhydrous sodium sulfate. The solvent was distilled off to leave 1-[(1-azido-1-methyl)ethyl]-4-bromobenzene as a yellow oily product (3.1 g).

NMR(CDCl$_3$) δ: 1.615(6H,s), 7.25–7.55(4H,m)

(2) Raney nickel (15 g) was suspended in ethanol (150 ml). To the suspension was added dropwise, while stirring at room temperature, 1-[(1-azido-1-methyl)ethyl]-4-bromobenzene (7.0 g). The reaction mixture was subjected to filtration, and the filtrate was concentrated. To the concentrate were added 1N hydrochloric acid (50 ml), hexane (50 ml) and ether (30 ml) for extraction. The aqueous layer was separated, which was made alkaline with 1N sodium hydroxide, followed by extraction with ethyl acetate (150 ml). The extract was dried over anhydrous sodium sulfate. The solvent was distilled off, and the residue was dissolved in tetrahydrofuran (80 ml) To the solution was added di-tert-butyl dicarbonate (6.5 g), and the mixture was stirred for 2 hours at room temperature. The reaction mixture was concentrated, which was subjected to extraction with ethyl acetate. The extract was washed with water and dried over anhydrous sodium sulfate. The solvent was distilled off to leave 1-[(1-tert-butoxycarbonylamino-1-methyl)ethyl]-4-bromobenzene as colorless crystalline product (6.7 g). m.p.: 89–90° C.

NMR(CDCl$_3$) δ: 1.37(9H,br), 1.591(6H,s), 4.92(1H,m), 7.20–7.60(4H,m)

(3) A solution of N-methyl-N-methyloxy 2-amino-5-chlorobenzamide (0.74 g) and the compound produced in (2) in tetrahydrofuran (20 ml) was cooled to −80° C. or below. To the solution was added dropwise, while stirring, a hexane solution of n-butyl lithium (1.6 mol/L (10 ml) over 30 minutes. The reaction mixture was hydrolyzed, which was subjected to extraction with ethyl acetate (100 ml). The organic layer was washed with water and dried over anhydrous sodium sulfate. The solvent was distilled off, and the residue was purified by means of a silica gel column chromatography to give 2-amino-4-(1-tert-butoxycarbonylamino-1-methyl)ethyl-5-chlorobenzophenone as a pale yellow crystalline product (0.35 g). m.p.: 165–166° C.

NMR(CDCl$_3$) δ: 1.44(9H,br), 4.98(1H,br), 6.005(2H,br), 6.71(1H,d,J=8.8 Hz), 7.20–7.70(6H,m)

(4) To a methanol (20 ml) solution of the compound produced in (3) (0.6 g) was added, while stirring at room temperature, sodium borohydride (0.1 g). The reaction mixture was diluted with ethyl acetate (50 ml), which was washed with water, followed by drying over anhydrous sodium sulfate. The solvent was distilled off, and the residue was purified by means of a silica gel column chromatography to give 2-amino-α-[4-[(1-tert-butoxycarbonylamino-1-methyl)ethyl]phenyl]-5-chloro-benzyl alcohol (0.5 g) as a colorless crystalline product. m.p.: 124–125° C.

NMR(CDCl$_3$) δ: 1.37(9H,br), 1.617(6H,s), 2.55(1h,m), 3.95(2H,m), 4.93(1H,br), 5.771(1H,s), 6.59(1H,d,J=8.8 Hz), 7.0–7.50(6H,m)

(5) In methanol (10 ml) were dissolved the compound produced in (4) (0.4 g), 4-biphenylcarbaldehyde (0.22 g) and acetic acid (0.08 g). To the solution was added sodium cyano borohydride (0.1 g), and the mixture was stirred for 40 minutes at 60° C. The reaction mixture was concentrated, to which were added ethyl acetate (50 ml) and water (80 ml). The mixture was subjected to extraction. The organic layer was washed with water and dried over anhydrous sodium sulfate. The solvent was distilled off, and the residue was purified by means of a silica gel column chromatography to give 2-(4-biphenylmethylamino)-α-[4-[(1-tert-butoxycarbonylamino-1-methyl)ethyl]phenyl]-5-chloro-benzyl alcohol as an oily product (0.55 g).

NMR(CDCl$_3$) δ: 1.35(9H,br), 1.639(6H,s), 4.313(2H,s), 4.93(1H,m), 5.85(H,br), 6.56(1H,d,J=9.2 Hz), 7.0–7.70 A (15H,m)

(6) To an ethyl acetate (15 ml) solution of the compound (0.55 g) produced in (5) was added 1N sodium hydroxide (5 ml). To the mixture was added dropwise, while stirring at room temperature, an ethyl acetate (1 ml) solution of mono-ethyl ester of fumaric chloride (0.24 g). The reaction mixture was stirred for 20 minutes, which was separated into two layers. The organic layer was washed with water and dried over anhydrous sodium sulfate. The solvent was distilled off, and the residue was dissolved in ethanol (15 ml). To the solution was added potassium carbonate (0.4 g). The mixture was stirred for 2 hours at 60° C. To the reaction mixture was added ethyl acetate. The mixture was washed with water and dried over anhydrous sodium sulfate. The solvent was distilled off. The residue was purified by means of a silica gel column chromatography to give 3,5-trans-5-[4-[(1-tert-butoxycarbonylamino-1-methyl)ethyl]phenyl]-1-(4-biphenylmethyl)-7-chloro-2-oxo-1,2,3,5-tertrahydro-4,1-benzoxazepine-3-acetic acid ethyl ester (0.35 g) as a colorless oily product.

NMR(CDCl$_3$) δ: 1.255(3H,t,J=7.2 Hz), 1.349(9H,br), 1.608 (6H,s), 2.77(1H,dd,J=5.4,16.6 Hz),. 3.13(1H,dd,J=8.2, 16.6 Hz), 4.16(2H,q,J=7.2), 4.51(1H,dd,J=5.4,8.4 Hz), 4.70–5.0 (2H,m), 5.34–5.55(2H,m), 6.59(1H,s), 7.0–7.70(15H,m)

(7) In a mixture of tetrahydrofuran (3 ml) and methanol (10 ml) was dissolved 3,5-trans-5-[4-[(tert-butoxycarbonylamino-1-methyl)ethyl]phenyl]-1-(4-biphenylmethyl)-7-chloro-2-oxo-1,2,3,5-tetrahydro-4,1-benzoxazepine-3-acetic acid ethyl ester (0.35 g) produced in (6). To the solution was added 1N sodium hydroxide (3 ml), and the mixture was stirred for 40 minutes at 60° C. The reaction mixture was concentrated, which was neutralized with a 5% aqueous solution of potassium hydrogensulfate, followed by extraction with ethyl acetate (50 ml). The organic layer was washed with water and dried over anhydrous sodium sulfate. The solvent was distilled off, and the residue was purified by means of a silica gel column chromatography to give 3,5-trans-5-[4-[(tert-butoxycarbonylamino-1-methyl)ethyl]phenyl]-1-(4-biphenylmethyl)-7-chloro-2-oxo-1,2,3,5-tetrahydro-4,1-benzoxazepine-3-acetic acid as an amorphous solid product (0.14 g).

NMR(CDCl$_3$) δ: 1.30(9H,br), 1.599(6H,s), 2.70–3.10 (1H,m), 3.16(1H,dd,J=8.4,16.0 Hz), 4.47(1H,m), 4.80–5.10 (1H,m), 5.30–5.60(2H,m), 6.598(1H,s), 7.0–7.70(15H,m)

(8) In N,N-dimethylformamide (5 ml) were dissolved 3,5-trans-5-[4-[(tert-butoxycarbonylamino-1-methyl)ethyl] phenyl]-1-(4-biphenylmethyl)-7-chloro-2-oxo-4,1-benzoxazepine-3-acetic acid (0.14 g) produced in (7) and 2-fluorobenzylamine (32 mg). To the solution were added, while stirring at 0° C., diethyl cyanophosphate (80 mg) and triethylamine (0.06 g). The reaction mixture was stirred for 30 minutes at room temperature, to which were added ice water and ethyl acetate (30 ml). The mixture was subjected to extraction. The organic layer was washed with water and dried over anhydrous sodium sulfate. The solvent was distilled off, and the residue was purified by means of a silica gel column chromatography to give 3,5-trans-N-(2-fluorobenzyl)-5-[4-[(1-tert-butoxycarbonylamino-1-methyl) ethyl]phenyl]-1-(4-biphenylmethyl)-7-chloro-2-oxo-1,2,3,5-tetrahydro-4,1-benzoxazepine-3-acetamide as a colorless oily product (80 mg).

NMR(CDCl$_3$) δ: 1.342(9H,br), 1.604(6H,s), 2.73(1H,dd, J=6.0,14.4 Hz), 2.93(1H,dd,J=7.0,14.4 Hz), 4.35–5.0 (5H, m), 5.380(1H,s), 5.50(1H,d,J=14.4 Hz), 6.261(1H,t, J=6.0 Hz), 6.562(1H,d,J=1.8 Hz), 6.90–7.65(19H,m)

EXAMPLE 146

3,5-Trans-N-(2-fluorobenzyl)-5-[4-[(1-amino-1-methyl) ethyl]phenyl]-1-(4-biphenylmethyl)-7-chloro-2-oxo-1,2,3,5-tetrahydro-4,1-benzoxazepine-3-acetamide•monohydrochloride A solution of the compound (80 mg) produced in Example 145 in a 4N hydrogen chloride (ethyl acetate solution) (2 ml) was stirred for 2 hours at room temperature. The solvent was distilled off to leave the titled compound (70 mg) as a colorless amorphous solid product.

NMR(CDCl$_3$) δ: 1.489(6H,s), 2.73(1H,dd,J=6.2,14.5 Hz), 2.93(1H,dd,J=7.2,14.5 Hz), 4.35–4.63(3H,m), 4.84(1H,d, J=14.8 Hz), 5.379(1H,s), 5.49(1H,d,J=14.8 Hz), 6.35(1H, m), 6.566(1H,d,J=1.8 Hz), 6.95–7.62(19H,m)

EXAMPLE 147

3,5-Trans-N-(2-fluorobenzyl)-1-(4-benzyloxybenzyl)-5-[3-[(1-tert-butoxycarbonylamino-1-methyl)ethyl]phenyl]-7-chloro-2-oxo-1,2,3,5-tetrahydro-4,1-benzoxazepine-3-acetamide (1) To a methanol (20 ml) solution of 2-amino-α-[3-[(1-tert-butoxycarbonylamino-1-methyl)ethyl]phenyl]-5-chlorobenzyl alcohol (1.0 g) produced in Example 92 and 4-benzyloxy benzaldehyde (0.6 g) were added acetic acid (0.18 g) and sodium cyano borohydride (0.2 g). The mixture was stirred for 30 minutes at 60° C. The reaction mixture was concentrated, to which were added ethyl acetate (50 ml) and water (60 ml), followed by extraction. The organic layer was washed with water and dried over anhydrous sodium sulfate. The solvent was distilled off, and the residue was purified by means of a silica gel column chromatography to give 2-(4-benzyloxybenzylamino)-α-[3-[(1-tert-butoxycarbonylamino-1-methyl)-ethyl]phenyl]-5-chlorobenzyl alcohol (1.3 g) as a colorless oily product.

NMR(CDCl$_3$) δ: 1.356(9H,br), 1.562(6H,s), 4.187(2H,s), 4.90(1H,m), 5.04(2H,s), 5.807(H,s), 6.53(1H,d,J=8.8 Hz), 6.83–7.50(15H,m)

(2) To a mixture of an acetic acid ethyl ester (25 ml) solution of the compound (1.3 g) produced in (1) and 1N sodium hydroxide (10 ml) was added, while stirring at room temperature, fumaric chloride monoethyl ester (0.38 g). The reaction mixture was washed with water and dried over anhydrous sodium sulfate. The solvent was distilled off, and the residue was dissolved in ethanol (20 ml). To the solution was added potassium carbonate, which was stirred for 2 hours at 60° C. The reaction mixture was diluted with acetic acid ethyl ester (50 ml), which was washed with water and dried over anhydrous sodium sulfate. The solvent was distilled off, and the residue was purified by means of a silica gel column chromatography to give 3,5-cis-1-(4-benzyloxybenzyl)-5-[3-[(1-tert-butoxycarbonylamino-1-methyl)ethyl]phenyl]-7-chloro-2-oxo-1,2,3,5-tetrahydro-4,1-benzoxazepine-3-acetic acid ethyl ester (0.21 g) (A) and 3,5-trans-1-(4-benzyloxybenzyl)-5-[3-[(1-tert-butoxycarbonylamino-1-methyl)ethyl]phenyl]-7-chloro-2-oxo-1,2,3,5-tetrahydro-4,1-benzoxazepine-3-acetic acid ethyl ester (1.02 g) (B) as colorless oily products, respectively.

Cis (A)

NMR(CDCl$_3$) δ: 1.240(3H,t,J=7.2 Hz), 1.363(9H,br), 2.89 (1H,dd,J=5.8,16.7 Hz), 3.23(1H,dd,J=7.8,16.7 Hz), 3.53 (1H,d,J=15.6 Hz), 4.05–4.20(2H,m), 5.015(2H,s), 6.70–7.50 (16H,m)

Trans (B)

NMR(CDCl$_3$) δ: 1.247(3H,t,J=7.2 Hz), 1.315(9H,br), 2.73 (1H,dd,J=5.6,16.5 Hz), 3.12(1H,dd,J=8.6,16.5 Hz), 4.15 (2H,q,J=7.2 Hz), 4.43(1H,dd,J=5.4,8.6 Hz), 4.67(1H,d, J=13.8 Hz), 5.0(1H,m), 5.057(2H,d,J=1.4 Hz), 5.248(1H,s), 5.52(1H,d,J=13.8 Hz), 6.539(1H,s), 6.9–7.5(15H,m)

(3) The trans-compound (B) (1.02 g) produced in (2) was dissolved in a mixture of tetrahydrofuran (5 ml) and methanol (10 ml). To the solution was added 1N sodium hydroxide (8 ml), and the mixture was stirred for 40 minutes at 60° C. The reaction mixture was concentrated, which was neutralized with a 5% aqueous solution of potassium hydrogensulfate, followed by extraction with acetic acid ethyl ester (50 ml). The extract was washed with water and dried over anhydrous sodium sulfate. The solvent was distilled off, and the residue was purified by means of a silica gel column chromatography to give 3,5-trans-i-(4-benzyloxybenzyl)-5-[3-[(1-tert-butoxycarbonylamino-1-methyl)ethyl]phenyl]-7-chloro-2-oxo-1,2,3,5-tetrahydro-4,1-benzoxazepine-3-acetic acid (0.55 g) as a colorless amorphous solid product.

NMR(CDCl$_3$) δ: 1.24(9H,m), 2.70–3.20(2H,m), 1.509(3H, s), 1.586(3H,s), 4.42(1H,m), 4.70(1H,d,J=13.0 Hz), 5.05 (2H, s), 5.31(1H,m), 5.50(1H,d,J=13.0 Hz), 6.51(1H,br), 6.80–7.50(15H,m)

(4) In N,N-dimethylformamide (10 ml) were dissolved the compound produced in (3) (0.5 g) and 2-fluorobenzylamine-(0.12 g). To the solution were added, while stirring at 0° C., diethyl cyanophosphate (0.15 g) and triethylamine (0.11 g). The reaction mixture was stirred for 20 minutes at room temperature, which was poured into water (50 ml). The mixture was subjected to extraction with ethyl acetate (60 ml). The organic layer was washed with 5% potassium hydrogensulfate, which was then washed with water, followed by drying over anhydrous sodium sulfate. The solvent was distilled off, and the residue was purified by means of a silica gel column chromatography to give the titled compound, 3.5-trans-N-(2-fluorobenzyl)-1-(4-benzyloxybenzyl)-5-[1-[(1-tert-butoxycarbonylamino) ethyl]phenyl]-7-chloro-2-oxo1,2,3,5-tetrahydro-4,1-benzoxazepine-3-acetamide (0.49 g) as a colorless crystalline product. m.p.: 120–121° C.

NMR(CDCl$_3$) δ: 1.29(9H,br), 1.573(3H,s), 1.598(3H,s), 2.68(1H,dd,J=6.0,14.4 Hz), 2.93(1H,ad,J=7.0,14.4 Hz), 4.35–4.70(4H,m), 5.045(2H,d,J=2.2 Hz), 5.222(1H,s), 5.51 (1H,d,J=14.8 Hz), 6.29(1H,m), 6.53(1H,d,J=2.0 Hz), 6.80–7.50(19H,m)

EXAMPLE 148

3,5-Trans-N-(2-fluorobenzyl)-5-[1-[1-(1-amino)ethyl]phenyl]-1-(4-benzyloxybenzyl)-7-chloro-2-oxo-1,2,3,5-tetrahydro-4,1-benzoxazepine-3-acetamide•hydrochloride To the compound produced in Example 147 (80 mg) was added 4N hydrogen chloride (ethyl acetate solution) (3 ml). The mixture was stirred for 90 minutes at room temperature. The solvent was distilled off to leave the titled compound (48 mg) as an amorphous solid product.
NMR(CDCl$_3$) δ: 1.479(3H,s), 1.500(3H,s), 2.72(1H,dd, J=6.0,14.5 Hz), 2.93(1H,dd,J=7.2,14.5 hz), 4.35–4.60(3H, m), 4.734(1H,d,J=14.6 Hz), 5.013(2H,s), 5.358(1H,s), 5.378 (1H,d,J=14.6 Hz), 6.444(1H,m), 6.513(1H,d,J=2.0 Hz), 6.85–7.60(19H,m)

EXAMPLE 149

3,5-Trans-N-(2-fluorobenzyl)-5-[3-[(1-tert-butoxycarbonylamino-1-methyl)ethyl]phenyl]-7-chloro-1-(4-hydoxybenzyl)-2-oxo-1,2,3,5-tetrahydro-4,1-benzoxazepine-3-acetamide The compound produced in Example 147 (0.35 g) was dissolved in a mixture of ethyl acetate (12 ml) and methanol (2 ml). To the solution was added 10% palladium-carbon (50 mg). The mixture was stirred for 2 hours at room temperature under hydrogen atmosphere. The reaction mixture was subjected to filtration. From the filtrate, the solvent was distilled off. The residue was subjected to extraction with ethyl acetate (60 ml). The organic layer was washed with water and dried over anhydrous sodium sulfate. The solvent was distilled off to leave the titled compound (0.3 g) as a colorless amorphous solid product.
NMR(CDCl$_3$) δ: 1.075(9H,br), 1.434(3H,s), 1.557(3H,s), 2.67(1H,dd,J=6.4,14.4 Hz), 2.88(1H,dd,J=6.8,14.4 Hz), 4.30–4.90(5H,m), 5.196(1H,s), 5.88(1H,m), 6.10–6.30 (2H, m), 6.430(1H,s), 6.65–7.50(12H,m), 8.52(1H,m)

EXAMPLE 150

3,5-Trans-N-(2-fluorobenzyl)-5-[3-[(1-amino)ethyl]phenyl]-7-chloro-1-(4-hydoxybenzyl)-2-oxo-1,2,3,5-tetrahydro-4,1-benzoxazepine-3-acetamide•hydrochloride To the compound produced in Example 149 (0.25 g) was added 4N hydrogen chloride (ethyl acetate solution) (4 ml). The mixture was stirred for one hour at room temperature. The solvent was distilled off to leave the titled compound (0.23 g) as a colorless amorphous solid product.
NMR(CDCl$_3$) δ: 1.482(6H,s), 2.70–2.95(2H,m), 4.20–4.80 (5H,m), 5.613(1H,d,J=13.6 Hz), 6.41(1H,d,J=2.2 Hz), 6.35–7.45(14H,m)

EXAMPLE 151

3,5-Trans-N-(2-fluorobenzyl)-1-(4-biphenylmethyl)-5-[2-(2-tert-butoxycarbonylaminoethyl)phenyl]-7-chloro-2-oxo-1,2,3,5-tetrahydro-4,1-benzoxazepine-3-acetamide (1) In tetrahydrofuran (30 ml) were dissolved 2-bromo-N-tert-butoxycarbonyl-2-bromo-phenethylamino (1.2 g) and N-methyl-N-methyloxy 2-amino-5-chloro-benzamide (0.85 g), The solution was cooled to −78° C., to which was added dropwise, while stirring, a hexane solution of n-butyl lithium (1.6 mol/L) (12 ml) over 30 minutes. The mixture was subjected to extraction with ethyl acetate (60 ml). The organic layer was washed with water and dried over anhydrous sodium sulfate. The solvent was then distilled off. The residue was purified by means of a silica gel column chromatography to give 2-amino-2'-(2-tert-butoxycarbonylaminoethyl)-5-chloro-benzophenone as a yellow oily product (0.7 g).
NMR(CDCl$_3$) δ: 1.407(9H,s), 2.777(2H,t,J=7 Hz), 3.25–3.50 (2H,m), 4.93(1H,m), 6.41(2H,br), 6.68(1H,d,J= 8.8 Hz), 7.10–7.50(6H,m)

(2) The compound (0.7 g) produced in (1) was dissolved in methanol (20 ml). To the solution was added, while stirring at room temperature, sodium borohydride (0.2 g). The reaction mixture was stirred for 20 minutes, which was then diluted with water (50 ml), followed by extraction with ethyl acetate (60 ml). The organic layer was washed with water and dried over anhydrous sodium sulfate. The solvent was distilled off to leave 2-amino-α-[ (2'-(2-tert-butoxycarbonylaminomethyl)phenyl]-5-chloro-benzyl alcohol as a yellow needle-like crystalline product (0.54 g).
NMR(CDCl$_3$) δ: 1.342(9H,s), 2.60–3.50(4H,m), 4.75(1H, m), 6.08(1H,d,J=3.4 Hz), 6.62(1H,d,J=8.6 Hz), 7.00–7.40 (6H,m)

(3) In methanol (12 ml) were dissolved the compound produced in (2) (0.3 g) and 4-phenyl benzaldehyde (0.16 g). To the solution was added acetic acid (0.06 g). To the mixture was added, while stirring at room temperature, cyano sodium borohydride (0.07 g). The reaction mixture was stirred for 40 minutes at 60° C., which was diluted with water (40 ml), followed by extraction with ethyl acetate (60 ml). The organic layer was washed with water and dried over anhydrous sodium sulfate. The solvent was distilled off, and the residue was purified by means of a silica gel column chromatography to give 2-(4-biphenylmethyl)-α-[2'-(2-tert-butoxycarbonylaminoethyl)phenyl]-5-chloro-benzyl alcohol (0.4 g) as a colorless oily product.
NMR(CDCl$_3$) δ: 1.316(9H,s), 2.60–3.50(4H,m), 4.35(2H, br), 6.10(1H,br), 6.58(1H,d,J=8.6 Hz), 7.00–7.70(15H,m)

(4) The compound (0.4 g) produced in (3) was dissolved in ethyl acetate (18 ml), to which was added 1N sodium hydroxide (8 ml). To the mixture was added dropwise, while stirring at room temperature, an ethyl acetate (1 ml) solution of fumaric chloride monoethyl ester (0.13 g). The reaction mixture was stirred for 20 minutes, which was then washed with water and dried over anhydrous sodium sulfate. The solvent was distilled off, and the residue was dissolved in ethanol (20 ml). To the solution was added potassium carbonate (0.3 g). The mixture was stirred for 2 hours at 60° C. The reaction mixture was diluted with ethyl acetate (60 ml), which was washed with water and dried over anhydrous sodium sulfate. The solvent was distilled off, and the residue was purified by means of a silica gel column chromatography to give 3,5-trans-1-(4-biphenylmethyl)-5-[2-(2-tert-butoxycarbonylaminoethyl)phenyl]-7-chloro-2-oxo-1,2,3,5-tetrahydro-4,1-benzoxazepine-3-acetic acid ethyl ester as a colorless oily product (0.45 g).
NMR(CDCl$_3$) δ: 1.262(3H,t,J=7.2 Hz), 1.370(9H,s), 2.00–2.20(2H,m), 2.70–3.05(3H,m), 3.14(1H,dd,J=7.4,16.7 Hz), 4.00–4.30(2H,m), 4.55(1H,dd,J=5.8,7.3 Hz), 4.94(1H, d, J=15.2 Hz), 5.713(1H,s), 7.10–7.70(15H,m)

(5) The compound (0.45 g) produced in (4) was dissolved in a mixture of tetrahydrofuran (5 ml) and methanol (15 ml). To the solution was added 1N sodium hydroxide (5 ml). The mixture was stirred for 50 minutes at 60° C. The reaction mixture was diluted with water (40 ml), which was neutralized with a 5% aqueous solution of potassium hydrogensulfate, followed by extraction with ethyl acetate (60 ml). The organic layer was washed with water and dried over anhydrous sodium sulfate. The solvent was then distilled off. The residue was purified by means of a silica gel column chromatography to give 3,5-trans-1-(4-biphenylmethyl)-5-[2-(2-tert-butoxycarbonylaminoethylphenyl]-7-chloro-2-oxo-1,2,3,5-tetrahydro-4,1-benzoxazepine-3-acetic acid as a colorless amorphous solid product (0.21 g).
NMR(CDCl$_3$) δ: 1.384(9H,s), 2.00–2.40(2H,m), 2.70–3.20 (4H,m), 4.32(1H,m), 4.539(1H,t,J=6.6 Hz), 4.93 (1H,d,J=15 Hz), 5.56(1H,d,J=15 Hz), 5.67(1H,br), 6.548(1H,s), 7.10–7.80(15H,m)
(6) In N,N-dimethylformamide (6 ml) were dissolved the compound produced in (5) (0.15 g) and 2-fluorobenzylamine (35 mg). To the solution were added, while stirring at 0° C., cyano diethyl phosphate (50 mg) and triethylamine (38 mg). The reaction mixture was stirred for 20 minutes at room temperature, which was then diluted with water (30 ml), followed by extraction with ethyl acetate (50 ml). The organic layer was washed with water and dried over anhydrous sodium sulfate. The solvent was distilled off, and the residue was purified by means of a silica gel column chromatography to give the titled compound, 3,5-trans-N-(2-fluorobenzyl)-1-(4-biphenylmethyl)-5-(2-tert-butoxycarbonylaminophenyl)-7-chloro-2-oxo-1,2,3,5-tetrahydro-4,1-benzoxazepine-3-acetamide (0.16 g) as a colorless amorphous solid product.
NMR(CDCl$_3$) δ: 1.362(9H,s), 2.00–2.30(2H,m), 2.60–3.10 (4H,m), 4.32(1H,m), 4.501(2H,t,J=6.4 Hz), 4.92(1H,d, J=15.6 Hz), 5.55(1H,d,J=15.6 Hz), 5.68(1H,s), 6.26(1H,m), 6.515(1H,s), 7.00–7.70(19H,m)

EXAMPLE 152

3,5-Trans-N-(2-fluorobenzyl)-5-[2-(2-aminoethyl)phenyl]-1-(4-biphenylmethyl)-7-chloro-2-oxo-1,2,3,5-tetrahydro-4,1-benzoxazepine-3-acetamide To an ethyl acetate (2 ml) solution of the compound produced in Example 151 (0.12 g) was added 4N hydrogen chloride (ethyl acetate solution) (2 ml). The mixture was stirred for 2 hours at room temperature. The solvent was distilled off to leave the titled compound (92 mg) as a colorless amorphous solid product.
NMR(CDCl$_3$) δ: 1.95(2H,m), 2.35(2H,m), 2.74(1H,dd, J=6.2,14.6 Hz), 2.95(1H,dd,J=6.8,14.6 Hz), 4.35–4.62 (3H, m), 4.73(1H,d,J=14.6 Hz), 5.717(1H,d,J=14.6 Hz), 5.700 (1H,s), 6.37(1H,m), 6.488(1H,s), 6.90–7.70(19H,m)

EXAMPLE 153

3,5-Trans-N-(2-fluorobenzyl)-1-(N-benzyloxycarbonylpiperidin-4-yl-methyl)-5-(3-tert-butoxycarbonylaminomethylphenyl)-7-chloro-2-oxo-1,2,3,5-tetrahydro-4,1-benzoxazepine-3-acetamide (1) In methanol (20 ml) were dissolved 2-amino-5-chloro-α-(3-tert-butoxycarbonylaminomethylphenyl)benzyl alcohol produced in Example 1-(2) (1.0 g) and N-benzyloxycarbonyl piperidine-4-carbaldehyde (0.82 g), followed by addition of acetic acid (0.2 g). To the mixture was added, while stirring at room temperature, cyano sodium borohydride (0.2 g). The reaction mixture was stirred for 30 minutes at 60° C., which was then concentrated. To the concentrate was added water (40 ml), followed by extraction with ethyl acetate (60 ml). The organic layer was washed with water and dried over anhydrous sodium sulfate. The solvent was distilled off, and the residue was purified by means of a silica gel column chromatography to give 2-(N-benzyloxycarbonylpiperidin-4-yl-methyl)amino-5-chloro-α-(3-tert-butoxycarbonylaminomethylphenyl) benzyl alcohol (1.5 g) as a colorless oily product.
NMR(CDCl$_3$) δ: 1.446(9H,s), 1.30–2.00(4H,m), 2.50–3.00 (7H,m), 4.30(2H,m), 5.12(2H,s), 5.76(1H,s), 7.00–7.50 (12H,m)

(2) The compound (1.5 g) produced in (1) was dissolved in ethyl acetate (20 ml), to which was added 1N sodium hydroxide (10 ml). To the mixture was added dropwise, while stirring at room temperature, an ethyl acetate (1 ml) solution of fumaric chloride monoethyl ester (0.45 g). The reaction mixture was washed with water and dried over anhydrous sodium sulfate. The solvent was distilled off. The residue was dissolved in ethanol (20 ml), to which was added potassium carbonate (0.8 g). The mixture was diluted with ethyl acetate (80 ml), which was washed with water and dried over anhydrous sodium sulfate. The solvent was purified by means of a silica gel column chromatography to give 3,5-trans-1-(N-benzyloxycarbonylpiperidin-4-yl-methyl)-5-(3-tert-butoxycarbonylaminomethylphenyl)-7-chloro-2-oxo-1,2,3,5-tetrahydro-4,1-benzoxazepine-3-acetic acid ethyl ester as a colorless oily product (0.9 g).
NMR(CDCl$_3$) δ: 1.00–2.20(8H,m), 1.438(9H,s), 2.60–2.90 (3H,m), 3.08(1H,dd,J=8.2,16.0 Hz), 3.50–3.70(1H,m), 4.00–4.50(7H,m), 5.107(2H,s), 5.777(1H,s), 6.60(1H,d, J=2.4 Hz), 7.10–7.50(11H,m)
(3) To a solution of the compound produced in (2) (1.3 g) in a mixture of tetrahydrofuran (5 ml) and methanol (10 ml) was added 1N sodium hydroxide (5 ml). The mixture was stirred for 40 minutes at 50° C., which was diluted with water (50 ml) and neutralized with 5% potassium hydrogensulfate, followed by extraction with ethyl acetate (60 ml). The organic layer was washed with water and dried over anhydrous sodium sulfate. The solvent was distilled off, and the residue was dissolved in N,N-dimethylformamide (8 ml). To the solution was added 2-fluorobenzylamine (0.22 g). To the mixture were added, while stirring at 0° C., diethyl cyanophosphate (0.33 g) and triethylamine (0.21 g). The mixture was stirred for 30 minutes at room temperature, to which was then added water (40 ml), followed by extraction with ethyl acetate (60 ml). The organic layer was washed with water and dried over anhydrous sodium sulfate. The solvent was then distilled off, and the residue was purified by means of a silica gel column chromatography to give the titled compound, 3.5-trans-N-(2-fluorobenzyl)-1-(N-benzyloxycarbonylpiperidin-4-yl-methyl)-5-(3-tert-butoxycarbonylaminomethylphenyl)-7-chloro-2-oxo-1,2,3, 5-tetrahydro-4,1-benzoxazepine-3-acetamide (0.46 g) as a colorless amorphous solid product.
NMR(CDCl$_3$) δ: 1.10–2.10(5H,m), 1.433(9H,s), 2.60–3.00 (4H,m), 3.55(1H,m), 4.00–4.60(8H,m), 5.107(2H,s), 5.756 (1H,s), 6.23(1H,m), 6.58(1H,m), 6.90–7.50(15H,m)

EXAMPLE 154

3,5-Trans-N-(2-fluorobenzyl)-5-(3-aminomethylphenyl)-1-(N-benzylozycarbonylpiperridin-4-yl-methyl)-7-chloro-2-oxo-1,2,3,5-tetrahydro-4,1-benzoxazepine-3-acetamide•hydrochloride To an ethyl acetate (2 ml) solution of the compound produced in Example 153 (0.1 g) was added 4N hydrogen chloride (ethyl acetate solution) (1 ml). The mixture was stirred for 2 hours at room temperature. The solvent was distilled off to leave the titled compound (60 mg) as a colorless amorphous solid product.
NMR(CDCl$_3$) δ: 1.00–2.20(5H,m), 2.60–3.00(4H,m), 3.55 (1H,m), 3.887(2H,s), 4.05–4.60(6H,m), 5.109(2H,s), 5.768 (1H,s), 6.37(1H,m), 6.60(1H,d,J=2.4 Hz), 6.80–7.50(15H, m)

EXAMPLE 155

3,5-Trans-N-(2-fluorobenzyl)-1-(3-benzyloxybezyl)-5-(3-tert-butoxycarbonylaminomethylphenyl)-7-chloro-2-oxo-1,2,3,5-tetrahydro-4,1-benzoxazepine-3-acetamide (1) In methanol (15 ml) were dissolved 2-amino-5-chloro-α-(3-tert-butoxycarbonylaminomethylphenyl)benzyl alcohol produced in Example 1-(2) (0.6 g) and 3-benzyloxybenzaldehyde (0.38 g). To the solution was added acetic acid (0.12 g). To the mixture was added dropwise, while stirring at room temperature, cyano sodium borohydride (0.13 g). The reaction mixture was stirred for one hour at 60° C., to which was then added water (50 ml), followed by extraction with ethyl acetate (80 ml). The organic layer was washed with water and dried over anhydrous sodium sulfate. The solvent was distilled off, and the residue was purified by means of a silica gel column chromatography to give 2-(3-benzyloxybenzyl)-5-chloro-α-(3-tert-butoxycarbonylaminomethylphenyl)benzyl alcohol (0.9 g) as a colorless oily product.

NMR(CDCl$_3$) δ: 1.432(9H,s), 4.15–4.32(3H,m), 4.996(2H, s), 5.790(1H,s), 6.489(1H,d,J=8.6 Hz), 6.68–7.50(15H,m)

(2) To an ethyl acetate (20 ml) solution of the compound (0.9 g) produced in (1) was added 1N sodium hydroxide (10 ml). To the mixture was added, while stirring at room temperature, fumaric chloride monoethyl-ester (0.27 g). The mixture was stirred for 20 minutes, which was washed with water and dried over anhydrous sodium sulfate, followed by distilling off the solvent. The residue was dissolved in ethanol (20 ml), to which was added potassium carbonate (0.6 g). The mixture was stirred for 1.5 hour at 60° C. The reaction mixture was diluted with ethyl acetate (60 ml), which was washed with water and dried over anhydrous sodium sulfate. The solvent was distilled off, and the residue was purified by means of a silica gel column chromatography to give 3,5-trans-1-(3-benzyloxybenzyl)-5-(3-tert-butoxycarbofiylaminomethylphenyl)-7-chloro-2-oxo-1,2,3,5-tetrahydro-4,1-benzoxazepine-3-acetic acid ethyl ester (0.62 g) as a colorless oily product.

NMR(CDCl$_3$) δ: 1.261(3H,t,J=7.2 Hz), 1.457(9H,s), 2.77 (1H,dd,J=5.2,16.8 Hz), 3.16(1H,d,J=9.6,16.8 Hz), 4.13(2H, q,J=7.2 Hz), 4.49(1H,dd,J=5.2,8.6 Hz), 4.73–4.87(1H,m), 4.986(1H,d,J=15.2 Hz), 5.038(2H,s), 5.261(1H,d,J=15.2 Hz), 5.470(1H,s), 6.517(1H,d,J=2.2 Hz), 6.82–7.46(15H,m)

(3) The compound produced in (2) (0.6 g) was dissolved in a mixture of tetrahydrofuran (5 ml) and methanol (10 ml). To the solution was added 1N sodium hydroxide (4 ml). The mixture was stirred for one hour at 60° C. The reaction mixture was concentrated, which was diluted with water (50 ml). The solution was neutralized with 5% potassium hydrogensulfate, followed by extraction with ethyl acetate (60 ml). The organic layer was washed with water and dried over anhydrous sodium sulfate. The solvent was then distilled off. The residue was dissolved in N,N-dimethylformamide (10 ml), to which was added 2-fluorobenzylamine (0.11 g). To the mixture were added, while stirring at 0° C., diethyl cyanophosphate (0.15 g) and triethylamine (0.1 g). The reaction mixture was stirred for 20 minutes at room temperature, to which was added water (50 ml), followed by extraction with acetic acid ester. The organic layer was washed with water and dried over anhydrous sodium sulfate. The solvent was then distilled off, and the residue was purified by means of a silica gel column chromatography to give the titled compound, 3,5-trans-N-(2-fluorobenzyl)-1-(3-benzyloxybenzyl)-5-(3-tert-butoxycarbonylaminomethylphenyl)-7-chloro-2-oxo-1,2,3, 5-tetrahydro-4,1-benzoxazepine-3-acetamide (0.47 g) as a colorless amorphous solid product.

NMR(CDCl$_3$) δ: 1.450(9H,s), 2.82(1H,dd,J=5.6,14.5 Hz), 2.95(1H,dd,J=7.4,14.5 Hz), 4.254(2H,d,J=6.2 Hz), 4.33–4.60(3H,m), 4.80(1H,m), 4.884(1H,d,J=14.8 Hz), 5.011(2H, s), 5.317(1H,d,J=14.8 Hz), 5.438(1H,s), 6.244 (1H,m), 6.498(1H,d,J=2.2 Hz), 6.78–7.40(19H,m)

EXAMPLE 156

3,5-Trans-N-(2-fluorobenzyl)-5-(3-aminomethylphenyl)-1-(3-benzyloxybenzyl)-7-chloro-2-oxo-1,2,3,5-tetrahydro-4,1-benzoxazepine-3-acetamide•hydrochloride To the compound produced in Example 155 (80 mg) was added 4N hydrogen chloride (ethyl acetate solution) (3 ml). The mixture was stirred for one hour at room temperature. The solvent was distilled off to leave the titled compound (63 mg).

NMR(CDCl$_3$) δ: 2.73(1H,dd,J=5.8,14.5 Hz), 2.96(1H,dd, J=7.4,14.5 Hz), 3.65–3.95(2H,m), 4.839(1H,d,J=15.0 Hz), 5.002(2H,s), 5.301(1H,d,J=15.0 Hz), 5.472(1H,s), 6.408 (1H,t,J=6.0 Hz), 6.515(1H,d,J=2.2 Hz), 6.75–7.40(18H,m)

EXAMPLE 157

3,5-Trans-N-(2-fluorobenzyl)-5-(3-tert-butoxycarbonylaminomethylphenyl)-7-chloro-1-(3-hydroxybenzyl)-2-oxo-1,2,3,5-tetrahydro-4,1-benzoxazepine-3-acetamide In a mixture of ethyl acetate (10 ml) and methanol (3 ml) was dissolved 3,5-trans-N-(2-fluorobenzyl)-1-(3-benzyloxybenzyl)-5-(3-tert-butoxycarbonylaminomethylphenyl)-7-chloro-2-oxo-1,2,3, 5-tetrahydro-4,1-benzoxazepine-3-acetamide (0.35 g). To the solution was added 10% palladium-carbon (50 mg). The mixture was stirred for 1.5 hour under hydrogen atmosphere. The reaction mixture was subjected to filtration, and the filtrate was concentrated. The concentrate was dissolved in ethyl acetate (50 ml), which was washed with water and dried over anhydrous sodium sulfate. The solvent was distilled off to leave the titled compound (0.29 g) as a colorless amorphous solid product.

NMR(CDCl$_3$) δ: 1.438(9H,s), 2.67(1H,dd,J=6.0,14.6 Hz), 2.89(1H,dd,J=7.6,14.6 hz), 4.15–4.62(5H,m), 4.62–5.75 (3H,m), 6.315(1H,m), 6.471(1H,br), 6.53–7.45(14H,m)

EXAMPLE 158

3,5-Trans-N-(2-fluorobenzyl)-5-(3-aminomethylphenyl)-7-chloro-1-(3-hydroxybenzyl)-2-oxo-1,2,3,5-tetrahydro-4,1-benzoxazepine-3-acetamide•hydrochloride To the compound produced in Example 157 (0.24 g) was added 4N hydrogen chloride (ethyl acetate solution) (2 ml). The mixture was stirred for 1.5 hour at room temperature. The reaction mixture was concentrated to leave the titled compound (0.17 g) as a colorless amorphous solid product.

NMR(CDCl$_3$) δ: 2.66(1H,dd,J=6.2,14.6 Hz), 2.87(1H,dd, J=7.2,14.6 Hz), 3.45–3.95(4H,m), 4.28–4.58(3H,m), 4.643 (1H,d,J=14.4 Hz), 5.336(1H,s), 5.416(1H,d,J=14.4 Hz), 6.395(1H,m), 6.512(1H,d,J=1.2 Hz), 6.64–7.42(14H,m)

EXAMPLE 159

3,5-Trans-N-(2-fluorobenzyl)-5-(3-tert-butoxycarbonylaminomethylphenyl)-7-chloro-1-[2-(4-hydroxyphenyl)ethyl]-2-oxo-1,2,3,5-tetrahydro-4,1-benzoxazepine-3-acetamide (1) In methanol (15 ml) were dissolved 2-amino-5-chloro-α-(3-tert-butoxycarbonylaminomethylphenyl)benzyl alcohol produced in Example 1-(2) (0.5 g) and 4-benzyloxyphenylacetaldehyde (0.4 g). To the solution were added acetic acid (0.1 g) and, subsequently, cyano sodium hydride (0.11 g). The mixture was stirred for 40 minutes at 60° C. The reaction mixture was diluted with ethyl acetate (60 ml), which was washed with water and dried over anhydrous sodium sulfate. The solvent was distilled off to leave 2-[2-(4-benzyloxyphenyl)ethyl]amino-α-(3-tert-butoxycarbonylaminomethylphenyl)-5-chloro-benzyl alcohol (0.45 g) as a colorless oily product.

NMR(CDCl$_3$) δ: 1.443(9H,s), 2.70–2.85(2H,m), 3.20–3.40 (2H,m), 4.20–4.40(2H,m), 4.7–4.90(1H,m), 5.053(2H,s), 5.662(1H,s), 6.61(1H,d,J=8.4H), 6.85–7.55(15H,m)

(2) The compound (0.45 g) produced in (1) was dissolved in ethyl acetate (20 ml), to which was added 1N sodium hydroxide (10 ml). To the mixture was added dropwise, while stirring at room temperature, an ethyl acetate (1 ml) solution of fumaric chloride monoethyl ester (0.13 g). The reaction mixture was stirred for 20 minutes, which was washed with water and dried over anhydrous sodium sulfate. The solvent was distilled off, and the residue was purified by means of a silica gel column chromatography. The oily product thus produced was dissolved in ethanol (15 ml), to which was added potassium carbonate (0.3 g). The mixture was stirred for 1.5 hour at 60° C., which was diluted with ethyl acetate (50 ml). The solution was washed with water and dried over anhydrous sodium sulfate, followed by purification by means of a silica gel column chromatography to give 3,5-trans-1-[2-(4-benzyloxyphenyl)ethyl]-5-(3-tert-butoxycarbonylaminomethylphenyl)-7-chloro-2-oxo-1,2,3,5-tetrahydro-4,1-benzoxazepine-3-acetic acid ethyl ester (0.3 g) as a colorless oily product.

NMR(CDCl$_3$) δ: 1.247(3H,t,J=7.2 Hz), 1.437(9H,s), 2.65–3.15(4H,m), 3.75–4.00(1H,m), 4.13(2H,q,J=7.2 Hz), 4.28 (2H,br), 4.37(1H,dd,J=5.6,7.6 Hz), 4.55–4.75(1H,m), 4.95 (1H,m), 5.019(2H,s), 5.305(1H,s), 6.512(1H,d,J=2.4 Hz), 6.85–7.50(15H,m)

(3) The compound (0.3 g) was dissolved in a mixture of tetrahydrofuran (3 ml) and methanol (8 ml). To the solution was added 1N sodium hydroxide (2 ml). The mixture was stirred for 40 minutes at 60° C. The reaction mixture was concentrated, which was neutralized with 5% sodium hydrogensulfate, followed by extraction with ethyl acetate (50 ml). The organic layer was washed with water and dried over anhydrous sodium sulfate. The solvent was distilled off, and the residue was dissolved in N,N-dimethylformamide (6 ml). To the solution was added 2-fluorobenzylamine (40 mg). To the mixture were added, while stirring at 0° C., cyano diethyl phosphate (55 mg) and triethylamine (50 ml). The reaction mixture was stirred for 30 minutes at room temperature, to which was added water, followed by extraction with ethyl acetate (60 ml). The organic layer was washed with water and dried over anhydrous sodium sulfate. The solvent was distilled off, and the residue was purified by means of a silica gel column chromatography to give 3,5-trans-N-(2-fluorobenzyl)-1-[2-(4-benzyloxyphenyl) ethyl]-5-(3-tert-butoxycarbonylaminomethylphenyl)-7-chloro-2-oxo-1,2,3,5-tetrahydro-4,1-benzoxazepine-3-acetamide (0.26 g) as a colorless oily product.

NMR(CDCl$_3$) δ: 1.43(9H,s), 2.62–3.05(4H,m), 2.85–3.98 (1H,m), 4.27(2H,d,J=6.0 Hz), 4.36–4.75(4H,m), 4.85–5.00 (1H,m), 5.018(2H,s), 5.286(1H,s), 6.297(1H,m), 6.50(1H,d, J=2.4 Hz), 6.85–7.55(19H,m)

(4) The compound (0.26 g) produced in (3) was dissolved in a mixture of ethyl acetate (10 ml) and methanol (5 ml). To the solution was added 10% palladium-carbon (30 mg). The mixture was stirred for 2 hours under hydrogen atmosphere. The reaction mixture was subjected to filtration, and the filtrate was concentrated. The concentrate was dissolved in ethyl acetate (30 ml), which was washed with water and dried over anhydrous sodium sulfate. The solvent was distilled off to leave the titled compound, 3,5-trans-N-(2-fluorobenzyl)-5-(3-tert-butoxycarbonylaminomethylphenyl)-7-chloro-1-[2-(4-hydroxyphenyl)ethyl]-2-oxo-1,2,3,5-tetrahydro-4,1-benzoxazepine-3-acetamide (0.19 g) as a colorless amorphous solid product.

NMR(CDCl$_3$) δ: 1.436(9H,s), 2.55–3.28(4H,m), 3.75–4.02 (1H,m), 4.15–4.60(5H,m), 4.75–5.20(3H,m), 6.39(1H,d, J=2.2 Hz), 6.55–7.45(14H,m)

EXAMPLE 160

3,5-Trans-N-(2-fluorobenzyl)-5-(3-aminomethylphenyl)-7-chloro-1-[2-(4-hydroxyphenyl)ethyl]-2-oxo-1,2,3,5-tetrahydro-4,1-benzoxazepine-3-acetamide•hydrochloride To the compound (0.19 g) produced in Example 159 was added 4N hydrogen chloride (ethyl acetate solution) (3 ml). The mixture was stirred for 50 minutes at room temperature. The solvent was distilled off to leave the titled compound (0.13 g) as a colorless amorphous solid product.

NMR(CDCl$_3$) δ: 2.55–3.30(4H,m), 3.70–4.60(6H,m), 4.639 (1H,s), 4.86–5.05(1H,m), 6.44(1H,d,J=2.6 Hz), 6.42–6.75 (14H,m)

EXAMPLE 161

3,5-Trans-N-(2-fluorobenzyl)-5-(3-tert-butoxycarbonylaminomethylphenyl)-7-chloro-1-(4-methoxybenzyl)-2-oxo-1,2,3,5-tetrahydro-4,1-benzoxazepine-3-acetamide A mixture of 3,5-trans-N-(2-fluorobenzyl) 5-(3-tert-butoxycarbonylaminomethylphenyl)-7-chloro-1-(4-hydroxybenzyl)-2-oxo-1,2,3,5-tetrahydro-4,1-benzoxazepine-3-acetamide produced in Example 101 (0.12 g), methyl iodide (0.15 g), potassium.carbonate (0.1 g) and N,N-dimethylformamide (4 ml) was stirred for 2.5 hours at 60° C. To the reaction mixture was added water, which was subjected to extraction with ethyl acetate (40 ml). The organic layer was washed with a 5% aqueous solution of potassium hydrogensulfate, which was washed with water and dried over anhydrous sodium sulfate. The solvent was distilled off to leave the titled compound (0.105 g) as a colorless amorphous solid product.

NMR(CDCl$_3$) δ: 1.445(9H,s), 2.71(1H,dd,J=6.2,14.6 Hz), 2.93(1H,dd,J=7.4,14.6 Hz), 3.792(3H,s), 4.22–4.63(5H,m), 4.699(1H,d,J=14.4 Hz), 4.76–4.95(1H,m), 5.300(1H,s), 5.435(1H,d,J=14.4 Hz), 6.18–6.33(1H,m), 6.476(1H,d, J=2.2 Hz), 6.78–7.45(14H,m)

EXAMPLE 162

3,5-Trans-N-(2-fluorobenzyl)-5-(3-aminomethylphenyl)-7-chloro-1-(4-methoxybenzyl)-2-oxo-1,2,3,5-tetrahydro-4,1-benzoxazepine-3-acetamide•hydrochloride The compound produced in Example 161 (70 mg) was dissolved in 4N hydrogen chloride (ethyl acetate solution) (2 ml). The solution was stirred for 40 minutes at room temperature. The solvent was distilled off to leave the titled compound (65 mg) as a colorless amorphous solid product.

NMR(CDCl$_3$) δ: 2.73(1H,dd,J=6.0,14.4 Hz), 2.93(1H,dd, J=7.2,14.4 Hz), 3.781(3H,s), 3.831(2H,br), 4.36–4.62 (3H, m), 4.678(1H,d,J=14.4 Hz), 5.307(1H,s), 5.445(1H,d, J=14.4 Hz), 6.44(1H,m), 6.482(1H,d,J=2.2 Hz), 6.78–7.42 (14H,m)

EXAMPLE 163

3,5-Trans-N-(2-fluorobenzyl)-5-[3-[(1-tert-butoxycarbonylamino-1-methyl)ethyl]phenyl]-7-chloro-1-(4-methoxybenzyl)-2-oxo-1,2,3,5-tetrahydro-4,1-benzoxazepine-3-acetamide (1) In methanol (30 ml) were dissolved 2-amino-α-[3'-[(1-tert-butoxycarbonylamino-1-methyl(ethyl]phenyl]-5-chlorobenzyl alcohol (2.0 g) produced in Example 92, 4-methoxybenzaldehyde (0.8 g) and acetic acid (0.37 g). To the solution was added cyano sodium borohydride (0.38 g), and the mixture was stirred for 1.5 hour at 60° C. The reaction mixture was concentrated, to which was added water, followed by extraction with ethyl acetate (80 ml). The organic layer was washed with water and dried over anhydrous sodium sulfate. The solvent was distilled off to leave,-2-(4-methoxybenzyl)amino-α-[3'-[(1-tert-butoxycarbonylamino-1-methyl)ethyl]phenyl]-5-chlorobenzyl alcohol (2.6 g) as a yellow oily product.

NMR(CDCl$_3$) δ: 1.35(9H,br), 1.577(6H,s), 3.784(3H,s), 4.183(2H,s), 5.798(1H,s), 6.5–7.5(11H,m)

(2) The compound (2.6 g) produced in (1) was dissolved in ethyl acetate (50 ml). To the solution was added 1N sodium hydride (15 ml). To the mixture was added dropwise, while stirring at room temperature, fumaric chloride monoethyl ester (0.85 g). The mixture was stirred for 10 minutes, and, then, the organic layer was separated, washed with water and dried over anhydrous sodium sulfate. The solvent was distilled off, and the residue was dissolved in ethanol (50 ml). To the solution was added potassium carbonate (20 g), and the mixture was stirred for 2 hours at 70° C. The reaction mixture was concentrated, which was dissolved in ethyl acetate (80 ml). The solution was washed with water and dried over anhydrous sodium sulfate. The solvent was distilled off to leave 3,5-cis- and 3,5-trans-5-[3-[1-tert-butoxycarbonylamino-1-methyl)ethyl]phenyl]-7-chloro-1-(4-methoxybenzyl)-2-oxo-1,2,3,5-tetrahydro-4,1-benzoxazepine-3-acetic acid ethyl ester (2.9 g) as an oily product.

NMR(CDCl$_3$) δ: 1.260(3H,t,J=7.2 Hz), 1.0–1.45(9H,m), 1.584(4H,s), 1.619(2H,s), 2.65–3.32(2H,m), 3.795(2H,s), 3.815(1H,s), 4.14(2H,dq), 4.43(⅔H,dd,J=5.6,8.3 Hz), 5.18 (⅔H,s), 5.534(⅔H,d,J=14.2 Hz), 5.885(⅓H,s), 6.75–7.50 (10⅓H,m)

(3) The compound (2.9 g) produced in (2) was dissolved in a mixture of tetrahydrofuran (20 ml) and methanol (30 ml). To the solution was added 1N sodium hydroxide (10 ml). The mixture was stirred for 40 minutes at 60° C. The reaction mixture was concentrated, which was neutralized with 5% potassium hydrogensulfate, followed by extraction with ethyl acetate (60 ml). The organic layer was washed with water and dried over anhydrous sodium sulfate. The solvent was distilled off, and the residue was purified by means of a silica gel column chromatography to give 3,5-trans-5-[3-[(1-tert-butoxycarbonylaminomethyl)ethyl] phenyl]-7-chloro-1-(4-methoxybenzyl)-2-oxo-1,2,3,5-tetrahydro-4,1-benzoxazepine-3-acetic acid (0.85 g) as a colorless amorphous solid product.

NMR(CDCl3) δ: 1.05–1.40(9H,m), 1.509(3H,s), 1.601(3H, s), 2.75–3.30(2H,m), 3.790(3H,s), 4.30–4.80(3H,m), 5.0–5.60(2H,m), 6.509(1H,s), 6.70–7.40(1H,m)

(4) In N,N-dimethylformamide (10 ml) were dissolved the compound produced in (3) (1.5 g) and 2-fluorobenzylamine (0.37 g). To the solution was added, while stirring at 0° C., cyano diethyl phosphate (0.5 g). To the mixture was further added triethylamine (0.35 g). The reaction mixture was stirred for 30 minutes at room temperature. To the reaction mixture was then added water, followed by extraction with ethyl acetate (100 ml). The organic layer was washed with water and dried over anhydrous sodium sulfate. The solvent was distilled off, and residue was purified by means of a silica gel column chromatography to give the titled compound, 3,5-trans-N-(2-fluorobenzyl)-5-[3-[(1-tert-butoxycarbonylamino-1-methyl)ethyl]phenyl]-7-chloro-1-(4-methoxybenzyl)-2-oxo-1,2,3,5-tetrahydro-4,1-benzoxazepine-3-acetamide (1.3 g) as a colorless amorphous solid product.

NMR(CDCl$_3$) δ: 1.29(9H,br), 1.478(3H,s), 1.604(3H,s), 2.69(1H,dd,J=6.0,14.4 Hz), 2.93(1H,dd,J=7.0,14.4 Hz), 3.791(3H,s), 4.36–4.70(4H,m), 4.85–5.10(1H,m), 5.15(1H, m), 5.537(1H,d,J=14.0 Hz), 6.301(1H,m), 6.513(1H,d, J=1.8 Hz), 6.75–7.42(14H,m)

EXAMPLE 164

3,5-Trans-N-(2-fluorobenzyl)-5-[3-[(1-amino-1-methyl) ethyl]phenyl]-7-chloro-1-(4-methoxybenzyl)-2-oxo-1,2, 3,5-tetrahydro-4,1-benzoxazepine-3-acetamide•hydrochloride 4N Hydrogen chloride (ethyl acetate solution) (6 ml) was added to 3,5-trans-N-(fluorobenzyl)-5-[3-[(1-tert-butoxycarbonylamino-1-methyl)ethyl]phenyl]-7-chloro-1-(4-methoxybenzyl)2-oxo-1,2,3,5-tetrahydro-4,1-benzoxazepine-3-acetamide produced in Example 163 (1.2 g). The mixture was stirred for 1.5 hour at room temperature. The solvent was distilled off. To the residue was added ethyl acetate (50 ml). The solvent was again distilled off to leave the titled compound (1.15 g) as a colorless amorphous solid product.

NMR(CDCl$_3$) δ: 1.452(3H,s), 1.468(3H,s), 2.73(1H,dd, J=6.0,14.4 Hz), 2.93(1H,dd,J=7.0,14.4 Hz), 3.773(3H,s), 4.35–4.62(3H,m), 4.673(1H,d,J=14.4 Hz), 5.293(1H,s), 5.458(1H,d,J=14.4 Hz), 6.335(1H,m), 6.510(1H,d,J=2.0 Hz), 6.75–7.55(14H,m)

EXAMPLE 165

3,5-Trans-N-(2-fluorobenzyl)-5-(3-tert-butoxycarbonylaminomethylphenyl)-1-(4-biphenylmethyl)-7-hydroxy-2-oxo-1,2,3,5-tetrahydro-4, 1-benzoxazepine-3-acetamide (1) In ethyl acetate (30 ml) were dissolved N-methyl-N-methyloxy-2-benzyloxycarbonylamino-5-hydroxybenzamide produced in Example 7-(1) (2.5 g) and 3,4-dihydro-2H-pyran (0.8 g). To the solution was added p-toluenesulfonic acid (10 mg). The mixture was stirred for 2 hours at room temperature. The reaction mixture was washed with a saturated aqueous solution of sodium hydrogencarbonate, which was then dried over anhydrous sodium sulfate. The solvent was distilled off, and the residue was purified by means of a silica gel column chromatography to give N-methyl-N-methyloxy-2-benzyloxycarbonylamino-5-(tetrahydcopyran-2-yl)oxy-benzamide (2.0 g) as a colorless oily product.

NMR(CDCl$_3$) δ: 1.40–2.10(6H,m), 3.338(3H,s), 3.557(3H, s), 3.45–3.95(2H,m), 5.176(2H,s), 5.36(1H,m), 7.08–7.45 (7H,m), 7.90–8.40(2H,m)

(2) The compound (2.0 g) produced in (1) was dissolved in a mixture of ethyl acetate (15 ml) and methanol (15 ml). To the solution was added 10% palladium-carbon (0.3 g). The mixture was stirred for 1.5 hour at room temperature in hydrogen streams. The reaction mixture was subjected to filtration. From the filtrate, the solvent was distilled off to leave N-methyl-N-methyloxy 2-amino-5-(tetrahydropyran-2-yl)oxy-benzamide (1.5 g).

NMR(CDCl$_3$) δ: 1.40–2.10(6H,m), 3.337(3H,s), 3.50–4.05 (2H,m), 3.617(3H,s), 5.23(1H,m), 6.60–7.15(3H,m)

(3) In tetrahydrofuran (30 ml) were dissolved N-methyl-N-methyloxy- 2-amino-5-(tetrahydropyran-2-yl) oxybenzamide produced in (2) (1.4 g) and N-tert-butoxycarbonyl-3-bromo-benzylamine (1.45 g). The solution was cooled to -78° C. To the solution was added dropwise, while stirring, n-butyl lithium (1.6 mol, hexane solution) (15.6 ml) over 40 minutes. To the reaction mixture was added water (50 ml), followed by extraction with ethyl acetate (70 ml). The organic layer was washed with waster and dried over anhydrous sodium sulfate. The solvent was distilled off. The residue was purified by means of a silica gel column chromatography to give 2-amino-3'-tert-butoxycarbonylaminomethyl-5-(tetrapyran-2-yl)oxy-benzophenone (0.8 g) as a yellow oily product.

NMR(CDCl$_3$) δ: 1.459(9H,s), 1.50–2.05(6H,m), 3.45–3.58 (1H,m), 3.82–3.94(1H,m), 4.34–4.43(2H,m), 4.95–5.10(1H, m), 5.153(1H,t,J=3.4 Hz), 5.80(2H,m), 6.703(1H,d,J=9.0 Hz), 7.07–7.62(6H,m)

(4) The compound (0.8 g) produced in (3) was dissolved in methanol (30 ml). To the solution was added sodium borohydride (0.2 g), and the mixtuke was stirred for 30 minutes at room temperature. The reaction mixture was concentrated, to which was added water, followed by extraction with ethyl acetate (50 ml). The organic layer was washed with water and dried over anhydrous sodium sulfate. The solvent was distilled off to leave 2-amino-α-(3'-tert-butoxycarbonylaminomethylphenyl)-5-(tetrahydropyran-2-yl)oxy-benzyl alcohol (0.8 g) as a colorless oily product.

NMR(CDCl$_3$) δ: 1.451(9H,s), 1.52–2.10(6H,m), 3.48–3.63 (1H,m), 3.85–4.0(1H,m), 4.305(2H,d,J=5.6 Hz), 4.75–4.95 (1H,m), 5.20–5.30(1H,m), 5.792(1H,s), 6.618(1H,d, J=8.0 Hz), 6.80–7.40(6H,m)

(5) In methanol (20 ml) were dissolved the compound produced in (4) and 4-phenyl benzaldehyde (0.38 g). To the solution was added acetic acid (0.13 g). The mixture was stirred for 5 minutes, followed by addition of cyano sodium borohydride (0.14 g). The reaction mixture was stirred for 30 minutes at 60° C., to which was added ethyl acetate (50 ml). The mixture was washed with water and dried over anhydrous sodium sulfate. The solvent was distilled off, and the residue was purified by means of a silica gel column chromatography to give 2-(4-biphenylmethyl)amino-α-(3-tert-butoxycarbonylaminomethylphenyl)-5-(tetrahydropyran-2-yl)oxybenzyl alcohol (0.7 g) as a yellow oily product.

NMR(CDCl$_3$) δ: 1.434(9H,s), 1.50–2.15(6H,m), 3.45–3.65 (1H,m), 3.86–4.0(1H,m), 4.257(2H,s), 4.299(2H,d, J=5.8 Hz), 4.70–4.90(1H,m), 5.856(1H,s), 6.621(1H,d, J=8.6 Hz), 6.83–7.65(15H,m)

(6) The compound (0.7 g) produced in (5) was dissolved in ethyl acetate (25 ml), to which was added 1N sodium hydroxide (8 ml). To the mixture was added dropwise, while stirring at room temperature, an ethyl acetate (1 ml) solution of fumaric chloride monoethyl ester (0.2 g). The reaction mixture was washed with water and dried over anhydrous sodium sulfate. The solvent was then distilled off. The residue was dissolved in ethanol (20 ml), to which was added potassium carbonate (0.05 g). The mixture was stirred for 50 minutes at 60° C. The reaction mixture was concentrated, to which was added ethyl acetate (60 ml). The mixture was washed with water and dried over anhydrous sodium sulfate, followed by distilling off the solvent. The residue was purified by means of a silica gel column chromatography to give 3,5-trans-5-(3-tert-butoxycarbonylaminomethylphenyl)-1-(4-biphenylmethyl)-2-oxo-1,2,3,5-tetrahydro-7-(tetrahydropyran-2-yl)oxy-4,1-benzoxazepine-3-acetic acid ethyl ester (0.6 g) as a colorless oily product.

NMR(CDCl$_3$) δ: 1.249(3H,t,J=7.2 Hz), 1.441(9H,s), 1.50–2.05(6H,m), 2.68–2.86(1H,m), 3.13(1H,dd,J=8.0,16.9 Hz), 3.37–3.56(1H,m), 3.67–3.86(1H,m), 4.06–4.27(4H,m), 4.53 (1H,dd,J=5.4,8.4 Hz), 4.70–4.86(1H,m), 4.913(1H,d, J=14.6 Hz), 5.07–5.23(1H,m), 5.35–5.50(2H,m), 6.15–6.23(1H,m), 6.90–7.62(15H,m)

(7) The compound (0.6 g) produced in (6) was dissolved in a mixture of tetrahydrofuran (5 ml) and methanol (10 ml). To the solution was added 1N sodium hydroxide (5 ml). The mixture was stirred for 30 minutes at 60° C. The reaction mixture was concentrated, which was neutralized with 5% potassium hydrogensulfate, followed by extraction with ethyl acetate (50 ml). The organic layer was washed with water and dried over over anhydrous sodium sulfate. The solvent was distilled off, and the residue was purified by means of a silica gel column chromatography to give 3,5-trans-5-(3-tert-butoxycarbonylaminomethylphenyl)-1-(4-biphenylmethyl)-2-oxo-1, 2,3,5-tetrahydro-7-(tetrahydropyran-2-yl)oxy-4,1-benzoxazepine-3-acetic acid (0.48 g) as a colorless amorphous solid product.

NMR(CDCl$_3$) δ: 1.436(9H,s), 1.50–2.05(6H,m), 2.75–3.25 (2H,m), 3.35–3.90(2H,m), 4.15–4.30(2H,m), 4.40–4.55 (1H,m), 4.70–5.55(6H,m), 6.168(1H,br), 6.80–7.65(15H,m)

(8) In N,N-dimethylformamide (8 ml) were dissolved the compound produced in (7) (0.43 g) and 2-luorobenzylamine (0.95 g). To the solution was added, while stirring at 0° C., cyano diethyl phosphate (0.12 g) and, subsequently, triethylamine (0.1 ml). The reaction mixture was stirred for 30 minutes at room temperature, to which was added water, followed by extraction with ethyl acetate (60 ml). The organic layer was washed with a 5% aqueous solution of sodium hydrogensulfate, a saturated aqueous solution of sodium hydrogencarbonate and a saturated aqueous saline solution, successively, followed by drying over anhydrous sodium sulfate. The solvent was distilled off, and the residue was purified by means of a silica gel column chromatography to give 3,5-trans-N-(2-fluorobenzyl) 5-(3-(tert-butoxycarbonylaminomethylphenyl)-1-(4-biphenylmethyl)-2-oxo-1,2,3,5-tetrahydro-7-(tetrahydropyran-2-yl)oxy-4,1-benzoxazepine-3-acetamide (0.4 g) as a colorless amorphous solid product.

NMR(CDCl$_3$) δ: 1.435(9H,s), 1.48–2.05(6H,m), 2.62–2.78 (1H,m), 2.94(1H,dd,J=7.4,17.0 Hz), 3.35–3.95(2H,m), 4.05–4.23(2H,m), 4.35–4.63(3H,m), 4.65–4.80(1H,m), 4.86 (1H,d,J=14.4 Hz), 5.07–5.52(3H,m), 6.13–6.22(1H,m), 6.32–6.46(1H,m), 6.85–7.63(19H,m)

(9) The compound (0.4 g) produced in (8) was dissolved in methanol (20 ml). To the solution was added a 10% aqueous solution of oxalic acid (2 ml). The mixture was stirred for 40 minutes at 50–60° C. The reaction mixture was concentrated, to which was added water, followed by extraction with ethyl acetate (60 ml). The organic layer was washed with water and dried over anhydrous sodium sulfate. The solvent was distilled off to leave the titled compound, 3,5-trans-N-(2-fluorobenzyl)-1-(4-biphenylmethyl)-5-(3-tert-butoxycarbonylaminomethylphenyl)-7-hydroxy-2-oxo-1,2,3,5-tetrahydro-4,1-benzoxazepine-3-acetamide (0.3 g) as a colorless crystalline product m.p.: 206–207° C.

NMR(CDCl$_3$) δ: 1.397(9H,s), 2.68(1H,dd,J=6.2,14.6 Hz), 2.93(1H,dd,J=7.8,14.6 Hz), 4.124(2H,d,J=7.0 Hz), 4.33–4.58(3H,m), 4.738(1H,d,J=14.8 Hz), 4.80(1H,m), 5.231 (1H,s), 5.450(1H,d,J=14.8 Hz), 5.901(1H,d,J=2.8 Hz), 6.551(1H,m), 6.78–7.68(19H,m)

EXAMPLE 166

3,5-Trans-N-(2-fluorobenzyl)-5-(3-aminomethylphenyl)-1-(4-biphenylmethyl)-7-hydroxy-2-oxo-1,2,3,5-tetrahydro-4,1-benzoxazepine-3-acetamide•hydrochloride 4N Hydrogen chloride (ethyl acetate solution) (2 ml) was added to 3,5-trans-N-(2-fluorobenzyl)-5-(3-tert-butoxycarbonylaminomethylphenyl)-1-(4-biphenylmethyl)-7-hydroxy-2-oxo-1,2,3,5-tetrahydro-4,1-benzoxazepine-3-acetamide (0.15 g). The mixture was stirred for 30 minutes at room temperature. The solvent was distilled off to leave the titled compound (0.14 g) as a colorless crystalline product. m.p.: 220–222° C.

NMR(CDCl$_3$) δ: 2.72(1H,dd,J=5.8,14.3 Hz), 2.82–3.52 (5H, m), 4.33–4.67(3H,m), 4.737(1H,d,J=14.2 Hz), 5.256 (1H,s), 5.504(1H,d,J=14.2 Hz), 5.854(1H,d,J=2.4 Hz), 6.48–6.60 (1H,m), 6.75–7.65(19H,m)

EXAMPLE 167

3,5-Trans-N-(2-fluorobenzyl)-1-(4-biphenylmethyl)-5-(3-tert-butoxycarbonyaminomethylphenyl)-7-(3-chloropropyloxy)-2-oxo-1,2,3,5-tetrahydro-4,1-benzoxazepine-3-acetamide In N,N-dimethylformamide (5 ml) were dissolved 3,5-trans-N-(2-fluorobenzyl)-5-(3-tert-2 butoxycarbonylaminomethylphenyl)-1-(4-biphenylmethyl)-7-hydroxy-2-oxo-1,2,3,5-tetrahydro-4,1-benzoxazepine-2-acetamide produced in Example 165 (0.2 g) and 1-bromo-3-chloropropane (0.1 g). To the solution was added potassium carbonate (0.1 g). The mixture was stirred for 40 minutes at 70° C. The reaction mixture was diluted with ethyl acetate (50 ml). The organic layer was washed with water and dried over anhydrous sodium sulfate. The solvent was distilled off, and the residue was purified by means of a silica gel column chromatography to give the titled compound (0.16 g) as a colorless oily product.
NMR(CDCl$_3$) δ: 1.423(9H,s), 2.05–2.18(2H,m), 2.713(1H, dd,J=6.0,14.4 Hz), 2.934(1H,dd,J=7.2,14.4 Hz), 3.648(1H, t,J=6.4 Hz), 3.78–4.02(2H,m), 4.05–4.02(2H,m), 4.36– 4.62 (3H,m), 4.63–4.76(1H,m), 4.808(1H,d,J=14.2 Hz), 5.312 (1H,s), 5.48(1H,d,J=14.2 Hz), 6.016(1H,d,J=2.8 Hz), 4.35–4.77(1H,M), 6.87–7.62(19H,m)

EXAMPLE 168

3,5-Trans-N-(2-fluorobenzyl)-5-(3-aminomethylphenyl)-1-(4-biphenylmethyl)-7-(3-chloropropyloxy)-2-oxo-1,2,3,5-tetrahydro-4,1-benzoxazepine-3-acetamide•hydrochloride 4N Hydrogen chloride (ethyl acetate solution) (1 ml) was added to 3,5-trans-N-(2-fluorobenzyl)-5-(3-tert-butoxycarbonylaminomethylphenyl)-1-(4-biphenylmethyl)-7-(3-chloropropyloxy)-2-oxo-1,2,3,5-tetrahydro-4,1-benzoxazepine-3-acetamide produced in Example 167 (70 mg). The mixture was stirred for 40 minutes at room temperature. The solvent was distilled off to leave the titled compound (45 mg) as a colorless amorphous solid product.
NMR(CDCl$_3$) δ: 2.05–2.18(2H,m), 2.22–2.66(2H,m), 2.724 (1H,dd,J=6.0,14.4 Hz), 2.930(1H,dd,J=7.0,14.4 Hz), 3.641 (2H,t,J=6.4 Hz), 3.68–3.97(4H,m), 4.35–4.63(3H,m), 4.799 (1H,d,J=14.6 Hz), 5.331(1H,s), 5.486(1H,d,J=14.6 Hz), 6.039(1H,d,J=2.8 Hz), 6.45–6.56(1H,m), 6.87–7.62(19H,m)

EXAMPLE 169

3,5-Trans-N-(2-fluorobenzyl)-1-(4-biphenylmethyl)-5-(3-tert-butoxycarbonyaminomethylphenyl)-7-benzoylmethyloxy-2-oxo-1,2,3,5-tetrahydro-4,1-benzoxazepine-3-acetamide An N,N-dimethylformamide (4 ml) solution of 3,5-trans-N-(2-fluorobenzyl)-5-(3-tert-butoxycarbonylaminomethylphenyl)-1-(4-biphenylmethyl)-7-hydroxy-2-oxo-1,2,3,5-tetrahydro-4,1-benzoxazepine-3-acetamide produced in Example 165 (0.1 g), phenacyl bromide (0.03 g) and potassium carbonate (0.04 g) was stirred for 2 hours at 70° C. The reaction mixture was diluted with water, which was subjected to extraction with ethyl acetate (40 ml). The organic layer was washed with water and dried over anhydrous sodium sulfate. The solvent was purified by means of a silica gel column chromatography to give the titled compound (0.105 g) as a colorless amorphous solid product.

NMR(CDCl$_3$) δ: 1.433(9H,s), 2.707(1H,dd,J=5.8,14.2 Hz), 2.941(1H,dd,J=7.4,14.2 Hz), 4.126(2H,d,J=6.2 Hz), 4.37–4.63(3H,m), 4.65–4.82(1H,m), 4.888(1H,d,J=14.8 Hz), 5.085(2H,s), 5.346(1H,s), 5.387(1H,d,J=14.8 Hz), 6.012(1H,d,J=3.0 Hz), 6.27–6.40(1H,m), 6.85–7.94(24H,m)

EXAMPLE 170

3,5-Trans-N-(2-fluorobenzyl)-5-(3-aminomethylphenyl)-7benzoylmethyloxy-1-(4-biphenylmethyl)-2-oxo-1,2,3,5-tetrahydro-4,1-benzoxazepine-3-acetamide•hydrochloride In ethyl acetate (1 ml) was dissolved 3,5-trans-N-(2-fluorobenzyl)-7-benzoylmethyloxy-1-(4-biphenylmethyl)-5-(3-tert-butoxycarbonylaminomethylphenyl)-2-oxo-1,2,3,5-tetrahydro-4,1-benzoxazepine-3-acetamide produced in Example 169 (70 mg). To the solution was added 4N hydrogen chloride (ethyl acetate solution) (1 ml). The mixture was stirred for 40 minutes at room temperature. The solvent was distilled off to leave the titled compound (65 mg) as a colorless amorphous solid product.
NMR(CDCl$_3$) δ: 1.899(2H,br), 2.721(1H,dd,J=6.0,14.3 Hz), 2.937(1H,dd,J=7.4,14.3 Hz), 0.656(2H,s), 4.35–4.62 (3H, m), 4.859(1H,d,J=14.4 Hz), 5.091(2H,s), 5.350(1H,s), 5.414 (1H,d,J=14.4 Hz), 6.058(1H,d,J=2.8 Hz), 6.35–6.52 (1H,m), 6.85–7.92(24H,m)

EXAMPLE 171

3,5-Trans-N-(2-fluorobenzyl)-5-(3-tert-butoxycarbonyaminomethylphenyl)-1-(4-biphenylmethy)-7-(2-hydroxyethyloxy)-2-oxo-1,2,3,5-tetrahydro-4,1 -benzoxazepine-3-acetamide A mixture of 3,5-trans-N-(2-fluorobenzyl)-5-(3-tert-butoxycarbonylaminomethylphenyl)-1-(4-biphenylmethyl)-7-hydroxy-2-oxo-1,2,3,5-tetrahydro-4,1-benzoxazepine-3-acetamide produced in Example 165 (50 mg), 2-bromoethyl acetate (60 mg), potassium carbonate (40 mg) and N,N-dimethylformamide (2 ml) was stirred for 15 hours at 80° C. To the reaction mixture was added water, followed by extraction with ethyl acetate (30 ml). The organic layer was washed with water and dried over anhydrous sodium sulfate. The solvent was distilled off. The residue was dissolved in methanol (3 ml), to which was added iN sodium hydroxide (0.5 ml). The mixture was stirred for 30 minutes at 60° C. The reaction mixture was diluted with ethyl acetate (20 ml), which was washed with water and dried over anhydrous sodium sulfate. The solvent was distilled off, and the residue was purified by means of a silica gel column chromatography to give the titled compound (40 mg) as a colorless oily product.
NMR(CDCl$_3$) δ: 1.414(9H,s), 2.709(1N,dd,J=6.0,14.3 Hz), 2.929(1H,d,J=7.4,14.3 Hz), 3.843(4H,br), 4.05–4.22 (2H, m), 4.35–4.63(3H,m), 4.65–4.87(2H,m), 5.302(1H,s), 5.477 (1H,d,J=14.8 Hz), 6.059(1H,d,J=2.8 Hz), 6.43–6.54 (1H,m), 6.85–7.62(19H,m)

EXAMPLE 172

3,5-Trans-N-(2-fluorobenzyl)-5-(3-aminomethylphenyl)-1-(4-biphenylmethy)-7-(2-hydroxyethyloxy)-2-oxo-1,2,3,5-tetrahydro-4,1-benzoxazepine-3-acetamide•hydrochloride The compound (40 mg) produced in Example 171 was dissolved in 4 N hydrogen chloride (ethyl acetate solution) (1 ml). The solution was stirred for one hour at room temperature. The solvent was distilled off. To the residue were added ethyl acetate and n-hexane to give the titled compound (25 mg) as a colorless amorphous solid product.

NMR(CDCl₃) δ: 2.156(2H,br), 2.73(1H,dd,J=6.2,14.3 Hz), 2.94(1H,dd,J=7.0,14.3 Hz), 3.63–4.02(5H,m), 4.27–4.63 (4H,m), 4.794(1H,d,J=14.4 Hz), 5.33(1H,d), 5.53(1H,dd), 6.09(1H,m), 6.87–7.63(19H,m)

EXAMPLE 173

3,5-Trans-N-(2-fluorobenzyl)-5-(3-tert-butoxycarbonylaminomethylphenyl)-1-(4-biphenylmethy)-7-methoxycarbonylmethyloxy-2-oxo-1,2,3,5-tetrahydro-4,1-benzoxazepine-3-acetamide A mixture of 3,5-trans-N-(2-fluorobenzyl)-5-(3-tert-butoxycarbonylaminomethylphenyl)-1-(4-biphenylmethyl)-7-hydroxy-2-oxo-1,2,3,5-tetrahydro-4,1-benzoxazepine-3-acetamide produced in Example 165 (50 mg), bromoacetic acid methyl ester (37 mg), potassium carbonate (30 mg) and N,N-dimethylformamide (3 ml) was stirred for 2 hours at 80° C. The reaction mixture was diluted with ethyl acetate (20 ml), which was washed with water and dried over anhydrous sodium sulfate. The solvent was distilled off, and the residue was purified by means of a silica gel column chromatography to give the titled compound (55 mg) as a colorless oily product.
NMR(CDCl₃) δ: 1.428(9H,s), 2.73(1H,dd,J=5.8,14.4 Hz), 2.96(1H,dd,J=7.4,14.4 Hz), 3.708(3H,s), 4.05–4.23(2H,m), 4.32–4.62(5H,m), 4.75–4.90(1H,m), 4.877(1H,d,J=14.6 Hz), 5.354(1H,s), 5.395(1H,d,J=14.6 Hz), 6.04(1H,d,J=2.8 Hz), 6.46(1H,t,J=6.2 Hz), 6.86–7.63(19H,m)

EXAMPLE 174

3,5-Trans-N-(2-fluorobenzyl)-5-(3-aminomethylphenyl)-1-(4-biphenylmethy)-7-methoxycarbonylmethyloxy-2-oxo-1,2,3,5-tetrahydro-4,1-benzoxazepine-3-acetamide•hydrochloride The compound (55 mg) produced in Example 173 was dissolved in 4N hydrogen chloride (ethyl acetate solution) (1 ml). The solution was stirred for one hour at room temperature. The solvent was distilled off to leave the titled compound (30 mg) as a colorless amorphous solid product.
NMR(CDCl₃) δ: 2.05–2.41(2H,m), 2.721(1H,dd,J=6.0, 14.3 Hz), 2.943(1H,dd,J=7.4,14.3 Hz), 3.719(3H,s), 3.75(2H,br), 4.35–4.62(5H,m), 4.861(1H,dd,J=14.8 Hz), 5.357(1H,s), 5.427(1H,d,J=14.8 Hz), 6.081(1H,d,J=2.8 Hz), 6.35–6.47 (1H,m), 6.85–7.62(19H,m)

EXAMPLE 175

3,5-Trans-N-(2-fluorobenzyl)-7-benzyloxy-1-(4-biphenylmethy)-5-(3-tert-butoxycarbonyaminomethylphenyl)-2-oxo-1,2,3,5-tetrahydro-4,1-benzoxazepine-3-acetamide A mixture of 3,5-trans-N-(2-fluorobenzyl)-5-(tert-butoxycarbonylaminomethylphenyl)-1-(4-biphenylmethyl)-7-hydroxy-2-oxo-1,2,3,5-tetrahydro-4,1-benzoxazepine-3-acetamide produced in Example 165 (0.1 g), benzyl bromide (28 mg), potassium carbonate (30 mg) and N,N-dimethylformamide (4 ml) was stirred for 1.5 hour at 70° C. To the reaction mixture was added water, followed by extraction with ethyl acetate (30 ml). The organic layer was washed with water and dried over anhydrous sodium sulfate. The solvent was distilled off, and the residue was purified by means of a silica gel column chromatography to give the titled compound (0.105 g) as a colorless crystalline solid product.
NMR(CDCl₃) δ: 1.420(9H,s), 2.708(1H,dd,J=5.8,14.4 Hz), 2.939(1H,dd,J=7.2,14.4 Hz), 4.157(2H,d,J=5.8 Hz), 4.38–4.73(4H,m), 4.76–4.93(3H,m), 5.329(1H,s), 5.434 (1H,d, J=14.4 Hz), 6.095(1H,d,J=2.8 Hz), 6.25–6.42(1H,m), 6.85–7.63(24H,m)

EXAMPLE 176

3,5-Trans-N-(2-fluorobenzyl)-5-(3-aminomethylphenyl)-7-benzyloxy-1-(4-biphenylmethy)-2-oxo-1,2,3,5-tetrahydro-4,1-benzoxazepine-3-acetamide•hydrochloride To the compound produced in Example 175 (70 mg) was added 4N hydrogen chloride (ethyl acetate solution) (1 ml). The mixture was stirred for 2 hours at room temperature. The solvent was distilled off. The residue was processed with ethyl acetate and n-hexane to give the titled compound (65 mg) as a colorless amorphous solid product.
NMR(CDCl₃) δ: 2.009(2H,br), 2.722(1H,d,J=6.0,14.3 Hz), 2.935(1H,dd,J=7.2,14.3 Hz), 3.726(2H,br), 4.35–4.62 (3H, m), 4.75–4.93(3H,m), 5.337(1H,s), 5.452(1H,d, J=14.4 Hz), 6.123(1H,d,J=3.0 Hz), 6.35–6.52(1H,m), 6.84–7.62(24H,m)

EXAMPLE 177

3,5-Trans-N-(2-fluorobenzyl)-1-(4-biphenylmethy)-5-(3-tert-butoxycarbonylaminomethylphenyl)-7-cyclohexylmethyloxy-2-oxo-1,2,3,5-tetrahydro-4,1-benzoxazepine-3-acetamide A solution of the compound produced in Example 165 (0.1 g), cyclohexyl methyl bromide (30 mg) and sodium hydride (7 mg) in N,N-dimethylformamide (3 ml) was stirred for 40 minutes at 60° C. To the reaction mixture was added water, which was subjected to extraction with ethyl acetate (20 ml). The organic layer was washed with water and dried over anhydrous sodium sulfate. The solvent was distilled off. The residue was purified by means of a silica gel column chromatography to give the titled compound (60 mg) as a colorless amorphous solid product.
NMR(CDCl₃) δ: 0.83–1.82(11H,m), 1.427(9H,s), 2.709(1H, dd,J=5.8,14.1 Hz), 2.931(1H,dd,J=7.2,14.1 Hz), 3.546(2H, d,J=6.0 Hz), 4.05–4.22(2H,m), 4.35–4.75(4H,m), 4.814(1H, d,J=14.6 Hz), 5.313(1H,s), 5.472(1H,d,J=14.6 Hz), 6.006 (1H,d,J=3.0 Hz), 6.28–6.42(1H,m), 6.85–7.62(19H,m)

EXAMPLE 178

3,5-Trans-N-(2-fluorobenzyl)-5-(3-aminomethylphenyl)-1-(4-biphenylmethy)-7-cyclohexylmethyloxy-2-oxo-1,2,3,5-tetrahydro-4,1-benzoxazepine-3-acetamide To the compound produced in Example 177 (50 mg) was added 4N hydrogen chloride (ethyl acetate solution) (1 ml). The mixture was stirred for 30 minutes at room 10 temperature. The solvent was distilled off to leave the titled compound (40 mg) as a colorless amorphous solid product.
NMR(CDCl₃) δ: 0.82–1.85(11H,m), 2.25–2.65(2H,m), 2.727(1H,dd,J=5.8,14.3 Hz), 2.926(1H,dd,J=5.8,14.3 Hz), 2.926(1H,dd,J=7.2,14.3 Hz), 3.543(2H,d,J=5.0 Hz), 3.747(2H,br), 4.35–4.62(3H,m), 4.796(1H,d,J=14.4 Hz), 5.319(1H,s), 5.462(1H,d,J=14.4 Hz), 6.02(1H,d,J=2.6 Hz), 6.54–6.66(1H,m), 6.85–7.62(19H,m)

EXAMPLE 179

3,5-Trans-N-(2-fluorobenzyl)-1-(4-biphenylmethy)-5-(3-tert-butoxycarbonylaminomethylphenyl)-7-[3-(imidazol-1-yl)propyloxy]-2-oxo-1,2,3,5-tetrahydro-4,1-benzoxazepine-3-acetamide A solution of the compound produced in Example 167 (50 mg), imidazole (15 mg) and potassium carbonate (20 mg) in N,N-dimethylformamide (3 ml) was stirred for 3 hours at 80° C. To the reaction mixture was added water, which was subjected to extraction with ethyl acetate (20 ml). The organic layer was washed with water and dried over anhydrous sodium sulfate. The solvent was distilled off, and the residue was purified by means of a silica gel column chromatography to give the titled compound (40 mg) as a colorless amorphous solid product.
NMR(CDCl$_3$) δ: 1.425(9H,s), 1.95–2.35(2H,m), 2.65–3.05 (2H,m), 3.65–3.75(2H,m), 4.03–4.32(4H,m), 4.38–4.62 (3H,m), 4.83(1H,d,J=14.4 Hz), 5.334(1H,s), 5.45(1H,d, J=14.4 Hz), 5.982(1H,d,J=2.8 Hz), 6.50–7.85(22H,m)

EXAMPLE 180

3,5-Trans-N-(2-fluorobenzyl)-5-(3-aminomethylphenyl)-1-(4-biphenylmethy)-7-[3-(imidazol-1-yl)propyloxy]-2-oxo-1,2,3,5-tetrahydro-4,1-benzoxazepine-3-acetamide•dihydrochloride To the compound produced in Example 179 (30 mg) was added 4N hydrogen chloride (ethyl acetate solution) (1 ml). The mixture was stirred for 50 minutes at room temperature. The solvent was distilled off to leave the titled compound (20 mg) as a yellow amorphous solid product.
NMR(CDCl$_3$) δ: 1.85–2.35(4H,m), 2.723(1H,dd,J=6.0, 14.4 Hz), 2.943(1H,dd,J=7.0,14.4 Hz), 3.65–3.85(4H,m), 4.03–4.16(2H,m), 4.35–4.63(3H,m), 4.814(1H,d,J=14.4 Hz), 5.348(1H,s), 5.484(1H,d,J=14.4 Hz), 6.026(1H,d,J=3.0 Hz), 6.36–6.47(1H,m), 6.83–7.85(22H,m)

EXAMPLE 181

3,5-Trans-N-(2-fluorobenzyl)-7-benzyloxycarbonylmethyloxy-1-(4-biphenylmethy)-5-(3-tert-butoxycarbonylaminomethylphenyl)-2-oxo-1,2,3,5-tetrahydro-4,1-benzoxazepine-3-acetamide A mixture of the compound produced in Example 165 (0.1 g), bromo benzyl acetate ester (38 mg), potassium carbonate (40 mg) and N,N-dimethylformamide (4 ml) was stirred for one hour at 60° C. To the reaction mixture was added water, which was subjected to extraction with ethyl acetate (20 ml). The organic layer was washed with water and dried over anhydrous sodium sulfate. The solvent was distilled off, and the residue was purified by means of a silica gel column chromatography to give the titled compound (0.11 g) as a colorless amorphous solid product.
NMR(CDCl$_3$) δ: 1.423(9H,s), 2.709(1H,dd,J=5.4,14.3 Hz), 2.948(1H,dd,J=7.2,14.3 Hz), 4.162(2H,d,J=5.6 Hz), 4.36–4.62(5H,m), 4.65–4.82(1H,m), 4.876(1H,d,J=14.4 Hz), 5.348(1H,s), 5.415(1H,d,J=14.4 Hz), 6.068(1H,d,J=2.8 Hz), 6.25–6.37(1H,m), 6.84–7.62(24H,m)

EXAMPLE 182

3,5-Trans-N-(2-fluorobenzyl)-5-(3-aminomethylphenyl)-7-benzyloxycarbonylmethyloxy-1-(4-biphenylmethy)-2-oxo-1,2,3,5-tetrahydro-4,1-benzoxazepine-3-acetamide•hydrochloride To the compound produced in Example 18 (80 mg) was added 4N hydrogen chloride (ethyl acetate solution) (1.5 ml). The mixture was stirred for 30 minutes at room temperature. The solvent was distilled off. The residue was processed with ethyl acetate and hexane to give the titled compound (50 mg) as a colorless amorphous solid product.
NMR(CDCl$_3$) δ: 2.721(1H,dd,J=5.8,14.4 Hz), 2.825(2H,br), 2.938(1H,dd,J=7.4,14.4 Hz), 3.723(2)H,s), 4.36–4.58(5H,), 4.850(1H,d,J=14.6 Hz), 5.138(2H,s), 5.348(1H,s), 5.405 (1H,d,J=14.6 Hz), 6.090(1H,d,J=3.0 Hz), 6.53–6.63(1H,m), 6.83–7.58(24H,m)

EXAMPLE 183

3,5-Trans-N-(2-fluorobenzyl)-1-(4-biphenylmethy)-5-[3-(2-tert-butoxycarbonylaminoethyl)phenyl]-7-chloro-2-oxo-1,2,3,5-tetrahydro-4,1-benzoxazepine-3-acetamide
(1) A solution of N-tert-butoxycarbonyl-3-bromophenethylamine (1.7 g) and N-methyl-N-methyloxy-2-amino-5-chloro-benzamide (1.9 g) in tetrahydrofuran (50 ml) was cooled to -70° C. To the solution was added dropwise, while stirring, a hexane solution of n-butyl lithium (1.6 mol/L) (18 ml). To the reaction mixture were added water (100 ml) and ethyl acetate (80 ml). The mixture was shaken. The organic layer was separated, which was washed with water and dried over anhydrous sodium sulfate. The solvent was distilled off, and the residue was purified by means of a silica gel column chromatography to give 2-amino-3'-(2-tert-butoxycarbonylaminoethyl)-5-chloro-benzophenone (1.5 g) as a yellow crystalline product. m.p.: 128–129° C.
NMR(CDCl$_3$) δ: 1.430(9H,s), 2.879(2H,t,J=7.2 Hz), 3.33–3.48 (2H,m), 4.48–4.67(1H,m), 6.068(2H,br), 6.701 (1H,d, J=8.8 Hz), 7.22–7.53(6H,m)
(2) The compound (1.5 g) produced in (1) was dissolved in methanol (30 ml), To the solution was added, while stirring at room temperature, sodium borohydride (0.3 g). The mixture was stirred for 30 minutes, which was concentrated. To the concentrate were added water (50 ml) and ethyl acetate (80 ml). The mixture was subjected to extraction. The organic layer was washed with water and dried over anhydrous sodium sulfate. The solvent was distilled off to leave 2-amino-α-[3'-(2-tert-butoxycarbonylaminoethyl) phenyl]-5-chloro-benzyl alcohol (1.45 g) as a colorless oily product.
NMR(CDCl$_3$) δ: 1.424(9H,s), 2.62–2.72(1H,m), 2.791(2H, t, J=7.2 Hz), 3.27–3.43(2H,m), 3.957(2H,br), 4.47–4.63 (1H,m), 5.776(1H,d,J=3.0 Hz), 6.593(1H,d,J=9.0 Hz), 7.03–7.46(6H,m)
(3) The compound (1.45 g) produced in (2) and 4-phenylbenzaldehyde (0.8 g) were dissolved in methanol (15 ml). To the solution was added acetic acid (0.28 g). To the mixture was added, while stirring at room temperature, cyano sodium borohydride (0.3 g). The reaction mixture was stirred for one hour at 60° C., which was then concentrated. To the concentrate were added water (60 ml) and ethyl acetate (80 ml). The mixture was subjected to extraction. The organic layer was washed with water and dried over anhydrous sodium sulfate. The solvent was distilled off to leave 2-(4-biphenylmethyl)-α-[3'-(2-tert-butoxycarbonylaminoethyl)phenyl]-5-chloro-benzyl alcohol (1.95 g) as a colorless oily product.
NMR(CDCl$_3$) δ: 1.414(9H,s), 2.788(2H,t,J=6.8 Hz), 3.25–3.45(2H,m), 4.299(2H,s), 5.836(1H,s), 6.560(1H,d, J=8.6 Hz), 7.05–7.73(15H,m)
(4) The compound (1.95 g) produced in (3) was dissolved in ethyl acetate (40 ml), to which was added 1N sodium hydroxide (15 ml). To the mixture was added, while stirring at room temperature, fumaric chloride monoethyl ester (0.6 g). The mixture was stirred for 10 minutes. The organic layer was then separated and washed with water, followed by drying over anhydrous sodium sulfate. The solvent was distilled off, and the residue was dissolved in ethanol (40 ml). To the solution was added potassium carbonate (1.5 g). The mixture was stirred for 3 hours at 60° C. The reaction mixture was concentrated, to which were added water (100 ml) and ethyl acetate (120 ml). The mixture was subjected to extraction. The organic layer was washed with water and dried over anhydrous sodium sulfate. The solvent was distilled off, and the residue was purified by means of a silica gel column chromatography to give 3,5-trans-1-(4-biphenylmethyl)-5-[3-(2-tert-butoxycarbonylaminoethyl) phenyl)-7-chloro-2-oxo-1,2,3,5-tetrahydro-4,1-benzoxazepine-3-acetic acid ethyl ester (1.2 g) as a colorless oily product.
NMR(CDCl$_3$) δ: 1.253(3H,t,J=7.0 Hz), 1.424(9H,s), 2.57–2.85(3H,m), 4.16(2H,q,J=7.0 Hz), 4.25–4.43(1H,m), 4.483 (1H,dd,J=5.2,8.4 Hz), 4.878(1H,d,J=14.6 Hz), 5.326 (1H,s), 5.497(1H,d,J=14.6 Hz), 6.615(1H,s), 6.789(1H,br), 6.95–7.64(14H,m)

(5) The compound produced in (4) (1.5 g) was dissolved in a mixture of tetrahydrofuran (8 ml) and methanol (20 ml). To the solution was added 1N sodium hydroxide (10 ml). The mixture was stirred for 40 minutes at 60° C. The reaction mixture was concentrated, which was neutralized with 5% potassium hydrogensulfate, followed by extraction with ethyl acetate (60 ml). The organic layer was washed with water and dried over anhydrous sodium sulfate. The solvent was distilled off, and the residue was purified by means of a silica gel column chromatography to give 3,5-trans-i-(4-biphenylmethyl)-5-[3-(2-tert-butoxycarbonylaminoethyl)phenyl]-7-chloro-2-oxo-1,2,3,5-tetrahydro-4,1-benzoxazepine-3-acetic acid (0.9 g) as a colorless amorphous solid produce.

NMR(CDCl$_3$) δ: 1.435(9H,s), 2.65–3.60(6H,m), 4.43–4.75 (2H,m), 4.891(1H,d,J=14.8 Hz), 5.35–5.62(2H,m), 6.323 (1H,s), 6.65–7.65(15H,m)

(6) In N,N-dimethylformamide (10 ml) were dissolved 7 the compound produced in (5) (0.6 g) and 2-fluorobenzylamine (0.15 g). To the solution were added, while stirring at 0° C., cyano diethyl phosphate (0.18 g) and triethylamine (0.15 g). The reaction mixture was stirred for 20 minutes at room temperature, which was poured into ice-water, fbllowed by extraction with ethyl acetate (50 ml). The organic layer was washed with water and dried over anhydrous sodium sulfate. The solvent was distilled off, and the residue was purified by means of a silica gel column chromatography to give the titled compound (0.45 g) as a colorless amorphous solid product.

NMR(CDCl$_3$) δ: 1.415(9H,s), 2.53–2.77(3H,m), 2.943 (1H, dd,J=7.4,14.5 Hz), 3.05–3.25(2H,m), 4.24–4.63(4H,m), 4.816(1H,d,J=14.4 Hz), 5.287(1H,s), 5.52(1H,d,J=14.4 Hz), 6.18–6.42(1H,m), 6.498(1H,d,J=2.0 Hz), 6.723(1H,br), 6.88–7.63(18H,m)

EXAMPLE 184

3,5-Trans-N-(2-fluorobenzyl)-5-[3-(2-aminoethylphenyl)]-1-(4-biphenylmethy)-7-chloro-2-oxo-1,2,3,5-tetrahydro-4,1-benzoxazepine-3-acetamide•hydrochloride To the compound produced in Example 183 (0.3 g) was added 4N hydrogen chloride (ethyl acetate solution) (5 ml). The mixture was stirred for 40 minutes at room temperature. The solvent was distilled off to leave the titled compound (0.28 g) as a colorless amorphous product.

NMR(CDCl$_3$) δ: 1.686(2H,br), 2.53–2.86(5H,m), 2.941(1H, dd,J=7.2,14.6 Hz), 4.34–4.58(3H,m), 4.797(1H,d,J=14.6 Hz), 5.300(1H,s), 5.509(1H,d,J=14.6 Hz), 6.508(1H,d, J=1.8 Hz), 6.55–6.67(1H,m), 6.747(1H,br), 6.88–7.62(18H, m)

EXAMPLE 185

3,5-Trans-N-(2-fluorobenzyl)-1-(4-biphenylmethy)-5-[3-[(1-tert-butoxycarbonylamino-1-methyl)ethyl]phenyl]-7-(3-phenylpropyl)oxy-2-oxo-1,2,3,5-tetrahydro-4,1-benzoxazepine-3-acetamide (1) In tetrahydrofuran (80 ml) were dissolved N-methyl-N-methyloxy 2-amino-5-(tetrahydropyran-2-yl)oxy-benzamide produced in Example 165-(2) (2.0 g) and 1-[(1-tert-butoxycarbonylamino-1-methyl)ethyl]-3-bromobenzene produced in Example 92-(1) (2.5 g). The solution was cooled to −80° C. or below. To the solution was added dropwise, while stirring, a hexane solution of n-butyl lithium (1.6 mol/L) (22 ml) over 40 minutes. To the reaction mixture were added water (150 ml) and ethyl acetate (200 ml). The mixture was subjected to extraction. The organic layer was washed with water and dried over anhydrous sodium sulfate. The solvent was distilled off, and the residue was purified by means of a silica gel column chromatography to give 2-amino-3'-(1-tert-butoxycarbonylamino-1-methyl)ethyl-5(tetrahydropyran-2-yl)oxy-benzophenone (0.6 g) as a yellow oily product.

NMR(CDCl$_3$) δ: 1.34(9H,br), 1.576(3H,s), 1.656(3H,s), 1.45–2.05(6H,m), 3.45–3.57(1H,m), 3.82–3.96(1H,m), 4.88–5.03(1H,m), 5.152(1H,br), 5.738(2H,br), 6.698(1H,d, J=8.8 Hz), 7.07–7.76(6H,m)

(2) The compound (0.6 g) produced in (1) was dissolved in methanol (20 ml). To the solution was added, while stirring at room temperature, sodium borohydride (0.2 g). The mixture was stirred for 20 minutes, which was then concentrated. To the concentrate were added water (50 ml) and ethyl acetate (60 ml). The mixture was subjected to extraction. The organic layer was washed with water and dried over anhydrous sodium sulfate. The solvent was distilled off, and the residue was purified by means of a silica gel column chromatography to give 2-amino-α-[3-[(1-tert-butoxycarbonylamino-1-methyl)ethyl]phenyl]-5-(tetrahydropyran-2-yl)oxy-benzyl alcohol (0.5 g) as a colorless oily product.

NMR(CDCl$_3$) δ: 1.522(9H,br), 1.609(6H,s), 1.50–2.15 (6H, m), 3.05–3.75(3H,m), 3.87–4.05(1H,m), 4.85–5.07 (1H,m), 5.20–5.27(1H,m), 5.784(1H,s), 6.55–7.57(7H,m)

(3) The compound (0.5 g) produced in (2) and 4-phenylbenzaldehyde (0.23 g) were dissolved in methanol (20 ml). To the solution was added acetic acid (0.08 g). To the mixture was added, while stirring at room temperature, cyano sodium borohydride (0.1 g). The reaction mixture was stirred for 30 minutes at 60° C., which was then concentrated. To the concentrate was added water (50 ml) and ethyl acetate (50 ml), followed by extraction. The organic layer was washed with water and dried over anhydrous sodium sulfate. The solvent was distilled off to leave 2-(4-biphenylmethyl)amino-α-[3-[(1-tert-butoxycarbonylamino-1-methyl)ethyl]phenyl]-5-(tetrahydropyran-2-yl)oxy-benzyl alcohol (0.5 h) as a colorless oily product.

NMR(CDCl$_3$) δ: 1.368(9H,br), 1.569(6H,s), 1.46–2.05 (6H, m), 3.45–3.62(1H,m), 3.85–4.02(1H,m), 4.947(1H,br), 5.18–5.26(1H,m), 5.863(1H,s), 6.613(1H,d,J=8.6 Hz), 6.83–7.75(15H,m)

(4) The compound (0.6 g) produced in (3) was dissolved in ethyl acetate (20 ml), to which was added 1N sodium hydroxide (8 ml). To the mixture was added, while stirring at room temperature, fumaric chloride monoethyl ester (0.17 g). The organic layer was separated, which was washed with water and dried over anhydrous sodium sulfate. The solvent was distilled off, and the residue was dissolved in ethanol (15 ml). To the solution was added potassium carbonate (0.3 g). The mixture was stirred for 2 hours at 60° C. To the reaction mixture was added ethyl acetate (50 ml). The mixture was washed with water and dried over anhydrous sodium sulfate. The residue was purified by means of a silica gel column chromatography to give 3,5-trans-1-(4-biphenylmethyl)-5-[3-[(1-tert-butoxycarbonylamino-1-methyl)ethyl]phenyl]-7-(tetrahydropyran-2-yl)oxy-2-oxo-1,2,3,5-tetrahydro-4,1-benzoxazepine-3-acetic acid ethyl ester (0.25 g) as a colorless crystalline product. m.p.: 150–151° C.

NMR(CDCl$_3$) δ: 1.05–1.35(12H,m), 1.34(3H,s), 1.578(3H, s), 1.43–2.05(6H,m), 2.65–2.83(1H,m), 3.03–3.20(1H,m), 3.38–3.53(1H,m), 3.67–3.85(1H,m), 4.13(2H,q), 4.46–4.55 (1H,m), 4.56–4.73(1H,m), 4.825(1H,d,J=14.2 Hz), 5.10–5.57(3H,m), 6.15–6.25(1H,m), 6.85–7.65(15H,m)

(5) The compound produced in (4) (0.32 g) was dissolved in a mixture of tetrahydrofuran (5 ml) and methanol (10 ml). To the solution was added 1N sodium hydroxide (5 ml). The mixture was stirred for 40 minutes at 60° C. The reaction mixture was concentrated, which was neutralized with a 5% aqueous solution of sodium hydrogensulfate, followed by extraction with ethyl acetate (50 ml). The organic layer was washed with water and dried over anhydrous sodium sulfate. The solvent was distilled off, and the residue was purified by means of a silica gel column chromatography to give 3,5-trans-1-(4-biphenylmethyl)-5-[3-[(1-tert-butoxycarbonylamino-1-methyl)ethyl]phenyl]-7-(tetrahydropyranyl-2-yl)oxy-2-oxo-1,2,3,5-tetrahydro-4,1-benzoxazepine-3-acetic acid (0.16 g) as a colorless amorphous solid product.
NMR(CDCl$_3$) δ: 0.9–2.05(21H,m), 2.65–3.25(2H,m), 3.35–3.85(2H,m), 4.35–4.95(3H,m), 5.05–5.65(3H,m), 6.12–6.23(1H,m), 7.03–7.67(15H,m)

(6) The compound produced in (5) (0.25 g) and 2-fluorobenzylamine (60 mg) were dissolved in N,N-dimethylformamide (4 ml). To the solution were added, while stirring at 0° C., cyano diethyl phosphate (80 mg) and triethylamine (50 mg). The reaction mixture was stirred for 20 minutes at room temperature, which was poured into ice-water, followed by extraction with ethyl acetate (50 ml). The organic layer was washed with water and dried over anhydrous sodium sulfate. The solvent was distilled off, and the residue was purified by means of a silica gel column chromatography to give 3,5-trans-N-(2-fluorobenzyl) 1-(4-biphenylmethyl)-5-[3-[(1-tert-butoxycarbonylamino-1-methyl)ethyl]phenyl]-7-(tetrahydropyranyl-2-yl)oxy-2-oxo-1,2,3,5-tetrahydro-4,1-benzoxazepine-3-acetamide (0.23 g) as a colorless amorphous solid product.
NMR(CDCl$_3$) δ: 0.95–2.05(21H,m), 2.73(1H,ddd), 2.934 (1H,dd,J=7.2,14.3 Hz), 3.38–3.85(2H,m), 4.25–4.85(5H,m), 5.10–5.28(2H,m), 5.502(1H,d,J=14.4 Hz), 6.15–6.25(1H, m), 6.45–6.62(1H,m), 6.85–7.65(19H,m)

(7) The compound (0.23 g) produced in (6) was dissolved in methanol (10 ml). To the solution was added a 10% aqueous solution of oxalic acid (2 ml). The mixture was stirred for one hour at 60° C. The reaction mixture was concentrated, to which was added water, followed by extraction with ethyl acetate (40 ml). The organic layer was washed with water and dried over anhydrous sodium sulfate. The solvent was distilled off to leave 3,5-trans-N-(2-fluorobenzyl)-1-(4-biphenylmethyl)-5-[3-[(1-tert-butoxycarbonylamino-1-methyl)ethyl]phenyl]-7-hydroxy-2-oxo-1,2,3,5-tetrahydro-4,1-benzoxazepine-3-acetamide (0.2 g) as an amorphous solid product.
NMR(CDCl$_3$) δ: 1.03–1.43(15H,m), 2.741(1H,dd,J=6.0, 14.6 Hz), 2.919(1H,dd,J=7.2,14.6 Hz), 4.25–4.57(3H,m), 4.60–4.95(2H,m), 5.116(1H,br), 5.45–5.62(1H,m), 6.75–7.64(19H,m)

(8) A mixture of the compound produced in (7) (0.1 g), 1-bromo-3-phenylpropane (35 mg), potassium carbonate (40 mg) and N,N-dimethylformamide (4 ml) was stirred for 2 hours at 80° C. To the reaction mixture was added water, and the mixture was subjected to extraction with ethyl acetate (30 ml). The organic layer was washed with water and dried over anhydrous sodium sulfate. The solvent was distilled off, and the residue was purified by means of a silica gel column chromatography to give the titled compound, 3,5-trans-N-(2-fluorobenzyl)-1-(4-biphenylmethyl)-5-(3-[(1-tert-butoxycarbonylamino-1-methyl)ethyl]phenyl]-7-(3-phenylpropyloxy)-2-oxo-1,2,3,5-tetrahydro-4,1-benzoxazepine-3-acetamide (0.11 g) as a colorless amorphous solid product.
NMR(CDCl$_3$) δ: 1.05–1.65(15H,m), 1.87–2.07(2H,m), 2.63–2.77(3H,m), 2.93(1H,dd,J=7.0,14.4 Hz), 3.746(2H,t, J=6.2 Hz), 4.35–4.82(4H,m), 5.219(1H,s), 5.537(1H,d, J=14.2 Hz), 6.04(1H,br), 6.34–6.45(1H,m), 6.85–7.65(24H, m)

EXAMPLE 186

3,5-Trans-N-(2-fluorobenzyl)-5-[3-[(1-amino-1-methyl) ethyl]phenyl]-1-(4-biphenylmethyl)-2-oxo-7-(3-phenylpropyloxy)-1,2,3,5-tetrahydro-4,1-benzoxazepine-3-acetamide•hydrochloride To the compound produced in Example 185 (0.1 g) was added 4N hydrogen chloride (ethyl acetate solution) (1 ml). The mixture was stirred for 30 minutes. The solvent was distilled off to leave the titled compound (92 mg) as a colorless amorphous solid product.
NMR(CDCl$_3$) δ: 1.399(3H,s), 1.413(3H,s), 1.88–2.05 (2H, m), 2.63–3.02(4H,m), 3.63–3.85(2H,m), 4.32–4.60(3H,m), 4.859(1H,d,J=14.6 Hz), 5.359(1H,s), 5.420(1H,d,J=14.6 Hz), 6.05(1H,d,J=2.8 Hz), 6.47–6.62(1H,m), 6.85–7.62 (24H,m)

EXAMPLE 187

3,5-Trans-N-(2-fluorobenzyl)-1-[4-(4-benzyloxy) biphenylmethyl]-5-(3-tert-butoxycarbonylaminomethylphenyl)-7-chloro-2-oxo-1,2, 3,5-tetrahydro-4,1-benzoxazepine-3-acetamide (1) 4-(41-Hydroxyphenyl)benzoic acid (2.0 g) was dissolved in N,N-dimethylformamide (30 ml). To the solution were added benzyl bromide (3.99 g) and potassium carbonate (3.86 g). The mixture was stirred for 3 hours at 80° C. The reactionmixture was poured into water (100 ml), which was subjected to extraction with ethyl acetate (150 ml). The organic layer was washed with 5% potassium hydrogensulfate, which was then washed with water and dried over anhydrous sodium sulfate. The solvent was distilled off to leave 4-(4'-benzyloxyphenyl)-benzoic acid benzyl ester as a scale-like crystalline product (3.4 g). m.p.: 138–140° C.
NMR(CDCl$_3$) δ: 5.121(2H,s), 5.384(2H,s), 7.066(2H,d, J=8.8 Hz), 7.28–7.67(14H,m), 8.119(2H,d,J=8.4 Hz)

(2) The compound produced in (1) (2.0 g) was added, while stirring at room temperature, to a suspension of aluminium lithium hydride (0.38 g) in tetrahydrofuran (40 ml). The reaction mixture was heated for 3 hours under reflux, which was then subjected to decomposition, under ice-cooling, with water (0.4 g) and 1N sodium hydroxide (1.2 ml). The reaction mixture was subjected to filtration. From the filtrate, the solvent was distilled off to leave 4-(4-benzyloxyphenyl) benzyl alcohol (1.2 g) as a scale-like crystalline product. m.p.: 194–195° C.
NMR(CDCl$_3$) δ: 3.72–3.88(1H,m), 4.691(2H,d,J=5.8 Hz), 5.113(2H,s), 7.02–7.12(2H,m), 7.18–7.58(11H,m)

(3) The compound produced in (2) (0.5 g) was added to a solution of chromic anhydride (0.32 g) in pyridine (10 ml). The mixture was stirred for 3 hours at room temperature, to which was added water, followed by extraction with ethyl acetate (50 ml). The organic layer was washed with 5% potassium hydrogensulfate, which was then washed with water and dried over anhydrous sodium sulfate. The solvent was distilled off to leave 4-(4-benzyloxyphenyl)-benzaldehyde (0.38 g) as a colorless crystalline product. m.p.: 124–126° C.
NMR(CDCl$_3$) δ: 5.134(2H,s), 7.04–7.97(13H,m), 10.04(1H, s)

(4) In methanol (15 ml) were dissolved the compound produced in (3) (0.33 g) and 2-amino-5-chloro-α-(3-tert-butoxycarbonylaminomethylphenyl)benzyl alcohol produced in Example (1). To the solution were added acetic acid (0.08 g) and cyano sodium borohydride (0.1 g). The mixture was stirred for 1.5 hour, which was then concentrated. To the concentrate were added water (50 ml) and ethyl acetate (60 ml). The mixture was subjected to extraction. The organic layer was washed with water and dried over anhydrous sodium sulfate. The solvent was distilled off to leave 2-[4-(4-benzyloxy)biphenylmethyl]amino-5-chloro-α-(3-tert-butoxycarbonylaminomethylphenyl)benzyl alcohol (0.54 g) as a colorless crystalline product. m.p.: 119–120° C.
NMR(CDCl$_3$) δ: 1.431(9H,s), 4.26–4.35(3H,m), 5.110(2H, s), 5.828(1H,s), 6.560(1H,d,J=8.6 Hz), 7.02–7.67(19H,m)
(5) The compound produced in (4) (0.5 h) was dissolved in ethyl acetate (15 ml). To the solution was added 1N sodium hydroxide (5 ml). To the mixture was added dropwise, while stirring at room temperature, an ethyl acetate (1 ml) solution of fumaric chloride monoethyl ester (0.13 g). The mixture was stirred for 10 minutes. The organic layer was then washed with water and dried over anhydrous sodium sulfate. The solvent was distilled off, and the residue was dissolved in ethanol (20 ml). To the solution was added potassium carbonate (0.3 g). The mixture was stirred for 1.5 hour at 60° C. The reaction mixture was diluted with ethyl acetate (50 ml), which was washed with water and dried over anhydrous sodium sulfate. The solvent was distilled off, and the residue was purified by means of a silica gel column chromatography to give 3,5-trans-1-[4-(4-benzyloxy)biphenylmethyl]-5-(3-tert-butoxycarbonylaminomethylphenyl)-7-chloro-2-oxo-1,2,3,5-tetrahydro-4,1-benzoxazepine-3-acetic acid ethyl ester (0.37 g) as a colorless oily product.
NMR(CDCl$_3$) δ: 1.255(3H,t,J=7.2 Hz), 1.435(9H,s), 2.771 (1H,dd,J=5.4,16.8 Hz), 3.145(1H,dd,J=8.4,16.8 Hz), 4.05–4.28(4H,m), 4.485(1H,dd,J=5.4,8.3 Hz), 4.65–4.82 (1H,m), 4.911(1H,d,J=15.0 Hz), 5.118(2H,s), 5.382(1H,s), 5.401(1H,d,J=15.0 Hz), 6.496(1H,br), 6.93–7.57(19H,m)
(6) The compound produced in (5) (0.36 g) was dissolved in a mixture of tetrahydrofuran (5 ml) and methanol (10 ml). To the solution was added 1N sodium hydroxide (5 ml). The mixture was stirred for 30 minutes at 60° C. The reaction mixture was concentrated, which was neutralized with 5% potassium hydrogensulfate, followed by extraction with ethyl acetate (30 ml). The organic layer was washed with water and dried over anhydrous sodium sulfate. The solvent was distilled off, and the residue was dissolved in N,N-dimethylformamide (6 ml). To the solution was added 2-fluorobenzylamine (0.05 g). To the mixture were added, while stirring at 0° C., cyano diethyl phosphate (0.07 g) and triethylamine (0.05 g). The reaction mixture was stirred for 20 minutes at room temperature, which was poured into ice-water, followed by extraction with ethyl acetate (50 ml). The organic layer was washed with water and dried over anhydrous sodium sulfate. The solvent was distilled off, and the residue was purified by means of a silica gel column chromatography to give the titled compound, 3,5-trans-N-(2-fluorobenzyl)-1-[4-(4-benzyloxy)biphenylmethyl]-5-(3-tert-butoxycarbonylmethylphenyl)-7-chloro-2-oxo-1,2,3,5-tetrahydro-4,1-benzoxazepine-3-acetamide (0.2 g) as a colorless oily product.
NMR(CDCl$_3$) δ: 1.424(9H,s), 2.711(1H,dd,J=6.0,14.5 Hz), 2.941(1H,dd,J=7.4,14.5 Hz), 4.05–4.25(2H,m), 4.35–4.62 (3H,m), 4.63–4.83(1H,m), 4.838(1H,d,J=14.6 Hz), 5.108 (2H,s), 5.345(1H,s), 5.448(1H,d,J=14.6 Hz), 6.32–6.47(1H, m), 6.484(1H,d,J=1.8 Hz), 6.85–7.54(23H,m)

EXAMPLE 188

3,5-Trans-N-(2-fluorobenzyl)-5-(3-aminomethylphenyl)-1-[4-(4-benzyloxy)biphenylmethyl]-7-chloro-2-oxo-1,2,3,5-tetrahydro-4,1-benzoxazepine-3-acetamide•hydrochloride The compound produced in Example 187 (70 mg) was dissolved in 4N hydrogen chloride (ethyl acetate solution) (1.5 ml). The solution was stirred for 2 hours at room temperature. The solvent was distilled off to leave the titled compound (60 mg) as a colorless amorphous solid product.
NMR(CDCl$_3$) δ: 2.723(1H,dd,J=6.0,14.4 Hz), 2.941(1H,dd, J=7.4,14.4 Hz), 3.759(2H,br), 4.37–4.62(3H,m), 4.825(1H, d,J=14.6 Hz), 5.113(2H,s), 5.363(1H,s), 5.475(1H,d, J=14.6 Hz), 6.354(1H,t,J=6.2 Hz), 6.506(1H,d,J=2.2 Hz), 6.85–7.55(23H,m)

EXAMPLE 189

3,5-Trans-N-(2-fluorobenzyl)-5-(3-tert-butoxycarbonylaminomethylphenyl)-7-chloro-1-[4-(4-hydroxy)biphenylmethyl]-2-oxo-1,2,3,5-tetrahydro-4,1-benzoxazepine-3-acetamide In a mixture of ethyl acetate (10 ml) and methanol (4 ml) was dissolved 3,5-trans-N-(2-fluorobenzyl)1-[4-(4-benzyloxy)biphenylmethyl]-5-(3-tert-butoxycarbonylaminomethylphenyl)-7-chloro-2-oxo-1,2,3,5-tetrahydro-4,1-benzoxazepine-3-acetamide (0.15 g) produced in Example 187. To the solution was added 10% palladium-carbon (0.08 g). The mixture was stirred for 1.5 hour in hydrogen streams. The reaction mixture was subjected to filtration. From the filtrate, the solvent was distilled off to leave the titled compound (95 mg) as a colorless amorphous solid product.
NMR(CDCl$_3$) δ: 1.43(9H,s), 2.66–3.04(2H,m), 4.02–4.26 (2H,m), 4.36–4.62(3H,m), 4.65–4.83(1H,m), 4.84–5.05(1H, m), 5.32–5.47(2H,m), 5.85–6.12(1H,m), 6.25–6.58(2H,m), 6.82–7.48(18H,m)

EXAMPLE 190

3,5-Trans-N-(2-fluorobenzyl)-5-(3-aminomethylphenyl)-1-[4-(4-hydroxy)biphenylmethyl]-7-chloro-2-oxo-1,2,3,5-tetrahydro-4,1-benzoxazepine-3-acetamide•hydrochloride The compound produced in Example 189 (65 mg) was dissolved in 4N hydrogen chloride (ethyl acetate solution) (1.5 ml). The solution was stirred for 2 hours. The solvent was distilled off to leave the titled compound (60 mg) as a colorless amorphous solid product.
NMR(CDCl$_3$) δ: 1.65–3.15(5H,m), 3.624(2H,br), 4.33–4.62 (3H,m), 4.654(⅔H,d,J=14.4 Hz), 4.743(⅓H,d, J=14.2 Hz), 5.147(⅔H,s), 5.224(⅓H,s), 5.579(⅓H, d,J=14.2 Hz), 5.591 (⅓H,d,J=14.4 Hz), 6.42–6.73(3H,m), 6.77–7.55(18H,m)

EXAMPLE 191

3,5-Trans-N-(2-fluorobenzyl)-5-(3-tert-butoxycarbonylaminomethylphenyl)-7-chloro-1-(4-fluorobenzyl)-2-oxo-1,2,3,5-tetrahydro-4,1-benzoxazepine-3-acetamide (1) In methanol (10 ml) were dissolved 2-amino-5-chloro-α-(3-tert-butoxycarbonylaminomethylphenyl)benzyl alcohol produced in Example (1) (0.5 g) and 4-fluorobenzaldehyde (0.2 g). To the solution were added acetic acid (0.1 g) and cyano sodium borohydride (0.1 g). The mixture was concentrated, to which were added water (60 ml) and ethyl acetate (50 ml), followed by extraction. The organic layer was washed with water and dried over anhydrous sodium sulfate. The solvent was then distilled off to leave 5-chloro-2-(4-fluorobenzylamino)-α-(3-tert-butoxycarbonylaminomethylphenyl)benzyl alcohol (0.56 g) as a colorless oily product.
NMR(CDCl$_3$) δ: 1.445(9H,s), 4.21(2H,br), 4.296(2H,d, J=6.0 Hz), 4.64–5.03(3H,m), 5.812(1H,s), 6.494(1H,d, J=8.8 Hz), 6.92–7.62(10H,m)

(2) The compound (0.56 g) produced in (1) was dissolved in ethyl acetate (15 ml), to which was added 1N sodium hydroxide (6 ml). To the mixture was added dropwise, while stirring, an ethyl acetate (1 ml) solution of fumaric chloride monoethyl ester (0.26 g). The organic layer was separated, washed with water and dried over anhydrous sodium sulfate. The solvent was distilled off, and the residue was dissolved in ethanol (20 ml). To the solution was added potassium carbonate (0.4 g). The mixture was stirred for 1.5 hour at 60° C. The reaction mixture was diluted with ethyl acetate (50 ml), which was washed with water and dried over anhydrous sodium sulfate. The solvent was distilled off, and the residue was purified by means of a silica gel column chromatography to give 3,5-trans-5-(3-tert-butoxycarbonylaminomethylphenyl)-7-chloro-1-(4-fluorobenzyl)-2-oxo-1,2,3,5-tetrahydro-4,1-benzoxazepine-3-acetic acid ethyl ester (0.45 g) as a colorless oily product.
NMR(CDCL$_3$) δ: 1.25(3H,t,J=7.0 Hz), 1.453(9H,s), 2.759 (1H,dd,J=5.2,16.7 Hz), 3.131(1H,dd,J=8.4,16.7 Hz), 4.143 (2H,q,J=7.0 Hz), 4.312(2H,d,J=5.4 Hz), 4.466(1H,dd,J=5.2, 8.6 Hz), 4.867(1H,d,J=14.8 Hz), 5.369(1H,s), 5.371(1H,d, J=14.8 Hz), 6.518(1H,d,J=2.2 Hz), 6.95–7.38(10H,m)

(3) To a solution of the compound (0.45 g) produced in (2) in a mixture of tetrahydrofuran (5 ml) and methanol (10 ml) was added 1N sodium hydroxide (5 ml). The mixture was stirred for 30 minutes at 60° C. The reaction mixture was concentrated, which was made acidic with 5% potassium hydrogensulfate, followed by extraction with ethyl acetate. The organic layer was washed with water and dried over anhydrous sodium sulfate. The solvent was distilled off, and the residue was purified by means of a silica gel column chromatography to give 3,5-trans-5-(3-tert-butoxycarbonylaminomethylphenyl)-7-chloro-1-(4-fluorobenzyl)-2-oxo-1,2,3,5-tetrahydro-4,1-benzoxazepine-3-acetic acid (0.24 g) as a colorless amorphous solid product.
NMR(CDCl$_3$) δ: 1.445(9H,s), 2.853(1H,dd,J=5.2,18.6 Hz), 3.06–3.24(2H,m), 4.311(2H,d,J=6.0 Hz), 4.45(1H,dd,J=4.8, 7.7 Hz), 4.908(1H,d,J=14.6 Hz), 5.342(1H,d,J=14.6 Hz), 5.407(1H,s), 6.525(1H,s), 6.83–7.52(10H,m)

(4) The compound produced in (3) (0.2 g) and 2-fluorobenzylamine (52 mg) were dissolved in N,N-dimethylformamide (6 ml). To the solution were added, while stirring under ice-cooling, cyano diethyl phosphate (65 mg) and triethylamine (50 mg). The reaction mixture was stirred for 20 minutes at room temperature, which was poured into ice-water, followed by extraction with ethyl acetate (40 ml). The organic layer was washed with water and dried over anhydrous sodium sulfate. The solvent was distilled off, and the residue was purified by means of a silica gel column chromatography to give 3,5-trans-N-(2-fluorobenzyl)-5-(3-tert-butoxycarbonylaminomethylphenyl)-7-chloro-1-(4-fluorobenzyl)-2-oxo-1,2,3,5-tetrahydro-4,1-benzoxazepine-3-acetamide (0.2 g) as a colorless amorphous solid product.
NMR(CDCl$_3$) δ: 1.447(9H,s), 2.694(1H,dd,J=6.0,14.5 Hz), 2.927(1H,dd,J=7.4,14.5 Hz), 4.281(2H,d,J=5.8 Hz), 4.37–4.62(3H,m), 4.798(1H,d,J=14.6 Hz), 5.334(1H,s), 5.395 (1H,d,J=14.6 Hz), 6.16–6.26(1H,m), 6.499(1H,d,J= 2.2 Hz), 6.93–7.42(14H,m)

EXAMPLE 192

3,5-Trans-N-(2-fluorobenzyl)-5-(3-aminomethylphenyl)-7-chloro-1-(4-fluorobenzyl)-2-oxo-1,2,3,5-tetrahydro-4,1-benzoxazepine-3-acetamide•hydrochloride The compound produced in Example 191 (0.16 g) was dissolved in 4N hydrogen chloride (ethyl acetate solution) (3 ml). The solution was stirred for 1.5 hour. The solvent was distilled off to leave the titled compound (0.13 g) as a colorless amorphous solid product.
NMR(CDCl$_3$) δ: 2.711(1H,dd,J=6.0,14.6 Hz), 2.927(1H,dd, J=7.2,14.6 Hz), 3.851(2H,br), 4.34–4.62(3H,m), 4.783(1H, d,J=14.6 Hz), 5.335(1H,s), 5.398(1H,d,J=14.6 Hz), 6.35–6.46(1H,m), 6.515(1H,d,J=2.4 Hz), 6.86–7.38(14H,m)

EXAMPLE 193

3,5-Trans-N-(2-fluorobenzyl)-5-(3-tert-butoxycarbonylaminomethylphenyl)-3-chloro-1-[3-(4-hydroxyphenyl)propyl]-2-oxo-1,2,3,5-tetrahydro-4,1-benzoxazepine-3-acetamide (1) A mixture of 4-hydroxyphenylpropionic acid (3.0 g), benzyl bromide (7.7 g), potassium carbonate (7.5 g) and N,N-dimethylformamide (30 ml) was stirred for 3 hours at 60° C. The reaction mixture was poured into water (200 ml), which was subjected to extraction with ethyl acetate (150 ml). The organic layer was washed with 5% potassium hydrogensulfate, which was further washed with a saturated sodium hydrogencarbonate and a saturated aqueous saline solution, followed by drying over anhydrous sodium sulfate. The solvent was distilled off, and the residue was dissolved in tetrahydrofuran (20 ml). The solution was added dropwise, while stirring, to a suspension of aluminium lithium hydride (1.05 g) in tetrahydrofuran (50 ml). The reaction mixture was heated for 30 minutes under reflux, which was cooled to 0° C., followed by hydrolysis with water (1 ml) and 1N sodium hydroxide (3 ml). Insolubles were filtered off. From the filtrate, the solvent was distilled off to leave 4-benzyloxyphenylpropanol (4.05 g) as a colorless crystalline product.
NMR(CDCl$_3$) δ: 1.78–1.95(2H,m), 2.657(2H,t,J=8.2 Hz), 3.63–3.73(2H,m), 5.044(2H,s), 6.78–7.48(9H,m)

(2) A solution of oxalyl chloride (1.15 g) in methylene chloride (20 ml) was cooled to −78° C., to which was added dimethyl sulfoxide (1.42 g). To this solution was added dropwise a solution of the compound produced in (1) (2.0 g) in methylene chloride (10 ml). To the mixture was then added triethylamine (4.17 g). The mixture was stirred for 40 minutes at room temperature, to which then added water (50 ml). The organic layer was separated and dried over anhydrous sodium sulfate. The solvent was distilled off, and the residue was purified by means of a silica gel column chromatography to give 4-benzyloxyphenylpropionaldehyde (1.1 g) as a colorless oily product.
NMR(CDCl$_3$) δ: 2.72–2.98(4H,m), 5.04(2H,s), 6.88–7.48 (9H,m), 9.812(1H,br)

(3) In methanol (20 ml) were dissolved 2-amino-5-chloro-α-(3-tert-butoxycarbonylaminomethylphenyl)benzyl alcohol (0.7 g) produced in Example (1) and 4-benzyloxyphenylpropionaldehyde produced in (2) (0.51 g). To the solution were added acetic acid (0.14 g) and cyano sodium borohydride (0.15 g). The mixture was stirred for 50 minutes at 60° C. To the reaction mixture were added water (80 ml) and ethyl acetate (100 ml), followed by extraction. The organic layer was washed with water and dried over anhydrous sodium sulfate. The solvent was distilled off to leave 2-[3-(4-benzyloxyphenyl)propyl]amino-5-chloro-α-(3-tert-butoxycarbonylaminomethylphenyl)benzyl alcohol (1.05 g) as a colorless oily product.
NMR(CDCl$_3$) δ: 1.443(9H,s), 1.72–1.78(2H,m), 2.473(2H, t, J=7.6 Hz), 3.004(2H,t,J=7.4 Hz), 4.23–4.36(2H,m), 4.38–4.86(1H,m), 5.033(2H,s), 5.738(1H,s), 6.516(1H,d, J=8.8 Hz), 6.82–7.47(15H,m)

(4) To a solution of the compound (1.05 g) produced in (3) in ethyl acetate (20 ml) was added 1N sodium hydroxide (10 ml). To the mixture was added, while stirring at room temperature, fumaric chloride monoethyl ester (0.31 g). The mixture was stirred for 20 minutes. Then, the organic layer was separated, which was washed with water and dried over anhydrous sodium sulfate. The solvent was distilled off, and the residue was dissolved in ethanol (20 ml). To the solution was added potassium carbonate (0.8 g), which was stirred for 30 minutes at 60° C. The reaction mixture was diluted with ethyl acetate (50 ml), which was washed with water and dried over anhydrous sodium sulfate. The solvent was distilled off, and the residue was purified by means of a silica gel column chromatography to give 3,5-cis and 3,5-trans-1-[3-(4-benzyloxyphenyl)propyl]-5-(3-tert-butoxycarbonylaminomethylphenyl)-7-chloro-2-oxo-1,2,3,5-tetrahydro-4,1-benzoxazepine-3-acetic acid ethyl ester (1.1 g) as a colorless oily product.

NMR(CDCl$_3$) δ: 1.258(3H,t,J=7.2 Hz), 1.432(9H,s), 1.85–2.27(3H,m), 2.55–3.15(4H,m), 3.55–3.75(2H,m), 4.13 (2H, q,J=7.2 Hz), 4.05–4.65(3H,m), 5.041(3/2H,s), 5.052 (1/2H, s), 5.753(2/3H,s), 5.835(1/3H,s), 6.581(2/3H,d, J=2.4 Hz), 6.84–7.48(15 1/3H,m)

(5) The compound (1.1 g) produced in (4) was dissolved in a mixture of tetrahydrofuran (10 ml) and methanol (15 ml). To the solution was added 1N sodium hydroxide (6 ml), which was stirred for 30 minutes at 60° C. The reaction mixture was concentrated, which was made acidic with a 5% aqueous solution of potassium hydrogensulfate, followed by extraction with ethyl acetate (60 ml). The organic layer was washed with water and dried over anhydrous sodium sulfate. The solvent was distilled off, and the residue was purified by means of a silica gel column chromatography to give 3,5-cis and 3,5-trans-1-[3-(4-benzyloxyphenyl)propyl]-5-(3-tert-butoxycarbonylaminomethylphenyl)-7-chloro-2-oxo-1,2,3,5-tetrahydro-4,1-benzoxazepine-3-acetic acid (0.55 g) as a colorless amorphous solid product.

NMR(CDCl$_3$) δ: 1.427(9H,s), 1.88–2.27(2H,m), 2.627(3/2H, t,J=7.4 Hz), 2.77–3.17(5/2H,m), 3.48–3.73(1H,m), 4.03–4.12 (1/3H,m), 4.23–4.45(1 1/3H,m), 5.037(4/3H,s), 5.049 (1/3H,m), 5.768(2/3H,s), 5.856(1/3H,s), 6.58(1H,br), 6.85–7.48(15 1/3H, m)

(6) The compound produced in (5) (0.5 g) and 2-fluorobenzylamine (0.11 g) were dissolved N,N-dimethylformamide (10 ml). To the solution were added, while stirring at 0° C., cyano diethyl phosphate (0.14 g) and triethylamine (0.13 g). The reaction mixture was stirred for 30 minutes at room temperature, to which were added ice-water and ethyl acetate (60 ml), followed by extraction. The organic layer was washed with water and dried over anhydrous sodium sulfate. The solvent was distilled off, and the residue was purified by means of a silica gel column chromatography to give 3,5-trans-N-(2-fluorobenzyl)-1-[3-4-benzyloxyphenyl)propyl]-5-(3-tert-butoxycarbonylaminomethylphenyl)-7-chloro-2-oxo-1,2,3,5-tetrahydro-4,1-benzoxazepine-3-acetamide (0.24 g) as a colorless amorphous solid product.

NMR(CDCl$_3$) δ: 1.435(9H,s), 1.85–2.05(2H,m), 2.57–2.76 (3H,m), 2.898(1H,dd,J=7.2,14.4 Hz), 3.53–3.75(1H,m), 4.02–4.58(6H,m), 4.73–4.88(1H,m), 5.043(2H,s), 5.732 (1H,s), 6.23–6.32(1H,m), 6.566(1H,d,J=2.4 Hz), 6.86–7.47 (19H,m)

(7) To a solution of the compound produced in (6) (0.43 g) in a mixture of ethyl acetate (12 ml) and methanol (3 m) was added 10% palladium-carbon (80 mg). The mixture was stirred for 30 minutes in hydrogen streams. The reaction mixture was subjected to filtration, and the filtrate was concentrated. To the concentrate was added water (30 ml), which was subjected to extraction with ethyl acetate (30 ml). The organic layer was washed with water and dried over anhydrous sodium sulfate. The solvent was distilled off to leave 3,5-trans-N-(2-fluorobenzyl)-5-(3-tert-butoxycarbonylaminomethylphenyl)-7-chloro-1-(4-hydroxyphenyl)propyl]-2-oxo-1,2,3,5-tetrahydro-4,1-benzoxazepine-3-acetamide (0.34 g) as a colorless amorphous solid product.

NMR(CDCl$_3$) δ: 1.437(9H,s), 1.83–2.06(2H,m), 2.55–3.60 (4H,m), 3.52–3.75(1H,m), 4.279(2H,d,J=6.2 Hz), 4.36–4.62 (4H,m), 4.75–4.95(1H,m), 5.702(1H,s), 6.23–6.38(1H,m), 6.553(1H,d,J=2.4 Hz), 6.68–7.47(14H,m)

EXAMPLE 194

3,5-Trans-N-(2-fluorobenzyl)-5-(3-aminomethylphenyl)-7-chloro-1-[3-(4-hydroxyphenyl)propyl]-2-oxo-1,2,3,5-tetrahydro-4,1-benzoxazepine-3-acetamide•hydrochloride To the compound produced in Example 193 (0.3 g) was added 4N hydrogen chloride (ethyl acetate solution) (4 ml). The mixture was stirred for 1.5 hour. The solvent was distilled off to leave the titled compound (0.24 g) as a colorless amorphous solid product.

NMR(CDCl$_3$) δ: 1.82–2.02(2H,m), 2.577(2H,t,J=7.4 Hz), 2.692(1H,dd,J=6.2,14.6 Hz), 2.833(1H,dd,J=6.8,14.6 Hz), 3.262(2H,br), 3.42–3.72(1H,m), 3.852(2H,s), 4.22–4.58 (4H,m), 5.69(1H,s), 6.52(1H,m), 6.558(1H,d,J=2.2 Hz), 6.62–7.48(14H,m)

EXAMPLE 195

3,5-Trans-N-(2-fluorobenzyl)-1-(4-biphenylmethyl)-5-[3-tert-butoxycarbonylaminomethylphenyl)-7-(3-(4-hydroxyphenyl)propyloxy]-2-oxo-1,2,3,5-tetrahydro-4,1-benzoxazepine-3-acetamide (1) 3-(4-Benzyloxyphenyl)propanol produced in Example 193-(1) (1.5 g) was dissolved in toluene (30 ml). To the solution were added thionyl chloride (0.88 g) and pyridine (0.1 ml). The mixture was stirred for 2 hours at 80° C. The reaction mixture was cooled, to which was added saturated sodium hydrogencarbonate to cause decomposition, followed by extraction with ethyl acetate. The organic layer was washed with water and dried over anhydrous sodium sulfate. The solvent was distilled off to leave 3-(4-benzyloxyphenyl)propyl chloride (1.3 g) as a colorless crystalline product. m.p.: 34–35° C.

NMR(CDCl$_3$) δ: 1.97–2.13(2H,m), 2.723(2H,t,J=7.6 Hz), 3.516(2H,t,J=6.4 Hz), 5.047(2H,s), 6.87–7.47(9H,m)

(2) A solution of the compound produced in (1) (70 mg), 3,5-trans-N-(2-fluorobenzyl)-1-(4-biphenylmethyl)- 5-(3-tert-butoxycarbonylaminomethylphenyl)-7-hydroxy-2-oxo-1,2,3,5-tetrahydro-4,1-benzoxazepine-3-acetamide produced in Example 165 (0.15 g) and potassium carbonate in N,N-dimethylformamide (6 ml) was stirred for 3 hours at 70° C. The reaction mixture was poured into water, which was subjected to extraction with ethyl acetate (40 ml). The organic layer was washed with water and dried over anhydrous sodium sulfate. The solvent was distilled off, and the residue was purified by means of a silica gel column chromatography to give 3,5-trans-N-(2-fluorobenzyl)-7-[3-(4-benzyloxyphenyl)propyl]oxy-1-(4-biphenylmethyl)-5-(3-tert-butoxycarbonylaminomethylphenyl)-2-oxo-1,2,3,5-tetrahydro-4,1-benzoxazepine-3-acetamide (0.17 g) as a colorless oily product.

NMR(CDCl$_3$) δ: 1.417(9H,s), 1.85–2.06(2H,m), 2.58–2.77 (3H,m), 2.938(1H,dd,J=7.4,14.3 Hz), 3.65–3.82(2H,m), 4.157(2H,d,J=7.0 Hz), 4.35–4.76(4H,m), 4.818(1H,d, J=14.2 Hz), 5.033(2H,s), 5.319(1H,s), 5.466(1H,d, J=14.2 Hz), 6.022(1H,d,J=2.8 Hz) 6.34–6.43(1H,m), 6.85–7.62 (28H,m)

(3) To a solution of the compound (0.17 g) produced in (2) in a mixture of ethyl acetate (5 ml) and methanol (10 ml) was added 10% palladium-carbon (80 mg). The mixture was stirred for 5 hours in hydrogen streams. The reaction mixture was subjected to filtration, and the filtrate was concentrated. The concentrate was dissolved in ethyl acetate (40 ml), which was washed with water and dried over anhydrous sodium sulfate. The solvent was distilled off to leave the titled compound (0.11 g) as a colorless amorphous solid product.
NMR(CDCl$_3$) δ: 1.456(9H,s), 1.83–2.12(2H,m), 2.52–2.97 (4H,m), 3.48–3.63(2H,m), 4.02–4.22(2H,m), 4.36–4.56 (3H,m), 4.783(1H,d,J=14.4 Hz), 5.272(1H,s), 5.475(1H,d, J=14.4 Hz), 5.777(1H,d,J=3.0 Hz), 6.25–6.42(1H,m), 6.65–7.60(23H,m)

EXAMPLE 196

3,5-Trans-N-(2-fluorobenzyl)-5-(3-aminomethylphenyl)-1-(4-biphenylmethyl)-7-[3-(4-hydroxyphenyl)propyl]-2-oxo-1,2,3,5-tetrahydro-4,1-benzoxazepine-3-acetamide•hydrochloride To the compound produced in Example 195 (80 mg) was added 4N hydrogen chloride (ethyl acetate solution) (2 ml). The mixture was stirred for 2 hours. From the reaction mixture, the solvent was distilled off to leave the titled compound (72 mg) as a colorless crystalline solid product.
NMR(CDCl$_3$) δ: 1.83–2.02(2H,m), 2.618(2H,t,J=7.0 Hz), 2.745(1H,dd,J=6.2,14.4 Hz), 2.909(1H,dd,J=6.8,14.4 Hz), 3.41(2H,br), 3.636(2H,t,J=5.8 Hz), 3.741(2H,br), 4.28–4.62 (3H,m), 4.771(1H,d,J=14.4 Hz), 5.269(1H,s), 5.475 (1H,d, J=14.4 Hz), 5.827(1H,d,J=2.8 Hz), 6.48–6.72(3H,m), 6.78–7.62(21H,m)

EXAMPLE 197

3,5-Trans-N-(2-fluorobenzyl)-1-(4-acetylamino)benzyl-5-[3-[(1-tert-butoxycarbonylamino-1-methyl)ethyl]phenyl]-7-chloro-2-oxo-1,2,3,5-tetrahydro-4,1-benzoxazepine-3-acetamide (1) In methanol (30 ml) were dissolved 2-amino-α-[3'-[(1-tert-butoxycarbonylamino-1-methyl)ethyl]phenyl]-5-chloro-benzyl alcohol produced in Example 92 (2.0 g) and 4-nitrobenzaldehyde (0.85 g). To the solution were added acetic acid (0.35 g) and cyano sodium borohydride (035 g). The mixture was stirred for 1.5 hour at 60° C. The reaction mixture was concentrated, to which were added water (80 ml) and ethyl acetate (100 ml), followed by subjecting the mixture to extraction. The organic layer was washed with water and dried over anhydrous sodium sulfate. The solvent was distilled off, and the residue was purified by means of a silica gel column chromatography to give 5-chloro-2-(4-nitrobenzylamino)-α-[3'-[(1-tert-butoxycarbonylamino-1-methyl)ethyl]phenyl]-benzyl alcohol (2.2 g) as a yellow oily product.
NMR(CDCl$_3$) δ: 1.341(9H,br), 1.599(6H,s), 2.67(1H,br), 4.385(2H,d,J=3.4 Hz), 4.97(1H,br), 5.23(1H,m), 5.826(1H, s), 6.333(1H,d,J=8.8 Hz), 6.90–7.60(8H,m), 8.085(2H,d, J=8.6 Hz)

(2) The compound (2.2 g) produced in (1) was dissolved in ethyl acetate (30 ml). To the solution was added IN sodium hydroxide (20 ml). To the mixture was added, a while stirring at room temperature, fumaric chloride monoethyl ester (0.7 g). The reaction mixture was stirred for 10 minutes, and, then, the organic layer was separated, which was washed with water and dried over anhydrous sodium sulfate. The solvent was distilled off, and the residue was dissolved in ethanol (30 ml). To the solution was added sodium carbonate (1.2 gm and the mixture was stirred for 2 hours at 60° C. The reaction mixture was diluted with ethyl acetate (80 ml), which was washed with water and dried over anhydrous sodium sulfate. The solvent was distilled off, and the residue was purified by means of a silica gel column chromatography to give 3,5-trans-5-[3-[(1-tert-butoxycarbonylamino-1-methyl)ethyl]phenyl]-7-chloro-1-(4-nitrobenzyl)-2-oxo-1,2,3,5-tetrahydro-4,1-benzoxazepine-3-acetic acid ethyl ester (0.9 g) as a yellow oily product.
NMR(CDCl$_3$) δ: 1.262(3H,t,J=7.2 Hz), 1.284(9H,br), 1.513 (3H,s), 1.562(3H,s), 2.77(1H,dd,J=5.0,16.4 Hz), 3.16(1H, dd,J=9.2,16.4 Hz), 4.14(2H,q,J=7.2 Hz), 4.53(1H,dd,J=4.6, 6.5 Hz), 4.80–5.50(4H,m), 6.62(1H,d,J=2.2 Hz), 7.0–7.60 (8H,m), 8.27(2H,d,J=8.6 Hz)

(3) The compound (0.9 g) produced in (2) was dissolved in ethyl acetate (15 ml), to which was added 10% palladium-carbon (0.1 g). The mixture was stirred for 3 hours in hydrogen streams. The reaction mixture was subjected to filtration, and the filtrate was concentrated. The concentrate was purified by means of a silica gel column chromatography to give 3,5-trans-1-(4-aminobenzyl)-5-[3-[1-tert-butoxycarbonylamino-1-methyl)ethyl]phenyl]-7-chloro-2-oxo-1,2,3,5-tetrahydro-4,1-benzoxazepine-3-acetic acid ethyl ester (0.5 g) as a colorless oily product.
NMR(CDCl$_3$) δ: 1.245(3H,t,J=7.2 Hz), 1.29(9H,br), 2.73 (1H,dd,J=5.6,16.7 Hz), 3.12(1H,dd,J=8.2,16.7 Hz), 4.14 (1H,q,J=7.2 Hz), 4.30–4.45(2H,m), 5.0–5.20(1H,m), 5.683 (1H,d,J=14.0 Hz), 6.45–6.70(4H,m), 6.95–7.50(8H,m)

(4) The compound (0.5 g) produced in (3) was dissolved in a mixture of tetrahydrofuran (5 ml) and methanol (10 ml). To the solution was added 1N sodium hydroxide (6 ml). The mixture was stirred for 40 minutes at 60° C. The reaction mixture was concentrated, to which was added water (20 ml). The mixture was neutralized with 10% potassium hydrogensulfate, which was then subjected to extraction with ethyl acetate (50 ml). The organic layer was washed with water and dried over anhydrous sodium sulfate. The solvent was distilled off, and the residue was dissolved in N,N-dimethylformamide (8 ml). To the solution was added 2-fluorobenzylamine (0.11 g). To the mixture were added, while stirring at 0° C., cyano diethyl phosphate (0.14 g) and triethylamine (0.1 g). The reaction mixture was stirred for 20 minutes at room temperature, which was diluted with ethyl acetate (50 ml). The solution was washed with water and dried over anhydrous sodium sulfate. The solvent was distilled off, and the residue was purified by means of a silica gel column chromatography to give 3,5-trans-N-(2-fluorobenzyl)-1-(4-aminobenzyl)-5-[3-[(1-tert-butoxycarbonylamino-1-methyl)ethyl]phenyl]-7-chloro-2-oxo-1,2,3,5-tetrahydro-4,1-benzoxazepine-3-acetamide (0.27 g). m.p.: 165–167° C.
NMR(CDCl$_3$) δ: 0.95–1.65(15H,m), 2.68(1 H,dd,J=6.4, 14.4 Hz), 2.89(1H,dd,J=7.0,14.4 Hz), 4.250–4.65(4H,m), 4.95–5.15(1H,m), 5.665(1H,d,J=14.0 Hz), 5.73–5.95(1H, m), 6.35–6.70(4H,m), 6.90–7.45(12H,m)

(5) The compound produced in (4) (0.25 g) was dissolved in methylene chloride (10 ml). To the solution were added acetic anhydride (0.2 ml) and triethylamine (0.2 ml). The reaction mixture was stirred for 30 minutes at room temperature, which was then concentrated. The concentrate was diluted with ethyl acetate (30 ml), which was washed with a 5% aqueous solution of potassium hydrogensulfate. The solution was further washed with a saturated aqueous solution of sodium hydrogencarbonate and a saturated aqueous saline solution, followed by drying over anhydrous sodium sulfate. The solvent was distilled off, and the residue was purified by means of a silica gel column chromatography to give the titled compound, 3,5-trans-N-(2-fluorobenzyl)-1-(4-acetylaminobenzyl-5-[3-[(1-butoxycarbonylamino-1-methyl)ethyl]phenyl]-7-chloro-2-oxo-1,2,3,5-tetrahydro-4,1-benzoxazepine-3-acetamide (0.26 g) as a colorless amorphous solid product.
NMR(CDCl$_3$) δ: 0.95–1.52(15H,m), 2.170(3H,m), 2.68(1H, dd,J=6.2,14.5 Hz), 2.89(1H,dd,J=6.8,14.5 Hz), 4.25–4.70 (4H,m), 5.152(1H,s), 5.45–5.95(2H,m), 6.268(1H,m), 6.489 (1H,s), 6.90–7.55(14H,m)

EXAMPLE 198

3,5-Trans-N-(2-fluorobenzyl)-1-(4-acetylaminobenzyl)-5-[3-[(1-amino-1-methyl)ethyl]phenyl]-7-chloro-2-oxo-1, 2,3,5-tetrahydro-4,1-benzoxazepine-3-acetamide•hydrochloride The compound produced in Example 197 (0.22 g) was dissolved in methanol (1 ml), to which was added 4N hydrogen chloride (ethyl acetate solution) (5 ml). The mixture was stirred for 40 minutes. The solvent was distilled off. To the residue were added methanol (10 ml) and ethyl acetate (20 ml). The mixture was again subjected to distillation to remove the solvent to leave the titled compound (0.2 g) as a colorless amorphous solid product.
NMR(CDCl$_3$) δ: 1.439(3H,s), 1.458(3H,s), 2.71(1H,dd, J=5.8,14.5 Hz), 2.91(1H,dd,J=7.2,14.5 Hz), 4.34–4.60 (3H, m), 4.681(1H,d,J=14.4 Hz), 5.226(1H,s), 5.435(1H,d, J=14.4 Hz), 6.413(1H,m), 6.495(1H,d,J=2.2 Hz), 6.95–7.52 (14H,m) 7.935(1H,br)

EXAMPLE 199

3,5-Trans-N-(2-fluorobenzyl)-1-(4-biphenylmethyl)-5-[3-[(1-tert-butoxycarbonylamino-1-methyl)ethyl]phenyl]-2-oxo-1,2,3,5-tetrahydro-4,1-benzoxazepine-3-acetamide (1) N,O-Dimethylhydroxylamine (102.5 g) was dissolved in 90% ethanol (40 ml). To the solution were added triethylamine (106 g) and isatoic anhydride (74 g). The mixture was heated for 1.5 hour under reflux. The reaction mixture was concentrated, to which was added a saturated aqueous saline solution, followed by extraction with ethyl acetate (500 ml). The organic layer was washed with water and dried over anhydrous sodium sulfate. The solvent was distilled off to leave N-methyl-N-methyloxy-2-aminobenzamide (81 g) as a yellow oily product. This compound (6.8 g) and 1-[(tert-butoxycarbonylamino-1-methyl)ethyl]-3-bromobenzene (10 g) were dissolved in tetrahydrofuran (200 ml). The solution was cooled to −80° C. or below, to which was added dropwise, while stirring, n-butyl lithium (1.6 mol/L) (128 ml) over 1.5 hour. To the reaction mixture was added water (200 ml), which was subjected to extraction with ethyl acetate (300 ml). The organic layer was washed with water and dried over anhydrous sodium sulfate. The solvent was distilled off, and the residue was purified by means of a silica gel column chromatography to give 2-amino-3'-(1-tert-butoxycarbonylamino-1-methyl)ethyl-benzophenone (2.2 g) as a yellow oily product.
NMR(CDCl$_3$) δ: 1.364(9H,s), 1.642(6H,s), 4.85–5.03 (1H, m), 6.075(2H,br), 6.55–6.77(2H,m), 7.22–7.72(4H,m)
(2) The compound produced in (1) (2.1 g) was dissolved in methanol (30 ml), to which was added sodium borohydride (0.4 g). The mixture was stirred for 30 minutes at room temperature. The reaction mixture was concentrated, to which was added water (50 ml), followed by extraction with ethyl acetate (60 ml). The organic layer was washed with water and dried over anhydrous sodium sulfate. The solvent was distilled off, and the residue was purified by means of a silica gel column chromatography to give 2-amino-α-[3-[(1-tert-butoxycarbonylamino-1-methyl )ethyl]phenyl] benzyl alcohol (2.0 g) as a pale yellow oily product.
NMR(CDCl$_3$) δ: 1.35(9H,br), 1.610(6H,s), 2.55–2.73 (1H, m), 3.96(2H,br), 4.84–5.03(1H,m), 5.859(1H,s), 6.63–7.57 (BH,m)
(3) The compound produced in (2) (1.2 g) and 4-phenyl benzaldehyde (0.64 g) were dissolved in methanol. To the solution were added acetic acid (0.24 g) and cyano sodium borohydride (0.25 g). The mixture was stirred for 30 minutes at 60° C. The reaction mixture was concentrated, which was subjected to extraction with water (30 ml) and ethyl acetate (50 ml). The organic layer was separated, washed with water and dried over anhydrous sodium sulfate. The solvent was distilled off, and the residue was purified by means of a silica gel column chromatography to give 2-(4-biphenylmethyl) amino-α-[3-[(1-tert-butoxycarbonylamino-1-methyl)ethyl] phenyl]benzyl alcohol (1.5 g) as a colorless oily product.
NMR(CDCl$_3$) δ: 1.34(9H,br), 1.556(3H,s), 1.583(3H,s), 2.38–2.57(1H,m), 4.345(2H,s), 4.83–5.17(2H,m), 5.921 (1H,s), 6.63–6.56(2H,m), 6.95–7.72(15H,m)
(4) The compound (1.5 g) produced in (3) was dissolved in ethyl acetate (20 ml), to which was added 1N sodium hydroxide (10 ml). To the mixture was added, while stirring at room temperature, fumaric chloride monoethyl ester (0.39 g). The reaction mixture was stirred for 10 minutes. The solvent was then separated, washed with water and dried over anhydrous sodium sulfate. The solvent was distilled off, and the residue was dissolved in ethanol (30 ml). To the solution was added potassium carbonate (1.0 g). The mixture was stirred for .1.5 hour at 60° C. The reaction mixture was concentrated, which was subjected to extraction with water (50 ml) and ethyl acetate (60 ml). The organic layer was washed with water and dried over anhydrous sodium sulfate. The solvent was distilled off, and the residue was purified by means of a silica gel column chromatography to give 3,5-trans-1-(4-biphenylmethyl)-5-[3-[(1-tert-butoxycarbonylamino-1-methyl)ethyl]phenyl]-2-oxo-1,2,3, 5-tetrahydro-4,1-benzoxazepine-3-acetic acid ethyl ester (1.12 g) as a colorless oily product.
NMR(CDCl$_3$) δ: 1.247(3H,t,J=7.0 Hz), 1.24–1.43(12H,m), 1.523(3H,s), 2.773(1H,dd,J=5.4,16.6 Hz), 3.144(1H,dd, J=8.4,16.6 Hz), 4.142(1H,q,J=7.0 Hz), 4.498(1H,dd,J=5.4, 8.4 Hz), 4.63–4.75(1H,m), 4.934(1H,d,J=14.8 Hz), 5.359 (1H,s), 5.495(1H,d,J=14.8 Hz), 6.572(1H,d,J=7.4 Hz), 6.97–7.66(16H,m)
(5) The compound produced in (4) (1.05 g) was dissolved in a mixture of tetrahydrofuran (10 ml) and methanol (10 ml). To the solution was added 1N sodium hydroxide (8ml). The mixture was stirred for 40 minutes at 60° C. The reaction mixture was concentrated, to which was added water (20 ml), followed by neutralization with a 5% aqueous solution of potassium hydrogensulfate. The solution was subjected to extraction with ethyl acetate (50 ml). The organic layer was washed with water and dried over anhydrous sodium sulfate. The solvent was distilled off, and the residue was purified by means of a silica gel column chromatography to give 3,5-trans-1-(4-biphenylmethyl)-5-[3-[(1-tert-butoxycarbonylamino-1-methyl)ethyl]phenyl]-2-oxo-1,2,3, 5-tetrahydro-4,1-benzoxazepine-3-acetic acid (0.9 g) as a colorless amorphous solid product.
NMR(CDCl$_3$) δ: 1.428(9H,br), 1.534(6H,s), 2.88–3.25 (2H, m), 4.72–5.08(2H,m), 5.33–5.62(2H,m), 6.551(1H,d, J=8.2 Hz), 6.83–7.65(16H,m)
(6) In N,N-dimethylformamide (10 ml) were dissolved the compound (0.9 g) produced in (5) and 2-fluorobenzyl amine (0.22 g). To the solution were added, while stirring at 0° C., cyano diethylphosphate (0.28 g) and, then, triethylamine (0.21 g). The reaction mixture was stirred for 20 minutes at room temperature, which was poured into water (40 ml), followed by extraction with ethyl acetate (60 ml). The organic layer was washed with water and dried over anhydrous sodium sulfate. The solvent was distilled off, and the residue was purified by means of a silica gel column chromatography to give the titled compound, 3,5-trans-N-(2-fluorobenzyl)-1-(4-biphenylmethyl)-5-[3-[(1-tert-butoxycarbonyl-1-methyl)ethyl]phenyl]-2-oxo-1,2,3,5-tetrahydro-4,1-benzoxazepine-3-acetamide (0.75 g) as a colorless amorphous solid product.

NMR(CDCl$_3$) δ: 1.294(3H,s), 1.311(9H,br), 1.579(3H,s), 2.720(1H,dd,J=5.8,14.2 Hz), 2.951(1H,dd,J=7.2,14.2 Hz), 4.38–4.73(3H,m), 4.877(1H,d,J=14.2 Hz), 5.325(1H,s), 5.507(1H,d,J=14.2 Hz), 6.32–6.42(1H,m), 6.555(1H,d, J=7.8 Hz), 6.94–7.63(20H,m)

EXAMPLE 200

3,5-Trans-N-(2-fluorobenzyl)-5-[3-[(1-amino-1-methyl)ethyl]phenyl]-1-(4-biphenylmethyl)-2-oxo-1,2,3,5-tetrahydro-4,1-benzoxazepine-3-acetamide•hydrochloride To the compound produced in Example 199 was added 4N hydrogen chloride (ethyl acetate solution) (6 ml). The mixture was stirred for 2 hours. The reaction mixture was concentrated, to which was added ethyl acetate (20 ml). The mixture was again concentrated to leave the titled compound (0.56 g) as a colorless amorphous solid product.

NMR(CDCl$_3$) δ: 1.379(3H,s), 1.392(3H,s), 2.746(1H,dd, J=5.8,14.3 Hz), 2.963(1H,dd,J=7.4,14.3 Hz), 4.37–4.58 (3H, s), 4.977(1H,d,J=14.6 Hz), 5.420(1H,d,J=14.6 Hz), 5.484 (1H,s), 6.504(1H,t,J=5.6 Hz), 6.565(1H,d,J=7.6 Hz), 6.95–7.58(20H,m)

EXAMPLE 201

3,5-Trans-N-(2-fluorobenzyl)-5-[3-[(1-tert-butoxycarbonyl-1-methyl)ethyl]phenyl]-7-chloro-1-(4-diethylamino)benzyl-2-oxo-1,2,3,5-tetrahydro-4,1-benzoxazepine-3-acetamide (1) In methanol (20 ml) were dissolved 2-amino-α-[3'-[(1-tert-butoxycarbonylamino-1-methyl)ethyl]phenyl]-5-chloro-benzyl alcohol produced in Example 92 (0.9 g) and 4-(diethylamino)benzaldehyde (0.45 g). To the solution was added acetic acid (0.16 g). To the mixture was added, while stirring at room temperature, cyano sodium borohydride (0.17 g). The reaction mixture was stirred for 40 minutes at 60° C., which was concentrated. To the concentrate were added water (4 ml) and ethyl acetate (50 ml). The mixture was subjected to extraction. The organic layer was washed with water and dried over anhydrous sodium sulfate. The solvent was distilled off, and the residue was dissolved in ethyl acetate (20 ml). To the solution was added IN sodium hydroxide (12 ml). To the mixture was added, while stirring, fumaric chloride monoethyl ester (0.26 g). The reaction mixture was stirred for 20 minutes. The organic layer was then separated, washed with water and dried over anhydrous sodium sulfate. The solvent was distilled off, and the residue was dissolved in ethanol (20 ml). To the solution was added potassium carbonate (0.4 g). The mixture was stirred for 1.5 hour at 60° C. The reaction mixture was diluted with ethyl acetate (50 ml), which was washed with water and dried over anhydrous sodium sulfate. The solvent was distilled off, and the residue was purified by means of a silica gel column chromatography to give 3,5-trans-5-[3-[(1-tert-butoxycarbonylamino-1-methyl)ethyl]phenyl]-1(4-diethylamino)benzyl-7-chloro-2-oxo-1,2,3,5-tetrahydro-4,1-benzoxazepine-3-acetic acid ethyl ester (0.32 g) as a yellowish green amorphous solid product.

NMR(CDCl$_3$) δ: 1.08–1.47(18H,m), 1.539(3H,s), 2.753(1H, dd,J=5.4,16.5 Hz), 3.106(1H,dd,J=8.0,16.5 Hz), 3.333(4H, q,J=7.2 Hz), 4.139(2H,q,J=7.2 Hz), 4.420(1H,dd,J=5.6, 8.1 Hz), 4.588(1H,d,J=14.2 Hz), 4.83–4.93(1H,m), 5.325(1H,s), 5.467(1H,d,J=14.2 Hz), 6.52–6.63(3H,m), 6.84–7.52(8H,m)

(2) The compound produced in (1) (0.3 g) was dissolved in a mixture of tetrahydrofuran (4 ml) and methanol (10 ml). To the solution was added 1N sodium hydroxide (5 ml), and the mixture was stirred for 40 minutes at 60° C. The reaction mixture was concentrated, to which was added water (20 ml). The mixture was neutralized with a 5% aqueous solution of potassium hydrogensulfate, which was subjected to extraction with ethyl acetate (50 ml). The organic layer was washed with water and dried over anhydrous sodium sulfate. The solvent was distilled off, and the residue was dissolved in N,N-dimethylformamide (6 ml). To the solution was added 2-fluorobenzylamine (40 mg). To the mixture were added, while stirring at 0° C., cyano diethyl phosphate (60 mg) and triethylamine (50 mg). The reaction mixture was stirred for 20 minutes at room temperature, which was poured into ice-water, followed by extraction with ethyl acetate. The organic layer was washed with water and dried over anhydrous sodium sulfate. The solvent was distilled off, and the residue was purified by means of a silica gel column chromatography to give the titled compound, 3,5-trans-N-(2-fluorobenzyl) 5-[3-[(1-tert-butoxycarbonyl-1-methyl)ethyl]phenyl]-7-chloro-1-(4-diethylamino)benzyl-2-oxo-1,2,3,5-tetrahydro-4,1-benzoxazepine-3-acetamide (0.21 g) as a colorless amorphous solid product.

NMR(CDCl$_3$) δ: 1.129(6H,t,J=6.8 Hz), 1.22–1.43(9H,m), 1.512(3H,s), 2.692(1H,dd,J=6.0,14.5 Hz), 2.925(1H,dd, J=7.2,14.5 Hz), 3.327(4H,q,J=6.8 Hz), 4.37–4.63(4H,m), 4.83–4.93(1H,m), 5.306(1H,s), 5.439(1H,d,J=14.0 Hz), 6.32–6.43(1H,m), 6.47–7.25(15H,m)

EXAMPLE 202

3,5-Trans-N-(2-fluorobenzyl)-5-[3-[(1-amino-1-methyl)ethyl]phenyl]-7-chloro-1-(4-diethylamino)benzyl-2-oxo-1,2,3,5-tetrahydro-4,1-benzoxazepine-3-acetamide•dihydrochloride To the compound produced in Example 201 (0.18 g) was added 4N hydrogen chloride (ethyl acetate solution) (3 ml). The mixture was stirred for 30 minutes at room temperature. The reaction mixture was concentrated, to which was added ethyl acetate (20 ml). The mixture was again concentrated to leave the titled compound (0.17 g) as a colorless amorphous solid product.

NMR(CDCl$_3$) δ: 1.121(6H,t,J=7.0 Hz), 1.469(3H,s), 1.490 (3H,s), 2.730(1H,dd,J=5.8,14.6 Hz, 3.310(3H,q,J=7.0 Hz), 4.35–4.53(3H,m), 4.597(1H,d,J=14.2 Hz), 5.359(1H,s); 5.40(1H,d,J=14.2 Hz), 6.45–6.62(4H,m), 6.87–7.55(12H,m)

EXAMPLE 203

N-(2-fluorobenzyl)-5-(3-tert-butoxycarbonylaminomethyl)phenyl-7-chloro-2-oxo-1-[(3-phenyl)-2-propenyl]-1,2,3,5-tetrahydro-4,1-benzoxazepine-3-acetamide (1) In methanol (15 ml) were dissolved 2-amino-5-chloro-α-(3-tert-butoxycarbonylaminomethylphenyl)benzyl alcohol (0.6 g) produced in Example (1) and cinnamaldehyde. (0.5 g). To the solution was added acetic acid (0.11 g). To the mixture was added, while stirring at room temperature, cyano sodium borohydride (0.12 g). The reaction mixture was stirred for 40 minutes at 60° C., which was concentrated. The concentrate was subjected to extraction by the addition of water (30 ml) and ethyl acetate (50 ml). The organic layer was washed with water and dried over anhydrous sodium sulfate. The solvent was distilled off, and the residue was purified by means of a silica gel column chromatography to give a-(3-tert-butoxycarbonylaminomethylphenyl)-5-chloro-2-[(3-phenyl)-2-propenyl]amino-benzyl alcohol (0.8 g) as a colorless oily product.

NMR(CDCl$_3$) δ: 1.445(9H,s), 3.83–3.89(2H,m), 4.291 (2H, d,J=5.6 Hz), 4.73–4.86(1H,m), 5.823(1H,s), 6.08–6.47(2H, m), 6.630(1H,d,J=8.6 Hz), 6.990(1H,d,J=2.0 Hz), 7.04–7.48 (10H,m)

(2) The compound (0.8 g) produced in (1) was dissolved in ethyl acetate (20 ml), to which was added 1N sodium hydroxide (10 ml). To the mixture was added, while stirring at room temperature, fumaric chloride monoethyl ester (0.29 g). The mixture was stirred for 10 minutes. The organic layer was then separated, washed with water and dried over anhydrous sodium sulfate. The solvent was distilled off, and the residue was dissolved in ethanol (20 ml). To the solution was added potassium carbonate (0.7 g). The mixture was stirred for 2 hours at 60° C. The reaction mixture was diluted with ethyl acetate (50 ml), which was washed with water and dried over anhydrous sodium sulfate. The solvent was distilled off, and the residue was purified by means of a silica gel column chromatography to give 3,5-cis and 3,5-trans-5-(3-tert-butoxycarbonylaminomethylphenyl)-7-chloro-1-[(3-phenyl)-2-propenyl]-2-oxo-1,2,3,5-tetrahydro-4,1-benzoxazepine-3-acetic ethyl ester (0.6 g) as an oily mixture.

NMR(CDCl$_3$) δ: 1.18–1.33(3H,m), 1.447(9H,s), 2.62–3.23 (2H,m), 3.93–4.92(8H,m), 5.760(½H,s), 5.866(½H,s), 6.12–6.72(2H,m), 6.95–7.63(11H,m)

(3) The compound (0.6 g) produced in (2) was dissolved in a mixture of tetrahydrofuran (5 ml) and methanol (10 ml). To the solution was added 1N sodium hydroxide (5 ml). The mixture was stirred for 40 minutes at 60° C. The reaction mixture was diluted with water (10 ml), which was neutralized with a 5% aqueous solution of potassium hydrogensulfate, followed by extraction with ethyl acetate (50 ml). The organic layer was washed with water and dried over anhydrous sodium sulfate. The solvent was distilled off, and the oily residue (0.3 g) was dissolved in N,N-dimethylformamide (6 ml). To the solution was added 2-fluorobenzylamine (65 mg). To the mixture were added, while stirring at 0° C., cyano diethyl phosphate (85 mg) and triethylamine (57 mg). The reaction mixture was stirred for 20 minutes at room temperature, which was diluted with ethyl acetate (30 ml). The solution was washed with water and dried over anhydrous sodium sulfate. The solvent was distilled off, and the residue was purified by means of a silica gel column chromatography to give the titled compound, N-(2-fluorobenzyl)-5-(3-tert-butoxycarbonylaminomethyl) phenyl- 7-chloro-2-oxo-1-[(3-phenyl)-2-propenyl]-1,2,3,5-tetrahydro-4,1-benzoxazepine-3-acetamide (0.22 g) as a colorless oily product.

NMR(CDClhd 3) δ: 1.419(3.6H,s), 1.439(5.4H,s), 2.63–3.07(2H,m), 3.959(0.8H,d,J=6.4 Hz), 4.25(1.2H,d, J=5.6 Hz), 4.33–4.92(5.4H,m), 5.26–5.93(0.6H,m), 5.738 (0.6H,s), 5.857(0.4H,s), 6.23–6.63(3.6H,m), 6.96–7.47 (15.4H,m)

EXAMPLE 204

A N-(2-fluorobenzyl)-5-(3-aminomethylphenyl)-7-chloro-2-oxo-1-[(3-phenyl)-2-propenyl]-1,2,3,5-tetrahydro-4,1-benzoxazepine-3-acetamide•hydrochloride To the compound (0.22 g) produced in Example 203 was added 4N hydrogen chloride (ethyl acetate solution) (3 ml), and the mixture was stirred for 40 minutes. The solvent was distilled off. To the residue was added ethyl acetate (30 ml). The solvent was again distilled off to leave the titled compound (0.21 g) as a colorless amorphous solid product.

NMR(CDCl$_3$) δ: 2.165(2H,br), 2.63–3.07(2H,m), 3.62–3.98 (2.6H,m), 4.33–4.83(4H,m), 5.25–5.42(0.4H,s), 5.746 (0.6H,s), 5.847(0.4H,s), 6.23–6.63(2.6H,m), 6.78–7.47 (15.4H,m)

EXAMPLE 205

3,5-Trans-N-(2-fluorobenzyl)-5-(3-tert-butoxycarbonylaminomethyl)phenyl-1-[2-(4-benzyloxycarbonylamino)phenylethyl]-7-chloro-2-oxo-1,2,3,5-tetrahydro-4,1-benzoxazepine-3-acetamide (1) 4-Aminophenethyl alcohol (3.5 g) was dissolved in ethyl acetate (60 ml), to which was added 1N sodium hydroxide (50 ml). To the mixture was added, while stirring at room temperature, carbobenzoxy chloride (4.5 g). The mixture was stirred for 30 minutes. The organic layer was then separated, washed with water and dried over anhydrous sodium sulfate. The solvent was distilled off to leave 4-benzyloxycarbonylaminophenethyl alcohol (4.5 g) as a liver brown crystalline product (4.5 g), NMR(CDCl$_3$) δ: 2.822(2H,t,J=6.6 Hz), 3.829(2H,t,J=6.6 Hz), 5.199(2H,s), 6.69(1H,br), 7.13–7.44(9H,m)

(2) A methylene chloride (40 ml) solution of oxalyl chloride (1.29 g) was cooled to −78° C., to which was added dimethyl sulfoxide (1.6 g). The mixture was stirred for 5 minutes, to which was then added dropwise a methylene chloride (10 ml) solution of the compound produced in (1) (2.5 g). The mixture was stirred for 30 minutes at room temperature. The reaction mixture was washed with water and dried over anhydrous sodium sulfate. The solvent was distilled off, and the residue was purified by means of a silica gel column chromatography to give 4-benzyloxycarbonylaminophenyl acetaldehyde (0.5 g) as a colorless oily product.

NMR(CDCl$_3$) δ: 3.62–3.68(2H,m), 5.206(2H,s), 6.63–6.77 (1H,m), 7.13–7.45(9H,m), 9.73(1H,br)

(3) In methanol (15 ml) were dissolved 2-amino-5-chloro-α-(3-tert-butoxycarbonylaminomethylphenyl)benzyl alcohol (0.6 g) produced in Example (1) and 4-(benzyloxycarbonylaminophenyl acetaldehyde (0.5 g). To the solution were added acetic acid (0.11 g) and cyano sodium borohydride (0.12 g). The mixture was stirred for one hour at 60° C. The reaction mixture was concentrated, to which was added water (20 ml) and ethyl acetate (30 ml), followed by extraction. The organic layer was separated, washed with water and dried over anhydrous sodium sulfate. The solvent was distilled off, and the residue was purified by means of a silica gel column chromatography to give 2-(2-(4-benzyloxycarbonylamino)phenylethyl]-5-chloro-α-(3-tert-butoxycarbonylaminomethyl)phenyl-benzyl alcohol (0.8 g)

NMR(CDCl$_3$) δ: 1.435(9H,s), 2.73–2.83(2H,m), 3.23–3.33 (2H,m), 4.255(2H,d,J=5.8 Hz), 5.194(2H,s), 5.623(1H,s), 6.85–7.45(11H,m)

(4) The compound (0.8 g) produced in (3) was dissolved in ethyl acetate (30 ml), to which was added 1N sodium hydroxide (10 ml). To the mixture was added, while stirring at room temperature, fumaric chloride monoethyl ester (0.24 g). The reaction mixture was stirred for 40 hours. The organic layer was separated, washed with water and dried over anhydrous sodium sulfate. The solvent was distilled off, and the residue was dissolved in ethanol (20 ml). To the solution was added potassium carbonate (0.4 g), and the mixture was stirred for 2 hours at 60° C. The reaction mixture was diluted with ethyl acetate (40 ml), which was washed with water and dried over anhydrous sodium sulfate, The solvent was distilled off, and the residue was purified by means of a silica gel column chromatography to give 3,5-trans-5-(3-tert-butoxycarbonylaminomethylphenyl)-1-[2-(4-benzyloxycarbonylamino)phenylethyl]-7-chloro-2-oxo-1,2,3,5-tetrahydro-4,1-benzoxazepine-3-acetic acid ethyl ester (0.25 g) as a colorless oily product.
NMR(CDCl$_3$) δ: 1.232(3H,t,J=7.2 Hz), 2.723(1H,dd,J=5.8, 16.6 Hz), 2.83–3.16(3H,m), 3.79–3.97(1H,m), 4.119(2H,q, J=7.2 Hz), 4.255(2H,d,J=5.8 Hz), 4.355(1H,dd,J=6.0, 7.7 Hz), 4.68–4.87(1H,m), 5.172(3H,s), 6.478(1H,d, J=2.4 Hz), 6.910(1H,s), 7.04–7.43(15H,m)

(5) The compound (0.25 g) produced in (4) was dissolved in a mixture of tetrahydrofuran (4 ml) and methanol (8 ml). To the solution was added 1N sodium hydroxide (2 ml). The mixture was stirred for 20 minutes at 60° C. The reaction mixture was concentrated, which was neutralized with 5% potassium hydrogensulfate, followed by extraction with ethyl acetate (50 ml). The organic layer was washed with water and dried over anhydrous sodium sulfate. The solvent was distilled off, and the residue was dissolved in N,N-dimethylformamide (6 ml). To the solution was added 2-fluorobenzylamine (42 mg). To the mixture were added, while stirring at 0° C., cyano diethyl phosphate (50 mg) and triethylamine (36 mg). The reaction mixture was stirred for 30 minutes at room temperature, which was diluted with ethyl acetate (5 ml). The solution was washed with water and dried over anhydrous sodium sulfate. The solvent was distilled off, and the residue was purified by means of a silica gel column chromatography to give the titled compound, 3,5-trans-N-(2-fluorobenzyl) 5-(3-tert-butoxycarbonylaminomethylphenyl)-[2-(4-benzyloxycarbonylamino)phenylethyl]-7-chloro-2-oxo-1,2,3,5-tetrahydro-4,1-benzoxazepine-3-acetamide (0.2 g) as a colorless amorphous solid product.
NMR(CDCl$_3$) δ: 1.419(9H,s), 2.642(1H,dd,J=6.2,14.6 Hz), 2.76–3.14(3H,m), 3.73–4.58(6H,m), 4.68–4.92(1H,m), 5.02–5.17(1H,m), 5.128(1H,s), 5.182(2H,s), 6.12–6.33(1H, m), 6.463(1H,d,J=2.4 Hz), 6.855(1H,s), 6.96–7.43(19H,m)

EXAMPLE 206

3,5-Trans-N-(2-fluorobenzyl)-5-(3-aminomethylphenyl)-1-[2-(4-benzyloxycarbonylamino)phenylethyl]-7-chloro-2-oxo-1,2,3,5-tetrahydro-4,1-benzoxazepine-3-acetamide•hydrochloride To the compound produced in Example 205 (45 mg) was added 4N hydrogen chloride (ethyl acetate solution) (2 ml). The mixture was stirred for 2 hours. The solvent was distilled off. To the residue was added ethyl acetate to give the titled compound (31 mg) as a colorless crystalline product. m.p.: 196–198° C.
NMR(CDCl$_3$) δ: 2.65–3.55(5H,m), 4.035(2H,br), 4.23–4.45 (3H,m), 4.52–4.72(1H,m), 5.142(2H,s), 5.244(1H,s), 6.366 (1H,d,J=2.0 Hz), 7.05–7.65(19H,m), 8.15–8.55(3H,m), 9.700(1H,s)

EXAMPLE 207

3,5-Trans-N-(2-fluorobenzyl)-5-(3-tert-butoxycarbonylaminomethyl)phenyl-7-chloro-1-(furan-2-yl)methyl-1,2,3,5-tetrahydro-4,1-benzoxazepine-3-acetamide (1) In methanol (15 ml) were dissolved 2-amino-5-chloro-α-(3-tert-butoxycarbonylaminomethylphenyl)benzyl alcohol (0.5 g) produced in Example (1) and furfural (0.15 g). To the solution were added acetic acid (0.1 g) and cyano sodium borohydride (0.11 g). The mixture was stirred for 40 minutes at 60° C. The reaction mixture was concentrated, to which were added water (30 ml) and ethyl acetate (50 ml), followed by subjecting the mixture to extraction. The organic layer was washed with water and dried over anhydrous sodium sulfate. The solvent was distilled off, and the residue was purified by means of a silica gel column chromatography to give 5-chloro-2-(furan-2-ylmethyl)amino-α-(3-tert-butoxycarbonylaminomethylphenyl)benzyl alcohol (0.6 g) as a colorless oily product.
NMR(CDCl$_3$) δ: 1.451(9H,s), 4.240(2H,s), 4.303(2H,d, J=6.2 Hz), 4.73–4.92(1H,m), 5.804(1H,s), 6.04–6.08 (1H, m), 6.26–6.33(1H,m), 6.652(1H,d,J=8.8 Hz), 6.97–7.43(7H, m)

(2) The compound (0.6 g) produced in (1) was dissolved in ethyl acetate (15 ml), to which was added 1N sodium hydroxide (8 ml). To the mixture was added, while stirring, fumaric chloride monoethyl ester (0.23 g). The reaction mixture was stirred for 10 minutes. The organic layer was then separated, washed with water and dried over anhydrous sodium sulfate. The solvent was distilled off, and the residue was dissolved in ethanol (20 ml). To the solution was added potassium carbonate (0.4 g). The mixture was stirred for 40 minutes at 60–70° C. The reaction mixture was diluted with ethyl acetate (50 ml), which was washed with water and dried over anhydrous sodium sulfate. The solvent was distilled off, and the residue was purified by means of a silica gel column chromatography to give 3,5-trans-5-(3-tert-butoxycarbonylaminomethylphenyl)-7-chloro-1-(furan-2-yl)methyl-2-oxo-1,2,3,5-tetrahydro-4,1-benzoxazepine-3-acetic acid ethyl ester (0.4 g) as a colorless oily product.
NMR(CDCl$_3$) δ: 1.232(3H,t,J=7.2 Hz), 1.454(9H,s), 2.769 (1H,dd,J=5.6,16.8 Hz), 3.091(1H,dd,J=8.0,16.8 Hz), 4.125 (2H,q,J=7.2 Hz), 4.328(2H,d,J=6.0 Hz), 4.441(1H,dd,J=5.8, 7.9 Hz), 4.638(1H,d,J=15.4 Hz), 5.411(1H,d,J=15.4 Hz), 5.566(1H,s), 6.27–6.36(2H,m), 6.537(1H,s), 7.08–7.43(7H, m)

(3) The compound (0.4 g) produced in (2) was dissolved in a mixture of tetrahydrofuran (3 ml) and methanol (6 ml). To the solution was added 1N sodium hydroxide (3 ml). The mixture was stirred for 30 minutes at 60° C. The reaction mixture was concentrated, which was diluted with a 5% aqueous solution of potassium hydrogensulfate, followed by extraction with ethyl. acetate (30 ml). The organic layer was washed with water and dried over anhydrous sodium sulfate. The solvent was distilled off, and the residue was dissolved in N,N-dimethylformamide (6 ml). To the solution was added 2-fluorobenzylamine (65 mg). To the mixture were added, while stirring at 0° C., cyano diethyl phosphate (88 mg) and triethylamine (58 mg). The reaction mixture was stirred for 20 minutes at room temperature, to which were added water (30 ml) and ethyl acetate (40 ml), followed by extraction. The organic layer was washed with water and dried over anhydrous sodium sulfate. The solvent was distilled off, and the residue was purified by means of a silica gel column chromatography to give the titled compound, 3,5-trans-N-(2-fluorobenzyl)-5-(3-tert-butoxycarbonylaminomethylphenyl)-7-chloro-1-(furan-2-yl)methyl-2-oxo-1,2,3,5-tetrahydro-4,1-benzoxazepine-3-acetamide (0.15 g) as a colorless amorphous solid product.
NMR(CDCl$_3$) δ: 1.443(9H,s), 2.699(1H,dd,J=6.2,14.5 Hz), 2.905(1H,dd,J=7.2,14.5 Hz), 4.293(2H,d,J=6.0 Hz), 4.33–4.58(3H,m), 4.796(1H,d,J=15.4 Hz), 4.85–4.97(1H, m), 5.393(1H,d,J=15.4 Hz), 5.538(1H,s), 6.24–6.44(3H,m), 6.516(1H,s), 6.97–7.38(11H,m)

EXAMPLE 208

3,5-Trans-N-(2-fluorobenzyl)-5-(3-aminomethylphenyl)-7-chloro-1-(furan-2-yl)methyl-2-oxo-1,2,3,5-tetrahydro-4,1-benzoxazepine-3-acetamide•hydrochloride To the compound produced in Example 207 (0.12 g) was added 4N hydrogen chloride (ethyl acetate solution) (2 ml).

The mixture was stirred for 2 hours. The solvent was distilled off. To the residue was added ethyl acetate (30 mg). The solvent was again distilled off to leave the titled compound (0.11 g) as a colorless amorphous solid product.
NMR(CDCl$_3$) δ: 2.196(2H,br), 2.712(1H,dd,J=6.0,14.5 Hz), 2.904(1H,dd,J=7.0,14.5 Hz), 3.859(2H,s), 4.33–4.58 (3H, m), 4.823(1H,d,J=15.4 Hz), 5.361(1H,d,J=15.4 Hz), 5.564 (1H,s), 6.25–6.57(4H,m), 6.97–7.37(11H,m)

EXAMPLE 209

3,5-Trans-N-(2-fluorobenzyl)-5-(3-tert-butoxycarbonylaminomethylphenyl)-7-chloro-2-oxo-1,2,3,5-tetrahydro-1-(thiazol-5-yl)methyl-4,1-benzoxazepine-3-acetamide (1) In methanol (10 ml) were dissolved 2-amino-α-(3-tert-butoxycarbonylaminomethylphenyl)-5-chlorobenzyl alcohol (1 g) produced in Example (1) and thiazole-5-carboxyaldehyde (0.34 g). To the solution were added acetic acid (0.33 g) and cyano sodium borohydride (0.21 g). The mixture was stirred for one hour at 60° C. The reaction mixture was added to a 5% aqueous solution of potassium hydrogensulfate, followed by extraction with ethyl acetate (50 ml). The organic layer was washed with water and dried over anhydrous sodium sulfate. The solvent was distilled off, and the residue was purified by means of a silica gel column chromatography to give α-(3-tert-butoxycarbonylaminomethylphenyl)-5-chloro-2-(thiazol-5-yl)methylamino-benzyl alcohol (1.22 g) as a colorless amorphous solid product.
NMR(CDCl$_3$) δ: 1.438(9H,s), 4.273(2H,d,J=5.4 Hz), 4.456 (2H,s), 4.89–5.17(2H,br), 5.773(1H,s), 6.580(1H,d, J=8.4 Hz), 7.01–7.36(6H,m), 7.539(1H,s), 8.624(1H,s)

(2) The compound produced in (1) (1.1 g) was dissolved in ethyl acetate (20 ml), to which was added sodium hydrogencarbonate (0.3 g). To the mixture was added, while stirring at room temperature, fumaric chloride monoethyl ester (0.41 g). The reaction mixture was stirred for one hour, which was then washed with water and dried over anhydrous sodium sulfate. The solvent was distilled off, and the residue was dissolved in ethanol (20 ml). To the solution was added potassium carbonate (0.24 g). The mixture was stirred for 20 minutes at room temperature. To the reaction mixture were added water (100 ml) and ethyl acetate (100 ml), which was subjected to extraction. The organic layer was washed with water and dried over anhydrous sodium sulfate. The solvent was distilled off, and the residue was purified by means of a silica gel column chromatography to give 3,5-cis and 3,5-trans-5-(3-tert-butoxycarbonylaminomethylphenyl)-7-chloro-1,2,3,5 -tetrahydro-2-oxo-1-(thiazol-5-yl)methyl-4,1-benzoxazepine-3-acetic acid ethyl ester (0.81 g) as a mixture of colorless amorphous solid products.
NMR(CDCl$_3$) δ: 1.249(3H,t,J=7.4 Hz), 1.435, 1.449(9H, each s), 2.767(⅔H,dd,J=5.4,16.8 Hz), 2.877(⅓H,dd, J=6.2, 16.8 Hz), 3.122(⅔H,dd,J=8.4,16.8 Hz), 3.164(⅓H, 1H,dd, J=8.4,16.8 Hz), 4.09–4.32(4H+⅔H,m), 4.444(⅔H, dd,J= 5.4,8.4 Hz), 4.540(⅓H,dd,J=6.2,8.4 Hz), 4.80–4.90 (1H,br), 5.034(⅔H,d,J=15.4 Hz), 5.401(⅔H,s), 5.658 (⅔H,d,J=15.4 Hz), 5.855(⅓H,s), 6.546(⅔H,d, J=2.2 Hz), 6.91–7.55(6H+ ⅓H,m), 7.777(1H,s), 8.790(1H,s)

(3) The compound produced in (2) (0.7 g) was dissolved in ethanol (7 ml), to which was added 1N sodium hydroxide (1.5 ml). The mixture was stirred for 30 minutes at 60° C. To the reaction mixture was added water (100 ml), which was neutralized with a 5% potassium hydrogensulfate, followed by extraction with ethyl acetate (100 ml×2). The organic layer was washed with water and dried over anhydrous sodium sulfate. The solvent was distilled off to leave a mixture of 3,5-cis and 3,5-trans-5-(3-tert-butoxycarbonylaminomethylphenyl)-7-chloro-1,2,3,5-tetrahydro-2-oxo-1-(thiazol-5-yl)methyl-4,1-benzoxazepine-acetic acid (0.36 g) as a mixture of colorless amorphous solid products.
NMR(CDCl$_3$) δ: 1.441(9H,s), 2.74–2.82(⅓H,m), 3.108 (⅔H,dd,J=7.6,16.2 Hz), 4.25–4.48(3H+⅓H,m), 5.05–5.15 (1H,br), 5.056(⅔H,d,J=16.2 Hz), 5.416(⅔H,s), 5.786(⅔H, d,J=16.2 Hz), 5.722(⅓H,s), 6.54–7.52(7H,m), 7.790(1H,s), 8.655(1H,br), 8.788(1H,s)

(4) The compound (0.29 g) produced in (3) and 2-fluorobenzylamine (67 mg) were dissolved in N,N-dimethylformamide (3 ml). To the solution were added, while stirring at room temperature, cyano diethyl phosphate (96 mg) and triethylamine (74 mg). The reaction mixture was stirred for 10 minutes, which was diluted with ethyl acetate (50 ml). The solution was washed with a 5% aqueous solution of potassium hydrogensulfate, a saturated sodium hydrogencarbonate and water, successively, followed by drying over anhydrous sodium sulfate. The solvent was distilled off, and the residue was purified by means of a silica gel column chromatography to give the titled compound, 3,5-trans-N-(2-fluorobenzyl) 5-(3-tert-butoxycarbonylaminomethylphenyl)-7-chloro-1,2,3,5-tetrahydro-1-(thiazol-5-yl)methyl-2-oxo-4,1-benzoxazepine-3-acetamide (0.2 g) as a colorless amorphous solid product.
NMR(CDCl$_3$) δ: 1.445(9H,s), 2.696(1H,dd,J=5.8,14.6 Hz), 2.929(1H,dd,J=6.8,14.6 Hz), 4.283(2H,d,J=5.6 Hz), 4.38–4.60(3H,m), 4.85–4.95(1H,br), 4.989(1H,d,J=15.2 Hz), 5.372(1H,s), 5.654(1H,d,J=15.2 Hz), 6.20–6.30(1H, br), 6.529(1H,d,J=1.8 Hz), 6.95–7.43(10H,m), 7.766(1H,s), 8.773(1H,s)

EXAMPLE 210

3,5-Trans-N-(2-fluorobenzyl)-5-(3-aminomethylphenyl)-7-chloro-1,2,3,5-tetrahydro-1-(thiazol-5-yl)methyl-4,1-benzoxazepine-3-acetamide•oxalate To the compound produced in Example 209 (0.1 g) was added trifluoroacetic acid (1 ml). The mixture was stirred for 30 minutes at room temperature. The reaction mixture was concentrated, which was dissolved in ethyl acetate (10 ml). To this solution was added a methanol (2 ml) solution of oxalic acid (11 mg). The solvent was distilled off. To the residue were added ether and hexane to cause precipitation of the titled compound (135 mg) as an amorphous solid product.
NMR(CD$_3$OD) δ: 2.72–2.95(2H,m), 4.094(2H,s), 4.416(2H, s), 4.46–4.53(1H,m), 5.184(1H,d,J=15.4 Hz), 5.440(1H,s), 5.724(1H,d,J=15.4 Hz), 6.435(1H,d,J=2.2 Hz), 7.01–7.65 (6H,m), 7.821(1H,s), 8.968(1H,s)

EXAMPLE 211

N-(2-fluorobenzyl)-5-(3-tert-butyloxycarbonylaminomethylphenyl)-7-chloro-2,3-dihydro-2,3-dihydro-2-oxo-1H-1,4-benzodiazepine-3-acetamide (1) A 1N aqueous solution of sodium hydroxide (1.5 ml) was added to a methanol solution (6 m.) of 5-(3-tert-butyloxycarbonylaminomethylphenyl)-7-chloro-2,3-dihydro-2-oxo-1H-1,4-benzodiazepine-3-acetic acid methyl ester (0.6 g), the compound produced in Example 97-(1). The mixture was stirred for 2 hours at 60° C. The reaction mixture was diluted with water (50 ml), which was acidified, followed by extraction with ethyl acetate (50 ml) twice. The extracts were combined and washed with a saturated aqueous saline solution, followed by drying over anhydrous sodium sulfate. The solvent was distilled off under reduced pressure to give 5-(3-tert-butyloxycarbonylaminomethylphenyl)-7-chloro-2,3-dihydro-2-oxo-1H-1,4-benzodiazepine-3-acetic acid (0.64 g) as a colorless amorphous solid product.
$^1$H-NMR(CDCl$_3$) δ: 1.44(9H,s), 3.10–3.49(2H,m), 4.11(1H, t,J=6.4 Hz), 4.20–4.36(2H,m), 4.90–5.00(1H,br), 7.16–7.49 (7H,m), 9.80(1H,br)

(2) To a dimethylformamide solution (5 ml) of the compound (0.57 g) produced in (1) and 2-fluorobenzylamine (0.16 g) were added cyano diethyl phosphate (0.22 g) and triethylamine (0.19 g). The mixture was stirred for 10 minutes at room temperature. The reaction mixture was diluted with ethyl acetate (50 ml), which was washed with water, a 5% aqueous solution of potassium hydrogensulfate, a saturated aqueous solution of sodium hydrogencarbonate and a saturated aqueous saline solution, successively, followed by drying over anhydrous sodium sulfate. The solvent was distilled off under reduced pressure, and the residue was purified by means of a silica gel column chromatography [eluent: AcOEt-hexane (1:1)] to give N-(2-fluorobenzyl)-5-(3-tert-butyloxycarbonylaminomethylphenyl)-7-chloro-2,3-dihydro-2-oxo-1H-1,4-benzodiazepine-3-acetamide (0.75 g) as an anhydrous amorphous solid product.
$^1$H-NMR(CDCl$_3$) δ: 1.44(9H,s), 3.06(1H,dd,J=6.6,14.6 Hz), 3.18(1H,dd,J=6.6,14.6 Hz), 4.16(1H,dd,J=6.0,6.6 Hz), 4.30 (2H,d,J=6.0 Hz), 4.47(1H,dd,J=5.0,15.4 Hz), 4.61(1H,dd, J=6.6,15.4 Hz), 4.84–4.96(1H,br), 6.70–6.80(1H,br), 7.00–7.41(11H,m), 8.65–8.75(1H,br)

EXAMPLE 212

N-(2-fluorobenzyl)-5-(3-aminomethylphenyl)-7-chloro-2,3-dihydro-2-oxo-1H-1,4-benzdiazepine-3-acetamide•monohydrochloride A trifluoroacetic solution (2 ml) of N-(2-fluorobenzyl)-5-(3-tert-butyloxycarbonylaminomethyl-phenyl)-7-chloro-2,3-dihydro 2-oxo-1H-1,4-benzodiazepine-3-acetamide•produced in Example 211 (0.16 g) was stirred for 10 minutes at room temperature. The reaction mixture was concentrated under reduced pressure, which was dissolved in ethyl acetate (20 ml). To this solution was added a 4N ethyl acetate solution of hydrogen chloride (0.2 ml). The solvent was distilled off under reduced pressure. The residue was washed with diethyl ether-hexane (1:1), which was subjected to filtration to collect N-(2-fluorobenzyl)-5-(3-aminomethylphenyl)-7-chloro-2,3-dihydro-2-oxo-1H-1,4-benzodiazepine-3-acetamide•monohydrochloride (0.13 g) as a colorless amorphous solid product.
$^1$H-NMR(CD$_3$OD) δ: 3.29–3.32(2H,m), 3.95–4.01(1H,m), 4.23(2H,s), 4.49(2H,s), 7.02–7.85(11H,m)

EXAMPLE 213

(3,5-Trans)-N-(2-fluorobenzyl)-5-(3-tert-butyloxycarbonylaminomethylphenyl)-7-chloro-2,3,4,5-tetrahydro-2-oxo-1H-1,4-benzodiazepine-3-acetamide Acetic acid (1 ml) and cyano sodium borohydride (17 mg) were added, at room temperature, to a methanol (2 ml) solution of N-(2-fluorobenzyl)-5-(3-tert-butyloxycarbonylaminomethylphenyl)-7-chlbro-2,3-dihydro-2-oxo-1H-1,4-benzodiazepine-3-acetamide produced in Example 211 (0.1 g). The mixture was stirred for 2 hours at 60° C. The reaction mixture was diluted with ethyl acetate, which was washed with a 1N aqueous solution of sodium hydroxide and a saturated aqueous saline solution, followed by drying over anhydrous sodium sulfate. The solvent was distilled off under reduced pressure. The residue was purified by means of a silica gel column chromatography [eluent: hexane-ethyl acetate (1:1)] to give (3,5-cis)-N-(2-fluorobenzyl)-5-(3-tert-butyloxycarbonylaminomethylphenyl)-7-chloro-2,3,4,5-tetrahydro-2-oxo-1H-1,4-benzodiazepine-3-acetamide (0.08 g) and (3,5-trans)-N-(2-fluorobenzyl)-5-(3-tert-butyloxycarbonylaminomethylphenyl)-7-chloro-2,3,4,5-tetrahydro-2-oxo-1H-1,4-benzodiazepine-3-acetamide (0.19 g) as colorless amorphous solid products, respectively.
3,5-Cis:
$^1$H-NMR(CDCl$_3$) δ: 1.43(9H,s), 2.62(1H,dd,J=7.0,15.0 Hz), 2.77(1H,dd,J=4.8,15.0 Hz), 4.01(1H,dd,J=4.8,7.0 Hz), 4.22 (2H,d,J=5.0 Hz), 4.46(2H,d,J=6.2 Hz), 4.84–4.98(1H,br), 5.19(1H,s), 6.55–6.65(1H,br), 6.82–7.31(11H,m), 7.55–7.65 (1H,br)
Anal. Calcd for C$_{30}$H$_{32}$N$_4$O$_4$ClF+0.3H$_2$O: C, 62.94; H, 5.74; N, 9.79.
Found: C, 62.87; H, 5.86; N, 9.67
3,5-Trans:
$^1$H-NMR(CDCl$_3$) δ: 1.44(9H,s), 2.56(1H,dd,J=6.4,15.0 Hz), 2.75(1H,dd,J=6.6,15.0 Hz), 3.82(1H,dd,J=6.4,6.6 Hz), 4.30 (2H,d,J=6.2 Hz), 4.46(2H,d,J=5.2 Hz), 4.90–5.00(1H,br), 5.31(1H,s), 6.62(1H,s), 6.70–6.80(1H,br), 6.94–7.38 (10 H,m), 8.10–8.20(1H,br)

EXAMPLE 214

(3,5-Trans)-N-(2-fluorobenzyl)-5-(3-aminomethylphenyl)-7-chloro-2,3,4,5-tetrahydro-2-oxo-1H-1,4-benzodiazepine-3-acetamide•dihydrochloride A trifluoroacetic acid solution (1 ml) of the compound produced in Example 213, i.e. (3,5-trans)-N-(2-fluorobenzyl)-5-(3-tert-butyloxycarbonylaminomethylphenyl)-7-chloro-2,3,4,5-tetrahydro-2-oxo-1H-1,4-benzodiazepine-3-acetamide (0.11 g), was stirred for 10 minutes at room temperature. The reaction mixture was concentrated under reduced pressure, which was dissolved in ethyl acetate (20 ml). To this solution was added a 4N ethyl acetate solution of hydrogen chloride (0.2 ml). The solvent was distilled off, and the residue was washed with diethyl ether-hexane (1:5), followed by filtration to give (3,5-trans)-N-(2-fluorobenzyl)-5-(3-aminomethylphenyl)-7-chloro-2,3,4,5-tetrahydro-2-oxo-1H-1,4-benzodiazepine-3-acetamide•dihydrochloride (97 mg) as a colorless amorphous solid product.
$^1$H-NMR(CD$_3$OD) δ: 2.92(1H,dd,J=4.0,16.2 Hz), 3.17(1H, dd, J=8.8,16.2 Hz), 4.22(2H,s), 4.38(1H,dd,J=4.0,8.8 Hz), 4.42(2H,s), 5.85(1H,s), 6.88(1H,d,J=2.2 Hz), 7.01–7.83 (10H,m)

EXAMPLE 215

(3,5-Trans)-N-(2-fluorobenzyl)-1-(4-biphenylmethyl)-5-(3-tert-butyloxycarbonylaminomethylphenyl)-7-chloro-2,3,4,5-tetrahydro-2-oxo-1H-1,4-benzodiazepine-3-acetamide (1) Acetic acid (3 ml) and cyano sodium borohydride (97 mg) were added, at room temperature, to a methanol solution (6 ml) of the compound produced in Example 97-(2), i.e. 1-(4-biphenylmethyl)-5-(3-tert-butyloxycarbonylaminomethylphenyl)-7-chloro-2,3-dihydro-2-oxo-1H-4,1-benzodiazepine-3-acetic acid methyl ester (0.66 g). The mixture was stirred for 2 hours at 60° C. The reaction mixture was diluted with ethyl acetate (10 ml), which was washed with a 1N aqueous solution of sodium hydroxide and a saturated aqueous saline solution, followed by drying over anhydrous sodium sulfate. The solvent was distilled off under reduced pressure to leave (3,5-trans)-1-(4-biphenylmethyl)-5-(3-tert-butyloxycarbonylaminomethylphenyl)-7-chloro-2,3,4,5- tetrahydro-2-oxo-1H-4,1-benzodiazepine-3-acetic acid methyl ester (0.65 g) as a colorless amorphous solid product.
$^1$H-NMR(CDCl$_3$) δ: 1.43, 1.44(total 9H, each s), 2.63 (1H, dd,J=4.6,16.4 Hz), 2.96(1H,dd,J=8.6,16.4 Hz), 3.70 (3H,s), 3.79(1H,dd,J=4.6,8.6 Hz), 4.20(2H,d,J=5.2 Hz), 4.25–4.30 (1H,br), 4.70–4.80(1H,br), 4.82(1H,s), 4.86(1H,d,J=14.4 Hz), 5.46(1H,d,J=14.4 Hz), 6.49(1H,s), 6.97–7.58(15H,m)

(2) To a methanol solution (6 ml) of the compound produced in (1) (0.6 g) was added a 1N sodium hydroxide (1.2 ml). The mixture was stirred for one hour at 60° C. The reaction mixture was diluted with water (50 ml), which was made acidic, followed by extraction with ethyl acetate (50 ml) twice. The total extract solution was washed with a saturated aqueous saline solution and dried over anhydrous sodium sulfate. The solvent was then distilled off under reduced pressure to give (3,5-trans)-1-(biphenyl-4-methyl)-5-(3-tert-butyloxycarbonylaminomethylphenyl)-2,3,4,5-tetrahydro-2-oxo-1H-1,4-benzodiazepine-3-acetic acid (0.62 g) as a colorless amorphous solid product.
$^1$H-NMR(CDCl$_3$) δ: 1.32, 1.34(total 9H, each s), 2.63 (1H,dd,J=6.0,17.0 Hz), 2.84(1H,dd,J=8.4,17.0 Hz), 3.68 (1H,dd,J=6.0,8.4 Hz), 4.10(2H,d,J=5.2 Hz), 4.15–4.20(1H, br), 4.70(1H,s), 4.72(1H,d,J=14.8 Hz), 5.39(1H,d,J=14.8 Hz), 6.40(1H,s), 6.84–7.47(15H,m)

(3) Cyano diethyl phosphate (0.15 g) and triethylamine (0.13 g) were added to a dimethylformamide solution (5 ml) of the compound produced in (2), i.e. (3,5-trans)-1-(4-biphenylmethyl)-5-(3-tert-butyloxycarbonylaminomethylphenyl)-2,3,4,5-tetrahydro-2-oxo-1H-1,4-benzodiazepine-3-acetic acid (0.53 g), and 2-fluorobenzylamine (0.11 g). The mixture was stirred for 10 minutes at room temperature. The reaction mixture was diluted with ethyl acetate, which was washed with water, a 5% aqueous solution of potassium hydrogensulfate, a saturated aqueous solution of sodium hydrogencarbonate and a saturated aqueous saline solution, followed by drying over anhydrous sodium sulfate. The solvent was distilled off under reduced pressure, and the residue was purified by means of a silica gel column chromatography [eluent: hexane-ethyl acetate (3:2)] to give (3,5-trans)-N-(2-fluorobenzyl)-1-(4-biphenylmethyl)-5-(3-tert-butyloxycarbonylaminomethylphenyl)-7-chloro-2,3,4,5-tetrahydro-2-oxo-1H-1,4-benzodiazepine-3-acetamide (0.48 g) as a colorless amorphous solid product.
1H-NMR(CDCl$_3$) 6: 1.43(9H,s), 2.56(1H,dd,J=5.4,15.0 Hz), 2.81(1H,dd,J=7.4,15.0 Hz), 3.82(1H,dd,J=5.4,7.4 Hz), 4.16(2H,d,J=7.0 Hz), 4.48(2H,t,J=4.8 Hz), 4.76(1H,s), 4.77 (1H,d,J=14.6 Hz), 5.49(1H,d,J=14.6 Hz), 6.46(1H,s), 6.65–6.75(1H,m), 6.89–7.56(19H,m)

EXAMPLE 216

(3,5-Trans)-N-(2-fluorobenzyl)-5-(3-aminomethylphenyl)-1-(4-biphenylmethyl)-7-chloro-2,3,4,5-tetrahydro-2-oxo-1H-1,4-benzdiaoxazepine-3-acetamide•dihydrochloride A trifluoroacetic acid solution (2 ml) of the compound produced in Example 215, (3,5-trans)-N-(2-fluorobenzyl)-1-(biphenyl-4-methyl)-5-(3-tert-butyloxycarbonylaminomethylphenyl)-7-chloro-2,3,4,5-tetrahydro-2-oxo-1H-1,4-benzodiazepine-3-acetamide (0.12 g), was stirred for 10 minutes at room temperature. The reaction mixture was concentrated under reduced pressure, which was dissolved in ethyl acetate (20 ml). To this solution was added a 4N ethyl acetate solution of hydrogen chloride (0.2 ml). The solvent was distilled off under reduced pressure, and the residue was recrystallized from ethanol-diethyl ether (1:10) to give (3,5-trans)-N-(2-fluorobenzyl)-5-(3-aminomethylphenyl)-1-(4-biphenylmethyl)-7-chloro-2,3,4,5-tetrahydro-2oxo-1H-1,4-benzodiazepine-3-acetamide•dihydrochloride (88 mg) as a colorless powdery crystalline product. m.p.: 210–216° C.
$^1$H-NMR(CDCl$_3$) δ: 2.97(1H,dd,J=3.6.,16.0 Hz), 3.28(1H, dd, J=9.4,16.0 Hz), 4.06(2H,s), 4.35(1H,dd,J=3.6,9.4 Hz), 4.43–4.45(2H,m), 4.98(1H,d,J=14.6 Hz), 5.12(1H,s), 5.58 (1H,d,J=14.6 Hz), 6.77(1H,d,J=2.2 Hz), 7.00–7.73(19H,m)

EXAMPLE 217

(3,5-Trans)-N-(2-fluorobenzyl)-1-(4-biphenylmethyl)-5-(3-tert-butyloxycarbonylaminomethylphenyl)-7-chloro-4-methyl-2,3,4,5-tetrahydro-2-oxo-1H-1,4-benzodiazepine-3-acetamide A mixture of the compound produced in Example 215, i.e. (3,5-trans)-N-(2-fluorobenzyl)-1-(4-biphenylmethyl)-5-(3-tert-butyloxycarbonylaminomethylphenyl)-7-chloro-2,3,4, 5-tetrahydro-2-oxo-1H-1,4-benzodiazepine-3-acetamide (0.2 g), iodomethane (42 mg), potassium carbonate (46 mg) and dimethylformamide (2 ml) was stirred for 2 hours at 60° C. The reaction mixture was diluted with ethyl acetate (50 ml), which was washed with water, a 5% aqueous solution of potassium hydrogensulfate, a saturated aqueous solution of sodium hydrogencarbonate and a saturated aqueous saline solution, followed by drying over anhydrous sodium sulfate. The solvent was distilled off under reduced pressure, and the residue was purified by means of a silica gel column chromatography [eluent: hexane-ethyl acetate (3:2)] to give (3,5-trans)-N-(2-fluorobenzyl)-1-(4-biphenylmethyl)-5-(3-tert-butyloxycarbonylaminomethylphenyl)-7-chloro-4-methyl-2,3,4,5-tetrahydro-2-oxo-1H-1,4-benzodiazepine-3-acetamide (0.21 g) as a colorless amorphous solid product.
$^1$H-NMR(CDCl$_3$) δ: 1.43(9H,s), 2.14(3H,s), 2.61(1H,dd, J=6.0,15.2 Hz), 2.87(1H,dd,J=8.4,15.2 Hz), 4.01(1H,s), 4.07 (1H,dd,J=6.0,8.4 Hz), 4.14–4.25(2H,m), 4.42(1H,dd, J=6.6, 15.4 Hz), 4.52(1H,dd,J=6.6,15.4 Hz), 4.70–4.80 (1H,br), 4.84(1H,d,J=14.6 Hz), 5.48(1H,d,J=14.6 Hz), 6.39(1H,s), 6.93–7.57(20H,m)

EXAMPLE 218

(3,5-Trans)-N-(2-fluorobenzyl)-5-(3-aminomethylphenyl)-1-(4-biphenylmethyl)-7-chloro-4-methyl-2,3,4,5-tetrahydro-2-oxo-1H-1,4-benzodiazepine-3-acetamide•dihydrochloride A trifluoroacetic acid solution (1 ml) of the compound produced in Example 217, (3,5-trans)-(2-fluorobenzyl)-1-(4-biphenylmethyl)-5-(3-tert-butyloxycarbonylaminomethylphenyl)-7-chloro-4-methyl-2,3,4,5-tetrahydro-2-oxo-1H-1,4-benzodiazepine-3-acetamide (0.1 g), was stirred for 10 minutes at room temperature. The reaction mixture was concentrated under reduced pressure, and the residue was dissolved in ethyl acetate (20 ml). To this solution was added a 4N ethyl acetate solution of hydrogen chloride (0.2 ml). The solvent was distilled off under reduced pressure, and the residue was washed with diethyl ether-hexane (1:1), followed by filtration to give (3,5-trans)-N-(2-fluorobenzyl)-5-(3-aminomethylphenyl)-1-(biphenyl-4-methyl)-7-chloro-4-methyl-2,3,4,5-tetrahydro-2-oxo-1H-1,4-benzodiazepine-3-acetamide•dihydrochloride (95 mg) as a colorless amorphous solid product.
$^1$H-NMR(CDCl$_3$) δ: 2.15(3H,s), 2.62(1H,dd,J=6.2,15.2 Hz), 2.87(1H,dd,J=8.6,15.2 Hz), 3.77(2H,s), 4.03(1H,s), 4.08 (1H,dd,J=6.2,8.6 Hz), 4.36–4.55(2H,m), 4.83(1H,d,J=14.6 Hz), 5.50(1H,d,J=14.6 Hz), 6.41(1H,s), 6.97–7.61(19H,m)

EXAMPLE 219

3,5-Trans-N-(2-fluorobenzyl)-1-(4-biphenylmethyl)-5-(3-tert-butoxycarbonylaminomethylphenyl)-7-chloro-1,2,3, 5-tetrahydro-2-oxo-4,1-benzothiazepine-3-acetamide (1) In toluene (10 ml) were suspended 2-(4-biphenylmethyl)amino-5-chloro-α-(3-tert-butoxycarbonylaminomethylphenyl) produced in Example (4)-(1), thiomalic acid (0.14 g) and p-toluenesulfonic acid (9 mg). The suspension was stirred for one hour at 80° C. The reaction mixture was diluted with ethyl acetate (50 ml), which was washed with water and dried over anhydrous sodium sulfate. The solvent was distilled off, and the residue was dissolved in xylene (10 ml). The solution was heated for 15 hours under reflux. The reaction mixture was concentrated, which was purified by means of a silica gel column chromatography to give 5-[3-(tert-butoxycarbonylaminomethyl)phenyl]-7-chloro-1,2,3,5-tetrahydro-2-oxo-1-(4-phenylbenzyl)-4,1-benzothiazepine-3-acetic acid (0.31 g) as a mixture of cis-compound and trans-compound.

NMR(CDCl$_3$) δ: 1.308, 1.338(9H, each s), 2.36–2.50 (1H, m), 2.616(½H,d,J=15.8 Hz), 3.03–3.27(1H,m), 3.57–3.72 (1H,m), 4.22–4.40(2H,m), 4.655(½×2H,s), 4.792(½×1H,s), 4.981(½×1H,s), 5.00–5.10(1H,br), 5.631(1H,d, J=14.0 Hz), 6.55–7.53(15H,m)

(2) The compound produced in (1) (5.0 g) and 2-fluorobenzylamine (1.0 g) were dissolved in N,N-dimethylformamide (50 ml). To the solution were added, while stirring at room temperature, cyano diethyl phosphate (1.4 g) and triethylamine (1.0 g). The reaction mixture was stirred for 10 minutes, which was diluted with ethyl acetate (200 ml). The solution was washed with a 5% aqueous solution of potassium hydrogensulfate, a saturated sodium hydrogencarbonate and water, successively, followed by drying over anhydrous sodium sulfate. The solvent was distilled off, and the residue was purified by means of a silica gel column chromatography to give the titled compound, 3,5-trans-N-(2-fluorobenzyl) 5-(3-tert-butoxycarbonylaminomethylphenyl)-7-chloro-1,2,3,5-tetrahydro-2-oxo-1-(4-phenylbenzyl)-4,1-benzodiazepine-3-acetamide (1.7 g) as a colorless crystalline product. m.p.: 123–125° C.

NMR(CDCl$_3$) δ: 1.437(9H,s), 2.353(1H,dd,J=4.0,14.6 Hz), 3.004(1H,dd,J=10.2,14.6 Hz), 3.849(1H,dd,J=4.0,10.2 Hz), 4.372(1H,d,J=14.0 Hz), 4.46–4.52(2H,m), 4.870(2H,s), 4.912(1H,s), 5.721(1H,d,J=14.0 Hz), 6.18–6.25(1H,br), 6.634(1H,s), 6.69–6.73(1H,br), 6.94–7.60(19H,m)

EXAMPLE 220

3,5-Trans-N-(2-fluorobenzyl)-5-(3-aminomethylphenyl)-1-(4-biphenylmethyl)-7-chloro-1,2,3,5-tetrahydro-2-oxo-4,1-benzothiazepine-3-acetamide•hydrochloride To the compound produced in Example 219 (0.35 g) was added trifluoroacetic acid (4 ml). The mixture was stirred for 10 minutes at room temperature. The solvent was distilled off, and the residue was dissolved in ethyl acetate (30 ml). The solution was washed with 1N sodium hydroxide, which was washed with water and dried over anhydrous sodium sulfate. The solvent was distilled off. To the residue was added 4N hydrogen chloride (ethyl acetate solution) to give hydrochloride, which was crystallized from a mixture of ether and hexane to afford a colorless crystalline product (0.32 g). m.p.: 280–283° C.

NMR(CDCl$_3$) δ: 2.355(1H,dd,J=3.2,14.2 Hz), 3.004(1H,dd, J=9.8,14.2 Hz), 3.80–3.90(1H,m), 4.331(1H,dd,J=6.2, 13.4 Hz), 4.381(1H,s), 4.46–4.52(2H,m), 4.874(2H,s), 5.762(1H, dd,J=5.0,13.4 Hz), 6.15–6.25(1H,br), 6.66–7.59(20H,m)

EXAMPLE 221

3,5-Trans-N-(2-fluorobenzyl)-1-(4-biphenylmethyl)-5-(3-tert-butoxycarbonylaminomethylphenyl)-7-chloro-1,2,3,5-tetrahydro-2-oxo-4,1-benzothiazepine-3-acetamide-5-oxide The compound produced in Example 219 (1.18 g) was dissolved in ethyl acetate, to which was added m-chlorobenzoic acid (0.27 g). The mixture was stirred for 5 minutes at 0° C., which was diluted with ethyl acetate (50 ml). The solution was washed with sodium hydrogensulfite, which was washed with 1N sodium hydroxide and water, successively, followed by drying over anhydrous sodium sulfate. The solvent was distilled off, and the residue was purified by means of a silica gel column chromatography to isolate diastereomer of the titled compound and to give non-polar isomer (0.3 g) as a colorless crystalline product and polar substance (0.5 g) as an amorphous solid product, respectively. Non-polar isomer: m.p.: 214–215° C.

NMR(CDCl$_3$) δ: 1.431(9H,s), 2.865(1H,dd,J=2.6,15.0 HZ), 3.369(1H,dd,J=11.4,15.0 Hz), 3.606(1H,dd,J=2.6,11.4 Hz), 4.02–4.08(2H,m), 4.210(1H,s), 4.39–4.53(3H,m), 4.61–4.70 (1H,br), 5.762(1H,d,J=14.4 Hz), 6.05–6.15(1H,br), 6.75–7.56(20H,m)

Polar isomer:

NMR(CDCl$_3$) δ: 1.434(9H,s), 2.773(1H,dd,J=5.0,15.0 Hz), 3.992(1H,dd,J=5.0,9.2 Hz), 4.05–4.11(2H,m), 4.46–4.52 (3H,m), 6.40–6.50(1H,br), 6.70–7.60(20H,m)

EXAMPLE 222

3,5-Trans-N-(2-fluorobenzyl)-5-(3-aminomethylphenyl)-1-(4-biphenylmethyl)-7-chloro-1,2,3,5-tetrahydro-2-oxo-4,1-benzothiazepine-3-acetamide-5-oxide-hydrochloride To the non-polar isomer produced in Example 221 (0.1 g) was added trifluoroacetic acid (2 ml). The mixture was stirred for 30 minutes at room temperature. The reaction mixture was concentrated, which was dissolved in ethyl acetate (10 ml). To the solution was added 4N hydrogen chloride (ethyl acetate solution) (0.1 ml). The mixture was again concentrated. The concentrate was processed with ether and ethanol to give a non-polar isomer of the titled compound (91 mg). m.p.: 182–186° C.

NMR(CD$_3$OD) δ: 2.850(1H,dd,J=2.2,14.8 Hz), 3.415(1H, dd, J=11.0,14.8 Hz), 3.560(1H,dd,J=2.2,11.0 Hz), 3.956(2H, s), 4.34–4.52(2H,m), 4.641(1H,d,J=14.2 Hz), 4.749(1H,s), 5.723(1H,d,J=14.2 Hz), 6.616(1H,d,J=8.0 Hz), 6.982(1H,d, J=2.0 Hz), 7.07–7.76(19H,m)

The non-polar isomer produced in Example 221 (0.1 g) was processed in substantially the same manner as above to give a polar isomer of the titled compound (63 mg). m.p.: 201–204° C.

NMR(CD$_3$OD) δ: 2.844(1H,dd,J=6.0,16.2 Hz), 3.200(1H, dd, J=9.6,16.2 Hz), 3.867(1H,d,J=13.0 Hz), 3.962(1H,d, J=13.0 Hz), 4.008(1H,dd,J=6.0,9.6 Hz), 4.421(2H,s), 4.652 (1H,d,J=14.4 Hz), 4.683(1H,s), 5.851(1H,d,J=14.4 Hz), 6.810(1H,br), 6.859(1H,d,J=2.0 Hz), 7.07–7.75(19H,m)

EXAMPLE 223

3,5-Trans-N-(2-fluorobenzyl)-1-(4-biphenylmethyl)-5-(3-tert-butoxycarbonylaminomethylphenyl)-7-chloro-1,2,3,5-tetrahydro-2-oxo-4,1-benzothiazepine-3-acetamide-5-dioxide In ethyl acetate (3 ml) was dissolved 3,5-trans-N-(2-fluorobenzyl) 5-(3-tert-butoxycarbonylaminomethylphenyl)-1-(4-biphenylmethyl)-7-chloro-1,2,3,5-tetrahydro-2-oxo-4,1-benzodiazepine-3-acetamide (0.3 g). To the solution was added m-chlorobenzoic acid (0.14 g)., The mixture was stirred for 30 minutes at 0° C. The reaction mixture was diluted with ethyl acetate (50 ml), which was washed with saturated sodium hydrogensulfite, 1N sodium hydroxide and water, successively, followed by drying over anhydrous sodium sulfate. The solvent was distilled off, and the residue was purified by means of a silica gel column chromatography to give a crystalline product. The product was recrystallized from ethyl. acetate and hexane to afford the titled compound (0.18 g) as a colorless crystalline product.
NMR(CDCl$_3$) δ: 1.432(9H,s), 2.827(1H,dd,J=3.4,15.8 Hz), 3.331(1H,dd,J=10.2,15.8 Hz), 4.03–4.06(2H,m), 4.443(1H, d,J=13.6 Hz), 4.48–4.62(4H,m), 5.897(1H,d,J=13.6 Hz), 6.15–6.25(1H,br), 6.87–7.57(21H,m)

EXAMPLE 224

3,5-Trans-N-(2-fluorobenzyl)-5-(3-aminomethylphenyl)-1-(4-biphenylmethyl)-7-chloro-1,2,3,5-tetrahydro-2-oxo-4,1-benzothiazepine-3-acetamide-1-dioxide-hydrochloride To the compound produced in Example 222 (0.1 g) was added trifluoroacetic acid (1 ml). The mixture was stirred for 10 minutes at room temperature. The reaction mixture was concentrated, which was dissolved in ethyl acetate (5 ml). To the solution was added 4N hydrogen chloride (ethyl acetate solution) (0.1 ml). The solvent was distilled off to leave a crystalline product, which was recrystallized from ethanol and ether to afford the titled compound (85 mg) as a colorless crystalline product.
NMR(CD$_3$OD) δ: 2.832(1H,dd,J=3.2,15.6 Hz), 3.348(1H, dd,J=11.2,15.6 Hz), 3.863(1H,d,J=13.6 Hz), 3.972(1H,d, J=13.6 Hz), 4.378(1H,d,J=15.8 Hz), 4.487(1H,d,J=15.8 Hz), 4.527(1H,dd,J=3.2,11.2 Hz), 4.682(1H,d,J=14.2 Hz), 4.733 (1H,s), 5.848(1H,d,J=14.2 Hz), 6.81–7.86(21H,m)

EXAMPLE 225

3,5-Trans-N-(2-fluorobenzyl)-5-(3-tert-butoxycarbonylaminomethylphenyl)-1-(3,4-dibenzyloxybenzyl)-7-chloro-2-oxo-1,2,3,5-tetrahydro-4,1-benzoxazepine-3-acetamide 3,4-dibenzyloxybenzaldehyde A mixture of 3,4-dihydroxybenzaldehyde (5.0 g), benzyl bromide (14.8 g), potassium carbonate (13 g) and N,N-dimethylformamide (120 ml) was stirred for two hours at 60° C. To the reaction mixture was added cold water (200 ml), which was subjected to extraction with ethyl acetate (150 ml). The organic layer was washed with a 5% aqueous solution of potassium hydrogencarbonate, which was washed with water and dried over anhydrous sodium sulfate. The solvent was distilled off to leave 3,4-dibenzyloxybenzaldehyde (10.5 g) as colorless crystals. m.p.: 87–88° C.

In methanol (20 ml) were dissolved 2-amino-5-chloro-α-(3-tert-butoxycarbonylaminomethylphenyl)benzyl alcohol (0.6 g) and 3,4-dibenzyloxybenzaldehyde (0.55 g). To the solution were added acetic acid (0.12 g) and cyano sodium borohydride (0.13 g). The mixture was stirred for 1.5 hour at 60° C. The reaction mixture was concentrated, to which were added water (50 ml) and ethyl acetate (80 ml), followed by extraction. The organic layer was washed with water and dried over anhydrous sodium sulfate. The solvent was distilled off to leave 2-(3,4-dibenzyloxybenzyl)amino-5-chloro-α-(3-tert-butoxycarbonylaminomethylphenyl) benzyl alcohol (0.83 g) as colorless crystals, m.p.: 118–120° C.
NMR(CDCl$_3$) δ: 1.436(9H,s), 4.125(2H,s), 4.267(2H,d, J=5.4 Hz), 4.75–4.92(1H,m), 5.071(2H,s), 5.137(2H,s), 5.741(1H,s6.44–7.52(10H,m).)

(2) In ethyl acetate (20 ml) was dissolved 2-(3,4-dibenzyloxybenzyl)-5-chloro-α-(3-tert-butoxycarbonylaminomethylphenyl)benzyl alcohol (0.75 g). To the solution was added 1N sodium hydroxide (10 ml). To the mixture was added, while stirring, fumaric chloride monoethyl ester (0.10 g). The reaction mixture was stirred for 30 minutes, which was washed with water and dried over anhydrous sodium sulfate, followed by distilling off the solvent. The residue was dissolved in ethanol (30 ml), to which was added potassium carbonate (0.6 g). The mixture was stirred for 40 minutes at 60° C. The reaction mixture was concentrated, to which were added ethyl acetate (50 ml) and water (60 ml). The mixture was subjected to extraction. The organic layer was washed with water and dried over anhydrous sodium sulfate. The solvent was distilled off, and the residue was purification by means of a silica gel column chromatography. From the initial eluate was obtained 3,5-cis-5-(3-tert-butoxycarbonylaminomethylphenyl)-7-chloro-1-(3,4-dibenzyloxybenzyl)-2-oxo-1,2,3,5-tetrahydro-4,1-benzoxazepine-3-acetic acid ethyl ester (0.15 g) as a colorless oily product.
NMR(CDCl$_3$) δ: 1.251(3H,t,J=7.2 Hz), 1.425(9H,s), 2.858 (1H,dd,J=5.2,16.7 Hz), 3.256(1H,dd,J=8.6,16.7 Hz), 3.456 (1H,d,J=15.8 Hz), 4.04–4.37(4H,m), 4.55–4.66(2H,m), 4.88–5.06(1H,m), 5.099(2H,s), 5.855(1H,s), 6.52–7.47 (20H,m)

From the subsequent eluate was obtained 3,5-trans-5-(3-tert-butoxycarbonylaminomethylphenyl)-7-chloro-1-(3,4-dibenzyloxybenzyl)-2-oxo-1,2,3,5-tetrahydro-4,1-benzoxazepine-3-acetic acid-ethyl ester (0.6 g) as a colorless oily product.
NMR(CDCl$_3$) δ: 1.259(3H,t,J=7.2 Hz), 1.443(9H,s), 2.760 (1H,dd,J=5.2,16.7 hz), 3.147(1H,dd,J=8.6,16.7 Hz), 4.124 (2H,q,J=7.2 Hz), 4.276(2H,d,J=6.2 Hz), 4.454(1H,dd, J=5.0, 8.7 Hz), 4.897(1H,d,J=14.8 Hz), 5.104(2H,s), 5.148(2H,s), 5.165(21H,d,J=14.8 Hz), 5.366(1H,s), 6.498(1H,d,J=2.2 Hz), 6.68–7.47(19H,m)

(3) The trans compound (0.6 g) obtained in (2) was dissolved in ethanol (15 ml), to which was added 1N sodium hydroxide (4 ml). The mixture was stirred for 50 minutes at 60° C. The reaction mixture was concentrated, which was neutralized with 5%-potassium hydrogensulfate, followed by extraction with ethyl acetate. The organic layer was washed with water and dried over anhydrous sodium sulfate. The solvent was distilled off, and the residue was purified by means of a silica gel column chromatography to give 3,5-trans-5-(3-tert-butoxycarbonylaminomethylphenyl)-7-chloro-1-(3,4-dibenzyloxybenzyl)-2-oxo-1,2,3,5-tetrahydro-4,1-benzoxazepine-3-acetic acid (0.38 g) as a colorless amorphous solid product.
NMR(CDCl$_3$) δ: 1.436(9H,s), 2.75–3.25(2H,m), 4.275(2H, d,J=6.2 Hz), 4.34–4.46(1H,m), 4.794(1H,d,J=14.6 Hz), 4.87–5.05(1H,m), 5.079(2H,s), 5.141(2H,s), 5.244(1H, d,J= 14.6 Hz), 5.341(1H,s), 6.488(1H,br), 6.68–7.47(19H,m)

(4) The compound obtained in (3) (0.35 g) and 2-fluorobenzylamine (68 mg) were dissolved in N,N-dimethylformamide (8 ml). To the solution were added, while stirring at OIC, cyano diethyl phosphate (90 mg) and triethylamine (60 mg). The reaction mixture was stirred for 30 minutes at room temperature, to which was added water (60 ml), followed by extraction with ethyl acetate (50 ml). The organic layer was washed with water and dried over anhydrous sodium sulfate. The solvent was distilled off, and the residue was purified by means of a silica gel column chromatography to give the titled compound (0.36 g) as a colorless amorphous solid product.
NMR(CDCl$_3$) δ: 1.433(9H,s), 2.698(1H,dd,J=5.8,14.6 Hz), 4.236(2H,d,J=5.8 Hz), 4.34–4.62(3H,m), 4.796(1H,d, J=14.6 Hz), 4.83–4.97(1H,m), 5.069(2H,s), 5.139(2H,s), 5.221(1H,d,J=14.6 Hz), 5.333(1H,s), 6.243(1H,t,J=6.0 Hz), 6.482(1H,d,J=2.4 Hz), 6.67–7.47(23H,m)

EXAMPLE 226

3,5-Trans-N-(2-fluorobenzyl)-5-(3-aminomethylphenyl)-7-chloro-1-(3,4-dibenzyloxybenzyl)-2-oxo-1,2,3,5- tetrahydro-4,1-benzoxazepine-3-
acetamide•hydrochloride

To the compound obtained in Example 225 (50 mg) was added 4N hydrochloric acid (ethyl acetate solution) (2 ml). The mixture was stirred for 30 minutes. The reaction mixture was concentrated, to which was added ethyl acetate (20 ml). The solvent was again distilled off to leave the titled compound (40 mg) as a colorless amorphous solid product.
NMR(CDCl$_3$) δ: 2.348(2H,br), 2.716(1H,dd,J=5.8,14.6 Hz), 2.933(1H,dd,J=7.2,14.6 Hz), 3.802(2H,br), 4.33–4.58 (3H, m), 4.775(1H,d,J=14.6 Hz), 5.055(2H,s), 5.124(2H,s), 5.234 (1H,d,J=14.6 Hz), 5.345(1H,s), 6.397(1H,t,J=5.8 Hz), 6.495 (1H,d,J=2.2 Hz), 6.68–7.47(23H,m)

EXAMPLE 227

3,5-Trans-N-(2-fluorobenzyl)-5-(3-tert-butoxycarbonylaminomethylphenyl)-7-chloro-1-(3,4-dihydroxybenzyl)-2-oxo-1,2,3,5-tetrahydro-4,1--benzoxazepine-3-acetamide In a mixture of ethyl acetate (10 ml) and methanol (2 ml) was dissolved 3,5-trans-N-(2-fluorobenzyl)-5-(3-tert-butoxycarbonylaminomethylphenyl)-7-chloro-1-(3,4-dibenzyloxybenzyl)-2-oxo-1,2,3,5-tetrahydro-4,1-benzoxazepine-3-acetamide obtained in Example 225 (0.26 g). To the solution was added 10% palladium carbon (50 mg). The mixture was stirred for 40 minutes under hydrogen atmosphere. The reaction mixture was subjected to filtration. The filtrate was washed with water and dried over anhydrous sodium sulfate. The solvent was distilled off to leave the titled compound (0.2 g) as a colorless amorphous solid product.
NMR(CDCl$_3$) δ: 1.438(9H,br), 2.669(1H,dd,J=6.0,14.4 Hz), 2.880(1H,dd,J=7.2,14.4 Hz), 4.05–4.62(5H,m), 4.92–5.25 (2H,m), 5.38–5.86(1H,m), 6.28–7.45(14H,m)

EXAMPLE 228

3,5-Trans-N-(2-fluorobenzyl)-5-(aminomethylphenyl)-7-chloro-1-(3,4-dihydroxybenzyl)-2-oxo-1,2,3,5tetrahydro-4,1-benzoxazepine-3-acetamide•hydrochloride To the compound obtained in Example 227 (0.17 g) was added 4N hydrogen chloride (ethyl acetate solution) (2 ml). The mixture was stirred for 30 minutes. The solvent was distilled off to leave the titled compound (0.16 g) as a colorless amorphous solid product.
NMR(DMSO-d$_6$) δ: 2.620(1H,dd,J=5.8,15.2 Hz), 2.833(1H, dd,J=7.4,15.2 Hz), 3.92–4.45(5H,m), 4.686(1H,d,J=14.4 Hz), 5.339(1H,d,J=14.4 Hz), 5.451(1H,s), 6.360(1H,d,J=2.0 Hz), 6.42–7.72(13H,m), 8.401(2H,br), 8.549(1H,br), 8.65–9.25(1H,m)

EXAMPLE 229

3,5-Trans-N-(2-fluorobenzyl)-5-(4-tert-butoxycarbonylaminomethylphenyl)-1-(4-benzyloxybenzyl)-7-chloro-2-oxo-1,2,3,5-tetrahydro-4,1-benzoxazepine-3-acetamide (1) In methanol (20 ml) were dissolved 2-amino-5-chloro-α-(4-tert-butoxycarbonylaminomethylphenyl)benzyl alcohol (1.0 g) and 4-benzyloxybenzaldehyde (0.65 g).

To the solution was added acetic acid (0.2 g) and cyano sodium borohydride (0.2 g). The mixture was stirred for 50 minutes at 60° C. The reaction mixture was concentrated, to which were added water (50 ml) and ethyl acetate (60 ml), followed by extraction. The organic layer was washed with water and dried over anhydrous sodium sulfate. The solvent was distilled off. The residue was purified by means of a silica gel column chromatography to give 2-(4-benzyloxybenzyl)amino-5-chloro-α-(4-tert-butoxycarbonylamino)benzyl alcohol (1.05 g) as colorless crystals.
NMR(CDCl$_3$) δ: 1.450(9H,s), 4.164(2H,s), 4.317(2H,d, J=5.4 Hz), 4.88–4.92(1H,m), 5.046(2H,s), 5.797(1H,s), 6.538(1H,d,J=8.6 Hz), 6.83–7.47(15H,m)

(2) The compound obtained in (1) was dissolved in ethyl acetate (30 ml), to which was added 1N sodium hydroxide (10 ml). To the mixture was added, while stirring, fumaric chloride monoethyl ester (0.29 g). The reaction mixture was stirred for 30 minutes. Then, the organic layer was separated, washed with water and dried over anhydrous sodium sulfate. The solvent was distilled off. The residue was dissolved in ethanol (20 ml), to which was added potassium carbonate (0.7 g). The mixture was stirred for 40 minutes at 60° C. The reaction mixture was concentrated, to which were added ethyl acetate (50 ml) and water (50 ml), followed by extraction. The organic layer was washed with water and dried over anhydrous sodium sulfate. The solvent was then distilled off. The residue was dissolved in ethanol (20 ml), to which was added potassium carbonate (0.7 g). The mixture was stirred for 40 minutes at 60° C. The reaction mixture was concentrated, to which were added water (60 ml) and ethyl acetate (50 ml), followed by extraction. The organic layer was washed with water and dried over anhydrous sodium sulfate. The solvent was distilled off. The residue was purified by means of a silica gel column chromatography. From the initial eluate was obtained 3,5-cis-1-(4-benzyloxybenzyl)-5-(4-tert-butoxycarbonylaminomethylphenyl)-7-chloro-2-oxo-1,2,3, 5-tetrahydro-4,1-benzoxazepine-3-acetic acid ethyl ester (0.2 g) as a colorless oily product.
NMR(CDCl$_3$) δ: 1.261(3H,t,J=7.2 Hz), 1.439(9H,s), 2.872 (1H,dd,J=7.8,16.7 Hz), 3.188(1H,dd,J=7.8,16.7 Hz), 3.722 (1H,d,J=16.0 Hz), 4.14(2H,q,J=7.2 Hz), 4.55–4.73(2H,m), 4.77–4.92(1H,m), 5.03(2H,s), 5.870(1H,s), 6.78–7.47(16H, m)

From the subsequent eluate was obtained 3,5-trans-1-(4-benzyloxybenzyl)-5-(4-tert-butoxycarbonylaminomethylphenyl)-7-chloro-2-oxo-1,2,3, 5-tetrahydro-4,1-benzoxazepine-3-acetic acid ethyl ester (0.85 g) as a colorless oily product.
NMR(CDCl$_3$) δ: 1.245(3H,t,J=7.2 Hz), 1.466(9H,s), 2.758 (1H,dd,J=5.6,16.8 Hz), 3.102(1H,dd,J=8.2,16.8 Hz), 4.124 (2H,q,J=7.2 Hz), 4.336(2H,d,J=6.0 Hz), 4.450(1H,dd,J=5.6, 8.2 Hz), 4.745(1H,d,J=14.6 Hz), 4.83–4.96(1H,m), 5.044 (2H,s), 5.365(1H,s), 5.430(1H,d,J=14.6 Hz), 6.508(1H,d,J= 1.8 Hz), 6.84–7.47(15H,m).

(3) In a mixture of tetrahydrofuran (5 ml) and methanol (10 ml) was dissolved 3,5-trans-1-(4-benzyloxybenzyl)-5-(4-tert-butoxycarbonylaminomethylphenyl)-7-chloro-2-oxo-1, 2,3,5-tetrahydro-4,1-benzoxazepine-3-acetic acid ethyl ester (0.85 g) obtained in (2). To the solution was added 1N sodium hydroxide (3 ml). The mixture was stirred for 50 minutes at 60° C. The reaction mixture was diluted with water (80 ml), which was neutralized with 5% potassium hydrogencarbonate, followed by extraction with ethyl acetate (60 ml). The organic layer was washed with water and dried over anhydrous sodium sulfate. The solvent was distilled off. The residue was purified by means of a silica gel column chromatography to give 3,5-trans-1-(4-benzyloxybenzyl)-5-(4-tert-butoxycarbonylaminomethylphenyl)-7-chloro-2-oxo-1,2,3, 5-tetrahydro-4,1-benzoxazepine-3-acetic acid (0.55 g) as a colorless amorphous solid product.
NMR(CDCl$_3$) δ: 1.462(9H,s), 2.831(1H,dd,J=5.0,16.7 Hz), 3.147(1H,dd,J=8.0,16.7 Hz), 4.333(2H,d,J=5.6 Hz), 4.412 (1H,dd,J=5.2,8.0 Hz), 4.776(1H,d,J=14.6 Hz), 4.83–4.98

(1H,m), 5.037(2H,s), 5.373(1H,s), 5.405(1H,d,J=14.6 Hz), 6.518(1H,d,J=2.0 Hz), 6.83–7.47(15H,m)

(4) In N,N-dimethylformamide (10 ml) were dissolved the compound (0.55 g) obtained in (3) and 2-fluorobenzylamine (0.13 g). To the solution were added, while stirring, cyanodiethyl phosphate (0.16 g) and triethylamine (0.11 g). The reaction mixture was stirred for 30 minutes at room temperature, to which were added water (50 ml) and ethyl acetate (80 ml), followed by extraction. The organic layer was washed with water and dried over anhydrous sodium sulfate. The solvent was distilled off. The residue was purified by means of a silica gel column chromatography to give the titled compound, 3,5-trans-N-(2-fluorobenzyl)-1-(4-benzyloxybenzyl)-5-(4-tert-butoxycarbonylaminomethylphenyl)-7-chloro-2-oxo-1,2,3,5-tetrahydro-4,1-benzoxazepine-3-acetamide (0.55 g) as a colorless amorphous solid product.

NMR(CDCl$_3$) δ: 1.472(9H,s), 2.694(1H,dd,J=6.4,14.5 Hz), 2.897(1H,dd,J=7.0,14.5 Hz), 4.333(2H,d,J=6.0 Hz), 4.38–4.62(2H,m), 4.691(1H,d,J=14.6 Hz), 5.036(2H,s), 5.332(1H,s), 5.436(1H,d,J=14.6 Hz), 6.23–6.35(1H,m), 6.481(1H,d,J=2.0 Hz), 6.83–7.47(19H,m)

EXAMPLE 230

3,5-Trans-N-(2-fluorobenzyl)-5-(4-aminomethylphenyl)-1-(4-benzyloxybenzyl)-7-chloro-2-oxo-1,2,3,5-tetrahydro-4,1-benzoxazepine-3-acetamide•hydrochloride In ethyl acetate (1 ml) was dissolved 3,5-trans-N-(2-fluorobenzyl)-1-(4-benzyloxybenzyl)-5-(4-tert-butoxycarbonylaminomethylphenyl)-7-chloro-2-oxo-1,2,3,5-tetrahydro-4,1-benzoxazepine-3-acetamide obtained in Example 229 (50 mg). To the solution was added 4N hydrogen chloride (ethyl acetate solution) (2 ml). The mixture was stirred for 30 minutes. The reaction mixture was concentrated, to which was added ethyl acetate (20 ml). The solvent was distilled off again to leave the titled compound (38 mg) as a colorless amorphous solid product.

NMR(CDCl$_3$) δ: 2.677(1H,dd,J=6.0,14.5 Hz), 2.894(1H,dd,J=7.2,14.5 Hz), 3.35–4.05(4H,m), 4.32–4.58(3H,m), 4.722(1H,d,J=14.8 Hz), 5.019(2H,s), 5.347(1H,d, J=14.8 Hz), 5.354(1H,s), 6.478(1H,d,J=2.2 Hz), 6.62–6.63(1H,m), 6.83–7.45(19H,m)

EXAMPLE 231

3,5-Trans-N-(2-fluorobenzyl)-5-(4-tert-butoxycarbonylaminomethylphenyl)-7-chloro-1-(4-hydroxybenzyl)-2-oxo-1,2,3,5-tetrahydro-4,1-benzoxazepine-3-acetamide In a mixture of ethyl acetate (20 ml) and methanol (5.ml) was dissolved 3,5-trans-N-(2-fluorobenzyl)-1-(4-benzyloxybenzyl)-5-(4-tert-butoxycarbonylaminomethylphenyl)-7-chloro-2-oxo-1,2,3,5-tetrahydro-4,1-benzoxazepine-3-acetamide obtained in Example 230 (0.45 g). To the solution was added 10% palladium carbon (0.1 g). The mixture was stirred for 50 minutes under hydrogen atmosphere. The reaction mixture was subjected to filtration. The filtrate was washed with water and dried over anhydrous sodium sulfate. The solvent was then distilled off to leave the titled compound (0.36 g) as a colorless amorphous solid product.

NMR(CDCl$_3$) δ: 1.465(9H,s), 2.732(1H,dd,J=6.4,14.6 Hz), 2.878(1H,dd,J=6.8,14.6 Hz), 4.296(2H,d,J=5.8 Hz), 4.33–4.67(4H,m), 4.85–5.03(1H,m), 5.263(1H,s), 5.403 (1H, d,J=14.4 Hz), 6.445(1H,d,J=2.2 Hz), 6.48–6.76(1H,m), 6.63–7.37(19H,m)

EXAMPLE 232

3,5-Trans-N-(2-fluorobenzyl)-5-(4-aminomethylphenyl)-7-chloro-1-(4-hydroxybenzyl)-2-oxo-1,2,3,5-tetrahydro-4,1-benzoxazepine-3-acetamide•hydrochloride In ethyl acetate (2 ml) was dissolved 3,5-trans-N-(2-fluorobenzyl)-5-(4-tert-butoxycarbonylaminomethylphenyl)-7-chloro-1-(4-hydroxybenzyl)-2-oxo-1,2,3,5-tetrahydro-4,1-benzoxazepine-3-acetamide obtained in Example 231 (0.16 g). To the-solution was added 4N hydrogen chloride (ethyl acetate solution) (3 ml). The mixture was stirred for 30 minutes. The reaction mixture was concentrated, which was processed with ether to give the titled compound (0.14 g) as a colorless amorphous solid product.

NMR(CDCl$_3$) δ: 2.734(1H,dd,J=6.2,14.8 Hz), 2.889(1H,dd, J=7.0,14.8 Hz), 3.93(2H,br), 4.32–4.50(3H,m), 4.639(1H, d,J=14.4 Hz), 5.325(1H,s), 5.434(1H,d,J=14.4 Hz), 6.448 (1H,s), 6.78–7.62(14H,m)

EXAMPLE 233

3,5-Trans-N-(2-fluorobenzyl)-1-(4-biphenylmethyl)-5-(5-tert-butoxycarbonylaminomethyl-2-methoxyphenyl)-7-chloro-2-oxo-1,2,3,5-tetrahydro-4,1-benzoxazepine-3-acetamide (1) 4-Tert-Butoxycarbonylaminomethyl-2-bromoanisole 3-Bromo-4-methoxybenzaldehyde (5.0 g) was dissolved in methanol (100 ml), to which was added sodium borohydride (0.5 g). The mixture was stirred for 30 minutes at room temperature. The reaction mixture was concentrated, to which were added water (100 ml) and ethyl acetate (15 ml) for extraction. The organic layer was washed with water and dried over anhydrous sodium sulfate. The solvent was distilled off, and the residue was dissolved in toluene (80 ml). To the solution were added thionyl chloride (2.8 g) and pyridine (0.5 ml). The mixture was stirred for 40 minutes at room temperature. The reaction mixture was decomposed by the addition, of a saturated aqueous solution of sodium hydrogencarbonate. The organic layer was separated, washed with water and dried over anhydrous sodium sulfate. The solvent was distilled off, and the residue was dissolved in N,N-dimethylformamide (50 ml). To the solution was added potassium phthalimide (5.2 g). The mixture was stirred for one hour at 80° C. To the reaction mixture was added cold water, which was subjected to extraction with ethyl acetate (150 ml). The organic layer was washed with water and dried over anhydrous sodium sulfate. The solvent was distilled off, and the residue was dissolved in a mixture of ethanol (150 ml) and tetrahydrofuran (20 ml). To the solution was added hydrazine hydrate (2 ml), and the mixture was stirred for 2 hours at 80° C. Insolubles were filtered off. The filtrate was concentrated, to which were added ethyl acetate (150 ml) and a saturated aqueous solution of sodium hydrogencarbonate (200 ml). The mixture was shaken. The organic layer was separated, washed with water and dried over anhydrous sodium sulfate. The solvent was distilled off, and the residue was dissolved in a mixture of ethyl acetate (60 ml) and tetrahydrofuran (20 ml). To the solution was added di-tert-butyl dicarbonate (4.6 g). The mixture was stirred for 40 minutes. The reaction mixture was washed with water and dried over anhydrous sodium sulfate. The solvent was distilled off, and the residue was purified by means of a silica gel column chromatography to give 4-tert-butoxycarbonylaminomethyl-2-bromoanisole (5.7 g) as a colorless oily product.

NMR(CDCl$_3$) δ: 1.460(9H,s), 3.885(3H,s), 4.227(2H,d, J=6.0 Hz), 4.70–4.93(1H,m), 6.853(1H,d,J=8.4 Hz), 7.198 (1H,dd,J=2.0,8.4 Hz), 7.472(1H,d,J=2.0 Hz)

(2)2-Amino-4-chloro-1-tert-butoxycarbonylaminomethyl-2'-methoxybenzophenone

In tetrahydrofuran (120 ml) were dissolved 4-tert-butoxycarbonylaminomethyl-2-bromoanisole obtained in (1) (5.5 g) and N-methyl-N-methyloxy-2-amino-4-chlorobenzamide (4.09 g). The solution was cooled to −78° C., to which was added dropwise, while stirring, n-butyl lithium (1.6 mol./L, hexane solution) (57 ml) over 40 minutes. To the reaction mixture were added water (150 ml) and ethyl acetate (200 ml). The mixture was subjected to extraction. The organic layer was washed with water and dried over anhydrous sodium sulfate. The solvent was distilled off, and the residue was purified by means of a silica gel column chromatography to give 2-amino-4-chloro-5'-tert-butoxycarbonylaminomethyl-21-methoxybenzophenone (5.5 g) as a yellowish oily product. NMR(CDCl$_3$) δ: 1.448(9H,s), 3.762(3H,s), 4.280(2H,d, J=6.0 Hz), 4.78–4.93(1H,m), 6.421(2H,br), 6.62–7.43(6H, m)

(3) The compound (5.5 g) obtained in (2) was dissolved in methanol (60 ml). To the solution was added, while stirring at temperature, sodium borohydride (1.5 g). The reaction mixture was concentrated, to which were added ethyl acetate (80 ml) and water (100 ml). The mixture was subjected to extraction. The organic layer was washed with water and dried over anhydrous sodium sulfate. The solvent was distilled off to leave 2-amino-5-chloro-α-(5-tert-butoxycarbonylaminomethyl-2-methoxy)-benzyl alcohol (5.6 g) as a colorless oily product. NMR(CDCl$_3$) δ: 1.438(9H,s), 3.857(3H,s), 4.217(2H,d, J=5.8 Hz), 4.73–4.92(1H,m), 5.981(1H,s), 6.607(1H,d, J=8.4 Hz), 6.85–7.33(5H,m)

(4) In methanol (40 ml) were dissolved the compound obtained in (3) (2.5 g) and 4-phenyl benzaldehyde (1.2 g). To the solution were added, while stirring, acetic acid (0.45 g) and cyano sodium borohydride (0.48 g). The reaction mixture was stirred for 30 minutes at 60° C., which was then concentrated. The concentrate was subjected to extraction by the addition of water (100 ml) and ethyl acetate (120 ml). The organic layer was washed with water and dried over anhydrous sodium sulfate. The solvent was distilled off to leave 2-(4-biphenylmethyl)-5-chloro-α-(5-tert-butoxycarbonylamino-2-methoxy)benzyl alcohol (3.3 g) as a colorless oily product. NMR(CDCl$_3$) δ: 1.426(9H,s), 3.732(3H,s), 4.210(2H,d, J=5.8 Hz), 4.35(2H,s), 4.65–4.85(1H,m), 6.035(1H,s), 6.701 (1H,d,J=8.6 Hz), 6.84–7.63(14H,m)

(5) The compound (3.3 g) obtained in (4) was dissolved in ethyl acetate (30 ml), to which was added 1N sodium hydroxide (20 ml). To the mixture was added, while stirring, fumaric chloride monoethyl ester (1.05 g). The reaction mixture was stirred for 20 minutes. Then, the organic layer was separated, washed with water and dried over anhydrous sodium sulfate. The solvent was distilled off, and the residue was dissolved in ethanol (80 ml). To the solution was added potassium carbonate (3.5 g). The mixture was stirred for 1.5 hour at 60° C. The reaction mixture was concentrated, to which were added ethyl acetate (100 ml) and water (80 ml). The mixture was subjected to extraction. The organic layer was washed with water and dried over anhydrous sodium sulfate. The solvent was then distilled off. The residue was purified by means of a silica gel column chromatography to give 3,5-trans-1-(4-biphenylmethyl)-5-(5-tert-butoxycarbonylaminomethyl-2-methoxyphenyl)-7-chloro-2-oxo-1,2,3,5-tetrahydro-4,1-benzoxazepine-3-acetic acid ethyl ester (3.5 g) as a colorless amorphous solid product. NMR(CDCl$_3$) δ: 1.260(3H,t,J=7.4 Hz), 1.466(9H,s), 2.805 (1H,dd,J=5.2,16.6 Hz), 3.173(1H,dd,J=8.6,16.6 Hz), 3.397 (3H,s), 4.160(2H,q,J=7.4 Hz), 4.298(2H,d,J=5.6 Hz), 4.507 (1H,dd,J=5.2,8.6 Hz), 4.72–4.92(1H,m), 4.965(1H, d,J=15.0 Hz), 5.505(1H,d,J=15.0 Hz), 5.911(1H,s), 6.546(1H,s), 6.752(1H,d,J=8.4 Hz), 7.23–7.63(13H,m)

(6) The compound obtained in (5) (3.3 g) was dissolved in a mixture of tetrahydrofuran (30 ml) and methanol (50 ml). To the solution was added 1N sodium hydroxide (20 ml). The mixture was stirred for 40 minutes at 60° C. The reaction mixture was concentrated, which was diluted with water (100 ml). The solution was neutralized with a 5% aqueous solution of potassium hydrogensulfate, followed by extraction with ethyl acetate (150 ml). The organic layer was washed with water and dried over anhydrous sodium sulfate. The solvent was distilled off. The residue was purified by means of a silica gel column chromatography to give 3,5-trans-1-(4-biphenylmethyl)-5-(5-tert-butoxycarbonylaminomethyl-2-methoxyphenyl)-7-chloro-2-oxo-1,2,3,5-tetrahydro-4,1-benzoxazepine-3-acetic acid (1.7 g) as a colorless amorphous solid product. NMR(CDCl$_3$) δ: 1.446(9H,s), 2.84–3.23(2H,m), 3.404(3H, s), 4.283(2H,d,J=5.6 Hz), 4.43–4.85(2H,m), 4.941(1H, d,J=15.0 Hz), 5.517(1H,d,J=15.0 Hz), 5.914(1H,s), 6.544(1H,s), 6.741(1H,d,J=8.4 Hz), 7.13–7.58(13H,m)

(7) In N,N-dimethylformamide (10 ml) were dissolved the compound obtained in (6) (0.3 g) and 2-fluorobenzylamine (68 mg). To the solution were added, while stirring at 0° C., cyano diethyl phosphate (90 mg) and triethylamine (80 mg). The reaction mixture was stirred for 20 minutes at room temperature, to which were then added ice-water and ethyl acetate (50 ml). The mixture was subjected to extraction. The organic layer was washed with water and dried over anhydrous sodium sulfate. The solvent was distilled off, and residue was purified by means of a silica gel column chromatography to give the titled compound, i.e. 3,5-trans-N-(2-fluorobenzyl)-1-(4-biphenylmethyl)-5-(5-tert-butoxycarbonyl-2-methoxyphenyl)-7-chloro-2-oxo-1,2,3,5-tetrahydro-4,1-benzoxazepine-3-acetamide (0.21 g) as a colorless amorphous solid product. NMR(CDCl$_3$) δ: 1.454(9H,s), 2.738(1H,dd,J=5.4,14.4 Hz), 2.994(1H,dd,J=7.8,14.4 Hz), 3.380(3H,s), 4.244(2H,d, J=6.0 Hz), 4.37–4.65(3H,m), 4.73–4.85(1H,m), 4.903(1H,d, J=15.2 Hz), 5.517(1H,d,J=15.2 Hz), 5.891(1H,s), 6.28–6.42 (1H,m), 6.542(1H,d,J=1.8 Hz), 6.750(1H,d,J=8.6 Hz), 6.96–7.58(17H,m)

EXAMPLE 234

3,5-Trans-N-(2-fluorobenzyl)-5-(5-aminomethyl-2-methoxyphenyl)-1-(4-biphenylmethyl)-7-chloro-2-oxo-1, 2,3,5-tetrahydro-4,1-benzoxazepine-3-acetamide•hydrochloride 4N Hydrogen chloride (an ethyl acetate solution) (2 ml) was added to 3,5-trans-N-(2-fluorobenzyl)-1-(4-biphenylmethyl)-5-(5-tert-butoxycarbonylaminomethyl-2-methoxyphenyl)-7-chloro-2-oxo-1,2,3,5-tetrahydro-4,1-benzoxazepine-3-acetamide obtained in Example 233 (0.16 g). The mixture was stirred for 30 minutes. The reaction mixture was concentrated, to which was added ethyl acetate (30 ml). The solvent was distilled off to leave the titled compound (0.14 g) as a colorless amorphous solid product. NMR(CDCl$_3$) δ: 2.765(1H,dd,J=5.6,14.4 Hz), 2.991(1H,dd, J=7.6,14.4 Hz), 3.391(3H,s), 3.62–4.05(2H,m), 4.38–4.62 (3H,m), 4.900(1H,d,J=15.2 Hz), 5.516(1H,d,J=15.2 Hz), 5.909(1H,s), 6.45–6.63(2H,m), 6.752(1H,d,J=8.4 Hz), 6.92–7.62(17H,m)

EXAMPLE 235

3,5-Trans-N-(2-fluorobenzyl)-1-(2-benzyloxybenzyl)-5-(3-tert-butoxycarbonylaminomethylphenyl)-7-chloro-2-oxo-1,2,3,5-tetrahydro-4,1-benzoxazepine-3-acetamide (1) In methanol (20 ml) were dissolved 2-amino-5-chloro-α-(3-tert-butoxycarbonylaminomethylphenyl)benzyl alcohol (0.5 g) obtained in Example 1 (2) and 2-benzyloxybenzaldehyde (0.7 g). To the solution were added acetic acid (0.15 g) and cyano sodium borohydride (0.16 g). The mixture was stirred for 40 minutes at 60° C. The reaction mixture was concentrated, to which were added water (50 ml) and ethyl acetate (60 ml), followed by subjecting the mixture to extraction. The organic layer was separated, washed with water and dried over anhydrous sodium sulfate. The solvent was distilled off, and the residue was purified by means of a silica gel column chromatography to give 2-(2-benzyloxybenzylamino)-5-chloro-α-(3-tert-butoxycarbonylaminomethylphenyl)benzyl alcohol (1.05 g) as a colorless oily product.

NMR(CDCl$_3$) δ: 1.441(9H,s), 4.248(2H,d,J=5.8 Hz), 4.328 (2H,br), 5.061(2H,s), 5.749(1H,s), 6.554(1H,d,J=8.8 Hz), 6.82–7.52(14H,m)

(2) The compound (1.05 g) obtained in (1) was dissolved in ethyl acetate. To the solution was added 1N sodium hydroxide (20 ml). To the mixture was added dropwise, while stirring, a solution of fumaric chloride monoethyl ester (0.33 g) in ethyl acetate (2 ml). The reaction mixture was stirred for 20 minutes. The organic layer was then separated, washed with water and dried over anhydrous sodium sulfate. The solvent was distilled off, and the residue was dissolved in ethanol (30 ml). To the solution was added potassium carbonate (0.7 g). The mixture was stirred for 1.5 hour at 60° C. The reaction mixture was concentrated, to which were added ethyl acetate (50 ml) and water (50 ml). The mixture was then subjected to extraction. The organic layer was washed with water and dried over anhydrous sodium sulfate. The solvent was distilled off, and the residue was purified by means of a silica gel column chromatography. From the initial eluate was obtained 3,5-cis-1-(2-benzyloxybenzyl)-5-(3-tert-butoxycarbonylaminomethylphenyl)-7-chloro-2-oxo-1,2,3,5-tetrahydro-4,1-benzoxazepine-3-acetic acid ethyl ester (0.15 g) as a colorless oily product.

NMR(CDCl$_3$) δ: 1.233(3H,t,J=7.2 Hz), 1.422(9H,s), 2.862 (1H,dd,J=5.8,16.6 Hz), 3.199(1H,dd,J=8.0, 16.6 Hz), 3.958 (1H,d,J=16.6 Hz), 4.03–4.22(4H,m), 4.465(1H,d, J=16.6 Hz), 4.666(1H,dd,J=5.8,8.0 Hz), 4.72–4.88(1H,m), 4.942 (2H,s), 5.876(1H,s), 6.82–7.45(16H,m)

From the subsequent eluate was obtained 3,5-trans-1-(2-benzyloxybenzyl)-5-(3-tert-butoxycarbonylaminomethylphenyl)-7-chloro-2-oxo-1,2,3,5-tetrahydro-4,1-benzoxazepine-3-acetic acid ethyl ester (0.45 g) as a colorless amorphous solid product.

NMR(CDCl$_3$) δ: 1.240(3H,t,J=7.2 Hz), 1.423(9H,s), 2.749 (1H,dd,J=5.2,16.7 Hz), 3.109(1H,dd,J=8.2,16.7 Hz), 4.132 (2H,q,J=7.2 Hz), 4.311(2H,d,J=6.0 Hz), 4.481(1H,dd,J=5.4, 8.4 Hz), 4.73–4.85(1H,m), 4.899(1H,d,J=11.4 Hz), 5.021 (1H,d,J=11.4 Hz), 5.178(1H,d,J=15.0 Hz), 5.289(1H,d, J=15.0 Hz), 5.583(1H,s), 6.465(1H,d,J=2.2 Hz), 7.83–7.48 (15H,m)

(3) A mixture (0.7 g) of 3,5-cis compound and 3,5-trans compound obtained in (2) was dissolved in a mixture of tetrahydrofuran (5 ml) and ethanol (10 ml). To the solution was added 1N sodium hydroxide (3 ml). The mixture was stirred for 30 minutes at 60° C. The reaction mixture was concentrated. The concentrate was diluted with water (20 ml), which was made acidic with a 5% aqueous solution of potassium hydrogensulfate, followed by extraction with ethyl acetate (50 ml). The organic layer was washed with water and dried over anhydrous sodium sulfate. The solvent was distilled off to leave 3,5-cis and 3,5-trans-1-(2-benzyloxybenzyl)-5-(3-tert-butoxycarbonylaminomethylphenyl)-7-chloro-2-oxo-1,2,3, 5-tetrahydro-4,1-benzoxazepine-3-acetic acid (0.62 g) as a mixture of colorless amorphous solid products.

NMR(CDCl$_3$) δ: 1.412(9×⅓H,s), 1.454(9×⅔H,s), 2.75–3.26(2H,m), 3.85–4.63(4H,m), 4.75–5.36(4H,m), 5.597(⅓H,s), 5.894(⅓H,s), 6.466(⅓,br), 6.75–7.45(15⅓H, m)

(4) In N,N-dimethylformamide (8 ml) were dissolved the compound obtained in (3) (0.6 g) and 2-fluorobenzylamine (0.14 g). To the solution were added, while stirring, cyano diethyl phosphate (0.16 g) and triethylamine (0.12 g). The reaction mixture was stirred for 30 minutes at room temperature, to which were added water (40 ml) and ethyl acetate (50 ml), followed by subjecting the mixture to extraction. The organic layer was washed with water and dried over anhydrous sodium sulfate. The solvent was distilled off. The residue was purified by means of a silica gel column chromatography to give the titled compound, 3,5-trans-N-(2-fluorobenzyl)-1-(2-benzyloxybenzyl)-5-(3-tert-butoxycarbonylaminomethylphenyl)-7-chloro-2-oxo-1, 2,3,5-tetrahydro-4,1-benzoxazepine-3-acetamide (0.5 g) as a colorless amorphous product.

NMR(CDCl$_3$) δ: 1.450(9H,s), 2.680(1H,dd,J=5.8,14.2 Hz), 2.912(1H,dd,J=7.21,14.2 Hz), 4.278(2H,d,J=6.0 Hz), 4.32–4.61(3H,m), 4.73–5.36(5H,m), 5.552(1H,s), 6,23–6.38 (1H,m), 6.442(1H,d,J=2.4 Hz), 6.88–7.43(19H,m) m.p.: 173–174° C.

EXAMPLE 236

3,5-Trans-N-(2-fluorobenzyl)-4-(3-aminomethylphenyl)-1-(2-benzyloxybenzyl)-7-chloro-2-oxo-1,2,3,5-tetrahydro-4,1-benzoxazepine-3-acetamide•hydrochloride 4N Hydrogen chloride (an ethyl acetate solution) (3 ml) was added to 3,5-trans-N-(2-fluorobenzyl)-1-(2-benzyloxybenzyl)-5-(tert-butoxycarbonylaminomethylphenyl)-7-chloro-2-oxo-1,2,3, 5-tetrahydro-4,1-benzoxazepine-3-acetamide obtained in Example 235 (0.1 g). The mixture was stirred for 40 minutes. The reaction mixture was concentrated, to which was added ethyl acetate (30 ml). The solvent was distilled off to leave the titled compound (92 mg) as a colorless amorphous solid product.

NMR(CDCl$_3$) δ: 2.701(1H,dd,J=5.8,14.4 Hz), 2.918(1H,dd, J=7.2,14.4 Hz), 3.846(2H,br), 4.33–4.62(3H,m), 4.899(1H, d,J=11.6 Hz), 5.016(1H,d,J=11.6 Hz), 5.154(1H,d,J=15.4 Hz), 5.276(1H,d,J=15.4 Hz), 5.584(1H,s), 6.385(1H,m), 6.473(1H,d,J=2.2 Hz), 6.82–7.45(19H,m)

EXAMPLE 237

3,5-Trans-N-(2-fluorobenzyl)-5-(tert-butoxycarbonylaminomethylphenyl)-7-chloro-1-(2-hydroxybenzyl)-2-oxo-1,2,3,5-tetrahydro-4,1-benzoxazepine-3-acetamide In a mixture of ethyl acetate (20 ml) and methanol (5 ml) was dissolved 3,5-trans-N-(2-fluorobenzyl)-1-benzyloxybenzyl)-5-(3-tert-butoxycarbonylaminomethylphenyl)- 7-chloro-2-oxo-1,2,3, 5-tetrahydro-4,1-benzoxazepine-3-acetamide obtained in Example 235 (0.45 g). To the solution was added 10% palladium-carbon (0.15 g). The mixture was stirred for 1.5 hour under hydrogen atmosphere. The reaction mixture was subjected to filtration. The filtrate was washed with water and dried over anhydrous sodium sulfate. The solvent was distilled off to leave the titled compound (0.32 g) as a colorless amorphous solid product.

NMR(CDCl$_3$) δ: 1.448(9H,s), 2.677(1H,dd,J=6.0,14.6 Hz), 2.919(1H,dd,J=7.6,14.6 Hz), 4.244(2H,d,J=5.6 Hz), 4.34–4.85(5H,m), 5.070(⅔H,s), 5.115(⅓H,s), 5.496(⅔H, s), 5.569(⅓H,s) 6.12–6.26(1H,m), 6.46–7.55(15H,m)

EXAMPLE 238

3,5-Trans-N-(2-fluorobenzyl)-5-(3-aminomethylphenyl)-7-chloro-1-(2-hydroxybenzyl)-2-oxo-1,2,3,5-tetrahydro-4, 1-benzoxazepine-3-acetamide•hydrochloride 4N hydrogen chloride (an ethyl acetate solution) (4 ml) was added the compound obtained in Example 237 (0.28 g). The mixture was stirred for 40 minutes. The reaction mixture was concentrated, to which was added ethyl acetate (30 ml). The solvent was distilled off to leave the titled compound (0.18 g) as a colorless amorphous solid product.
NMR(CDCl$_3$) δ: 2.62–2.98(2H,m), 3.72–3.95(2H,m), 4.25–4.66(4H,m), 5.231(1h,s), 5.47–5.62(1H,m), 6.32–6.44 (1H,m), 6.48–7.55(15H,m)

EXAMPLE 239

3,5-Trans-N-(2-fluorobenzyl)-1-(4-biphenylmethyl)-5-(N-tert-butoxycarbonyl-1,2,3,4-tetrahydroisoquinolin-5-yl)-7-chloro-2-oxo-1,2,3,5-tetrahydro-4,1-benzoxazepine-3-acetamide (1) In tetrahydrofuran (15 ml) were dissolved N-tert-butoxycarbonyl- 5-bromo-1,2,3,4-tetrahydroisoquinoline (0.9 g) and N-methyl-N-methyloxy-2-amino-5-chlorobenzamide (0.68 g). The solution was cooled to −78° C., to which was added dropwise, while stirring, n-butyl lithium (1.6 mol, hexane solution) (9 ml) over 30 minutes. To the reaction mixture was added water (50 ml) to decompose, followed by extraction with ethyl acetate (80 ml). The organic layer was washed with water and dried over anhydrous sodium sulfate. The solvent was distilled off, and the residue was purified by means of a silica gel column chromatography to give 2-(N-tert-butoxycarbonyl-1,2,3,4-tetrahydroisoquinolin-5-yl)carbonyl-4-chloro-aniline (0.26 g) as a yellow crystalline product. m.p.: 159–160° C.
NMR(CDCl$_3$) δ: 1.490(9H,s), 2.730(2H,t,J=5.8 Hz), 3.593 (2H,t,J=6.0 Hz), 4.648(2H,s), 6.425(2H,br), 6.685(1H,d,J=8.8 Hz), 7.08–7.32(5H,m)
(2) The compound obtained in (1) (0.24 g) was dissolved in methanol (3 ml). To the solution was added, while stirring, sodium borohydride (0.05 g). The reaction mixture was stirred for 20 minutes, which was then concentrated. The concentrate was subjected to extraction with a mixture of ethyl acetate (20 ml) and water (30 ml). The organic layer was washed with water and dried over anhydrous sodium sulfate. The solvent was distilled off to leave 2-amino-5-chloro-α-(N-tert-butoxycarbonyl-1,2,3,4-tetrahydroisoquinolin-5-yl)benzyl alcohol (0.22 g) as a colorless oily product.
NMR(CDCl$_3$) δ: 1.476(9H,s), 2.46–2.93(2H,m), 3.57(2H, t,J=5.8 Hz), 3.85–4.20(2H,m), 4.606(2H,s), 5.955(1H,s), 6.60–7.42(6H,m)
(3) In methanol (10 ml) were dissolved the compound (0.22 g) obtained in (2) and 4-phenyl benzaldehyde (0.13 g). To the solution were added acetic acid (0.05 g) and cyano sodium borohydride (0.05 g). The mixture was stirred for 30 minutes at 60° C. The reaction mixture was diluted with water (30 ml), which was subjected to extraction with ethyl acetate (4 ml). The organic layer was washed with water and dried over anhydrous sodium sulfate. The solvent was distilled off, and the residue was purified by means of a silica gel column chromatography to give 2-(4-biphenylmethylamino)-5-chloro-α-(N-tert-butoxycarbonyl-1,2,3,4-tetrahydroisoquinolin-5-yl)benzyl alcohol (0.26 g) as a colorless oily product.
NMR(CDCl$_3$) δ: 1.466(9H,s), 2.45–2.92(2H,m), 3.40–3.70 (2H,m), 4.387(2H,br), 4.610(2H,s), 5.0–5.2(1H,m), 6.004 (1H,s), 6.629(1H,d,J=8.6 Hz), 6.735(1H,d,J=2.4 Hz), 7.05–7.65(13H,m)
(4) The compound (0.26 g) obtained in (3) was dissolved in ethyl acetate (10 ml), to which was added 1N sodium hydroxide (3 ml). To the mixture was added, while stirring, fumaric chloride monoethyl ester (0.095 mg). The reaction mixture was stirred for 20 minutes. Then, the organic layer was separated, washed with water and dried over anhydrous sodium sulfate. The solvent was distilled off, and the residue was dissolved in ethanol (12 ml). To the solution was added potassium carbonate (0.2 g). The mixture was stirred for one hour at 60° C. The reaction mixture was concentrated, to which were added water (20 ml) and ethyl acetate. The mixture was subjected to extraction. The organic layer was washed with water and dried over anhydrous sodium sulfate. The solvent was distilled off, and the residue was purified by means of a silica gel column chromatography to give 3,5-trans-1-(4-biphenylmethyl)-5-(N-tert-butoxycarbonyl-1,2,3,4-tetrahydroisoquinolin-5-yl)-7-chloro-2-oxo-1,2,3,5-tetrahydro-4,1-benzoxazepine-3-acetic acid ethyl ester (0.28 g) as a colorless oily product.
NMR(CDCl$_3$) δ: 1.268(3H,t,J=7.2 Hz), 1.316(9H,br), 2.50–3.50(4H,m), 2.83(1H,dd,J=5.4,16.7 Hz), 4.17(2H,q,J=7.2 Hz), 4.341 (1H,d,J=17.0 Hz), 4.48(1H,dd,J=5.4,8.0 Hz), 4.592(1H,d, J=17.0 Hz), 4.75(1H,m), 5.545(1H,s), 5.62–5.85(1H,m), 6.462(1H,s), 7.0–7.7(14H,m)
(5) To a solution of the compound (0.28 g) obtained in (4) in a mixture of tetrahydrofuran (5 ml) and methanol (10 ml) was added 1N sodium hydroxide. The mixture was stirred for 40 minutes at 60° C. The reaction mixture was concentrated, which was diluted with water (10 ml) and neutralized with 5% potassium hydrogensulfate, followed by extraction with ethyl acetate (30 ml). The organic layer was washed with water and dried over anhydrous sodium sulfate. The solvent was distilled off, and the residue was purified by means of a silica gel column chromatography to give 3,5-trans-1-(4-biphenylmethyl)-5-(N-tert-butoxycarbonyl-1,2,3,4-tetrahydroisoquinolin-5-yl)-7-chloro-2-oxo-1,2,3,5-tetrahydro-4,1-benzoxazepine-3-acetic acid (0.2 g) as a colorless amorphous solid product.
NMR(CDCl$_3$) δ: 1.375(9H,br), 2.80–3.40(4H,m), 2.88 (1H, dd,J=5.2,16.8 Hz), 3.18(1H,dd,J=8.0,16.8 Hz), 4.341(1H, d,J=16.8 Hz), 4.44(1H,dd,J=5.4,7.9 Hz), 4.596(1h,d, J=16.8 Hz), 4.66–4.90(1H,m), 5.550(1H,s), 5.62–5.82(1H,m), 6.475(1H,s), 7.0–7.65(14H,m)
(6) The compound obtained in (5) (0.15 g) and 2-fluorobenzylamine (0.035 g) were dissolved in N,N-dimethylformamide (5 ml). To the solution was added cyano diethyl phosphate (0.45 g), to which was further added triethylamine (0.05 g). The reaction mixture was stirred for 30 minutes, which was diluted with water (20 ml), followed by extraction with ethyl acetate (30 ml). The organic layer was washed with water and dried over anhydrous sodium sulfate. The solvent was distilled off, and the residue was purified by means of a silica gel column chromatography to give the titled compound, 3,5-trans-N-(2-fluorobenzyl)-1-(4-biphenylmethyl)-5-(N-tert-butoxycarbonyl-1,2,3,4-tetrahydroisoquinolin-5-yl)-7-chloro-2-oxo-1,2,3,5-tetrahydro-4,1-benzoxazepine-3-acetamide (0.16 g), as a colorless crystalline product.
NMR(CDCl$_3$) δ: 1.369(9H,br), 2.55–3.40(2H,m), 2.75(1H, dd,J=6.0,14.6 Hz), 2.96(1H,dd,J=7.0,14.6 Hz), 4.25–4.85 (6H,m), 5.20(1H,s), 5.55–5.80(1H,m), 6.256(1H,br), 6.43 (1H,br), 6.95–7.65(18H,m) m.p.: 125–127° C.

EXAMPLE 240

3,5-Trans-N-(2-fluorobenzyl)-1-(4-biphenylmethyl)-1,2,3,5-tetrahydro-5-(1,2,3,4-tetrahydroisoquinolin-5-yl)-7-chloro-2-oxo-4,1-benzoxazepine-3-acetamide•hydrochloride 4N Hydrogen chloride (an ethyl acetate solution) (3 ml) was added to 3,5-trans-N-(2-fluorobenzyl)-1-(4-biphenylmethyl)-5-(N-tert-butoxycarbonyl-1,2,3,4- tetrahydroisoquinolin-5-yl)-7-chloro-2-oxo-1,2,3,5-tetrahydro-4,1-benzoxazepine-3-acetamide obtained in Example 239 (0.13 g). The mixture was stirred for 2 hours. The reaction mixture was concentrated, to which was added ethyl acetate (30 ml), followed by distilling off the solvent to leave the titled compound (0.1 g) as a colorless amorphous solid product.
NMR(CDCl$_3$) δ: 1.10–1.17(2H,m), 2.508(2H,t,J=6.0 Hz), 2.74(1H,dd,J=6.2,14.4 Hz), 2.96(1H,dd,J=7.0,14.4 Hz), 3.882(2H,s), 4.35–4.70(4H,m), 5.446(1H,s), 5.828(1H, d,J=14.4 Hz), 6.15–6.35(1H,m), 6.464(1H,d,J=1.6 Hz), 6.92–7.60(18H,m) m.p. (free form): 184–185° C.

EXAMPLE 241

3,5-Trans-N-isopropyl-1-(4-biphenylmethyl)-5-(3-tert-butoxycarbonylaminomethylphenyl)-7-chloro-2-oxo-1,2,3,5-tetrahydro-4,1-benzoxazepine-3-acetamide In N,N-dimethylformamide (3 ml) were dissolved 3,5-trans-1-(4-biphenylmethyl)-5-(3-tert-butoxycarbonylaminomethylphenyl)-7-chloro-2-oxo-1,2,3,5-tetrahydro-4,1-benzoxazepine-3-acetic acid (0.11 g) obtained in Example 4 (2) and isopropylamine (15 mg). To the solution were added, while stirring at 0° C., cyano diethyl phosphate (35 mg) and triethylamine (22 mg). The reaction mixture was stirred for 20 minutes at room temperature, followed by extraction with ethyl acetate (30 ml). The organic layer was washed with water and dried over anhydrous sodium sulfate. The solvent was distilled off, and the residue was purified by means of a silica gel column chromatography to give the titled compound (0.12 g) as a colorless amorphous solid product.
NMR(CDCl$_3$) δ: 1.126(3H,d,J=4.2 Hz), 1.158(3H,d,J=4.2 Hz), 1.439(9H,s), 2.621(1H,dd,J=6.0,14.0 Hz), 2.842(1H, dd, J=7.4,14.0 Hz), 4.221(2H,d,J=5.4 Hz), 4.525(1H,dd,J=6.2, 7.3 Hz), 4.65–4.85(1H,m), 4.936(1H,d,J=14.8 Hz), 5.378(1H,s), 5.413(1H,d,J=14.8 Hz),6.495(1H,d,J=2.0 Hz), 6.95–7.62(15H,m)

EXAMPLE 242

3,5-Trans-N-isopropyl-1-(3-aminomethylphenyl)-1-(4-biphenylmethyl)-7-chloro-2-oxo-1,2,3,5-tetrahydro-4,1-benzoxazepine-3-acetamide•hydrochloride A solution of the compound obtained in Example 241 (90 mg) in 4N hydrogen chloride (an ethyl acetate solution) (2 ml) was stirred for 30 minutes, which was then concentrated. To the concentrate was added ethyl acetate (10 ml). The mixture was again concentrated to leave the titled compound (72 mg) as a colorless amorphous solid product.
NMR(CDCl$_3$) δ: 1.125(3H,d,J=4.0 Hz), 1.158(3H,d,J=4.0 Hz), 2.631(1H,dd,J=6.2,14.2 Hz), 2.836(1H,dd,J=7.6,14.2 Hz), 3.798(2H,br), 4.526(1H,dd,J=6.6,6.6 Hz), 4.905(1H,d, J=14.6 Hz), 5.383(1H,s), 5.440(1H,d,J=14.6 Hz), 5.683(1H, d,J=8.0 Hz), 6.515(1H,d,J=1.8 Hz), 6.88–7.63(15H,m)

EXAMPLE 243

N-[3,5-Trans-1-(4-biphenylmethyl)-5-(3-tert-butoxycarbonylaminomethylphenyl)-7-chloro-2-oxo-1,2,3,5-tetrahydro-4,1-benzoxazepine-3-acetyl]-pyrrolidine In N,N-dimethylformamide (4 ml) were dissolved 3,5-trans-i-(4-biphenylmethyl)-5-(3-tert-butoxycarbonylaminomethylphenyl)-7-chloro-2-oxo-1,2,3,5-tetrahydro-4,1-benzoxazepine-3-acetic acid (0.1 g) obtained in Example 4 (2) and pyrrolidine (15 mg). To the solution were added, while stirring at 0° C., cyano diethyl phosphate (35 mg) and triethylamine (30 mg). The reaction mixture was stirred for 20 minutes at room temperature, to which were added water (20 ml) and ethyl acetate (30 ml), followed by extraction. The organic layer was washed with water and dried over anhydrous sodium sulfate. The solvent was distilled off, and the residue was purified by means of a silica gel column chromatography to give the titled compound (0.15 g) as a colorless oily product.
NMR(CDCl$_3$) δ: 1.435(9H,s), 1.65–2.08(4H,m), 2.692(1H, dd,J=4.6,16.0 Hz), 3.05–3.65(6H,m), 4.225(2H,d,J=6.0 Hz), 4.635(1H,dd,J=4.6,8.7 Hz), 4.68–4.83(1H,m), 4.892(1H,d, J=14.6 Hz), 5.371(1H,s), 5.491(1H,d,J=14.6 Hz), 6.485(1H, s), 6.88–7.63(15H,m)

EXAMPLE 244

N-(3,5-Trans-5-(3-aminomethylphenyl)-1(4-biphenylmethyl)-7-chloro-2-oxo-1,2,3,5-tetrahydro-4,1-benzoxazepine-3-acetyllpyrrolidine hydrochloride A solution of the compound (0.15 g) obtained in Example 243 in 4N hydrogen chloride (an ethyl acetate solution) (2 ml) was stirred for 30 minutes, which was then concentrated. To the concentrate was added ethyl acetate (20 ml). The solvent was again distilled off to leave the titled compound (55 mg) as a colorless amorphous solid product.
NMR(CDCl$_3$) δ: 1.76–2.05(4H,m), 2.706(1H,dd,J=4.8, 15.7 Hz), 3.139(1H,dd,J=8.6,15.7 Hz), 3.33–3.63(4H,m), 3.791 (2H,br), 4.640(1H,dd,J=4.8,8.8 Hz), 4.866(1H,d, J=14.6 Hz), 5.379(1H,s), 5.513(1H,d,J=14.6 Hz), 6.511(1H,br), 6.93–7.63(15H,m)

EXAMPLE 245

3,5-Trans-N-(2-methoxyphenyl)-1-(4-biphenylmethyl)-5-(3-tert-butoxycarbonylaminomethylphenyl)-7-chloro-2-oxo-1,2,3,5-tetrahydro-4,1-benzoxazepine-3-acetamide In N,N-dimethylformamide (3 ml) was dissolved 3,5-trans-1-(4-biphenylmethyl)-5-(3-tert-butoxycarbonylaminomethylphenyl)-7-chloro-2-oxo-1,2,3, 5-tetrahydro-4,1-benzoxazepine-3 acetic acid (0.3 g) obtained in Example 4 (2). To the solution were added 2-anisidine (0.118 g), 1-ethyl-3-(3-dimethylaminopropyl) carbodiimide hydrochloride (91 mg) and 4-dimethylaminopyridine (58 mg). The mixture was stirred for 12 hours. The reaction mixture was diluted with ethyl acetate (30 ml), which was washed with water and dried over anhydrous sodium sulfate. The solvent was distilled off to leave the titled compound (0.29 g) as a colorless amorphous solid product.
NMR(CDCl$_3$) δ: 1.43(9H,s), 2.89(1H,dd,J=6.8,14.8 Hz), 3.12(1H,dd, J=6.8,14.6 Hz), 3.76(3H,s), 4.16(2H,d, J=5:2 Hz), 4.57(1H,d,J=6.8 Hz), 4.68(1H,br), 4.91(1H, d,J=14.6 Hz), 5.43(1H,s), 5.48(1H,d,J=14.6 Hz), 6.49(1H,d,J=1.6 Hz), 6.83–7.59(18H,m), 8.21(1H,s), 8.36(1H,dd,J=1.8,7.6 Hz)

EXAMPLE 246

3,5-Trans-N-(2-methoxyphenyl)-5-(3-aminomethylphenyl)-1-(4-biphenylmethyl)-7-chloro-2-oxo-1,2,3,5-tetrahydro-4,1-benzoxazepine-3-acetamide To a solution of the compound obtained in Example 245 (0.219 g) in ethyl acetate (1 ml) was added 4N hydrogen chloride (an ethyl acetate solution) (1 ml). The mixture was stirred for one hour. The reaction mixture was concentrated. To the concentrate was added ether to cause precipitation to afford the titled compound (0.172 g) as a colorless amorphous solid product.
NMR(DMSO-d$_6$) δ: 2.89(1H,dd,J=7.4,15.4 Hz), 3.16(1H, dd, J=7.4,15.4 Hz), 3.80(3H,s), 4.07(2H,s), 4.55(1H,t,J=7.4 Hz), 5.14(1H,d,J=15.6 Hz), 5.40(1H,d,J=15.6 Hz), 5.62(1H, s), 6.43(1H,d,J=2.0 Hz), 6.88–7.71(18H,m), 7.95(1H,d,J= 7.8 Hz), 8.30(3H,br), 9.33(1H,s)

EXAMPLE 247

3,5-Trans-N-cyclohexyl-1-(4-biphenylmethyl)-5-(3-tert-butoxycarbonylaminomethylphenyl)-7-chloro-2-oxo-1,2,3,5-tetrahydro-4,1-benzoxazepine-3-acetamide In N,N-dimethylformamide (3 ml) were dissolved 3,5-trans-1-(4-biphenylmethyl)-5-(3-tert-butoxycarbonylaminomethylphenyl)-7-chloro-2-oxo-1,2,3,5-tetrahydro-4,1-benzoxazepine-3-acetic acid (0.3 g) obtained in Example 4 (2) and cyclohexylamine (0.12 g). To the solution were added 1-ethyl-3-(3-dimethylaminopropyl) carbodiimide•hydrochloride (91 mg) and 4-dimethylaminopyridine (58 mg). The mixture was stirred for 12 hours. The reaction mixture was diluted with ethyl acetate (20 ml), which was washed with water and dried over magnesium sulfate. The solvent was distilled off, and the residue was purified by means of a silica gel column chromatography to give the titled compound (34 mg) as a colorless oily product.

NMR(CDCl$_3$) δ: 1.06–1.37(5H,m), 1.44(9H,m), 1.62–1.94(4H,m), 2.62(1H,dd,J=6.0,14.0 Hz), 2.84(1H,dd,J=7.6, 14.0 Hz), 3.65–3.72(1H,m), 4.21(2H,d,J=5.6 Hz), 4.51(1H, dd,J=6.0,7.6 Hz), 4.74(1H,br), 4.91(1H,d,J=14.8 Hz), 5.37 (1H,s), 5.41(1H,d,J=14.8 Hz), 5.37(1H,s), 5.41(1H,d, J=14.8 Hz), 5.70(1H,d,J=7.6 Hz), 6.49(1H,d,J=1.8 Hz), 6.97–7.60(15H,m)

EXAMPLE 248

3,5-Trans-N-cyclohexyl-5-(3-aminomethylphenyl)-7-chloro-1,2,3,5-tetrahydro-4,1-benzoxazepine-3-acetamide•hydrochloride A To a solution of the compound (34 mg) obtained in Example 247 in ethyl acetate (1 ml) was added 4N hydrogen chloride (an ethyl acetate solution) (1 ml). The mixture was then stirred for one hour. The reaction mixture was concentrated, which was processed with ether to give the titled compound (28 mg) as a colorless amorphous solid product.

NMR(DMSO-d$_6$) δ: 1.07–1.31(6H,m), 1.43–1.78(4H,m), 2.56(1H,dd,J=6.6,15.4 Hz), 2.72(1H,dd,J=6.6,15.4 Hz), 3.45–3.51(1H,m), 4.00–4.09(2H,m), 4.44(1H,t,J=6.6 Hz), 5.10(1H,d,J=8.0,15.4 Hz), 5.37(1H,d,J=15.4 Hz), 5.56(1H, s), 6.39(1H,d,J=1.8 Hz), 7.11(1H,d,J=7.4 Hz), 7.38–7.69 (13H,m), 7.89(1H,d,J=7.6 Hz), 8.30(3H,br)

EXAMPLE 249

3,5-Trans-N-(thiazol-2-yl)-1-(4-biphenylmethyl)-5-(3-tert-butoxycarbonylaminomethylphenyl)-7-chloro-2-oxo-1,2,3,5-tetrahydro-4,1-benzoxazepine-3-acetamide In N,N-dimethylformamide (2 ml) were dissolved 3,5-trans-i-(4-biphenylmethyl)-5-(3-tert-butoxycarbonylaminomethylphenyl)-7-chloro-2-oxo-1,2,3,5-tetrahydro-4,1-benzoxazepine-3-acetic acid (0.2 g) obtained in Example 4 (2) and 2-aminothiazole (63 mg). To the solution were added 1-ethyl-3-(3-dimethylaminopropyl) carbodiimide.hydrochloride (73 mg) and 4-dimethylaminopyridine (40 mg). The reaction mixture was stirred for 12 hours, which was then diluted with ethyl acetate (20 ml). The solution was washed with water and dried over anhydrous sodium sulfate. The solvent was then distilled off to leave the titled compound (144 mg) as a colorless amorphous solid product.

NMR(CDCl$_3$) δ: 1.42(9H,s), 3.02–3.23(2H,m), 4.22(2H,br), 4.60(1H,t,J=6.6 Hz), 4.90(1H,d,J=14.6 Hz), 5.22(1H,br), 5.42(1H,s), 5.50(1H,d,J=14.6 Hz), 6.52(1H,s), 6.85(1H, br), 6.95(1H,d,J=3.2 Hz), 7.09(1H,s), 7.25–7.59(14H,m), 11.19 (1H,s)

EXAMPLE 250

3,5-Trans-N-(thiazol-2-yl)-5-(3-aminomethylphenyl)-1-(4-biphenylmethyl)-7-chloro-2-oxo-1,2,3,5-tetrahydro-4,1-benzoxazepine-3-acetamide•hydrochloride To a solution of the compound (144 mg) obtained in Example 249 in ethyl acetate was added 4N hydrogen chloride (an ethyl acetate solution) (1 ml). The mixture was stirred for one hour. The reaction mixture was concentrated, which was processed with ether to give the titled compound (120 mg) as a colorless amorphous solid product.

NMR(DMSO-d$_6$) δ: 2.97(1H,dd,J=5.4,16.6 Hz), 3.17(1H, dd, J=8.0,16.6 Hz), 4.01(2H,d,J=5.8 Hz), 4.58(1H,dd,J=5.4, 8.0 Hz), 5.14(1H,d,J=15.8 Hz), 5.62(1H,s), 6.43(1H,d, J=1.8 Hz), 7.12(1H,d,J=7.2 Hz), 7.24(1H,d,J=3.6 Hz), 7.44–7.80 (15H,m), 8.41(3H,br)

EXAMPLE 251

3,5-Trans-N-(2-fluorobenzyl)-5-(3-tert-butoxycarbonylaminomethylphenyl)-7-chloro-2-oxo-1,2,3,5-tetrahydro-1-(4-trifluoromethylbenzyl)-4,1-benzoxazepine-3-acetamide (1) In methanol (20 ml) were dissolved 2-amino-5-chloro-α-(3-tert-butoxycarbonylaminomethylphenyl)benzyl alcohol (0.5 g) obtained in Example 1 (2) and 4-trifluoromethylbenzaldehyde (0.28 g). To the solution were added acetic acid (0.1 g) and cyano sodium borohydride (0.17 g). The mixture was stirred for 40 minutes at 60° C. The reaction mixture was concentrated, to which were added ethyl acetate (30 ml) and water (20 ml), followed by extraction. The organic layer was washed with water and dried over anhydrous sodium sulfate. The solvent was distilled off, and the residue was purified by means of a silica gel column chromatography to give 5-chloro-2-(4-trifluoromethylbenzylamino)-α-(3-tert-butoxycarbonylaminomethylphenyl)benzyl alcohol (0.6 g) as a colorless oily product.

NMR(CDCl$_3$) δ: 1.426(9H,s), 2.848(1H,d,J=3.6 Hz), 4.18–4.37(4H,m), 4.767(1H,d,J=5.6 Hz), 4.83–4.94(1H,m), 5.15–5.25(1H,m), 5.825(1H,d,J=3.0 Hz), 6.419(1H,d,J=8.6 Hz), 6.98–7.76(10H,m)

(2) To a solution of the compound (0.6 g) obtained in (1) in ethyl acetate (15 ml) was added 1N sodium hydroxide (5 ml). To the mixture was added dropwise, while stirring at room temperature, a solution of fumaric chloride monoethyl ester (0.21 g) in ethyl acetate (2 ml). The reaction mixture was stirred for 20 minutes. The organic layer was then separated, which was washed with water and dried over anhydrous sodium sulfate. The solvent was distilled off, and the residue was dissolved in ethanol (20 ml). To the solution was added potassium carbonate (0.3 g). The mixture was stirred for 40 minutes at 60° C. The reaction mixture was diluted with water (50 ml), which was washed with water and then dried over anhydrous sodium sulfate. The solvent was distilled off, and the residue was purified by means of a silica gel column chromatography. From the initial eluate, 3,5-cis-5-(3-tert-butoxycarbonylaminomethylphenyl)-7-chloro-2-oxo-1,2,3,5-tetrahydro-1-(4-trifluoromethylbenzyl)-4,1-benzoxazepine-3-acetic acid ethyl ester (0.12 g) was obtained as a colorless oily product.

NMR(CDCl$_3$) δ: 1.267(3H,t,J=7.2 Hz), 1.429(9H,s), 2.871 (1H,dd,J=5.4,16.8 Hz), 3.250(1H,dd,J=8.4,16.8 Hz), 3.790 (1H,d,J=16.2 Hz), 4.05–4.35(2H,m), 4.56–4.72(2H,m), 4.75–5.02(1H,m), 5.896(1H,s), 6.88–7.58(11H,m) From the subsequent eluate, 3,5-trans-5-(3-tert-butoxycarbonylaminomethylphenyl)-7-chloro-2-oxo-1,2,3,5-tetrahydro-1-(4-trifluoromethylbenzyl)-4,1-benzoxazepine-3-acetic acid ethyl ester (0.36 g) was obtained as a colorless oily product.

NMR(CDCl₃) δ: 1.259(3H,t,J=7.2 Hz), 1.437(9H,s), 2.768 (1H,dd,J=5.0,16.9 Hz), 3.154(1H,dd,J=8.8,16.9 Hz), 4.14 (2H,q,J=7.2 Hz), 4.306(2H,d, J=5.8 Hz), 4.512(1H,dd, J=5.0,8.8 Hz), 5.109(1H,d, J=15.2 Hz), 5.294(1H,d, J=15.2 Hz), 5.416(1H,s), 6.546(1H,d,J=2.2 Hz), 6.97–7.68(10H,m)

(3) A mixture (0.42 g) of the trans-compound and the cis-compound obtained in (2) was dissolved in a mixture of tetrahydrofuran (5 ml) and methanol (10 ml). To the solution was added 1N sodium hydroxide (3 ml). The mixture was stirred for 40 minutes at 60° C. The reaction mixture was diluted with water (20 ml), which was neutralized with 5% potassium hydrogensulfate, followed by extraction with ethyl acetate (40 ml). The organic layer was washed with water and dried over anhydrous sodium sulfate. The solvent was distilled off, and the residue was purified by means of a silica gel column chromatography to give 3,5-trans-5-(3-tert-butoxycarbonylaminomethylphenyl)-7-chloro-2-oxo-1,2,3,5-tetrahydro-4,1-benzoxazepine-3-acetic acid as a colorless amorphous solid product.

NMR(CDCl₃) δ: 1.499(9H,s), 2.854(1H,dd,J=4.8,17.0 Hz), 3.05–3.32(1H,m), 4.309(2H,d,J=5.6 Hz), 4.43–4.56(1H,m), 4.95–5.03(1H,m), 5.04–5.42(2H,m), 5.453(1H,s), 6.548 (1H,br), 6.85–7.66(10H,m)

(4) In N,N-dimethylformaldehyde (4 ml) were dissolved the compound obtained in (3) (0.16 g) and 2-fluorobenzylamine (38 mg). To the solution were added, while stirring at 0° C., cyano diethyl phosphate (40 mg) and triethylamine (35 mg). The reaction mixture was stirred for 20 minutes at room temperature, which was then diluted with ethyl acetate (20 ml). The solution was washed with a 5% aqueous solution of potassium hydrogensulfate, then, with water, followed by drying over anhydrous sodium sulfate. The solvent was distilled off, and the residue was purified by means of a silica gel column chromatography to give the titled compound, 3,5-trans-N-(2-fluorobenzyl)-5-(3-tert-butylcarbonylphenyl)-7-chloro-2-oxo-1,2,3,5-tetrahydro-1-(4-trifluoromethylbenzyl)-4,1-benzoxazepine-3-acetamide (0.11 g), as a colorless crystalline product.

NMR(CDCl₃) δ: 1.446(9H,s), 2.708(1H,dd,J=5.6,14.6 Hz), 4.277(2H,d,J=5.8 Hz), 4.37–4.62(3H,m), 4.75–4.93(1H,m), 5.027(1H,d,J=14.8 Hz), 5.335(1H,d,J=14.8 Hz), 5.372(1H, s), 6.14–6.27(1H,m), 6.524(1H,d,J=2.2 Hz), 6.93–7.65(14H, m) m.p.: 100–101° C.

EXAMPLE 252

3,5-Trans-N-(2-fluorobenzyl)-5-(3-aminomethylphenyl)-7-chloro-2-oxo-1,2,3,5-tetrahydro-1-(4-trifluorobenzyl)-4,1-benzoxazepine-3-acetamide•hydrochloride To the compound obtained in Example 251 was added a 4N hydrogen chloride solution (ethyl acetate) (2 ml). The mixture was stirred for 30 minutes. The reaction mixture was concentrated, to which was added ethyl acetate (20 ml). The solvent was distilled off, and the residue was processed with ether to give the titled compound as a colorless amorphous solid product.

NMR(CDCl₃) δ: 2.45–2.65(2H,m), 2.788(1H,d,J=5.6, 14.7 Hz), 3.851(2H,br), 4.33–4.62(3H,m), 4.995(1H, d,J=15.8 Hz), 5.339(1H,d,J=15.8 Hz), 5.362(1H,s), 6.37–6.47(1H,m), 6.526(1H,d,J=2.4 Hz), 6.85–7.63(14H,m)

The following are some examples of the pharmacological actions of the compounds of the present invention, which should not be construed as limiting to them. The genetic operation using *E. coli* was conducted in accordance with the method described in "Sambrook, J., E. F. Fritsch, and T. Maniatis, *Molecular Cloning: A Laboratory Manual*, 2nd ed. Cold Spring Harbor Laboratory Press, Cold Spring Harbor, N. Y., 1989."

(1) Cloning of Human Somatostatin Receptor Protein Subtype 1 (SSTR1) DNA

DNA oligomers S1-1 and S1-2 were synthesized based on the known human SSTRic DNA sequence (Proc. Natl. Acad. Sci., USA 89: 251–255, 1992). The sequence of S1-1 is 5'-GGTCGACCTCAGCT AGGATGTTCCCCAATG-3' and that of S1-2 is 5'-GGTCGACCCGGGCTCAGAGCtTCGTGAT-3'. Human chromosome DNA (Clone Tech Inc. Catalog No. CL 6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to said PfuDNA polymerase. The conditions of the reaction were as follows: One cycle consisted of the reactions at 94° C. for 1 minute, at 63° C. for 1 minute and at 75° C. for 2 minutes, and 35 cycles were repeated. The reaction mixture was subjected to electrophoresis on 1% agarose gel to find that the DNA fragments of the intended size (about 1.2 kb) was specifically amplified. Said DNA fragments were recovered from the agarose gel after the usual manner and connected to pUC118 cleaved at the Hinc 11 site to transform into the competent cells, *Escherichia coli* JM109. The transformant having plasmid containing said DNA fragments was selected out and confirmed about the sequence of the intercalated DNA fragments by the automatic sequence analyzer employing fluorochroming, ALF DNA Sequencer (Pharmacia). As the result, the amino acid sequence expected from the base sequence was completely in agreement with the sequence described in the above-mentioned literature.

(2) Organization of the Expression Plasmid of Human Somatostatin Receptor Protein Subtype 1 (SSTR1) DNA pAKKO-111 was used as the expression vector in CHO (Chinese Hamster Ovary) cells. PAKKO-111 was organized as follows: The 1.4 kb DNA fragment containing SRa promoter and poly A appositional signal was obtained from pTB1417 described in the official gazette JPA-H5(1993)-076385 by treatment with Hind III and Cla I. On the other hand, the 4.5 kb DNA fragment containing dihydrofolic acid reductase (DHFR) gene was obtained from pTB348 [Biochem. Biophys. Res. Commun., 128, 256–264, 1985) by treatment with Cla I and Sal I. These DNA fragments were treated with T4 polymerase to make the terminal blunt-ended and connected with T4 ligase to organize pAKKO-111 plasmid. 5 gg of the plasmid having human SSTR1 DNA fragment obtained under the above (1) was digested with the restriction enzyme Sal I and subjected to electrophoresis on 1% agarose gel to recover the 1.2 kb DNA fragment coded with human SSTR1. Next, 1 μg of the above-mentioned expression vector pAKKO-111 (5.5 kb) was digested with Sal I to prepare the cloning site for intercalation of human SSTR1 DNA fragment. Said expression vector and the 1.2 kb DNA fragment were combined using T4DNA ligase. The reaction mixture was transduced into *E. coli* JM 109 by the calcium chloride method to obtain the expression plasmid pA1-11-SSTRI in which human SSTR1 DNA fragment was intercalated from the transformants in regular sequence against the promoter. This transformant is expressed as *Escherichia coli* JM109/pA-1-11-SSTR1.

(3) Transfection and Expression of Human Somatostatin Receptor Protein Subtype 1 (SSTR1) DNA in CHO (dhfr⁻) Cells 1×10⁶ CHO (dhfr⁻) cells were cultured for 24 hours in HAM F12 medium containing 10% bovine fetal serum on a laboratory dish of 8 cm in diameter. To the cultured cells was transfected 10 μg of the human SSTR1c DNA expression plasmid 1, pA-1-11-SSTR1, obtained under the above (2) by the calcium phosphate method (Cell Phect Transfection Kit: Pharmacia). The medium was switched to DMEM medium containing 10% bovine fetal serum 24 hours after the transfection to select the colony-forming cells (i.e. DHFR$^+$ cells) in this medium. Further, the selected cells were cloned from a single cell by the limiting dilution method and the somatostatin protein activity was measured as follows: Human SSTRc DNA expression cell strain was diluted with a buffer solution for assay [50 mM of tris hydrochloride, 1 mM of EDTA, 5 mM of magnesium chloride, 0.1% of BSA, 0.2 mg/ml of bacitracin, 10μg/ml of leupeptin, 1μg/ml of pepstatin and 200 units/ml of aprotinin (pH 7.5)) to adjust the cell count to $2\times10^4/200$ μl. 200 μl of the dilution was placed in a tube and to this was added 2 μl of 5 nM[$^{125}$I]-somatostatin-14 (2000 Ci/mmol, Amersham). The mixture was incubated at 25° C. for 60 minutes. For measurement of non-specific binding (NSB), the tube to which 2 μl of somatostatin-14 ($10^{-4}$ M) was added was also incubated. To the tube was added 1.5 ml of a buffer solution for washing [50 mM of tris hydrochloride, 1 mM of EDTA and 5 mM of magnesium chloride (pH 7.5)] and the mixture was filtered by GF/F glass fiber filter paper (Whatman) and washed further with 1.5 ml of the same buffer solution. [25 I] of the filter was measured by a γ-counter. Thus, a highly somatostatin-binding cell strain, SSTR1-8-3, was selected.

(4) Cloning of Human Somatostatin Receptor Protein Subtype 2 (SSTR2) DNA

DNA oligomers PT-1 and PT-2 were synthesized based on the known human SSTR2c DNA sequence (Proc. Natl. Acad. Sci., USA 89: 251–255, 1992). The sequence of PT-1 is 5'-GGTCGACACCATGGACATGGCGGATGAG-3' and that of PT-2 is 5'-GGTCGACAGTTCAGATACTGGTTTGG-3'. Human pituitary gland cDNA (Clone Tech Inc. Catalog No. 7173-1) was used as the template. To 1 ng of said cDNA was added 25 pmol of each of the above mentioned DNA oligomers and the polymerase chain reaction was carried out using 2.5 units of TaqDNA polymerase (Takara Shuzo). The composition of the reaction mixture was in accordance with the directions attached to said TaqDNA polymerase. The conditions of the reaction were as follows: One cycle consisted of the reactions at 94° C. for 30 seconds, at 52° C. for 20 seconds and at 72° C. for 60 seconds, and 30 cycles were repeated. The reaction mixture was subjected to electrophoresis on 1% agarose gel to find that the DNA fragments of the intended size (about 1.1 kb) was specifically amplified. Said DNA fragments were recovered from the agarose gel after the usual manner and connected to pUC118 cleaved at the Hinc 11 site to transform into the competent cells, Escherichia coli JM109. Two strains (No. 5 and No. 7) of the transformant having plasmid containing said DNA fragments were selected out and confirmed about the sequence of the intercalated DNA fragments by the automatic sequence analyzer employing fluorochroming, 373A DNA Sequencer (Applied Biosystem). As the result, point mutation was confirmed at one site in the sequence of the 770 base fragment of No. 5 strain between Sal I and Bst PI, and point mutation was also confirmed at one site in the sequence of the 360 base fragment of No. 7 strain between Bst PI and Sal I. Therefore, the fragments remaining after removing the Bst PI-Sal I fragment of No. 5 strain and the Bst PI-Sal I fragment of No. 7 strain were purified by electrophoresis on agarose to organize a plasmid in which these fragments were bound by the ligation reaction. Confirmation of the insertion sequence of the DNA fragment of this plasmid revealed that it was completely in agreement with the sequence described in the above literature.

(5) Organization of the Expression Plasmid of Human Somatostatin Receptor Protein Subtype 2 (SSTR2) DNA pAKKO-111 mentioned under the above (2) was used as the expression vector in CHO (Chinese Hamster Ovary) cells. 5 μg of the plasmid having human SSTR2 cDNA fragment obtained under the above (4) was digested with the restriction enzyme Sal I and subjected to electrophoresis on 1% agarose gel to recover the 1.1 kb DNA fragment coded with human SSTR2. Next, 1 μg of the above-mentioned expression vector pAKKO-111 (5.5 kb) was digested with Sal I to prepare the cloning site for intercalation of human SSTR2 DNA fragment. Said expression vector and the 1.1 kb DNA fragment were combined using T4DNA ligase. The reaction mixture was transduced into E. coli JM 109 by the calcium chloride method to obtain the expression plasmid pA1-11-SSTR1 in which human SSTR1 DNA fragment was intercalated from the transformants in regular sequence against the promoter. This transformant was expressed as Escherichia coli JM109/pAC-01.

(6) Transfection and Expression of Human Somatostatin Receptor ) Protein Subtype 2 (SSTR2) DNA in CHO (dhfr$^-$) Cells $1\times10^6$ CHO (dhfr$^-$) cells were cultured for 24 hours in HAM F12 medium containing 10% bovine fetal serum on a laboratory dish of 8 cm in diameter. To the cultured cells was transfected 10 μg of the human SSTR2 cDNA expression plasmid, pA-CO1, obtained under the above (5) by the calcium phosphate method (Cell Phect Transfection Kit: Pharmacia). The medium was switched to DMEM medium containing 10% bovine fetal serum 24 hours after the transfection to select the colony-forming cells (i.e. DHFR cells) in this medium. Further, the selected cells were cloned from a single cell by the limiting dilution method and a cell strain which highly expresses human SSTR2, SSTR2-HS5-9, was selected.

(7) Cloning of Human Somatostatin Receptor Protein Subtype 3 (SSTR3) DNA

DNA oligomers S3-1 and S3-2 were synthesized based on the known human SSTR3c DNA sequence (Mol. Endocrinol., 6:2136–2142, 1992). The sequence of S3-1 is 5'-GGTCGACCTCAACCATGGACATGCTTCATC-3' and that of S3-2 is 5'-GGTCGACTTTCCCCAGGCCCCTAtAGGTA-3'. Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to said PfuDNA polymerase. The conditions of the reaction were as follows: One cycle consisted of the reactions at 94° C. for 1 minute, at 63° C. for 1 minute and at 75° C. for 2 minutes, and 35 cycles were repeated. The reaction mixture was subjected to electrophoresis on 1% agarose gel to find that the DNA fragments of the intended size (about 1.3 kb) was specifically amplified. As a result, the amino acid sequence expected from the base sequence was completely in agreement with the sequence described in the above-mentioned literature.

(8) Organization of the Expression Plasmid of Human Somatostatin Receptor Protein Subtype 3 (SSTR3) DNA pAKKO-111 mentioned under the above (2) was used as the expression vector in CHO cells. 5 μg of the plasmid having human SSTR3 DNA fragment obtained under the above (7) was digested with the restriction enzyme Sal I and subjected to electrophoresis on 1% agarose gel to recover the 1.3 kb DNA fragment coded with human SSTR3. Next, 1 μg of the above-mentioned expression vector pAKKO-111 (5.5 kb) was digested with Sal I to prepare the cloning site for intercalation of human SSTR3 DNA fragment. Said expression vector and the 1.3 kb DNA fragment were combined using T4DNA ligase. The reaction mixture was transduced into *E. coli* JM 109 by the calcium chloride method to obtain the expression plasmid pAl-11-SSTR3 in which human SSTR3 DNA fragment was intercalated from the transformants in regular sequence against the promoter. This transformant is expressed as *Escherichia coli* JM109/pA-1-11-SSTR3.

(9) Transfection and Expression of Human Somatostatin Receptor Protein Subtype 3 (SSTR3) DNA in CHO (dhfr⁻) Cells 1×10⁶ CHO (dhfr⁻) cells were cultured for 24 hours in HAM F12 medium containing 10% bovine fetal serum on a laboratory dish of 8 cm in diameter. To the cultured cells was transfected 10 μg of the human SSTR3 DNA expression plasmid, pA-1-11-SSTR3, obtained under the above (5) by the calcium phosphate method. The medium was switched to DMEM medium containing 10% bovine fetal serum 24 hours after the transfection to select the colony-forming cells (i.e. DHFR cells) in this medium. Further, the selected cells were cloned from a single cell by the limiting dilution method and the somatostatin receptor protein expression activity was measured by the binding assay mentioned under the above (3). Thus, a highly somatostatin-binding cell strain, SSTR3-15-19, was selected.

(10) Cloning of Human Somatostatin Receptor Protein Subtype 4 (SSTR4) DNA

DNA oligomers S4-1 and S4-2 were synthesized based on the known human SSTR4 DNA sequence (Proc. Natl, Acad. Sci., USA 90: 4196–4200, 1993). The sequence of S4-1 is 5'-GGCTCGAGTCACCATGAGCGCCCCCTCG-3' and that of S4-2 is 5'-GGGCTCGAGCTCCTCAGAAGGTGGTGG-3'. Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to said PfuDNA polymerase. The conditions of the reaction were as follows: One cycle consisted of the reactions at 94° C. for 1 minute, at 66° C. for 1 minute and at 75° C. for 2 minutes, and 35 cycles were repeated. The reaction mixture was subjected to electrophoresis on 1% agarose gel to find that the DNA fragments of the intended size (about 1.2 kb) was specifically amplified. Confirmation of the insertion sequence of said DNA by the method mentioned under the above (1) revealed that the amino acid sequence expected from the base sequence was completely in agreement with the sequence described in the above-mentioned literature.

(11) Organization of the Expression Plasmid of Human Somatostatin Receptor Protein Subtype 4 (SSTR4) DNA pAKKO-111 mentioned under the above (2) was used as the expression vector in CHO cells. 5 μg of the plasmid having human SSTR4 DNA fragment obtained under the above (10) was digested with the restriction enzyme XhoI and subjected to electrophoresis on 1% agarose gel to recover the 1.2 kb DNA fragment coded with human SSTR4. Next, 1 pg of the above-mentioned expression vector pAKKO-111 (5.5 kb) was digested with Sal I to prepare the cloning site for intercalation of human SSTR4 DNA fragment. Said expression vector and the 1.2 kb DNA fragment were combined using T4DNA ligase. The reaction mixture was transduced into *E. coli* JM 109 by the calcium chloride method to obtain the expression plasmid pA1-11-SSTR4 in which human SSTR4 DNA fragment was intercalated from the transformants in regular sequence against the promoter. This transformant is expressed as *Escherichia coli* JM109/pA-1-11-SSTR4.

(12) Transfection and Expression of Human Somatostatin Receptor Protein Subtype 4 (SSTR4) DNA in CHO (dhfr⁻) Cells 1×10⁶ CHO (dhfr⁻) cells were cultured for 24 hours in HAM F12 medium containing 10% bovine fetal serum on a laboratory dish of 8 cm in diameter. To the cultured cells was transfected 10 μg of the human SSTR4 DNA expression plasmid, pA-1-11-SSTR4, obtained under the above (8) by the calcium phosphate method. The medium was switched to DMEM medium containing 10% bovine fetal serum 24 hours after the transfection to select the colony-forming cells (i.e. DHFR⁺ cells) in this medium. Further, the selected cells were cloned from a single cell by the limiting dilution method and the somatostatin receptor protein expression activity was measured by binding assay mentioned under the above (3). Thus, a highly somatostatin-biding cell strain, SSTR4-1-2, was selected.

(13) Cloning of Human Somatostatin Receptor Protein Subtype (SSTR5) DNA

DNA oligomers S5-1 and S5-2 were synthesized based on the known human SSTR5c DNA sequence (Biochem Biophys. Res. Commun., 195: 844–852, 1993). The sequence of S5-1 is 5'-GGTCGACCACCATGGAGCCCCTGTTCCC-3' and that of S5-2 is 5'-CCGTCGACACTCTCACAGCTTGCTGG-3'. Human chromosome DNA (Clone Tech Inc. Catalog No. CL6550-1) was used as the template. To 0.5 ng of said DNA was added 25 pmol of each of the above mentioned DNA oligomers and the polymerase chain reaction was carried out using 2.5 units of PfuDNA polymerase (Strata gene). The composition of the reaction mixture was in accordance with the directions attached to PfuDNA polymerase. The conditions of the reaction were as follows: One cycle consisted of the reactions at 94° C. for 1 minute, at 66° C. for 1 minute and at 75° C. for 2 minutes, and 35 cycles were repeated. The reaction mixture was subjected to electrophoresis on 1% agarose gel to find that the DNA fragments of the intended size (about 1.1 kb) was specifically amplified. Confirmation of the insertion sequence of said DNA fragment by method mentioned under the above (1). As the results, the amino acid sequence expected from the base sequence was completely in agreement with the sequence described in the above-mentioned literature.

(14) Organization of the Expression Plaismid of Human Somatostatin Receptor Protein Subtype 5 (SSTR5) DNA.

pAKKO-111 mentioned under the above (2) was used as the expression vector in CHO cells. 5 μg of the plasmid having human SSTR5 DNA fragment obtained under the above (13) was digested with the restriction enzyme Sal I and subjected to electrophoresis on 1% agarose gel to recover the 1.1 kb DNA fragment coded with human SSTR5. Next, 1 μg of the above-mentioned expression vector pAKKO-111 (5.5 kb) was digested with Sal I to prepare the cloning site for intercalation of human SSTR5 DNA fragment. Said expression vector and the 1.1 kb DNA fragment were combined using T4DNA ligase. The reaction mixture was transduced into *E. coli* JM 109 by the calcium chloride method to obtain the expression plasmid pA1-11-SSTR5 in which human SSTR5 DNA fragment was intercalated from the transformants in regular sequence against the promoter. This transformant was expressed as *Escherichia coli* JM109/pA-1-11-SSTR5.

(15) Transfection and Expression of Human Somatostatin Receptor Protein Subtype 5 (SSTR5) DNA in CHO (dhfr⁻) Cells $1 \times 10^6$ CHO (dhfr⁻) cells were cultured for 24 hours in HAM F12 medium containing 10% bovine fetal serum on a laboratory dish of 8 cm in diameter. To the cultured cells was transfected 10 μg of the human SSTR5c DNA expression plasmid, pA-1-11-SSTR5, obtained under the above (11) by the calcium phosphate method. The medium was switched to DMEM medium containing 10% bovine fetal serum 24 hours after the transfection to select the colony-forming cells (i.e. DHFR cells) in this medium. Further, the selected cells were cloned from a single cell by the limiting dilution method and the somatostatin receptor protein expression activity was measured by binding assay mentioned under the above (3). Thus, a highly somatostatin-biding cell strain, SSTR5-3-2-4, was selected.

Experiment 1

Preparation of CHO Cell Membrane Fraction Containing Human Somatostatin Receptor A human somatostatin receptor expression CHO cell strain, SSTR1-8-3, SSTR2-HS5-9, SSTR3-15-19, SSTR4-1-2 or SSTR5-32-4 ($10^9$), was suspended in a phosphate buffered saline containing 5mM of EDTA (PBS-EDTA). The suspension was centrifuged. To the cell pellet was added 10 ml of a homogenation buffer solution for cells (10 mM NaHCO₃, 5 mM EDTA, pH=7.5). The mixture was homogenized by a Politron homogenizer and centrifuged at 400×g for 15 minutes. The supernatant obtained was farther centrifuged at 100,000×g for an hour to obtain a precipitate of the membrane fraction. The precipitate was suspended in 2 ml of a buffer solution for assay (25 ml of tris hydrochloride, 1 ml of EDTA, 0.1% of BSA (bovine serum albumin) and 0.25 ml of PMSF, 1 μ/ml of pepstatin, 20 μg/ml of leupeptin, 10 μg/ml of phosphoramide, pH=7.5). The suspension was centrifuged at 1000,000×g for an hour. The membrane fraction recovered as precipitate was suspended again in 20 ml of buffer solution for assay. The suspension was placed in tubes and stored at −80° C. The suspension was thawed when used, and used at every use.

Experiment 2

Measurement of the Binding Inhibition Rate of $^{125}$I-Somatostatin

The membrane fraction prepared in Example 1 was diluted with a buffer solution for assay to adjust the concentration to 3 μg/ml. The diluate was placed in tubes each in quantity of 173 μl. To this were simultaneously added 2 μl of a solution of a compound in DMSO and 25μl of a 200pM radioisotope-labeled somatostatin ($^{125}$I-somatostatin: Amersham) solution. For measurement of the maximum binding, a reaction mixture added with 2 μl of DMSO and 25μl of a 200pM $^{125}$I-somatostatin solution was prepared. For measurement of non-specific binding, a reaction mixture added with 2 μl of a 100 μM somatostatin solution diluted in DMSO and 25 μl of a 200pM $^{125}$I-somatostatin solution was prepared at the same time. The mixtures were allowed to react at 25° C. for 60 minutes. Then, the reaction mixture was filtered by aspiration using a GF/B glass fiber filter paper (Whatman) treated with polyethylenimine. After filtration, the radioactivity of 125I-somatostatin remaining on the filter paper was measured by a γ-counter.

The binding rate (%) of each compound was calculated by the formula:

$$PBM = (B-NSB)/(BO-NSB) \times 100$$

(where PBM: Percent maximum Binding, B: radioactivity when a compound was added, Bo: maximum binding radioactivity, NSB: non-specific binding radioactivity). The binding rates were calculated by changing the concentrations of the compound to obtain the 50% inhibiting concentration of the compound ($IC_{50}$ value) by the Hil 1 plots.

The activities ($IC_{50}$ value, μM) of the compounds for each human somatostatin receptor obtained by the above method are shown in the following Table 5.

TABLE 5

Activities for human somatostatin receptor ($IC_{50}$ value, μM)

| Compound | SSTR1 | SSTR2 | SSTR3 | SSTR4 | SSTR5 |
|---|---|---|---|---|---|
| Ex. 5 | 1 | 0.1 | 0.003 | 0.3 | 0.0007 |
| Ex. 25 | 8 | 6 | 0.3 | 4 | 0.007 |
| Ex. 26 | 10 | >10 | 7 | 4 | 0.6 |
| Ex. 87 | 0.8 | 0.8 | 0.02 | 0.3 | 0.001 |
| Ex. 91 | >1 | >1 | 0.04 | 1 | 0.007 |
| Ex. 93 | 0.9 | 0.5 | 0.004 | 0.2 | 0.009 |
| Ex. 102 | >1 | 0.06 | 0.08 | 0.3 | 0.0001 |

Experiment 3

Inhibitory Effect on Forskolin-stimulated Accumulation of cAMP in Human Somatostatin Receptor Expression CHO Cells For measurement of the accumulated intracellular adenosine 3′,5′-monophosphate (cAMP), the human somatostatin receptor expression cell strains, SSTR2-HS5-9, SSTR-3-15-19, SSTR4-1-2 and SSTR5-32-4, mentioned in Reference Examples 2-3, 3-3,4-3 and 5-3, respectively, were proliferated in 24-well plate until they were confluent. Said cells were washed twice with 1 ml of Medium A [Dulbecco's Modified Eagle Medium (DMEM), 20 mM 2-(4-(2-hydroxyethyl)-1-piperazinyl]ethanesulfonic acid (HEPES) (pH 7.5), 0.2% bovine serum albumin and 0.2 mM 3-isobutyl-1-methylxanthine (IBMX)]. The medium A was placed in wells each in quantity of 400 μl and incubated at 37° C. for an hour. A solution of the compounds of Example 5 and Example 102 (solution obtained by diluting with Medium A to the 10-fold concentration of the final concentration) and a forskolin solution (final concentration 10 μM) were placed in wells each in quantities of 50 μl and 50 μl, respectively, and incubated at 37° C. for 30 minutes. The cells were washed twice with 1 ml of Medium A. Medium A (500 μl) and 100 μl of a 20% aqueous perchloric acid solution were placed in each well and left standing for 20 minutes at 4° C. to lyse the cells. The lyzate was placed in an Eppendorf's tube and centrifuged (15.000 rpm, for 10 minutes). The supernatant was placed in another Eppendorf's tube in quantity of 500 μl and neutralized with 60 mM of a HEPES aqueous solution containing 1.5 M of potassium chloride. The content of cAMP contained in this extract was determined by the Amersham kit (cAMP EIA system). The results ($ED_{50}$ value, nM) are shown in Table 6.

TABLE 6

Inhibitory effect on forskolin-stimulated accumulation of cAMP in human somatostatin receptor expression CHO cells ($ED_{50}$ value, nM)

| Compound | SSTR2 | SSTR3 | SSTR4 | SSTR5 |
|---|---|---|---|---|
| Ex. 5 | 300 | 2 | 200 | 0.7 |
| Ex. 102 | 200 | 0.3 | 100 | 0.3 |

The above results made it clear that the compounds of Example 5 and Example 102 have an agonistic effect on the human somatostatin receptor.

Experiment 4
Inhibition of the Growth Hormone (GH) Secretion from the Primary Cell Culture of the Rat Anterior Pituitary The anterior pituitaries were excised from the decapitated skull of 40 unanesthetized male rats of 8 weeks of age. The anterior pituitaries were placed in a laboratory dish containing the buffer A (consisting of 137 mM of sodium chloride, 5 mM of potassium chloride, 0.7 mM of disodium hydrogen phosphate, 25 mM of 2-[4-(2-hydroxyethyl)-1-piperazinyl] ethane sulfonic acid (HEPES) (pH 7.3), and 50 µg/ml of gentamicin sulfate] and washed once with the buffer A. Each anterior pituitary was cut into 4 pieces by scissors and washed twice again. The pieces of the anterior pituitaries were incubated in 30 ml of Enzyme Solution I [buffer A solution containing 0.4% of collagenase (Boehringer Mannheim), 0.4% of bovine serum albumin, 10 µg/ml of deoxyribonuclease (Sigma) and 0.2% of glucose] at 37° C. under shaking for 1 hour. After dispersion of the pieces of the anterior pituitaries by a Komagome pipette, the solution was centrifuged (480×g, for 6 minutes). The supernatant was discarded. The sediment was suspended in 30 ml of Enzyme Solution II [buffer A solution containing 0.25% of pancreatin (Sigma)] and incubated at 37° C. under shaking for 8 minutes. After adding 2 ml of fetal calf serum, the cell suspension was centrifuged (480×g, for 6 minutes) again and the supernatant was discarded. The sediment was suspended in 10 ml of Medium I [Dulbecco modified Eagle's Medium (DMEM) containing 10% of fetal calf serum, 20 mM of HEPES (pH 7.3), 50 U/ml of penicillin G and 50 µg/ml of streptomycin] and filtered through nylon mesh. The cells thus obtained were washed twice with 10 ml of Medium I. The number of the cells was counted, and the cells were suspended in Medium I in the cell density of $1.5 \times 10^5$ cells/ml. The aliquots of 1 ml each of the cell suspension were placed in the wells of 24-well plate and incubated at 37° C. for 3 days in the carbon dioxide incubator under 5% carbon dioxide-95% air environment. The cells were washed twice with 1 ml of Medium II (Medium I containing 0.2% bovine serum albumin instead of 10% fetal calf serum) and then incubated in 1 ml of Medium II for 1 hour. The supernatant was discarded. To each well of the 24-well plate 0.8 ml each of Medium II was added, and 0.1 ml of Medium II containing somatostatin-14 (SS-14) or the compound of Example 5 or the compound of Example 102 in the concentration of 10 times the final concentration and 0.1 ml of 10 nM growth hormone releasing hormone (GHRH) were added thereto. After incubation at 37° C. for 3 hours, 0.6 ml of the supernatant of the each well was collected to obtain a supernatant solution by the centrifugation on 1,000×g for 8 minutes. GH concentrations in the supernatant were determined by radioimmunoassay (RIA) kit of Amersham.

The GH secretion from the primary cell culture of rat anterior pituitary was inhibited dose-dependently. by the compounds of Example 5 and Example 102. The $ED_{50}$ values of the compounds of Example 5 and Example 102 were 8 nM and 10 nM, respectively.

The results revealed that the compounds of Example 5 and Example 102 had the effect of inhibiting the GH secretion from the primary cell culture of rat anterior pituitary.

Experiment 5
Study on Inhibition of GH Secretion Using Sprague-Dawley (SD) Rats

Male rats of SD strain were divided into the compound treatment group (n=5) and the control group (n=4). The rats in the compound treatment group were administered intraperitoneally with 0.5% methylcellulose saline solution containing the compound of Example 5 in the concentration of 3 mg/kg/5 ml, and the animals of the control group were administered intraperitoneally with 5 ml/kg of 0.5% methylcellulose saline solution. Four hours after administration, the rats were decapitated without anesthesia and whole blood was collected. The aliquots of 1 ml each of the plasma were obtained from the blood by centrifugation at 2,500 rpm at 4° C. for 30 minutes and stored at −20° C. Plasma GH concentrations were determined by RIA using the rat GH [ I] assay system (Amersham). The results are shown in Table 7.

TABLE 7

|  | Plasma GH concentrations (ng/ml) mean ± SD |
|---|---|
| Control (n = 4) | 92.0 ± 56.0 |
| Compound (Ex. 5) treatment group (n = 5) | 11.2 ± 6.5 |

Plasma GH concentration in rats treated with the compound of Example 5 declined significantly ($p<0.05$). The results clarified that the compound of Example 5 has inhibitory activity on GH secretion.

Experiment 6
Insulin Secretion Inhibition Study Using SD Rats

In order to study the inhibitory effect of the compound of Example 5 on the insulin secretion after the stimulation by glucose, blood was withdrawn at various time intervals after the simultaneous intravenous administration of the compound of Example 5 and glucose. Serum insulin concentrations were determined by RIA.

Male rats of SD strain (8 weeks of age, n=3) were weighed and anesthetized by the intraperitoneal administration of 50 mg/kg of pentobarbital. As blood clotting inhibitor 30 mg of EDTA was dissolved in 300 µl of 50,000 units/ml Trasylol (Bayer) solution, and the solution was placed into Eppendorf blood collecting tubes each in quantity of 3 Ξl. After fixing the rat on the rat fixing apparatus, the unilateral jugular vein was exposed and 100 µl of the blood was withdrawn from the vein by using a 25G injection needle. The test solution for the control group [without glucose] was saline containing 5% propylene glycol and 30% hydroxypropyl-β-cyclodextrin. The test solution for the control group [with glucose] was saline containing 5% propylene glycol, 30% hydroxypropyl-β-cyclodextrin, and 300 mg/kg/ml of glucose. The test solution for compound [compound (I)] treatment group was saline containing 5% propylene glycol, 30% hydroxypropyl-β-cyclodextrin, 300 mg/kg/ml of glucose, and the compound of Example 5 in dose of 0.003, 0.03, 0.3 or 3 mg/kg/ml. These solutions were administered into contralateral jugular vein and 100 µl each of the blood was withdrawn 1, 2, 4, 6, 8, and 10 minutes after the administration. The blood samples collected were centrifuged at 10,000 rpm at 4° C. for 15 minutes and the supernatants were stored at −20° C.

Plasma insulin concentrations were determined by RIA using the rat insulin [125I] assay system (Amersham). 50 µl each of the 25-fold diluted rat plasma samples were placed in tubes in duplicate. Then, 50 µl of primary antibody and 50 µl of [125I] rat insulin were added to each tube and agitated. The sample solutions and similarly processed serial dilutions of the standard rat insulin solution were left standing at room temperature for 4 hours. To this was added 125 µl of the secondary antibody. The mixture was agitated, and then left standing at room temperature for 10 minutes. The solutions were then centrifuged at 3,000 rpm at 4° C. for 10 minutes. After decanting the supernatant, the droplets of the solution remaining on the tube's inner walls were eliminated by means of swab. The radioactivity of the sediment was measured by gamma counter. The plasma insulin concentration was elevated in the rats by administration of glucose, but the elevation of the plasma insulin concentration was dose-dependently inhibited by simultaneous administration of the compound. The dosage of the compound which inhibited the elevation of insulin concentration by 50% was about 0.03 mg/kg. The results revealed that the compound of Example 5 has an inhibitory effect on insulin secretion in rats.

Industrial Applicability

The compounds (I) or salts thereof of the present invention have an excellent somatostatin receptor agonistic action with low toxicity and therefore, may be useful for the prophylaxis and therapy of the diseases related to this effect.

What is claimed is:

1. A compound of the formula:

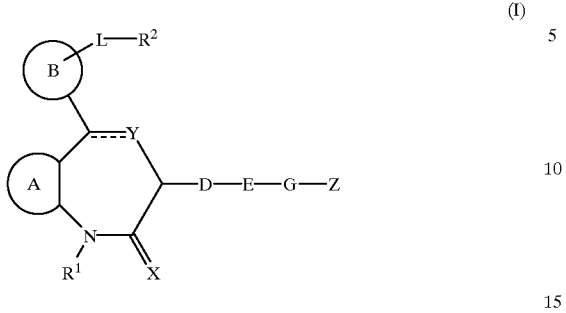

(I)

wherein ring A is $C_{6-14}$ aromatic hydrocarbon ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, ring B is 1) $C_{6-14}$ aromatic hydrocarbon ring, 2) 5- or 6-membered monocyclic aromatic heterocyclic ring having 1 to 4 hetero atoms selected from nitrogen, oxygen and sulfur in addition to carbon atoms or 3) bi- or tricyclic aromatic condensed heterocyclic ring which is formed by the condensation of benzene ring and the said 5- or 6-membered monocyclic aromatic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, mono- or di-$C_{1-6}$ alkylamino-$C_{1-6}$ alkoxy and mono- or di-$C_{1-6}$ alklamino-carbonyloxy, ring B may form, by combining with $R^2$, bi-cyclic non-aromatic condensed nitrogen-containing heterocyclic ring which is formed by the condensation of benzene ring and the 5- or 6-membered monocyclic non-aromatic heterocyclic ring having 1 to 3 hetero atoms selected from nitrogen, oxygen and sulfur, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, Z is 1) a $C_{3-14}$ cycloalkyl group, a $C_{3-14}$ cycloalkenyl group, a $C_{3-14}$ cycloalkadienyl group, an indanyl group or a $C_{6-14}$ aryl group, a 5- or 6-membered monocyclic aromatic or non-aromatic heterocyclic ring having 1 to 4 hetero atoms selected from nitrogen, oxygen and sulfur in addition to carbon atoms, or a bi- or tri-cyclic aromatic condensed heterocyclic ring which is formed by the condensation of benzene ring and the said 5- or 6-membered monocyclic aromatic heterocyclic ring or these partial reduction, which may have 1 to 5 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy, $C_{7-14}$ aralkyloxy-carbonyl, oxo and thioxo, or 2) a $C_{1-10}$ alkyl group, a $C_{2-10}$ alkenyl group or a $C_{2-10}$ alkynyl group, which may have 1 to 5 substituents selected from (1)halogen, (2)nitro, (3)cyano, (4)imino, (5)(i)amino which may have 1 to 2 substituents selected from $C_{1-6}$ alkyl which may be substituted with 1 to 5 halogen, phenyl, benzyl, formyl, $C_{1-6}$ alkyl-carbonyl, benzoyl, C16 alkoxy-carbonyl, $C_{7-14}$ aralkyloxy-carbonyl, sulfo, $C_{1-6}$ alkyl-sulfonyl and $C_{1-6}$ alkylamino-carbonyl, (ii) pyrrolidinyl, (iii)piperidyl, (iv)morpholinyl, (v)thio-morpholinyl, (vi) 4-methylpiperidyl, (vii) 4-phenylpiperidyl, (viii)4-benzyloxycarbonylpiperidyl, (6)hydroxy which may have substituents selected from (i)$C_{1-6}$ alkyl which may have 1 to 3 substituents selected from halogen, hydroxy, C16 alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (ii)$C_{6-10}$ aryl which may be have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl, (iii)$C_{714}$ aralkyl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkylcarbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl and (iv)formyl, $C_{1-6}$ alkyl-carbonyl, benzoyl, $C_{1-6}$ alkoxy-carbonyl, benzyloxycarbonyl, $C_{1-6}$ alkylsulfonyl, carbamoyl, mono- or di-$C_{1-6}$ alkyl-carbamoyl, which may have 1 to 3 substitutents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkylcarbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (7)carboxy which may be substituted with $C_{1-6}$ alkyl, benzyl or mono- or di-$C_{1-6}$ alkylamino, (8)$C_{3-6}$ cycloalkyl, (9)$C_{3-6}$ cycloalkenyl, (10)5- or 6-membered monocyclic aromatic heterocyclic ring having 1 to 4 hetero atoms selected from nitrogen, oxygen and sulfur in addition to carbon atoms or bi- or tri-cyclic aromatic condensed heterocyclic ring which is formed by the condensation of benzene ring and the said S- or 6-membered monocyclic aromatic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, (11)oxo and (12)pyrrolidinyl, $R^1$ is 1) a hydrogen atom, 2) a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{5-10}$ cycloalkadienyl group, a $C_{6-14}$ aryl group or a $C_{7-14}$ aralkyl group, which may have 1 to 5 substituents selected from (1)halogen, (2)nitro, (3)cyano, (4)imino, (5)(i) amino which may have 1 to 2 substituents selected from $C_{1-6}$ alkyl which may have 1 to 5 substituents selected from halogen, phenyl, benzyl, formyl, $C_{1-6}$ alkyl-carbonyl, benzoyl, $C_{1-6}$ alkoxy-carbonyl, $C_{7-14}$ aralkyloxy-carbonyl, sulfo, $C_{1-6}$ alkylsulfonyl and $C_{1-6}$ alkylamino-carbonyl, (ii)pyrrolidinyl, (iii)piperidyl, (iv)morpholinyl, (v)thio-morpholinyl, (vi)4-methylpiperidyl, (vii)4-phenylcarbonylpiperidyl, (viii) 4-benzyloxycarbonylpiperidyl,(6)hydroxy which may have substituents selected from (i)$C_{1-6}$ alkyl which may have 1 to 3 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (ii)$C_{6-10}$ aryl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl, (iii)$C_{7-14}$ aralkyl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl and (iv)formyl, $C_{1-6}$ alkyl-carbonyl, benzoyl, $C_{1-6}$ alkoxy-carbonyl, benzyloxycarbonyl, $C_{1-6}$ alkylsulfonyl, carbamoyl or mono- or di-$C_{1-6}$ alkyl-carbamoyl, which may have 1 to 3 substitutents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (7)carboxy which may be substituted with $C_{1-6}$ alkyl, benzyl or mono- or di-$C_{1-6}$ alkylamino, (8)$C_{3-6}$ cycloalkyl, (9)$C_{3-6}$ cycloalkenyl, (10)5- or 6-membered monocyclic aromatic heterocyclic ring having 1 to 4 hetero atoms selected from nitrogen, oxygen and sulfur in addition to carbon atoms or bi- or tri-cyclic aromatic condensed heterocyclic ring which is formed by the condensation of benzene ring and the said 5- or 6-membered monocyclic aromatic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-4}$ aralkyloxy, formyloxy, $C_{1-6}$ alkyl-carbonyloxy, $C_{1-5}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, and in addition to these substituents, a $C_{6-14}$ aryl group or a $C_{7-14}$ aralkyl group which may have 1 to 5 substituents selected from $C_{1-6}$ alkyl, halogeno-$C_{1-6}$ alkyl and $C_{6-14}$ aryl which may have 1 to 5 substituents selected from halogen, $C_{1-6}$ alkyl, halogeno-$C_{1-6}$ alkyl, $C_{1-6}$ alkoxy, $C_{7-14}$ aralkyloxy, hydroxy, amino, mono- or di-$C_{1-6}$ alkylmino, carboxy, $C_{1-6}$ alkyl-carbonyl, $C_{1-6}$ alkoxy-carbonyl, nitro and cyano, or 3) 5- or 6-membered monocyclic aromatic heterocyclic ring having 1 to 4 hetero atoms selected from nitrogen, oxygen and sulfur in addition to carbon atoms or bi- or tri-cyclic aromatic condensed heterocyclic ring which is formed by the condensation of benzene ring and the said 5- or 6-membered monocyclic aromatic heterocyclic ring, which may have 1 to 4 substituents selected from halogen, C16 alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-4}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, $R^2$ is (A) an unsubstituted amino group, (B) an amino group which have 1 to 2 substituents selected from 1) a $C_{1-10}$ alkyl group, a $C_{2-10}$ alkenyl group, a $C_{2-10}$-alkynyl group, a $C_{3-10}$ cycloalkyl group, a $C_{3-10}$ cycloalkenyl group, a $C_{5-10}$ cycloalkadienyl group, a $C_{6-14}$ aryl group or a $C_{7-14}$ aralkyl group, which may have 1 to 5 substituents selected from (1)halogen, (2)nitro, (3)cyano, (4)imino, (5)(i)amino which may have 1 to 2 substituents selected from $C_{1-6}$ alkyl which may be substituted with 1 to 5 halogen, phenyl, benzyl, formyl, $C_{1-6}$ alkyl-carbonyl, benzoyl, $C_{1-6}$ alkoxy-carbonyl, $C_{7-14}$ aralkyloxy-carbonyl, sulfo, $C_{1-6}$ alkyl-sulfonyl and $C_{1-6}$ alkylamino-carbonyl, (ii) pyrrolidinyl, (iii)piperidyl, (iv)morpholinyl, (v) thio-morpholinyl, (vi) 4-methylpiperidyl, (vii)4-phenylpiperidyl, (viii)4-benzyloxycarbonylpiperidyl, (6)hydroxy which may have substituents selected from (i)$C_{1-6}$ alkyl which may have 1 to 3 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (ii)$C_{6-10}$ aryl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl, (iii)$C_{7-14}$ aralkyl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl and (iv)formyl, $C_{1-6}$ alkyl-carbonyl, benzoyl, $C_{1-6}$ alkoxy-carbonyl, benzyloxycarbonyl, $C_{1-6}$ alkylsulfonyl, carbamoyl or mono- or di-$C_{1-6}$ alkyl-carbamoyl, which may have 1 to 3 substitutents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (7)carboxy which may be substituted with $C_{1-6}$ alkyl, benzyl or mono- or di-$C_{1-6}$ alkylamino, (8)$C_{3-6}$ cycloalkyl, (9)$C_{3-6}$ cycloalkenyl, (10)5- or 6-membered monocyclic aromatic heterocyclic ring having 1 to 4 hetero atoms selected from nitrogen, oxygen and sulfur in addition to carbon atoms or bi- or tri-cyclic aromatic condensed heterocyclic ring which is formed by the condensation of benzene ring and the said 5- or 6-membered monocyclic aromatic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, and in addition to these substituents, a $C_{6-14}$ aryl group or a $C_{7-14}$ aralkyl group which may have 1 to 5 substituents selected from $C_{1-6}$ alkyl, halogeno-$C_{1-6}$ alkyl and $C_{1-4}$ aryl which may have 1 to 5 substituents selected from halogen, $C_{1-6}$ alkyl, halogeno-$C_{1-6}$ alkyl, $C_{1-6}$ alkoxy, $C_{7-14}$ aralkyloxy, hydroxy, amino, mono- or di-$C_{1-6}$ alkylmino, carboxy, $C_{1-6}$ alkyl-carbonyl, $C_{1-6}$ alkoxy-carbonyl, nitro and cyano, 2) 5- or 6-membered monocyclic heterocyclic ring having 1 to 4 hetero atoms selected from nitrogen, oxygen and sulfur in addition to carbon atoms or bi- or tri-cyclic condensed heterocyclic ring which is formed by the condensation of benzene ring and the said 5- or 6-membered monocyclic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl and 3) formyl, $C_{1-6}$ alkyl-carbonyl, benzoyl, $C_{1-6}$ alkoxy-carbonyl, $C_{7-14}$ aralkyloxy-carbonyl, piperidin-4-ylcarbonyl, $C_{1-6}$ alkylsulfonyl, carbamoyl or mono- or di-$C_{1-6}$ alkyl-carbamoyl, which may have 1 to 3 substitutents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, or (C) 5 to 7-membered nitrogen-containing heterocyclic group having 1 to 4 heteroatoms selected from nitrogen, oxygen and sulfur or condensed nitrogen-containing heterocyclic group which is formed by the condensation of the said 5 to 7-membered nitrogen-containing heterocyclic ring and benzene or pyridine, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, D is a bond, or a $C_{1-10}$ alkylene group which may have $C_{3-6}$ cycloalkylene or phenylene and may have 1 to 3 substituents selected from $C_{1-6}$ alkyl, halogeno-$C_{1-6}$ alkyl, phenyl and benzyl, E is a bond, —CON($R^a$), —N($R^a$)CO—, —N($R^b$)CON($R^c$)—, —N($R^d$)COO—, —N($R^e$)SO$_2$—, —COO—, —N($R^f$)—, —O—, —S— —SO—, —SO$_2$—,

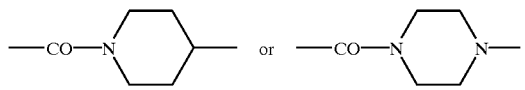

in which $R^a$, $R^b$, $R^c$, $R^d$, $R^e$ and $R^f$ are respectively a hydrogen atom or a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{5-10}$ cycloalkadienyl group, a $C_{6-14}$ aryl group or a $C_{7-14}$ aralkyl group, which may have 1 to 5 substituents selected from (1)halogen, (2)nitro, (3)cyano, (4)imino, (5)(i)amino which may have 1 to 2 substituents selected from $C_{1-6}$ alkyl which may have 1 to 5 substituents selected from halogen, phenyl, benzyl, formyl, $C_{1-6}$ alkyl-carbonyl, benzoyl, $C_{1-6}$ alkoxy-carbonyl, $C_{7-14}$ aralkyloxy-carbonyl, sulfo, $C_{1-6}$ alkylsulfonyl and $C_{1-6}$ alkylamino-carbonyl, (ii)pyrrolidinyl, (iii)piperidyl, (iv)morpholinyl, (v)thio-morpholinyl, (vi) 4-methylpiperidyl, (vii) 4-phenylpiperidyl, (viii)4-benzyloxycarbonylpiperidyl, (6)hydroxy which may have substituents selected from (i)$C_{1-6}$ alkyl which may have 1 to 3 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (ii)$C_{6-10}$ aryl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl, (iii) $C_{7-14}$ aralkyl which may have 1 to 5 substituents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkyl-carbamoyl, phenoxy, mono- or di-$C_{1-6}$ alkyl-carbamoyloxy, formylamino, $C_{1-6}$ alkyl-carbonylamino, formyloxy, $C_{1-6}$ alkyl-carbonyloxy, $C_{1-6}$ alkyl and halogeno-$C_{1-6}$ alkyl and (iv)formyl, $C_{1-6}$ alkyl-carbonyl, benzoyl, $C_{1-6}$ alkoxy-carbonyl, benzyloxycarbonyl, $C_{1-6}$ alkylsulfonyl, carbamoyl, mono- or di-$C_{1-6}$ alkyl-carbamoyl, which may have 1 to 3 substitutents selected from halogen, hydroxy, $C_{1-6}$ alkoxy, formyl, $C_{1-6}$ alkyl-carbonyl, carboxy, $C_{1-6}$ alkoxy-carbonyl, amino, mono- or di-$C_{1-6}$ alkylamino, pyrrolidinyl, piperidyl, morpholinyl, thio-morpholinyl, 4-methylpiperidyl, 4-phenylpiperidyl, carbamoyl, mono- or di-$C_{1-6}$ alkylcarbamoyl, phenoxy, mono- or di-$C_{1-6}$ alkyl-carbamoyloxy, formylamino, $C_{1-6}$ alkyl-carbonylamino, formyloxy and $C_{1-6}$ alkyl-carbonyloxy, (7)carboxy which may be substituted with $C_{1-6}$ alkyl, benzyl or mono- or di-$C_{1-6}$ alkylamino, (8)$C_{3-6}$ cycloalkyl, (9)$C_{3-6}$ cycloalkenyl, (10)5- or 6-membered monocyclic aromatic heterocyclic ring having 1 to 4 hetero atoms selected from nitrogen, oxygen and sulfur in addition to carbon atoms or bi- or tri-cyclic aromatic condensed heterocyclic ring which is formed by the condensation of benzene ring and the said 5- or 6-membered monocyclic aromatic heterocyclic ring, which may have 1 to 4 substituents selected from halogen, $C_{1-6}$ alkyl, halogeno-$C_{1-6}$ alkyl, phenyl, benzyl, $C_{1-6}$ alkoxy, halogeno-$C_{1-6}$ alkoxy, phenoxy, $C_{7-14}$ aralkyloxy, formyloxy, $C_{1-6}$ alkyl-carbonyloxy, $C_{1-6}$ alkylthio, halogeno-$C_{1-6}$ alkylthio, hydroxy, mercapto, cyano, nitro, carboxy, formyl, $C_{1-6}$ alkyl-carbonyl, benzoyl, $C_{1-6}$ alkoxy-carbonyl, phenoxycarbonyl, amino, mono- or di-$C_{1-6}$ alkylamino, formylamino, $C_{1-6}$ alkyl-carbonylamino, carbamoyl, mono- or di-$C_{1-6}$ alkyl-carbamoyl, sulfo, $C_{1-6}$ alkylsulfonyl, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy, hydroxyphenyl-$C_{1-6}$ alkoxy and $C_{7-14}$ aralkyloxy-carbonyl, and in addition to these substituents, a $C_{6-14}$ aryl group or a $C_{7-14}$ aralkyl group which may have 1 to 5 substituents selected from $C_{1-6}$ alkyl, halogeno-$C_{1-6}$ alkyl and $C_{6-14}$ aryl which may have 1 to 5 substituents selected from halogen, $C_{1-6}$ alkyl, halogeno-$C_{1-6}$ alkyl, $C_{1-6}$ alkoxy, $C_{7-14}$ aralkyloxy, hydroxy, amino, mono- or di-$C_{1-6}$ alkylmino, carboxy, $C_{1-6}$ alkyl-carbonyl, $C_{1-6}$ alkoxy-carbonyl, nitro and cyano, G is a bond, or a $C_{1-10}$ alkylene group which may have $C_{3-6}$ cycloalkylene or phenylene and may have 1 to 3 substituents selected from $C_{1-6}$ alkyl, halogeno-$C_{1-6}$ alkyl, phenyl and benzyl, L is a $C_{1-10}$ alkylene group which may be mediated by —O— or —S—, may have $C_{3-6}$ cycloalkylene or phenylene and may have 1 to 3 substituents selected from $C_{1-6}$ alkyl, halogeno-$C_{1-6}$ alkyl, phenyl and benzyl, X is two hydrogen atoms, an oxygen atom or a sulfur atom, ==== is a single bond, and Y is an oxygen atom, or a salt thereof.

2. A compound of claim 1, wherein Z is an optionally substituted cyclic group, G is an optionally divalent substituted hydrocarbon group and ring B do not form non-aromatic condensed nitrogen-containing heterocyclic ring by combining with $R^2$.

3. A compound of claim 1, wherein ring B is an optionally substituted benzene ring.

4. A compound of claim 1, wherein ring B is an optionally substituted aromatic heterocyclic ring.

5. A compound of claim 1, wherein ring B is a benzene ring or a thiophene ring.

6. A compound of claim 1, wherein ring A is an optionally substituted benzene ring.

7. A compound of claim 1, wherein ring A is a benzene ring which may be substituted with halogen, hydroxy or $C_{1-6}$ alkoxy.

8. A compound of claim 1, wherein $R^1$ is an optionally substituted hydrocarbon group.

9. A compound of claim 1, wherein $R^1$ is a $C_{1-6}$ alkyl group or a $C_{7-14}$ aralkyl group, which may be substituted with hydroxy, phenyl or amino which may be substituted with $C_{1-6}$ alkyl-carbonyl or $C_{1-6}$ alkylsulfonyl.

10. A compound of claim 1, wherein X is an oxygen atom.

11. A compound of claim 1, wherein L is an optionally substituted divalent hydrocarbon group.

12. A compound of claim 1, wherein L is a $C_{1-6}$ alkylene group.

13. A compound of claim 1, wherein Z is an optionally substituted phenyl group.

14. A compound of claim 1, wherein Z is a phenyl group which is substituted with halogen.

15. A compound of claim 1, wherein D is an divalent hydrocarbon group.

16. A compound of claim 1, wherein D is a $C_{1-6}$ alkylene group.

17. A compound of claim 1, wherein E is —CON($R^a$)— (in which $R^a$ is a hydrogen atom or an optionally substituted hydrocarbon group).

18. A compound of claim 1, wherein E is —CONH—.

19. A compound of claim 1, wherein G is a $C_{1-6}$ alkylene group.

20. A compound of claim 1, wherein $R^2$ is an unsubstituted amino group.

21. A compound of claim 1, wherein ring B form a tetrahydroisoquinoline ring by combining with $R^2$.

22. A compound of claim 1, wherein ring A is an optionally substituted benzene ring, ring B is an optionally substituted benzene ring, Z is an optionally substituted phenyl group, D is a $C_{1-6}$ alkylene group, G is a $C_{1-6}$ alkylene group, $R^1$ is an optionally substituted hydrocarbon group, $R^2$ is an unsubstituted amino group, E is —CONH—, L is a $C_{1-6}$ alkylene group, and X is an oxygen atom.

23. A compound of claim 22, wherein ring A is a benzene ring which may be substituted with halogen, hydroxy or $C_{1-6}$ alkoxy, ring B is a benzene ring, Z is a phenyl group which may be substituted with halogen and $R^1$ is a $C_{7-14}$ aralkyl group which may be substituted with hydroxy, phenyl or amino which may be substituted with $C_{1-6}$ alkyl-carbonyl or $C_{1-6}$ alkylsulfonyl.

24. A compound of claim 1, wherein ring A is an optionally substituted benzene ring, ring B is an optionally substituted aromatic heterocyclic ring, Z is an optionally substituted phenyl group, D is a $C_{1-6}$ alkylene group, G is a $C_{1-6}$ alkylene group, $R^1$ is an optionally substituted hydrocarbon group, $R^2$ is an unsubstituted amino group, E is —CONH—, L is a $C_{1-6}$ alkylene group, and X is an oxygen atom.

25. A compound of claim 1, wherein ring A is a benzene ring which may be substituted with halogen, hydroxy or $C_{1-6}$ alkoxy, ring B is a thiophene ring, Z is a phenyl group which may be substituted with halogen and $R^1$ is a $C_{7-14}$ aralkyl group which may be substituted with hydroxy, phenyl or amino which may be substituted with $C_{1-6}$ alkyl-carbonyl or $C_{1-6}$ alkylsulfonyl.

26. A compound of claim 1, wherein ring A is a benzene ring which may be substituted with halogen, hydroxy, $C_{1-6}$ alkoxy, halogeno-$C_{1-6}$ alkoxy, $C_{7-14}$ aralkyloxy, benzoyl-$C_{1-6}$ alkoxy, hydroxy-$C_{1-6}$ alkoxy, $C_{1-6}$ alkoxy-carbonyl-$C_{1-6}$ alkoxy, $C_{3-14}$ cycloalkyl-$C_{1-6}$ alkoxy, imidazol-1-yl-$C_{1-6}$ alkoxy, $C_{7-14}$ aralkyloxy-carbonyl-$C_{1-6}$ alkoxy or hydroxyphenyl-$C_{1-6}$ alkoxy, ring B is a benzene ring or a thiophene ring, which may be substituted with $C_{1-6}$ alkoxy, Z is a $C_{6-14}$ aryl group, a $C_{3-10}$ cycloalkyl group, a piperidyl group, a thienyl group, a furyl group, a pyridyl group, a thiazolyl group, an indolyl group or a $C_{1-6}$ alkyl group, which may have 1 to 3 substituents selected from halogen, formyl, halogeno-$C_{1-6}$ alkyl, $C_{1-6}$ alkoxy, $C_{1-6}$ alkoxy-carbonyl, oxo and pyrrolidinyl, D is a $C_{1-6}$ alkylene group, G is a bond or a $C_{1-6}$ alkylene group which may have phenylene and which may be substituted with phenyl, $R^1$ is a hydrogen atom, a $C_{1-6}$ alkyl group, a $C_{2-6}$ alkenyl group, a $C_{6-14}$ aryl group or a $C_{7-14}$ aralkyl group, which may be substituted with (1)halogen, (2)nitro, (3)amino which may have 1 to 2 substituents selected from $C_{1-6}$ alkyl which may be substituted with $C_{1-6}$ alkyl-carbonyl, benzyloxycarbonyl and $C_{1-6}$ alkylsulfonyl, (4)hydroxy which may be substituted with (i)$C_{1-6}$ alkyl which may be substituted with hydroxy, $C_{1-6}$ alkyl-carbonyl, carboxy or $C_{1-6}$ alkoxy-carbonyl, (ii)phenyl which may be substituted with hydroxy, (iii)benzoyl or (iv)mono- or di-$C_{1-6}$ alkylamino-carbonyl, (5)$C_{3-6}$ cycloalkyl, (6)phenyl which may be substituted with hydroxy or halogeno-$C_{1-6}$ alkyl, or (7)thienyl, furyl, thiazolyl, indolyl or benzyloxycarbonylpiperidyl, $R^2$ is an unsubstituted amino group, a piperidyl group or an amino group which have 1 to 2 substitutents selected from benzyl, $C_{1-6}$ alkyl which may be substituted with amino or phenyl, mono- or di-$C_{1-6}$ alkyl-carbamoyl, $C_{1-6}$ alkoxy-carbonyl, $C_{1-6}$ alkylsulfonyl, piperidylcarbonyl and $C_{1-6}$ alkyl-carbonyl which may be substituted with halogen or amino, E is a bond, —CON($R^a$)—, —N($R^a$)CO—, —N($R^b$)CON($R^c$)—, —COO—,

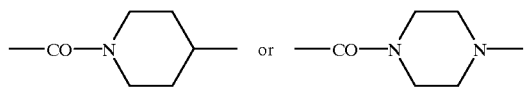

in which $R^a$, $R^b$ and $R^c$ is a hydrogen atom or a $C_{1-6}$ alkyl group,

L is a $C_{1-6}$ alkylene group which may be mediated by —O— and may be substituted with $C_{1-6}$ alkyl, X is an oxygen atom, and ring B may form a tetrahydroisoquinoline ring by combining with $R^2$.

27. A compound of claim 1, which is 3,5-trans-N-(2-fluorobenzyl)-5-(3-aminomethylphenyl)-1-(4-biphenylmethyl)-7-chloro-2-oxo-1,2,3,5-tetrahydro-4,1-benzoxazepine-3-acetamide or a salt thereof, (3S,5S)-N-(2-fluorobenzyl)-5-(3-aminomethylphenyl)-7-chloro-1-neopenthyl-2-oxo-1,2,3,5-tetrahydro-4,1-benzoxazepine-3-acetamide or a salt thereof, 3,5-trans-N-(2-fluorobenzyl)-5-(3-aminomethylphenyl)-1-{2-(4-biphenyl)ethyl}-7-chloro-2-oxo-1,2,3,5-tetrahydro-4,1-benzoxazepine-3-acetamide or a salt thereof, 3,5-trans-N-(2-fluorobenzyl)-5-(4-aminomethylphenyl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(2-aminomethylthiophen-5-yl)-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-{3-{(1-amino-1-methyl)ethyl}phenyl}-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-hydroxybenzyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-acetylaminobenzyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-(4-methanesulfonylaminobenzyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-hydroxybenzyl)-7-methyloxy-2-oxo-1,2,3,5-tetrahydro-4,1-benzoxazepine-3-acetamide or a salt thereof, 3,5-trans-N-(2-fluorobenzyl)-5-{4-{(1-amino-1-methyl)ethyl}phenyl}-1-(4-biphenylmethyl)-7-chloro-2-oxo-1,2,3,5-tetrahydro-4,1-benzoxazepine-3-acetamide or a salt thereof, 3,5-trans-N-(2-fluorobenzyl)-5-(3-aminomethylphenyl)-7-chloro-1-{2-(4-hydroxyphenyl)ethyl}-2-oxo-1,2,3,5-tetrahydro-4,1-benzoxazepine-3-acetamide or a salt thereof, 3,5-trans-N-(2-fluorobenzyl)-5-(3-aminomethylphenyl)-1-(4-biphenylmethyl)-7-hydroxy-2-oxo-1,2,3,5-tetrahydro-4,1-benzoxazepine-3-acetamide or a salt thereof, or 3,5-trans-N-(2-fluorobenzyl)-1-(4-biphenylmethyl)-5-(1,2,3,4-tetrahydroisoquinolin-5-yl)-7-chloro-2-oxo-1,2,3,5-tetrahydro-4,1-benzoxazepine-3-acetamide or a salt thereof.

28. A process for producing a compound of claim 1, or a salt thereof, which comprises reacting a compound of the formula: or a salt thereof, with a compound of the formula:

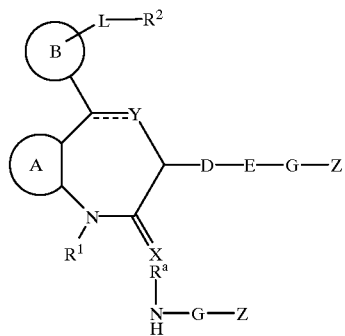

(1)

or a salt thereof.

29. A pharmaceutical composition which comprises a compound of claim 1 or a salt thereof in admixture with a pharmaceutically acceptable carrier or excipient.

30. A method for manufacturing a pharmaceutical composition, said method comprising combining a compound of claim 1, or a salt thereof with a pharmaceutically acceptable carrier or excipient.

31. A method for treating, diabetes, obesity, or inveterate diarrhea in a mammal which comprises administering an effective amount of a compound of claim 1 or a salt thereof to said mammal in need of such treatment.

* * * * *